United States Patent [19]

Klar et al.

[11] Patent Number: 5,235,072

[45] Date of Patent: Aug. 10, 1993

[54] 2-OXABICYCLO(2,2,1)HEPTANE DERIVATIVES AND PHARMACEUTICAL

[75] Inventors: Ulrich Klar; Helmut Vorbruggen; Hartmut Rehwinkel; Karl H. Thierauch; Claus S. Sturzebecher, all of Berlin, Fed. Rep. of Germany

[73] Assignee: Schering Aktiengesellschaft, Berlin, Fed. Rep. of Germany

[21] Appl. No.: 679,054

[22] PCT Filed: Sep. 7, 1989

[86] PCT No.: PCT/DE89/00585

§ 371 Date: May 7, 1991

§ 102(e) Date: May 7, 1991

[87] PCT Pub. No.: WO90/02740

PCT Pub. Date: Mar. 22, 1990

[30] Foreign Application Priority Data

Sep. 7, 1988 [DE] Fed. Rep. of Germany ....... 3830878

[51] Int. Cl.$^5$ ................. C07D 307/00; C07D 405/00; C07D 407/00; C07D 413/00; C07F 7/18; C07C 405/00; A61K 31/34; A61K 31/557

[52] U.S. Cl. .................................. 549/355; 514/233.5; 514/374; 514/307; 514/314; 514/320; 514/397; 544/147; 544/187; 546/139; 546/146; 546/152; 546/269; 549/422; 549/462; 549/463; 549/465

[58] Field of Search ............. 549/463, 462, 465, 355, 549/422; 514/456, 147, 187, 233.5, 374, 391, 307, 314, 320; 548/525, 311.4; 546/139, 146, 152, 169; 544/147, 187; 428/202.2

[56] References Cited

U.S. PATENT DOCUMENTS

| | | | |
|---|---|---|---|
| 3,950,363 | 4/1976 | Bundy | 549/463 |
| 4,028,350 | 6/1977 | Bundy | 549/463 X |
| 4,606,753 | 8/1986 | Powell | 549/415 |

FOREIGN PATENT DOCUMENTS

56-110685 9/1981 Japan .................. 549/463

OTHER PUBLICATIONS

Bundy III, Tetrahedron Letters, No. 24, pp. 1957–1960 (1975).
Hecker et al, Eur. J. Biochem., vol. 169 (3), pp. 563 to 569 (1987).
Morita et al, Chemical Abstracts, vol. 92, #69937c (1980).
Sakai et al I, Chem. Pharm. Bull., vol. 28, Nr. 6, pp. 1814 to 1819 (1980).
Sakai et al II, Chemical Abstracts, vol. 88, #152121v (1978).
Sakai et al III, Chemical Abstracts, vol. 93, #238875j (1980).
Toray, Chemical Abstracts, vol. 95, #150445z (1981).

*Primary Examiner*—Floyd D. Higel
*Attorney, Agent, or Firm*—Millen, White, Zelano & Branigan

[57] ABSTRACT

The invention relates to 2-oxabicyclo[2.2.1]heptane derivatives of formula I

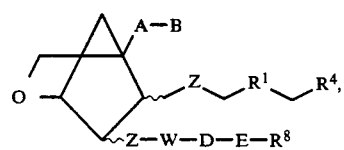

as well as their enantiomers, in which, e.g., A means —(CH$_2$)$_n$—, (E)— or (Z)—CH=CH—, —C≡C, —O— or —S—, B means hydrogen, C$_1$-C$_{10}$ alkyl, —OR$^2$, halogen, —C≡N, —N$_3$, —COOR$^3$, R$^1$ means oxygen or a —CH$_2$ group, R$^4$ means

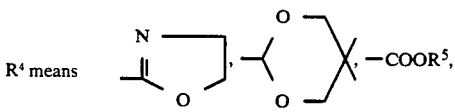

Z means —(CH$_2$)$_p$—, (E)—CH=CH—, —C≡C—,
W means a direct bond, a free or functionally modified

ABSTRACT—Continued hydroxymethylene group or a free or functionally modified

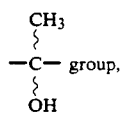

in which the OH group can be respectively in alpha- or beta-position,

D means a direct bond, a saturated alkylene group with 1-5 C atoms, a branched saturated or a straight-chain on branched unsaturated alkylene group with 2-5 C atoms, E means a direct bond, $-C\equiv C-$ or $-CH=CR^7$, $R^8$ means hydrogen, $C_1-C_{10}$ alkyl, $C_3-C_{10}$ cycloalkyl, optionally substituted $C_6-C_{12}$ aryl or a 5- or 6-member heterocyclic radical, and if $R^5$ means hydrogen, their salts with physiologically compatible bases, as well as the alpha-, beta- or gamma-cyclodextrin clathrates, as well as the compounds of formula I encapsulated with liposomes, process for their production and the pharmaceutical agents containing these compounds.

The compounds are thromboxane antagonists.

7 Claims, No Drawings

2-OXABICYCLO(2,2,1)HEPTANE DERIVATIVES AND PHARMACEUTICAL

DESCRIPTION

The invention relates to 2-oxabicyclo[2.2.1]heptane derivatives of formula I

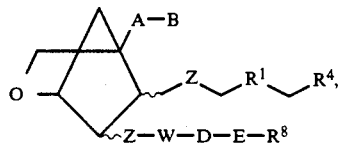

(I)

as well as their enantiomers, in which

A means —($CH_2$)$_n$—, (E)— or (Z)—CH=CH—, —C≡C—, —O— or —S—, n means 0-7,

B means hydrogen, $C_1$-$C_{10}$ alkyl, —$OR^2$, halogen, —C≡N, —$N_3$, —$COOR^3$,

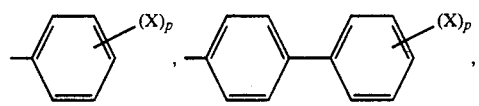

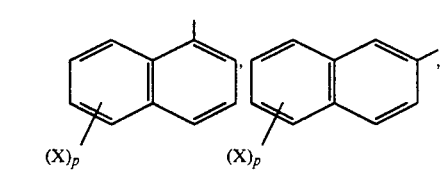

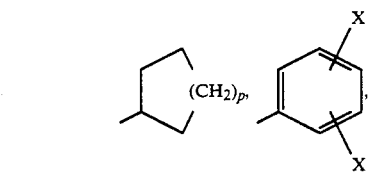

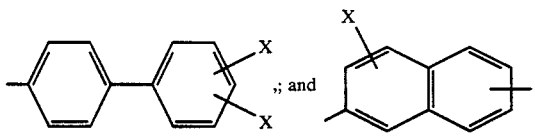

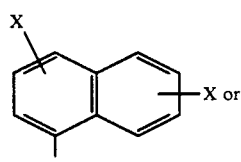

a 5- or 6-member heterocyclic radical with at least one N, O or S atom, $R^1$ means oxygen, a direct bond or a —$CH_2$ group, $R^2$ means hydrogen, $C_1$-$C_{10}$ alkyl, $C_6$-$C_{12}$ aryl substituted by X or $C_7$-$C_{16}$ aralkyl substituted by X, $R^3$ means hydrogen, $C_1$-$C_{10}$ alkyl, $C_5$-$C_6$ cycloalkyl, $C_6$-$C_{12}$ aryl or $C_7$-$C_{16}$ aralkyl, x means hydrogen, $C_1$-$C_5$ alkyl,

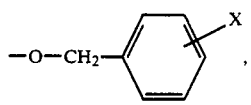

—$OR^2$, halogen, 'C≡N, —$N_3$, —$NO_2$, —$COOR^3$, trifluoromethyl, or phenyl;

$R^4$ means

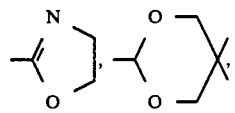

—$COOR^5$, in which $R^5$ can means hydrogen or $C_1$-$C_{10}$ alkyl optionally substituted by halogen, phenyl, $C_1$-$C_4$ alkoxy or di-($C_1$-$C_4$)-alkylamino, $C_5$-$C_6$ cycloalkyl, $C_7$-$C_{16}$ aralkyl, phenacyl or $C_6$-$C_{16}$ aryl substituted by X or a 5- or 6-member heterocyclic radical with at least one N, O or S atom, or —$CONHR^6$, with $R^6$ meaning hydrogen, can be $C_1$-$C_{10}$ alkanoyl or $C_1$-$C_{10}$ alkanesulfonyl or —$CONR^2R^3$ or the radical —CON ($CH_2$)$_t$ or the radical

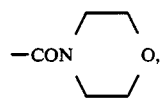

t means 2 or 3,

Z means —($CH_2$)$_p$—, (E)—CH=CH. —CH=$CR^7$—, —C≡C—, p means 0 to 5,

W means a direct bond

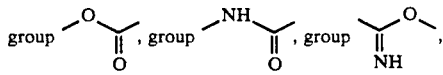

a free or functionally modified hydroxymethylene group or a free or functionally modified

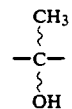

group, in which the OH group can be respectively in alpha- or beta-position

D means a direct bond,

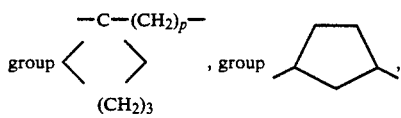

a straight-chain saturated alkylene group with 1-5 C atoms, a branched saturated or a straight-chain or branched unsaturated alkylene group with 2-5 C atoms, which optionally can be substituted by fluorine atoms, s means 2 to 4, E means a direct bond, —C≡C— or —CH=CR⁷—, in which R⁷ means hydrogen, C₁-C₅ alkyl, halogen, or trifluoromethyl, R⁸ means hydrogen, C₁-C₁₀ alkyl, C₃-C₁₀ cycloalkyl, C₇-C₁₆ aralkyl optionally substituted by X, C₆-C₁₂ aryl optionally substituted by X or a 5- or 6-membered heterocyclic radical with at least one N, O or S atom or, if E represents a direct bond.

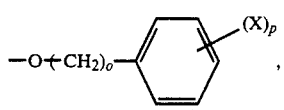

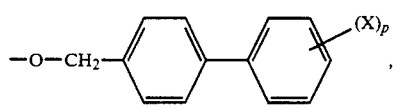

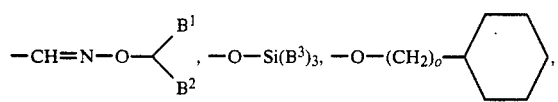

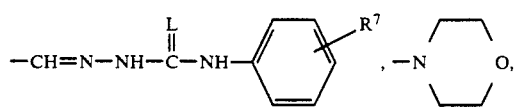

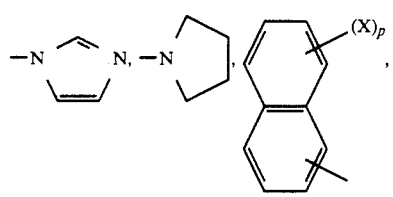

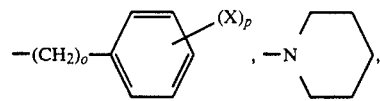

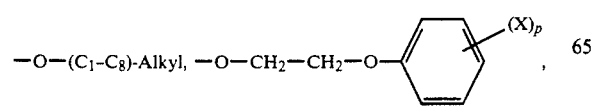

-continued

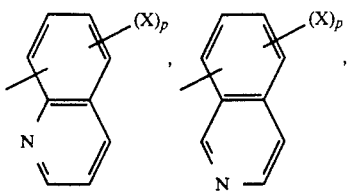

—O—(CH₂)ₛ—L—(CH₂)ₒ—X, in which X can be the same or different in radicals —(X)ₚ, if p=2 or 3, o means 0 to 5, R¹ means oxygen, a direct bond or a —CH₂ group, R² means hydrogen, C₁-C₁₀ alkyl, C₆-C₁₂ aryl substituted by X or C₇-C₁₆ aralkyl substituted by X, R³ means hydrogen, C₁-C₁₀ alkyl, C₅-C₆ cycloalkyl, C₆-C₁₂ aryl or C₇-C₁₆ aralkyl, x means hydrogen, C₁₆-C₅ alkyl, —O—CH₂—

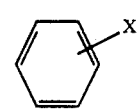

—OR², halogen, —C≡N, —N₃, —NO₂, —COOR³ or trifluoromethyl

R⁴ means

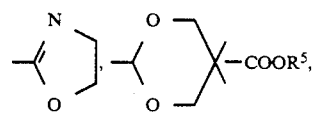

in which R⁵ can means hydrogen or C₁-C₁₀ alkyl optionally substituted by halogen, phenyl, C₁-C₄ alkoxy or di-(C₁-C₄)-alkylamino, C₅-C₆ cycloalkyl, C₇-C₁₆ aralkyl, phenacyl or C₆-C₁₂ aryl substituted by X or a 5- or 6-member heterocyclic radical with at least one N, O or S atom, or —CONHR⁶, with R⁶ meaning hydrogen, can be C₁-C₁₀ alkanoyl or C₁-C₁₀ alkanesulfonyl or CONR²R³ or the radical.

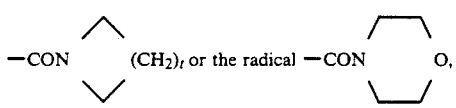

t means 2 or 3,

Z means —(CH₂)p—, (E)—CH=CH, —CH=CR⁷—, —C≡C, p means 0 to 5,

W means a direct bond,

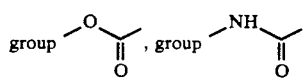

a free or functionally modified hydroxymethylene group or a free or functionally modified

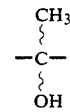

group, in which the OH group can be respectively in alpha- or beta-position, $B^1$ and $B^2$ are the same or different and mean, except for halogen, B, and $B^3$ are the same or different and mean $C_1$–$C_4$ alkyl, phenyl or $C_7$–$C_{16}$ aralkyl, L means oxygen or sulfur, and, if $R^5$ means hydrogen, their salts with physiologically compatible bases, as well as the alpha-, beta- or gamma-cyclodextrin clathrates, as well as the compounds of formula I encapsulated with liposomes.

The definition "5- or 6-member heterocyclic radicals" relates to heterocycles, which contain at least 1 heteroatom, preferably nitrogen, oxygen or sulfur and are monocyclic or bicyclic. For example, there can be mentioned 2-furyl, 3-furyl, 2-thienyl, 3-thenyl, 2-pyridyl, 4-pyridyl, quinolyl, isoquinolyl.

As alkyl groups $R^2$, $R^3$, $R^5$, $R^8$ and B, straight-chain or branched-chain alkyl groups with 1-10 C atoms, such as, for example, methyl, ethyl, propyl, isopropyl, butyl, isobutyl, tert-butyl, pentyl, isopentyl, neopentyl, heptyl, hexyl, decyl, are suitable.

Alkyl groups $R^2$, $R^3$, $R^5$, $R^8$ and B can be substituted by halogen atoms, hydroxy groups. $C_1$–$C_4$ alkoxy groups, $C_6$–$C_{12}$ aryl groups, which can be substituted by halogen, di-$C_1$–$C_4$-alkylamines and tri-$C_1$–$C_4$-alkylammonium. Those alkyl groups which are easily substituted are preferred.

As substituents, for example, there can be mentioned fluorine, chlorine or bromine atoms, phenyl, dimethylamino, diethylamino, methoxy, ethoxy.

As preferred alkyl groups $R^2$, $R^3$, $R^5$, $R^8$ and B, those with 1-4 C atoms, such as, e.g., methyl, ethyl, propyl, isobutyl, butyl, can be mentioned.

Alkyl group $R^7$ with 1-5 C atoms also represents straight-chain or branched-chain alkyl groups, as well already mentioned for $R_2$.

Preferred alkyls ($R^7$) are methyl and ethyl.

As aryl groups $R^2$, $R^3$, $R^5$ and $R^8$ with 6-12 C atoms, for example, phenyl, diphenyl, 1-naphthyl and 2-naphthyl, which can be substituted by 1-3 halogen atoms, a phenyl group, 1-3 alkyl groups each with 1-4 C atoms, a chloromethyl group, fluoromethyl group, trifluoromethyl group, carboxyl group, $C_1$–$C_4$ alkoxy group or hydroxy group, are suitable. The substitution in 3- and 4-position in the phenyl ring is preferred, for example, by fluorine, chlorine, $C_1$–$C_4$ alkoxy or trifluoromethyl or in 4-position by hydroxy.

Cycloalkyl groups $R^3$ and $R^5$ can contain 5 and 6 carbon atoms in the ring. The rings can be substituted by alkyl groups with 1-4 carbon atoms. For example, there can be mentioned cyclopentyl, cyclohexyl, methylcyclohexyl.

Cycloalkyl group $R^8$ can contain 3-10 carbon atoms, preferably 3-6 carbon atoms in the ring. The rings can be substituted by alkyl groups with 1-4 carbon atoms. For example, there can be mentioned cyclopropyl, cyclobutyl, cyclopentyl, cyclohexyl, methylcyclopentyl and methylcyclohexyl.

An aralkyl with 7-16 C atoms for $R^2$, $R^3$, $R^4$ and $B^3$ means one of the above-mentioned lower alkyl radicals with 1-4 C atoms with a phenyl substituent such as, e.g., benzyl, phenethyl, which can be substituted by 1-3 halogen atoms, a fluoromethyl group or a trifluoromethyl group.

The $C_1$–$C_4$ alkyl groups or the $C_1$–$C_5$ alkyl groups or the $C_1$–$C_8$ alkyl groups mentioned under the definitions are to be straight-chain or branched alkyl groups, as have already been mentioned for the above alkyl groups.

As alkylene group D, straight-chain or branched-chain, saturated and unsaturated alkylene radicals, preferably saturated ones, with up to 5 C atoms, which optionally can be substituted by fluorine atoms, are suitable. For example, there can be mentioned: methylene, fluoromethylene, ethylene, 1,2-propylene, ethylethylene, trimethylene, tetramethylene, pentamethylene, 1-methyltetramethylene, 1-methyl trimethylene.

The hydroxy groups in W can be functionally modified, for example, by etherification or esterification, and the free or modified hydroxy groups can be in alpha- or beta-position, and free hydroxy groups are preferred.

As ether and acyl radicals, the radicals known to one skilled in the art are suitable. Easily cleavable ether radicals, such as, for example, the tetrahydropyranyl radical, tetrahydrofuranyl radical, tribenzylsilyl radical, are preferred. As acyl radicals, e.g., acetyl, propionyl, butyryl, benzoyl are suitable.

A halogen in the definitions for B, X and $R^5$ means fluorine, chlorine and bromine.

Radicals $C_1$–$C_{10}$ alkanoyl or $C_1$–$C_{10}$ alkanesulfonyl for $R^6$ correspond to the already mentioned alkyl groups of the same length with the difference that they are connected to a carboxyl group. $C_1$–$C_4$ alkanoyl or $C_1$–$C_4$ alkanesulfonyl are preferred.

Inorganic and organic bases are suitable for salt formation with the free acids ($R^5$=H), as they are known to one skilled in the art for forming physiologically compatible salts. For example, there can be mentioned: alkali hydroxides, such as sodium hydroxide and potassium hydroxide, alkaline earth hydroxides, such as calcium hydroxide, ammonia, amines, such as ethanolamine, diethanolamine, triethanolamine, n-methylglucamine, morpholine, tris-(hydroxymethyl)methylamine, etc.

The compounds of formula I are preferred, in which

A means the groups —$(CH_2)_n$— with n=0-2 and —C≡C—,

B means hydrogen (for n=1-2), alkyl with 1-4 C atoms, phenyl, p-halogenphenyl (especially p-fluorophenyl), diphenyl, Z means the groups —$(CH_2)_p$— with p=0 to 2 and (E)—CH=CH—, —CH=CR$^7$—, —C≡C—, W means a direct bond or the group —CH(OH)—, —O—CO— and —NH—CO—, D means a direct bond or an alkylene group with 1-3 C atoms in the chain which is straight-chain or substituted by $C_1$–$C_2$ alkyl groups, the groups —N($R^2$)— and —NH—SO$_2$—, E means a direct bond, or the group —C≡C—, $R^8$ means hydrogen, $C_1$–$C_4$ alkyl, $C_5$–$C_6$ cycloalkyl, $C_1$–$C_7$ alkoxy, a benzyloxy group optionally substituted p' times by halogen (especially fluorine), CN, OH, trifluoromethyl or phenyl, an anilino group optionally substituted p' times by halogen (preferably fluorine), CN, OH or phenyl, a 5- or 6-member heterocyclic group with 1 or 2 heteroatoms (N or O) optionally substituted p times by halogen (preferably fluorine), CN, OH or phenyl, which can be monocyclic or bicyclic, as were already mentioned in detail for $R^8$, e.g.,

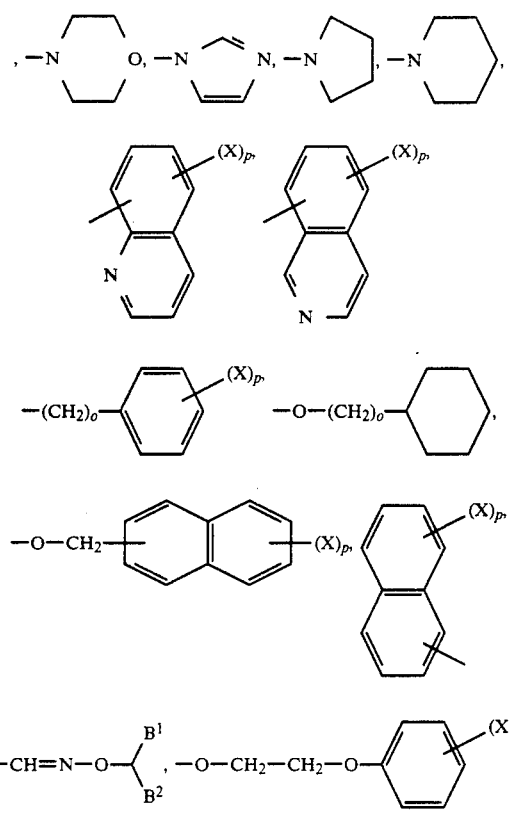

in which X can be the same or different in radicals
—(X)$_p$, if p=2 or 3,
o means 0 to 5,
p means 0 to 5,
p' means 1 to 5,
x means halogen (especially fluorine), CN, OH, trifluoromethyl or phenyl,
B$^1$ and B$^2$ are different and means hydrogen,
R$^1$ means —CH$_2$— and

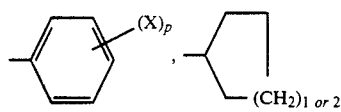

R$^4$ means the radicals —COOR$^5$ with R$^5$ as hydrogen, C$_1$-C$_4$ alkyl or C$_7$-C$_8$ aralkyl optionally substituted by halogen (fluorine) or

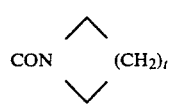

with t=2 or 3.

The combination of all definitions of the radicals A, n, B, R$^1$, R$^2$, R$^3$, R$^4$, X, p, R$^5$, R$^6$, t, Z, R$^7$, W, D, s, E, o, B$^1$, B$^2$, B$^3$, L disclosed by the examples is especially preferred.

The compounds of formula I according to the application can be produced as described in more detail below:

A.

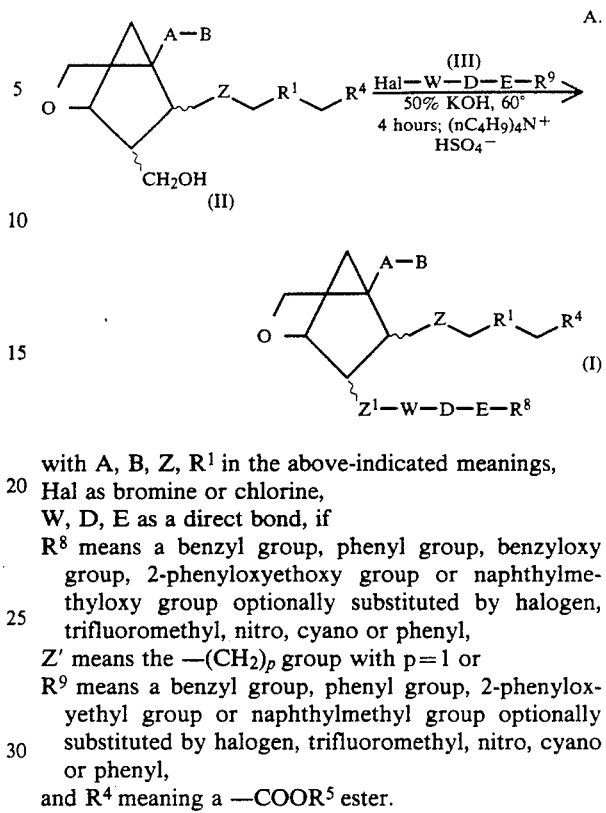

with A, B, Z, R$^1$ in the above-indicated meanings,
Hal as bromine or chlorine,
W, D, E as a direct bond, if
R$^8$ means a benzyl group, phenyl group, benzyloxy group, 2-phenyloxyethoxy group or naphthylmethyloxy group optionally substituted by halogen, trifluoromethyl, nitro, cyano or phenyl,
Z' means the —(CH$_2$)$_p$ group with p=1 or
R$^9$ means a benzyl group, phenyl group, 2-phenyloxyethyl group or naphthylmethyl group optionally substituted by halogen, trifluoromethyl, nitro, cyano or phenyl,
and R$^4$ meaning a —COOR$^5$ ester.

B.

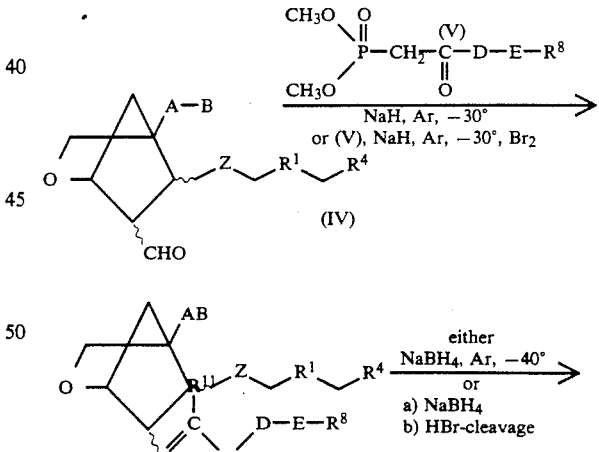

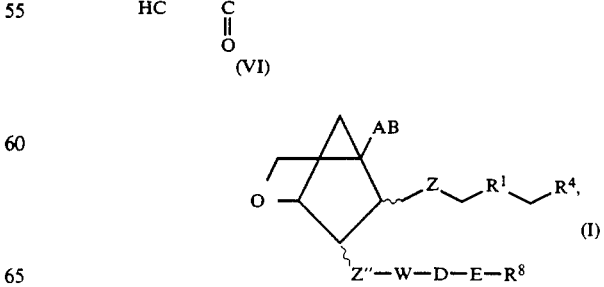

with A, B, Z, R$^1$ in the above-indicated meanings,
D as an alkylene optionally substituted by alkyl, E as a direct bond, as a —C≡C— group or as an optionally substituted phenoxy group,
R⁸ as hydrogen, alkyl,
R⁴ meaning a —COOR⁵ ester,
R¹¹ as hydrogen or bromine,
Z" means (E)—CH=CH— or —C≡C—,
W means CH(OH)— or
D and E as a direct bond, if Z' means the group —CH=CH—, R⁸ means the radicals C₁-C₁₀ alkyl or C₇-C₁₆ aralkyl and W means a hydroxymethylene group or W means the radical $$-\underset{\underset{OH}{|}}{\overset{\overset{CH_3}{|}}{C}}-,$$

or
D means a straight-chain or branched, saturated alkylene group with 2-5 C atoms,
E means group —CH=CH—, if
Z' represents groups —CH=CH— or —CH=C—
R⁸ represents C₁-C₁₀ alkyl.

C.

II $\xrightarrow[\text{process B}]{\text{analogously to}}$

IV $\xrightarrow[\substack{\text{Ar, 50°,}\\\text{pyridine}}]{H_2N-R^{10}}$ (I)

with A, B, Z, R¹ in the above-indicated meanings,
Z' as —(CH₂)ₚ— with p=0,
W, D, E as a direct bond
R⁸ as —CH=N—O—CH(C₆H₅)₂ or

—CH=N—NH—CO—NH—⌬

R⁴ as a —COOR⁵ ester and
R¹⁰ as —O—CH(B¹)B² or

—NH—CO—NH—⌬

B¹ and B² as different radicals meaning hydrogen,

⌬(X)ₚ  ,  ⌬(CH₂)₁ or 2

II $\xrightarrow[\text{collidine, Ar}]{CBr_4/\text{triphenylphosphine}}$

D.

-continued (VII) $\xrightarrow[\text{Ar, 100°}]{H-R^8}$ (I)

with A, B, Z, R¹, X in the above-indicated meanings,
Z''' as —(CH₂)ₚ— with p=1
W, D, E as a direct bond, R⁸ as —N⟨CH=CH—CH=CH⟩, —N⟨⟩, —N⟨⟩, —N⟨⟩O, —HN—⌬X ,  —O—⌬X  and R⁴ as a —COOR⁵ ester.

E.

II $\xrightarrow[\text{process D}]{\text{analogously to}}$

VII $\xrightarrow[\text{Ar, 100°}]{H-R^8}$ (I)

with A, B, R¹, Z, Z''', W, D, E, R⁸ in the meanings indicated under process D and
R⁴ as

—CON⟨(CH₂)ₜ⟩ and t meaning 2 or 3.

F.

(II) $\xrightarrow[\substack{\text{SOCL}_2, \text{Ar} \\ \text{NaN}_3, \\ (nC_4H_9)_4N^+HSO_4^- \\ CF_3COOH \\ K_2CO_3}]{\text{Oxidation}}$ -continued

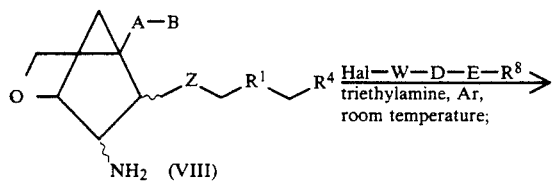

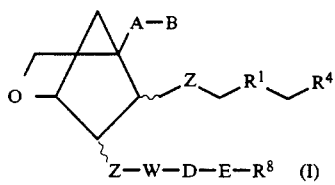

Hal as Cl, Br
W means a direct bond
or —CO—
D means a direct bond
or —SO$_2$—
E means a direct bond
R$^8$ as indicated in formula I with A, B, Z, R$^1$, R$^4$ in the above-indicated meanings, Z' means —(CH$_2$)$_p$— with p=0
W means a direct bond or the group —NH—CO—
D means a direct bond or the group —NH—SO$_2$—
E means a direct bond and
R$^8$ means an alkyl with 1–10 C atoms, aralkyl with 7–16 C atoms, cycloalkyl and aryl, as they were mentioned at the beginning of the description or aromatic, carbocyclic or heterocyclic, monocyclic or bicyclic radicals already substituted by 1–5 X radicals, as they were already mentioned above.

The compounds of formula I can be produced according to claim 3 in accordance with the above-described process alternatives.

The initial compounds of formula II are produced in accordance with the instructions indicated in examples 1a–1 1 or in the subsequent examples (e.g., 274a–274m, 276a–276u and 327a).

Lactols IX used as intermediate products for the production of the initial compounds of formula II as well as the related enantiomers.

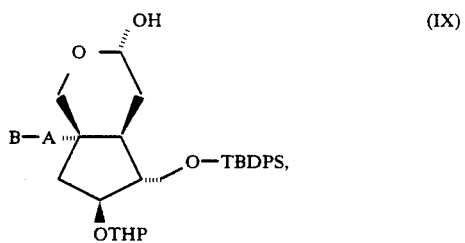

in which A and B have the above-mentioned meanings and THP stands for tetrahydropyranyl and TBDPS stands for tert-butyldiphenylsilyl, can be produced from enantiomeric Corey lactone in accordance with the indication provided in example 274m analogously to examples 17a to 17g and 1f to 1 1. Lactols IX are then reacted to compounds of formula II, as was shown, for example, in examples 274m (and following examples 274l–274) and 276f (and following examples 276e–276).

The saponification of the esters in —COOR$^5$ takes place, for example, with alkali or alkaline-earth carbonates or hydroxides in an alcohol or the aqueous solution of an alcohol. As alcohols, aliphatic alcohols, such as, for example, methanol, ethanol, butanol, etc., preferably methanol, are suitable. As alkali carbonates and alkali hydroxides, there can be mentioned potassium and sodium salts, but the potassium salts are preferred. As alkaline earth carbonates and alkaline earth hydroxides, for example, calcium carbonate, calcium hydroxide and barium carbonate are suitable. The reaction takes place at −10° C. to 70°C., preferably at 25° C.

The reaction conditions of the following process steps are:

1) II→I (Process A)

In the presence of aqueous alkali hydroxide solutions or alkaline earth hydroxide solutions and with use of phase transfer catalysts (such as, e.g., tetrabutylammonium hydrogen phosphate or tetrabutylammonium hydrogen sulfate), compounds of formula II are reacted at 20°–100° C. in 1–8 hours with reactant III as an organic phase or a solution of III in an inert, organic solvent which is not water-miscible.

2) II→IV (Process B)

The oxidation of compounds of formula II takes place according to known processes, such as, e.g., according to that of Swern, Collins as well as with the use of pyridinium dichromate or pyridinium chlorochromate in solvents such as methylene chloride, diethyl ether, tetrahydrofuran, benzene or toluene at −80° to −50° (Swern) or to +30° (in the case of the remaining oxidations) within 10 minutes to 24 hours, preferably 30 minutes to 2 hours.

IV→VI (Process B), VI→I (Process B)

The reaction of compounds IV with phosphonates V as well as the subsequent reduction or HBr-elimination take place analogously to the conditions mentioned in DE-OS 28 45 770.

3) IV→I (Process C)

The reaction of compounds of formula IV with compounds of formula H$_2$N—R$^{10}$ (or of the hydrochloride) is performed in an alcoholic (preferably ethanolic) solution in the presence of catalytic (equimolar) amounts of an organic base (e.g., pyridine, DABCO, DBN, DBU, triethylamine, DMAP, etc.) at 20°–100° C. (preferably 40°–60° C.) in 2–24 hours (preferably 5–10 hours).

4) II→VII (Process D)

As a bromation agent for the reaction II VII, thionyl bromide, CBr$_4$ or C$_2$Br$_6$/triphenylphosphine in the presence of an organic base (such as, e.g., pyridine, collidine, aniline, etc.) are suitable. The reaction is performed at 0°–80° C. (preferably 20°–50° C.) in 30 minutes to 2 hours. As solvents, inert organic solvents such as, e.g., methylene chloride, diethyl ether, chloroform, etc., are used.

5) VII→I (Processes D and E)

The reaction of the bromides of formula VII with H—R$^8$ takes place either with excess H—R$^8$ or with adding an inert solvent such as toluene at 60°–120° C. (preferably 80°–100° C.) in 2–28 hours (preferably 2–12 hours). If H—R$^8$ represents a phenol, the reaction optionally has to be performed with adding a copper salt with use of an additional deprotonation agent (such as, e.g., NaH, BuLi, sodium methanolate).

6) II→VIII (Process F)

The oxidation of the compounds of formula II preferably is performed with Jones reagent or pyridinium chlorochromate keeping in mind the reaction conditions required for this purpose. Then, it is converted to chloride under the usual conditions with SOCl$_2$, brought to reaction under phase transfer catalysis with aqueous NaN$_3$ solution and converted to compounds VIII as described in the related examples.

7) VIII→I (Process F)

The reaction of compounds VIII with the compounds of formula Hal—WDE—R$^8$ takes place as indicated in the examples mentioned in this respect.

The salts of the acids of formula I according to the invention are obtained by the reaction of a solution of the acid in an inert solvent, such as, e.g., methanol, or in aqueous solutions or water-containing solutions and the addition of a salt former [e.g., tris-(hydroxymethyl-)aminomethane] and subsequent evaporation of the solvent. Cyclodextrin clathrates are obtained analogously to the instructions in WO 87/05294.

Liposomes are produced according to the production process described in "Pharmazie in unserer Zeit" [Pharmacy in our Times] 11, 98 (1982).

All stereoisomeric forms also belong to the object of the invention.

Biological action and area of use of the new TXA2 antagonists:

The compounds of this invention are suitable for the treatment of diseases of the cardiovascular system, the stomach, the pancreases, the liver and the kidney. They have an antihypertensive and bronchodilatoric effect. They are suitable for inhibiting the activation of platelets. Consequently, the new TXA2 antagonists of formula I represent valuable pharmaceutical active ingredients. Moreover the compounds with a similar range of action as compared with corresponding TXA2 antagonists are marked by a significantly longer effectiveness and a greater stability through a higher specificity and selectivity (in the absence of partial agonism).

The new TXA2 antagonists have the properties typical for this compound family, such as, e.g., reduction of peripheral arterial, coronary and pulmonary vascular resistance, reduction of pulmonary blood pressure, reduction of systemic blood pressure without decreasing cardiac output and coronary circulation at the same time, promotion for renal circulation and circulation of other peripheral organs, increase of cerebral circulation, inhibition of platelet activation and dissolution of blood clots, inhibition of bronchial constriction, inhibition of hydrochloric acid secretion, cytoprotection of the heart, gastric and intestinal mucous membrane, of the liver, cytoprotection in the pancreas and in the kidney, as well as antiallergic properties. Therefore, the new TXA2 antagonists are suitable on principle for the treatment of stroke, prophylaxis and treatment of coronary heart diseases, for example, coronary thrombosis, for treatment of myocardial infarctions, peripheral arterial diseases, for prophylaxis and treatment of other thromboembolic diseases and of arterial sclerosis, in ischemic attacks of the central nervous system and other circulation disturbances of the brain, for treatment of hypertonia and for treatment of diseases whcih are accompanied by an increase of pulmonary vascular resistance, such as, e.g., pulmonary hypertonia and for treatment of shock and asthma. They can further be used for inhibition of labor and for treatment of toxicoses in pregnancies.

The new TXA2 antagonists further can be used to improve the organ function after transplantation, for example in kidney transplants, to prevent rejection reactions, instead of heparin or as an adjuvant in dialysis or hemofiltration and in the preservation of dried blood plasma, for example of dried platelet.

The new thromboxane antagonists have an antimetastatic effect and antiproliferative properties.

The new TXA2 antagonists can be used combined with, for example, carbacyclins, prostacyclin and its analogs, 7-oxoprostacyclins, prostaglandins and their derivatives and 6-keto-PGE$_1$ derivatives, with TXA$_2$-synthetase inhibitors, with phosphodiesterase inhibitors, with antagonists and receptor antagonists of different platelet stimulators (e.g., ADP, thrombin, collagen, PAF, adrenaline, serotonin, fibrinogen) with calcium antagonists, with fibrinolytic agents and thrombolytic agents, e.g., t-PA, with heparin and other anticoagulants, with cyclooxygenase inhibitors, e.g., acetylsalicyclic acid, with inhibitors of lipoxygenases as well as antagonists from lipoxygenase products, with vasodilators such as, e.g., nitro-compounds, with antihypertensive agents such as, e.g., beta-blocking substances or with diuretics.

The does of the compounds is 0.1-500 mg/per day, also in several partial dosages, if they are administered to human patients. The unit dose for the pharmaceutically acceptable vehicle is 0.1-100 mg. For parenteral administration, sterile, injectable, aqueous or oily solutions are used. For oral administration, for example, tablets, coated tablets or capsules are suitable.

The invention thus also relates to the pharmaceutical agents based on compounds of the general formula I and usual auxiliary agents and vehicles.

The active ingredients according to the invention are to be used in connection with the auxiliary agents known and usual in galenicals e.g. for the production of hypotensors.

The unit dosage range for the ampoule is 0.1-100 gm; the range for the tablet is 0.1-100 mg.

EXAMPLE 1

(4S,5R(5Z),6S,1R)-7-[4-Methyl-6-benzyloxymethyl-2-oxabicyclo[2.2.1]hepta-5-yl]-5-heptenoic acid methyl (or benzyl) ester 16 mg (56.7 micromol) of the alcohol produced according to example 1a was mixed with 160 microliters of a 50% aqueous potassium hydroxide solution, 100 microliters of benzyl chloride and 1.5 mg of tetrabutylammonium hydrogen sulfate. The heterogeneous mixture was heated to 60° C., allowed to react for 4 hours, the cooled mixture was extracted several times with a total of 4 ml of diethyl ether and purified by chromatography on an analytic thin-layer slab. A separation of the methyl ester from likewise-formed benzyl ester was dispensed with. After elution with diethyl ether, 18 mg of the title compounds was isolated as a colorless oil.

IR (film): 3080, 3060, 3020, 3000, 2960, 2940, 2870, 1735, 1455, 1125, 1020, 965, 895, 740 and 700 cm$^{-1}$.

EXAMPLE 1a (4S,5R(5Z),6S,1R)-7-[4-Methyl-6-hydroxymethyl-2-oxabicyclo[2.2.1]heptan-5-yl]-5-heptenoic acid methyl ester 400 mg (768 micromol) of the bicyclic compound produced in example 1b was dissolved in 4 ml of anhydrous tetrahydrofuran, mixed with 4.0 ml of a 1 molar solution of tetrabutylammonium fluoride in tetrahydrofuran and the yellow homogeneous solution was stirred for 1 hour at 23° C. under an atmosphere of dry argon. It was poured on 20 ml of an ice-cold 10% ammonium chloride solution, extracted several times with a total of 25 ml of diethyl ether, washed with water and, after drying on magnesium sulfate, filtration and concentration by evaporation in a water jet vacuum 432 mg of crude oil, which was purified by chromatography on about 70 ml of silica gel by a gradient system of acetone in n-hexane was isolated. 206 mg (730 micromol, 95%) of the title compound was isolated as a colorless oil.

IR (film): 3200–3600, 2950, 2930, 2870, 1735, 1450, 1435, 1155, 1010, 960 and 890 cm$^{-1}$.

EXAMPLE 1b (4S,5R(5Z),6S,1R)-7-[4-Methyl-6-tert-butyldiphenylsilyloxymethyl-2-oxabicyclo[2.2.1]heptan-5-yl]-5-heptenoic acid methyl ester The colorless solution of 598 mg (1.11 mmol) of the diol, produced in example 1c, in 5 ml of anhydrous toluene was mixed in succession with 780 mg of triphenylphosphine, 0.7 ml of diazodicarboxylic acid diethyl ester and stirred for 7 hours at 23° C. under an atmosphere of dry argon. It was mixed with 15 ml of diethyl ether, washed several times with water, dried on magnesium sulfate and, after filtration, concentration by evaporation in a water jet vacuum and chromatography on silica gel with a gradient system of diethyl ether in n-hexane, 403 mg (774 micromol, 70%) of the title compound was isolated as a colorless oil.

IR (film): 3070, 3050, 2950, 2930, 2860, 1735, 1590, 1425, 1110, 1015, 895, 820, 740 and 705 cm$^{-1}$.

EXAMPLE 1c (1S,2R(5Z),3S,4R)-7-[1-Hydroxymethyl-1-methyl-3-tert-butyldiphenylsilyloxymethyl-4-hydroxy-cyclopentan-2-yl]-5-heptenoic acid methyl ester The colorless solution of 921 mg (1.48 mmol) of the compound produced in example 1d, in 25 ml of anhydrous ethyl alcohol was mixed with 185 mg of Pyridium p-toluenesulfonate and the homogeneous solution was stirred for 3 hours at 55° C. under an atmosphere of dry argon. It was mixed with 50 ml of diethyl ether, filtered from precipitated solid, the filtrate was evaporated to dryness in a water jet vacuum and purified by chromatography on silica gel with use of a gradient system of acetone in n-hexane. 616 mg (1.14 mmol, 77%) of the title compound was isolated as a colorless oil.

IR (film): 3100–3600, 3070, 3050, 2940, 2855, 1735, 1590, 1425, 1110, 820, 740 and 705 cm$^{-1}$.

EXAMPLE 1d (1S,2R(5Z),3S,4R)-7-[1-Hydroxymethyl-1-methyl-3-tert-butyldiphenylsilyloxymethyl-4-(tetrahydropyran-2-yloxy)cyclopentan-2-yl]-5-heptenoic acid methyl ester The colorless solution of 11.7 ml of hexamethyldisilazane in 40 ml of anhydrous tetrahydrofuran was cooled under an atmosphere of dry argon to 0° C. to 3° C., mixed with 42 ml of a 1.33M solution of n-butyllithium in n-hexane and subsequently stirred for another 20 minutes. 40 ml of this solution was added with exclusion of moisture to a well stirred suspension of 5.52 g of carboxybutyltriphenylphosphonium bromide in 55 ml of anhydrous tetrahydrofuran and stirred for 30 minutes at room temperature. Then, the solution of 744 mg (1.42 mmol) of the polar lactols, produced in example 1e, was instilled in 15 ml of anhydrous tetrahydrofuran and stirred for another 2 hours at 35° C. It was quenched by pouring into 200 ml of an ice-cold 10% ammonium chloride solution, acidified with 10% citric acid and extracted several times with a total of 300 ml of diethyl ether. The combined organic extracts were washed with water and saturated sodium chloride solution, dried on magnesium sulfate and, after filtration and removal of the solvent in a water jet vacuum, 3.5 g of a colorless oil was isolated. It was mixed with 5 ml of diethyl ether, precipitated triphenylphosphine oxide was filtered and the filtrate was mixed with an ethereal solution of diazomethane at 0° C. The crude product (3.32 g) was again concentrated by evaporation and purified by chromatography on about 300 ml of a fine silica gel under pressure by a gradient system of n-hexane/diethyl ether. 848 mg (1.36 mmol, 96%) of the title compound was isolated as a colorless oil.

IR (film): 3200–3600, 3070, 3050, 2940, 2855, 1735, 1590, 1425, 1360, 1200, 1110, 870, 820, 740 and 705 cm$^{-1}$.

EXAMPLE 1e (1S,4RS,6R,7S,8R)-1-Methyl-4-hydroxy-7-tert-butyldiphenylsilyloxymethyl-8-(tetrahydropyran-2-yloxy)-3-oxabicyclo[4.3.0]nonane (A) and
(1R,3RS,6R,7S,8R)-1-methyl-3-hydroxy-7-tert-butyldiphenylsilyloxymethyl-8-(tetrahydropyran-2-yloxy)-4-oxabicyclo[4.3.0]nonane (B)

The colorless solution of an approximately 1:1 mixture of 1.71 g (3.26 mmol) of the regioisomeric lactones, produced in example 1f, in 45 ml of an anhydrous methyl benzene was cooled under an atmosphere of dry argon to −70° C., mixed with 6 ml of a 1M solution of dissobutylaluminum hydride in methyl benzene, allowed to react for 45 minutes and the excess reducing agent was decomposed by the addition of 3.3 ml of isopropanol. It was allowed to heat to 0° C., mixed with 3.0 ml of water, stirred until a fine-grain precipitate resulted, filtered, the precipitate was rewashed with 50 ml of dichloromethane, the solvent was removed in a vacuum and 1.68 mg (3.21 mmol, 98%) of a mixture of both title compounds A and B was isolated. By repeated chromatography on 400 ml of a fine silica gel under pressure by a gradient system of diethyl ether/n-hexane, the regioisomeric lactol mixture was separated:

nonpolar compound B: 930 mg (1.77 mmol, 54%, colorless oil.

polar compound A: 755 mg (1.44 mmol, 44%), colorless oil.

IR (film): 3200–3600, 3070, 3045, 2940, 2860, 1590, 1425, 1110, 1020, 865, 820, 740 and 705 cm$^{-1}$.

EXAMPLE 1f (1S,6R,7S,8R)-1-Methyl-7-tert-butyldiphenylsilyloxymethyl-8-(tetrahydropyran-2-yloxy)-3-oxabicyclo[4.3.0]nonan-4-one and
(1R,6R,7S,8R)-1-methyl-7-tert-butyldiphenylsilyloxymethyl-8-(tetrahydropyran-2-yloxy)-4-oxabicyclo[4.3.0]nonan-3-one The solution of 1.8 g (3.55 mmol) of the bicyclic ketone, produced in example 1g, in 30 ml of anhydrous dichloromethane was mixed with 870 mg of a finely pulvarized sodium bicarbonate, 1.43 g of m-chloroperbenzoic acid, and allowed to stir for 6 hours at room temperature under an atmosphere of dry argon. It was mixed with 100 ml of a 10% sodium thiosulfate solution, the organic phase was separated after 15 minutes, washed with 50 ml of a 1N sodium hydroxide solution, then several times with water until the neutral reaction of the washing solution and dried on magnesium sulfate. 1.9 g of a colorless oil, which was chromatographically purified under pressure on about 400 ml of a fine silica gel with an 8:2 mixture of n-hexane/ethyl acetate, was isolated. 1.72 g (3.28 mmol, 93%) of a 1:1 mixture of both title compounds was obtained as a colorless oil.

IR (film): 3070, 3045, 2940, 2855, 1750, 1590, 1470, 1425, 1214, 1110, 1075, 1060, 1035, 975, 910, 870, 820, 740 and 705 cm$^{-1}$.

EXAMPLE 1g (1R,5R,6S,7R)-1-Methyl-6-tert-butyldiphenylsilyloxymethyl-7-(tetrahydropyran-2-yloxy)-bicyclo[3.3.0]octan-3-one The solution of 3.04 g (6.2 mmol) of the bicyclic, unsaturated ketone, produced in example 1h, in 70 ml of anhydrous tetrahydrofuran was mixed with 103 mg of copper(II) acetate, cooled under an atmosphere of dry argon to −20° C. and 8.2 ml of a 3M methylmagnesium bromide solution was instilled steadily in tetrahydrofuran. It was allowed to react 20 minutes at −20° C. to −15° C., poured into 300 ml of an ice-cold 10% ammonium chloride solution and extracted several times with a total of 400 ml of diethyl ether. The combined organic extracts were washed with water and saturated sodium chloride solution until the neutral reaction, dried on magnesium sulfate and 3.34 g of a yellow oil, which was chromatographically purified on about 400 ml of a fine silica gel under pressure by a gradient system of n-hexane/ethyl acetate, was isolated after filtration and removal of the solvent in a water jet vacuum. 1.81 g (3.6 mmol, 58%) of the title compound was obtained as a colorless oil.

IR (film): 3070, 3045, 2970, 2930, 1740, 1590, 1425, 1110, 1075, 1020, 970, 870, 820, 740 and 700 cm$^{-1}$.

EXAMPLE 1h (5R,6S,7R)-7-(Tetrahydropyran-2-yloxy)-6-tert-butyldiphenyl-silyloxymethyl-bicyclo[3.3.0]oct-1-en-3-one The solution of 8.79 g (17.2 mmol) of keto acid, produced in example 1i, in 200 ml of anhydrous ethyl acetate as mixed with 7.14 g of triphenyl(phenyliminovinylidene)phosphorane and refluxed for 3 hours under an atmosphere of dry argon. After the cooling, it was concentrated by evaporation in a water jet vacuum to a residual volume of about 30 ml, mixed with 200 ml of anhydrous toluene, 5 ml of anhydrous ethanol, and again refluxed for 20 hours under argon. After the cooling, the solvent was removed in a water jet vacuum and the brown oil was chromatographed on about 600 ml of a fine silica gel under pressure with a gradient system of a n-hexane and ethyl acetate. 4.81 g (9.8 mmol, 57%) of the title compounds was isolated as a pale yellow oil.

IR (film): 3070, 3045, 2940, 2850, 1775, 1705, 1630, 1470, 1425, 1110, 1075, 1030, 970, 915, 870, 820, 740 and 705 cm$^{-1}$.

EXAMPLE 1i (2R,3S,4R)-2-Carboxymethyl-3-tert-butyldiphenyl-silyloxymethyl-4-(tetrahydropyran-2-yloxy)-cyclopentan-1-one The solution of 8.83 g (17.8 mmol) of the lactone, produced in example 1j, in 80 ml of diethyl ether was mixed with 80 ml of a 1 n sodium hydroxide solution and the two-phase system was stirred vigorously at room temperature. After 24 hours, the aqueous phase was separated, cooled to 0° to +3° C. and adjusted to pH 4–5 by adding an ice-cold, saturated citric acid solution. The precipitated hydroxy acid was extracted several times with a total of 200 ml of −5° C. cold trichloromethane, the combined organic extracts were filtered quickly on magnesium sulfate, rewashed twice with 20 ml of −5° C. cold trichloromethane each and mixed with 150 ml of −20° C. cold acetone. It was cooled to −30° C. and mixed with 9.2 ml of a standardized chromosulfuric acid solution. After stirring for 4 hours at −30° C. to −20° C., excess oxidizing agent was decomposed by adding 10 ml of isopropanol, it was allowed to heat to room temperature and diluted by adding 200 ml of water. The organic phase was separated, the aqueous phase was extracted several times with a total of 350 ml of trichloromethane and the combined extracts were washed with water and saturated sodium chloride solution until the washing solution reacted neutrally. After drying on magnesium sulfate, filtration and removal of the solvent in a vacuum, 8.79 g (17.2 mmol, 96%) of the title compound was isolated as a pale green oil, which was further reacted without purification.

IR (film): 2500–3600, 3070, 3040, 2940, 2860, 1745, 1710, 1590, 1428, 1110, 1075, 1035, 1020, 970, 870, 820, 758, 740 and 705 cm$^{-1}$.

EXAMPLE 1j (1S,5R,6S,7R)-7-(Tetrahydropyran-2-yloxy)-6-tert-butyldiphenylsilyloxymethyl-2-oxabicyclo[3.3.0]octan-3-one The solution of 7.74 g (18.9 mmol) of the compound, produced according to example 1k, in 110 ml of anhydrous dichloromethane was mixed with 95 mg of p-toluenesulfonic acid and 3.1 ml of dihydropyran. It was allowed to stir for 1 hour at room temperature under an atmosphere of dry argon, the clear violet solution was quenched by adding 20 ml of a 10% sodium bicarbonate solution, the organic phase was separated, rewashed several times with water and dried on magnesium sulfate. After filtration and removal of the solvent in a water jet vacuum, 12.4 g of a yellow oil, which was purified chromatographically on about 400 ml of a fine silica gel with use of a gradient system of n-hexane/ethyl acetate and under pressure, was isolated. 8.86 g (17.9 mmol, 95%) of the title compound was isolated as a colorless oil.

IR (film): 3065, 3045, 2940, 2850, 1770, 1590, 1425, 1175, 1110, 1075, 1035, 1000, 970, 870, 820, 740 and 705 cm$^{-1}$.

EXAMPLE 1k (1S,5R,6S,7R)-7-Hydroxy-6-tert-butyldiphenylsilyloxymethyl-2-oxabicyclo[3.3.0]octan-3-one The colorless solution of 93 g (181 mmol) of the compound, produced according to example 1l, in 800 mo of anhydrous methyl alcohol was mixed with 32.5 g of finely pulvarized potassium carbonate and stirred for 5.5 hours at room temperature under an atmosphere of dry argon. After filtration and concentration by evaporation of the filtrate to about 200 ml in a water jet vacuum, 600 ml of water was added, it was adjusted to pH 3 to 4 with 1 n hydrochloric acid and extracted several times with a total of 1 l of dichloromethane. The combined organic extracts were washed with water and saturated sodium chloride solution until the neutral reaction, dried on magnesium sulfate and the crude product obtained after removal of the solvent in a water jet vacuum was purified by chromatography under pressure on about 1.5 l of fine silica gel by a gradient system of n-hexane/ethyl acetate. 59 g (144 mmol, 80%) of the title compound was obtained as a crystalline solid.

IR (KBr): 3440, 3070, 3040, 2955, 2930, 2855, 1740, 1590, 1470, 1425, 1390, 1370, 1200, 1110, 1045, 1030, 995, 900, 865, 820, 795, 740, 705 and 615 cm$^{-1}$.

$a_D{}^{23} = -6.2°$ (c=1, CHCl$_3$)

Melting point: 90°-91° C.

EXAMPLE 11

(1S,5R,6S,7R)-7-Benzoyloxy-6-tert-butyldiphenyl-silyloxymethyl-2-oxabicyclo[3.3.0]octan-3-one The colorless solution of 50 g (181 mmol) of Corey lactone in 850 ml of anhydrous dimethylformamide was mixed with 25 g of imidazole and then 47.5 ml of tert-butyldiphenylchlorosilane was instilled within 1 hour, it was refluxed with anhydrous dimethylformamide and allowed to react for 2.5 hours at room temperature under an atmosphere of dry argon. The crude product rubberlike precipitating after pouring in 1 l of ice water, was extracted several times with a total of 1 l of diethyl ether, the combined organic extracts were washed with water and saturated sodium chloride solution until the neutral reaction of the washing solution and dried on magnesium sulfate. After filtration and removal of the solvent in a water jet vacuum, 93 g (181 mmol, 100%) of the title compound was isolated after intensive drying as a colorless oil solidifying at $-20°$ C., which was further reacted with purification.

IR (film): 3070, 3045, 2955, 2930, 2855, 1770, 1715, 1600, 1585, 1425, 1270, 1175, 1110, 820, 740 and 750 cm$^{-1}$.

$a_D{}^{23} = -52°$ (c=1.0, CHCl$_3$)

EXAMPLE 2

(4S,5R(5Z),6S,1R)-7-[4-Methyl-6-benzyloxymethyl-2-oxabicyclo[2.2.1]heptan-3-yl]-5-heptenoic acid 18 mg of the ester mixture produced according to example 1 was dissolved in 0.5 ml of methanol, mixed with 0.5 ml of a 5% aqueous lithium hydroxide solution and stirred for 4 to 6 hours at room temperature. It was acidified with a 1 n hydrochloric acid, extracted several times with a total of 30 ml of chloroform, filtered on magnesium sulfate and purified by chromatography on an analytic thin-layer slab. A mixture of n-hexane/ethyl acetate was used as a mobile solvent, a mixture of chloroform/i-propanol was used as an eluant. 15 mg (41.8 micromol, 74%, relative to the initial material in example 1) of the title compound was isolated as a colorless oil.

IR (film): 3600-2400, 3080, 3060, 3030, 3000, 2950, 2930, 2870, 1730, 1710, 1455, 1125, 1100, 1020, 965, 885, 875, 740 and 700 cm$^{-1}$.

EXAMPLE 3

(4S,5R(5Z),6S,1R)-7-[4-Phenyl-6-benzyloxymethyl-2-oxabicyclo[2.2.1]heptan-5-yl]-5-heptenoic acid methyl (or benzyl) ester 16 mg (46.5 micromol) of the alcohol produced according to example 3a was reacted analogously to example 1 and 19 mg of the title compounds was isolated as a colorless oil after working up and purification.

IR (film): 3090, 3060, 3030, 300, 2930, 2870, 1735, 1605, 1500, 1455, 1075, 970, 895, 740 and 700 cm$^{-1}$.

EXAMPLE 3a (4S,5R(5Z),6S,1R)-7-[4-Phenyl-6-hydroxymethyl-2-oxabicyclo[2.2.1]heptan-5-yl]-5-heptenoic acid methyl ester 460 mg (785 micromol) of the bicyclic compound produced according to example 3b was reacted analogously to example 1a and, after working up and purification, 254 mg (737 micromol, 93%) of the title compound was isolated as a colorless oil.

IR (film): 3600-3400, 3080, 3060, 3030, 2940, 2870, 1735, 1600, 1495, 1445, 1435, 1200, 1150, 1070, 1035, 1000, 895, 760 and 700 cm$^{-1}$.

EXAMPLE 3b (4S,5R(5Z),6S,1R)-7-[4-Phenyl-6-tert-butyldiphenyl-silyloxymethyl-2-oxabicyclo[2.2.1]heptan-5-yl]-5-heptenoic acid methyl ester 570 mg (949 micromol) of the diol produced according to example 3c was cyclized analogously to example 1b and, after working up and purification, 452 mg (776 micromol, 82%) of the title compound was isolated as a colorless oil.

IR (film): 3070, 3050, 3020, 2950, 2930, 2855, 1735, 1600, 1590, 1425, 1110, 895, 820, 760, 740 and 700 cm$^{-1}$.

EXAMPLE 3c (1S,2R(5Z),3S,4R)-7-[1-Hydroxymethyl-1-phenyl-3-tert-butyldiphenylsilyloxymethyl-4-hydroxy-cyclopentan-2-yl]-5-heptenoic acid methyl ester 436 mg (662 micromol) of the compound produced in example 3d was reacted analogously to example 1c and, after working up and purification, 359 mg (359 micromol, 90%) of the title compound was isolated as a colorless oil.

IR' (film): 3100-3600, 3070, 3050, 3000, 2950, 2930, 2855, 1735, 1600, 1590, 1425, 1110, 1055, 820, 740 and 700 cm$^{-1}$.

EXAMPLE 3d (1S,2R(5Z),3S,4R)-7-[1-Hydroxymethyl-1-phenyl-3-tert-butyldiphenylsilyloxymethyl-4-(methoxyethyl-1-oxy)-cyclopentan-2-yl]-5-heptenoic acid methyl ester 716 mg (1.28 mmol) of the nonpolar lactols produced in example 3e were reacted analogously to example 1d. After esterification and purification, 705 mg (1.07 mmol, 84%) of the title compound was isolated as a colorless oil.

IR (film): 3200-3600, 3070, 3050, 2950, 2930, 2860, 1740, 1600, 1590, 1430, 1110, 820, 740, 700 and 505 cm$^{-1}$.

EXAMPLE 3e (1S,4RS,6R,7S,8R)-1-Phenyl-4-hydroxy-7-tert-butyldiphenylsilyloxymethyl-8-(methoxyethyl-1-oxy)-3-oxabicyclo[4.3.0]nonane (A) and
(1S,3RS,6R,7S,8R)-1-phenyl-3-hydroxy-7-tert-butyldiphenylsilyloxymethyl-8-(methoxyethyl-1-oxy)-4-oxabicyclo[4.3.0]nonane (B)

Analogously to example 1e, 1.43 (2.56 mmol) of an approximately 1:1 mixture of the regioisomeric lactones produced in example 3f was reacted. After working up, 1.42 g (2.53 mmol, 99%) of a mixture of both title compounds A and B was isolated.

IR (film): 3200–3600, 3070, 3050, 3025, 2930, 2860, 1605, 1590, 1495, 1470, 1425, 1390, 1110, 1040, 990, 900, 825, 735 and 700 cm⁻¹.

Chromatographic separation yielded 716 mg (1.28 mmol, 50%) of compound A as a more nonpolar component as well as 629 mg (1.23 mmol, 48%) of more polar compound B.

Example 3f (1S,6R,7S,8R)-1-Phenyl-7-tert-butyldiphenylsilyloxymethyl)-8-(methoxyethyl-1-oxy)-3-oxabicyclo[4.3.0-]nonan-4-one and
(1S,6R,7S,8R)-1-phenyl-7-tert-butyldiphenylsilyloxymethyl-8-(methoxyethyl-1-oxy)-4-oxabicyclo[4.3.0-]nonan-3-one:

1.59 g (2.93 mmol) of the bicyclic ketone produced according to example 3g was oxidized analogously to example 1f and 1.43 g (2.56 mmol, 87%) of an approximately 1:1 mixture of both title compounds was isolated as a crystalline solid after working up and purification.

Melting point: 113°–114° C. (n-hexane/diisopropyl ether)

EXAMPLE 3g (1S,5R,6S,7S)-1-Phenyl-6-tert-butyldiphenylsilyloxymethyl-7-(methoxyethyl-1-oxy)-bicyclo[3.3.0]octan-3-one 1.19 g (2.56 mmol) of (5R,6S,7R)-7-(methoxyethyl-1-oxy)-6-tert-butyldiphenylsilyloxymethyl-bicyclo[3.3.-0]oct-1-en-3-one, which had been produced analogously to examples 1h, 1i and 1j with use of methyl vinyl ether from (1S,5R,6S,7R)-7-hydroxy-6-tert-butyldiphenylsilyloxymethyl-2-oxabicyclo[3.3.0]octan-3-one, was reacted analogously to example 1g with phenylmagnesium iodide with copper catalysis. After working up and purification, 995 mg (1.83 mmol, 72%) of the title compound was isolated as a colorless oil.

IR (film): 3070, 3050, 2940, 2855, 1740, 1600, 1490, 1470, 1430, 1390, 1110, 995, 900, 825, 740 and 705 cm⁻¹.

EXAMPLE 4

(4S,5R,(5Z),6S,1R)-Z-[4-Phenyl-6-benzyloxymethyl-2-oxabicyclo[2.2.1]heptan-5-yl]-5-heptenoic acid 19 mg of the ester mixture produced according to example 3 was saponified analogously to example 2 and, after working up and purification, 16 mg (38 micromol, 82%, relative to the initial material in example 3) of the title compound was isolated as a colorless oil.

IR (film): 3600–2500, 3090, 3060, 3030, 3000, 2930, 2870, 1730, 1710, 1605, 1500, 1455, 1210, 1120, 1075, 970, 900, 760, 740 and 700 cm⁻¹.

EXAMPLE 5

(4R,5S(5Z),6R,1S)-7-[4-Phenyl-6-benzyloxymethyl-2-oxabicyclo[2.2.1]heptan-5-heptenoic acid methyl (or benzyl) ester 19 mg (55 micromol) of the alcohol produced according to example 5a was reacted analogously to example 1 and, after working up and purification, 22 mg of the title compounds was isolated as a colorless oil.

IR (film): 3090, 3060, 3030, 2940, 2870, 1735, 1605, 1500, 1455, 1075, 970, 895, 740 and 700 cm⁻¹.

EXAMPLE 5a (4R,5S(5Z),6R,1S)-7-[4-Phenyl-6-hydroxymethyl-2-oxabicyclo[2.2.1]heptan-5-yl]-5-heptenoic acid methyl ester 2.81 g (10.2 mmol) of enantiomeric Corey lactone was reacted analogously to examples 1a to 1l and 228 mg (662 micromol, 6.5%) of the title compound was isolated as a colorless oil.

IR (film): 3600–3200, 3040, 3030, 3000, 2940, 2870, 1735, 1600, 1495, 1440, 1435, 1220, 1200, 1035, 1000, 895, 760 and 700 cm⁻¹.

EXAMPLE 6

(4R,5S(5Z),6R,1S)-7-[4-Phenyl-6-benzyloxymethyl-2-oxabicyclo[2.2.1]heptan-5-yl]-5-heptenoic acid 22 g of the ester mixture produced according to example 5 was saponified analogously to example 2 and, after working up and purification, 20 mg (48 micromol, 86%, relative to the initial material in example 5) of the title compound was isolated as a colorless oil.

IR (film): 3600–2300, 3080, 3060, 3030, 3000, 2930, 2670, 1730, 1705, 1600, 1500, 1450, 1240, 1210, 1115, 1095, 1070, 1040, 895, 760, 735 and 700 cm⁻¹.

EXAMPLE 7

(4S,5R(5Z),6S,1R)-7-[4-Benzyl-6-benzyloxymethyl-2-oxabicyclo[2.2.1]heptan-5-yl]-5-heptenoic acid methyl (or benzyl) ester 20 mg (55.8 micromol) of the alcohol produced according to example 7a was etherified analogously to example 1 and, after working up and purification, 21 mg of the title compound was isolated as a colorless oil.

IR (film): 3090, 3060, 3030, 3000, 2930, 2870, 1735, 1605, 1500, 1455, 1120, 1100, 1075, 1005, 895, 670, 740 and 700 cm⁻¹.

EXAMPLE 7a (4S,5R(5Z),6S,1R)-7-[4-Benzyl-6-hydroxymethyl-2-oxabicyclo[2.2.1]heptan-5-yl]-5-heptenoic acid methyl ester 364 mg (611 micromol) of the bicyclic compound produced according to example 7b was reacted analogously to example 1a and, after working up and purification, 210 mg (586 micromol, 96%) of the title compound was isolated as a colorless oil.

IR (film): 3600–3200, 3060, 3020, 2940, 1920, 2870, 1735, 1600, 1450, 1435, 1245, 1200, 1150, 1030, 1000, 890, 765 and 705 cm⁻¹.

EXAMPLE 7b (4S,5R(5Z),6S,1R)-7-[4-Benzyl-6-tert-butyldiphenylsilyloxymethyl-2-oxabicyclo[2.2.1]heptan-5-yl]-5-heptenoic acid methyl ester 554 mg (901 micromol) of the diol produced in example 7c was cyclized analogously to example 1b and, after working up and purification, 364 mg (610 micromol, 68%) of the title compound was isolated as a colorless oil.

IR (film): 3070, 3030, 2950, 2930, 2860, 1735, 1600, 1590, 2536, 2220, 2070, 1005, 895, 820, 740 and 700 cm⁻¹.

EXAMPLE 7c (1S,2R(5Z),3S,4R)-7-[1-Hydroxymethyl-1-benzyl-3-tert-butyldiphenylsilyloxymethyl-4-hydroxy-cyclopentan-2-yl]-5-heptenoic acid methyl ester 766 mg 1.10 micromole of the compound produced in example 7d was reacted analogously to example 1c and, after working up and purification, 554 mg (901 micromol, 82%) of the title compound was isolated as a colorless oil.

IR (film): 3200–3600, 3070, 3050, 3020, 3000, 2950, 2925, 2855, 1735, 1600, 1590, 1425, 1110, 820, 740 and 700 cm$^{-1}$.

EXAMPLE 7d (1S,2R(5Z),3S,4R)-7-[1-Hydroxymethyl-1-benzyl-3-tert-butyldiphenylsilyloxymethyl-4-(tetrahydropyran-2-yloxy)cyclopentan-2-yl]-5-heptenoic acid methyl ester 742 mg (1.23 mmol) of the nonpolar lactols produced in example 7e was reacted analogously to example 1d. After esterification and purification, 766 mg (1.10 mmol, 89%) of the title compound was isolated as a colorless oil.

IR (film): 3200–3600, 3070, 3050, 3020, 3000, 2940, 2855, 1735, 1600, 1590, 1425, 1265, 1200, 1100, 1030, 870, 820, 740 and 705 cm$^{-1}$.

EXAMPLE 7e (1S,4RS,6R,7S,8R)-1-Benzyl-4-hydroxy-7-tert-butyldiphenylsilyloxymethyl-8-(tetrahydropyran-2-yloxy)-3-oxabicyclo[4.3.0]nonane (A) and
(1S,3RS,6R,7S,8R)-1-benzyl-3-hydroxy-7-tert-butyldiphenylsilyloxymethyl-8-(tetrahydropyran-2-yloxy)-4-oxabicyclo[4.3.0]nonane (B)

1.86 g (3.11 mmol) of an approximately 1:1 mixture of the regioisomeric lactones produced in example 7f was reduced analogously to example 1 e and 1.85 g (3.08 mmol, 99%) of a mixture of title compounds A and B was isolated after working up.

IR (film): 3200–3600, 3070, 3045, 3020, 2940, 2855, 1600, 1590, 1425, 1110, 1040, 870, 820, 740 and 705 cm$^{-1}$.

Chromatographic separation yielded 764 mg (1.27 mmol, 41%) of compound A as a more nonpolar component in addition to 897 mg (1.49 mmol, 48%) of compound B.

EXAMPLE 7f (1S,6R,7S,8R)-1-Benzyl-7-tert-butyldiphenylsilyloxymethyl-8-(tetrahydropyran-2-yloxy)-3-oxabicyclo[4.3.0]nonan-4-one and
(1R,6R,7S,8R)-1-benzyl-7-tert-butyldiphenylsilyloxymethyl-8-(tetrahydropyran-2yloxy)-4-oxabicyclo[4.3.0]nonan-3-one 3.86 g (6.62 mmol) of the bicyclic ketone produced according to example 7g was oxidized analogously to example 1f. After working up and purification, 3.04 g (5.08 mmol, 77%) of an approximately 1:1 mixture of both title compounds was isolated as a colorless oil.

IR (film): 3070, 3045, 3010, 2940, 2855, 1745, 1600, 1590, 1425, 1110, 1035, 970, 870, 820, 740 and 705 cm$^{-1}$.

EXAMPLE 7g (1R,5R,6S,7R)-1-Benzyl-6-tert-butyldiphenylsilyloxymethyl-7-(tetrahydropyran-2-yloxy)-bicyclo[3.3.0]octan-3-one 2.01 g (4.18 mmol) of the bicyclic, unsaturated ketone produced according to example 1h was reacted with benzylmagnesium chloride with copper catalysis analogously to example 1g. After working up and purification, 1.90 g (3.23 mmol, 83%) of the title compound was isolated as a colorless oil.

IR (film): 3070, 3050, 3025, 2930, 2855, 1740, 1600, 1590, 1425, 1265, 1110, 1075, 1020, 870, 820, 740 and 705 cm$^{-1}$.

EXAMPLE 8

(4S,5R(5Z),6S,1R)-7-[4-Benzyl-6-benzoyloxymethyl-2-oxabicyclo[2.2.1]heptan-5-yl]-5-heptenoic acid 21 mg of the ester mixture produced according to example 7 was saponified analogously to example 2 and, after working up and purification, 10.7 mg (24.6 micromol, 44%, relative to the initial material in example 7) of the title compound was isolated as a colorless oil.

IR (film): 3600–2400, 3090, 3060, 3030, 3000, 2930, 2860, 1730, 1710, 1600, 1495, 1455, 1115, 1100, 1075, 1010, 895, 765, 740 and 705 cm$^{-1}$.

EXAMPLE 9

(4S,4R(5Z),6S,1R)-7-[4-(p-Phenyl-benzyl)-6-benzoyloxymethyl-2-oxabicyclo[2.2.1]heptan-5-yl]-5-heptenoic acid methyl (or benzyl) ester 29 mg (66.7 micromol) of the alcohol produced according to example 9a was etherified analogously to example 1 and, after working up and purification, 24 mg of the title compounds was isolated as a colorless oil.

IR (film): 3060, 3030, 3000, 2930, 2870, 1735, 1600, 1490, 1455, 1115, 1075, 1005, 895, 850, 770, 740 and 700 cm$^{-1}$.

EXAMPLE 9a (4S,5R(5Z),6S,1R)-7-[4-(p-Phenyl-benzyl)-6-hydroxymethyl-2-oxabicyclo[2.2.1]heptan-5-yl]-5-heptenoic acid methyl ester 210 mg (312 micromol) of the bicyclic compound produced according to example 9b was reacted analogously to example 1a and, after working up and purification, 126 mg (290 micromol, 93%) of the title compound was isolated as a colorless oil.

IR (KBr): 3200–3600, 3020, 2920, 2880, 2850, 1715, 1490, 1440, 1200, 1005, 890, 770, 740 and 695 cm$^{-1}$.

Melting point: 61.5°–63° C.

EXAMPLE 9b (4S,5R(5Z),6S,1R)-7-[4-(p-Phenyl-benzyl)-6-tert-butyldiphenylsilyloxymethyl-2-oxabicyclo[2.2.1]heptan-5-yl]-5-heptenoic acid methyl ester 296 mg (428 micromol) of the diol produced in example 9c was cyclized analogously to example 1b and, after working up and purification, 220 mg (327 micromol, 76%) of the title compound was isolated as a colorless oil.

IR (film): 3070, 3050, 3020, 3000, 2950, 2920, 2850, 1735, 1600, 1590, 1485, 1425, 1110, 1070, 1005, 900, 845, 820, 765, 740 and 700 cm$^{-1}$.

EXAMPLE 9c (1S,2R(5Z),3S,4R)-7-[1-Hydroxymethyl-1-(p-phenyl-benzyl)-3-tert-butyldiphenylsilyloxymethyl-4-hydroxy-cyclopentan-2-yl]-5-heptenoic acid methyl ester 469 mg (605 micromol) of the compound produced in example 9d was reacted analogously to example 1c and, after working up and purification, 308 mg (446 micromol, 74%) of the title compound was isolated as a colorless oil.

IR (film): 3200–3600, 3070, 3050, 3030, 3000, 2950, 2930, 2860, 1735, 1600, 1590, 1490, 1430, 1115, 825, 770, 740, 705 and 505 cm$^{-1}$.

EXAMPLE 9d (1S,2R(5Z),3S,4R)-7-[1-Hydroxymethyl-1-(p-phenyl-benzyl)-3-tert-butyldiphenylsilyloxymethyl-4-(tetrahydropyran-2-yloxy)cyclopentan-2-yl]-5-heptenoic acid methyl ester (A) and
(1R(5Z),2R,3S,4R)-7-[1-(p-phenyl-benzyl)-2-hydroxymethyl-3-tert-butyldiphenylsilyloxymethyl-4-(tetrahydropyran-2-yloxy)cyclopentan-1-yl]-5-heptenoic acid methyl ester (B)

0.77 g (1.14 mmol) of an approximately 1:1 mixture of the regioisomeric lactols produced in example 9e was reacted analogously to example 1d. After esterification, purification and chromatographic separation, 355 mg (458 micromol, 40%) of title compound B as a nonpolar component as well as 509 mg (657 micromol, 58%) of title compound A as a polar component were respectively isolated as colorless oil.

IR (film) of A: 3200–3600, 3070, 3050, 3020, 3000, 2950, 2855, 1735, 1600, 1590, 1430, 1110, 1025, 860, 820, 765, 740 and 700 cm$^{-1}$.

EXAMPLE 9e (1S,4RS,6R,7S,8R)-1-(p-Phenyl-benzyl)-4-hydroxy-7-tert-butyldiphenylsilyloxymethyl-8-(tetrahydropyran-2-yloxy)-3-oxabicyclo[3.4.0]nonane (A) and
(1S,3RS,6R,7S,8R)-1-(p-phenyl-benzyl)-3-hydroxy-7-tert-butyldiphenylsilyloxymethyl-8-(tetrahydropyran-2-yloxy)-4-oxabicyclo[4.3.0]nonane (B)

1.62 g (2.40 mmol) of an approximately 1:1 mixture of the regioisomeric lactones produced in example 9f was reduced analogously to example 1e. After working up, 1.37 g (2.03 mmol, 84%) of a mixture of the title compounds, which was further reacted without separation, was obtained.

IR (film): 3200–3600, 3070, 3050, 3020, 2940, 2855, 1600, 1590, 1485, 1425, 1265, 1200, 1110, 1075, 1020, 870, 820, 765, 740 and 700 cm$^{-1}$.

EXAMPLE 9f (1S,6R,7S,8R)-1-(p-Phenyl-benzyl)-7-tert-butyldiphenylsilyloxymethyl-8-(tetrahydropyran-2-yloxy)-3-oxabicyclo[4.3.0]nonan-4-one and
(1R,6R,7S,8R)-1-(p-phenyl-benzyl)-7-tert-butyldiphenylsilyloxymethyl-8-(tetrahydropyran-2-yloxy)-4-oxabicyclo[4.3.0]nonan-3-one 2.20 g (3.34 mmol) of the bicyclic ketone produced in example 9g was oxidized analogously to example 1f. After working up and purification, 1.69 g (2.51 mmol, 75%) of an approximately 1:1 mixture of both title compounds was isolated as a colorless oil.

IR (film): 3070, 3050, 3020, 2940, 2850, 1745, 1600, 1590, 1485, 1425, 1260, 1110, 1075, 1030, 870, 820, 735 and 700 cm$^{-1}$.

EXAMPLE 9g (1R,5R,6S,7R)-1-(p-Phenyl-benzyl)-6-tert-butyldiphenylsilyloxymethyl-7-(tetrahydropyran-2-yloxy)-bicyclo[3.3.0]octan-3-one 1.91 g (3.88 mmol) of the bicyclic, unsaturated ketone produced according to example 1h was reacted with p-phenylbenzylmagnesium chloride with copper catalysis analogously to example 1g. After working up and purification, 2.29 g (3.48 mmol, 98%) of the title compound was isolated as a colorless oil.

IR (film): 3070, 3050, 3000, 2940, 2855, 1730, 1600, 1590, 1485, 1425, 1110, 1075, 1020, 856, 820, 740 and 700 cm$^{-1}$.

EXAMPLE 10

(4S,5R(5Z),6S,1R)-7-[4-(p-Phenyl-benzoyl)-6-benzoyloxymethyl-2oxabicyclo[2.2.1]heptan-5-yl]-5-heptenoic acid 24 mg of the ester mixture produced according to example 9 was saponified analogously to example 2 and, after working up and purification, 16.2 mg (31.7 micromol, 48%, relative to the initial material in example 9) of the title compound was isolated as a colorless oil.

IR (KBr): 3600–2400, 3060, 3030, 3000, 2920, 2860, 1730, 1705, 1600, 1485, 1450, 1110, 1075, 1005, 895, 845, 770, 740 and 695 cm$^{-1}$.

EXAMPLE 11

(4S,5R(5Z),6S,1R)-7-[4-(1-Pentinyl)-6-benzyloxymethyl-2-oxabicyclo[2.2.1]heptan-5-yl]-5-heptenoic acid methyl (or benzyl) ester 12.3 mg (36.8 micromol) of the alcohol produced according to example 11a was etherified analogously to example 1 and, after working up and purification, 16.4 mg of the title compounds was isolated as a colorless oil.

IR (film): 3060, 3015, 2960, 2930, 2870, 1734, 1450, 1155, 1010, 895, 735 and 700 cm$^{-1}$.

EXAMPLE 11a (4S,5R(5Z),6S,1R)-7-[4-(1-Pentinyl)-6-hydroxymethyl-2-oxabicyclo[2.2.1]heptan-5-yl]-5-heptenoic acid methyl ester 22 mg (38 micromol) of the bicyclic compound produced according to example 11b was reacted analogously to example 1a and, after working up and purification, 12 mg (37 micromol, 96%) of the title compound was isolated as a colorless oil.

IR (film): 3200–3600, 2955, 2930, 2870, 1735, 1450, 1435, 1220, 1190, 1155, 1030, 1000, 950 and 890 cm$^{-1}$.

EXAMPLE 11b (4S,5R(5Z), 6S,1)-7-[4-(1-Pentinyl)-6-tert-butyldiphenylsilyloxymethyl-2-oxabicyclo[2.2.1]heptan-5-yl]-5-heptenoic acid methyl ester 46 mg (78 micromol) of the diol produced in example 11c was cyclized analogously to example 1b. After working up and purification, 22 mg (38 micromol, 49%) of the title compound was isolated as a colorless oil.

IR (film): 3070, 3050, 2960, 2930, 1735, 1590, 1425, 1245, 1110, 1005, 890, 820, 740 and 705 cm$^{-1}$.

EXAMPLE 11c (1S,2R(5Z),3S,4R)-7-[1-Hydroxymethyl-1-(1-pentinyl)-3-tert-butyldiphenylsilyloxymethyl-4-hydroxy-cyclopentan-2-yl]-5-heptenoic acid methyl ester 75 mg (111 micromol) of the compound produced in example 11d was reacted analogously to example 1c and, after working up and purification, 46 mg (78 micromol, 70%) of the title compound was isolated as a colorless oil.

IR (film): 3100–3600, 3070, 3050, 3000, 2950, 2930, 2855, 1735, 1590, 1425, 1110, 820, 740 and 705 cm$^{-1}$.

EXAMPLE 11d (1S,2R(5Z),3S,4R)-7-[1-Hydroxymethyl-1-(1-pentinyl)-3-tert-butyldiphenylsilyloxymethyl-4-(tetrahydropyran-2-yloxy)cyclopentan-2-yl]-5-heptenoic acid methyl ester 78 mg (135 micromol) of the polar lactols produced in example 11e was reacted analogously to example 1d and, after esterification and purification, 75 mg (111 micromol, 72%) of the title compound was isolated as a colorless oil.

IR (film): 3200–3600, 3070, 3050, 2950, 2930, 2860, 1735, 1590, 1430, 1200, 1110, 1030, 870, 820, 740 and 705 cm$^{-1}$.

EXAMPLE 11e (1S,4RS,6R,7S,8R)-1-(1-Pentinyl)-4-hydroxy-7-tert-butyldiphenylsilyloxymethyl-8-(tetrahydropyran-2-yloxy)-3-oxabicyclo[4.3.0]nonane (A) and
(1S,3RS,6R,7S,8R)-1-(1-pentinyl)-3-hydroxy-7-tert-butyldiphenylsilyloxymethyl-8-(tetrahydropyran-2-yloxy)-4-oxabicyclo[4.3.0]nonane (B)

330 mg (574 micromol) of an approximately 1:1 mixture of the regioisomeric lactones produced in example 11f was reduced analogously to example 1e. 325 mg (563 micromol, 98%) of a mixture of both title compounds A and B was isolated.

IR (film): 3200–3600, 3070, 3050, 2940, 2860, 1590, 1425, 1265, 1200, 1110, 1075, 1020, 870, 820, 740 and 705 cm$^{-1}$.

After chromatographic separation, 125 mg (218 micromol, 38%) of compound B was obtained in addition to 80 mg (139 micromol, 24%) of more polar component A.

EXAMPLE 11f (1S,6R,7S,8R)-1-(1-Pentinyl)-7-tert-butyldiphenylsilyloxymethyl-8-(tetrahydropyran-2-yloxy)-3-oxabicyclo[4.3.0]nonan-4-one and
(1S,6R,7S,8R)-1-(1-pentinyl)-7-tert-butyldiphenylsilyloxymethyl-8-(tetrahydropyran-2-yloxy)-4-oxabicyclo[4.3.0]nonan-3-one 770 mg (1.38 mmol) of the bicyclic ketone produced in example 11g was oxidized analogously to example 1f and, after working up and purification, 570 mg (992 micromol, 72%) of an approximately 1:1 mixture of both title compounds was isolated as a colorless oil.

IR (film): 3070, 3050, 2940, 2860, 1750, 1590, 1425, 1260, 1110, 1075, 1035, 970, 870, 820, 740 and 705 cm$^{-1}$.

EXAMPLE 11g (1S,5R,6S,7R)-1-(-1-Pentinyl)-6-tert-butyldiphenylsilyloxymethyl-7-(tetrahydropyran-2-yloxy)bicyclo[3.3.0]octan-3-one The solution of 587 mg of 1-pentine in 10 ml of anhydrous diethyl ether cooled to −40° C. under an atmosphere of dry argon was mixed with 7.2 ml of a 1.18M solution of n-butyllithium in n-hexane, allowed to stir for 30 minutes at −10° C., cooled again to −40° C., mixed with 8.5 ml of a 1M solution of diethylaluminum chloride in toluene and stirred for another 40 minutes at 0° C. to 3° C. The formed emulsion was added with exclusion of moisture of a mixture of 104 mg of nickel acetylacetonate, which had been suspended in 20 ml of anhydrous diethyl ether and had been mixed with 400 microliters of a 1M solution of diisobutylaluminum hydride in toluene, cooled to −10° C., the solution of 1.85 g (3.77 mmol) of the bicyclic, unsaturated ketone produced according to example 1h was instilled continuously in 25 ml of anhydrous diethyl ether. It was allowed to react for another 1.5 hours at −15° C. to −5° C., quenched by pouring into a well-stirred mixture of about 200 ml of finely crushed ice and 50 ml of a 1 n HCl, extracted several times with a total of 250 ml of diethyl ether, the combined organic extracts were washed with water and saturated sodium chloride solution until the neutral reaction, dried on magnesium sulfate and the solvent was removed in a water jet vacuum. The brown crude oil (2.41 g) was chromatographed under pressure on about 400 ml of silica gel with use of an n-hexane/ethyl acetate gradient system. 890 mg (1.59 mmol, 42%) of the title compound was isolated as a colorless oil.

IR (film): 3070, 3045, 2970, 2930, 1740, 1590, 1428, 1155, 1110, 1075, 1020, 870, 740 and 705 cm$^{-1}$.

EXAMPLE 12

(4S,5R(5Z),6S,1R)-7-[4-(1-Pentinyl)-6-benzyloxymethyl-2-oxabicyclo[2.2.1]heptan-5-yl]-5-heptenoic acid 16.4 mg of the ester mixture produced according to example 11 was saponified analogously to example 2 and, after working up and purification, 10.9 mg (26.5 micromol, 72%, relative to the initial material in example 11) of the title compound was isolated as a colorless oil.

IR (film): 3600–2400, 3090, 3060, 3030, 3000, 2930, 2870, 1730, 1710, 1605, 1455, 1115, 1090, 1075, 1010, 895, 735 and 700 cm$^{-1}$.

EXAMPLE 13

(4S,5R(5Z),6S,1R)-7-[4-Phenylacetylene-6-benzoyloxymethyl-2-oxabicyclo[2.2.1]heptan-5-yl]-5-heptenoic acid methyl (or benzyl) ester 11.7 mg (31.8 micromol) of the alcohol produced according to example 13a was reacted analogously to example 1 and, after working up and purification, 14 mg of the title compounds was isolated as a colorless oil.

IR (film): 3080, 3060, 3030, 3000, 2930, 2870, 2230, 1735, 1605, 1490, 1455, 1110, 1075, 1005, 895, 755, 740 and 695 cm$^{-1}$.

EXAMPLE 13a (4S,5R(5Z),6S,1R)-7-[4-Phenylacetylene-6-hydroxy-2-oxabicyclo[2.2.1]heptan-5-yl]-5-heptenoic acid methyl ester 91 mg (150 micromol) of the bicyclic compound produced according to example 13b was reacted analogously to example 1a and, after working up and purification, 55 mg (148 micromol, 99%) of the title compound was isolated as a colorless oil.

IR (CHCl$_3$): 3200-3700, 3080, 3060, 3030, 3000, 2950, 2880, 2230, 1725, 1600, 1490, 1440, 1365, 1300, 1220, 1175, 1025, 995, 890 and 690 cm$^{-1}$.

EXAMPLE 13b (4S,5R(5Z),6S,1R)-7-[4-Phenylacetylene-6-tert-butyldiphenylsilyloxymethyl-2-oxabicyclo[2.2.1]heptan-5-yl]-5-heptenoic acid methyl ester 120 mg (192 micromol) of the diol produced in example 13c was cyclized analogously to example 1b and, after working up and purification, 91 mg (150 micromol, 62%) of the title compound was isolated as a colorless oil.

IR (film): 3070, 3050, 3000, 2950, 2930, 2860, 2215, 1735, 1600, 1590, 1425, 1110, 1005, 895, 820, 755, 740 and 705 cm$^{-1}$.

EXAMPLE 13c (1S,2R(5Z),3S,4R)-7-[1-Hydroxymethyl-1-phenylacetylene-3tert-butyldiphenylsilyloxymethyl-4-hydroxy-cyclopentan-2-yl]-5-heptenoic acid methyl ester 205 mg (289 micromol) of the compound produced in example 13d was reacted analogously to example 1c and, after working up and purification, 120 mg (192 micromol, 66%) of the title compound was isolated as a colorless oil.

IR (film): 3200-3600, 3070, 3050, 3010, 2950, 2930, 2860, 2220, 1735, 1600, 1590, 1425, 1110, 820, 755, 740 and 705 cm$^{-1}$.

EXAMPLE 13d (1S,2R(5Z),3S,4R)-7-[1-Hydroxymethyl-1-phenylacetylene-3-tert-butyldiphenylsilyloxymethyl-4-(tetrahydropyran-2-yloxy)cyclopentan-2-yl]-5-heptenoic acid methyl ester (A) and
(1R(5Z),2R,3S,4R)-7-[1-phenylacetylene-2-hydroxymethyl-3-tert-butyldiphenylsilyloxymethyl-4-tetrahydropyran-2-yloxy)cyclopentan-1-yl]-5-heptenoic acid methyl ester (B)

512 mg (838 micromol) of an approximately 1:1 mixture of the regioisomeric lactols produced in example 13e was reacted analogously to example 1d and, after formation of methyl ester, purification and chromatographic separation, 220 mg (310 micromol, 37%) of title compound B as a nonpolar component as well as 205 mg (289 micromol, 35%) of title compound A as a polar component were isolated respectively as colorless oil.

IR (film) of A: 3200-3600, 3070, 3050, 3010, 2940, 2850, 2220, 1735, 1600, 1590, 1430, 1240, 1110, 1035, 1020, 870, 820, 760, 740 and 705 cm$^{-1}$.

EXAMPLE 13e (1S,4RS,6R,7S,8R)-1-Phenylacetylene-4-hydroxy-7-tert-butyldiphenylsilyloxymethyl-8-(tetrahydropyran-2-yloxy)-3-oxabicyclo[4.3.0]nonane and
(1S,3RS,6R,7S,8R)-1-phenylacetylene-3-hydroxy-7-tert-butyldiphenylsilyloxymethyl-8(tetrahydropyran-2-yloxy)-4-oxabicyclo[4.3.0]nonane 1.01 g (1.66 mmol) of an approximately 1:1 mixture of the regioisomeric lactones produced in example 13f was reduced analogously to example 1e. After working up and purification, 512 mg (838 micromol, 51%) of a mixture of both title compounds was isolated as a colorless oil.

IR (CHCl$_3$): 3400-3600, 3070, 3050, 3000, 2940, 2860, 2220, 1600, 1590, 1425, 1255, 1110, 1075, 1020, 910, 865, 820 and 700 cm$^{-1}$.

EXAMPLE 13f (1S,6R,7S,8R)-1-Phenylacetylene-7-tert-butyldiphenylsilyloxymethyl-8-(tetrahydropyran-2-yloxy)-3-oxabicyclo[4.3.0]nonan-4-one and (1S,6R,7S,8R)-1-phenylacetylene-7-tert-butyldiphenylsilyloxymethyl-8-(tetrahydropyran-2-yloxy)-4-oxabicyclo[4.3.0]nonan-3-one.

1.7 g (2.87 mmol) of the bicyclic ketone produced according to example 13g was oxidized analogously to example 1f. After working up and purification, 1.01 g (1.66 mmol, 58%) of an approximately 1:1 mixture of both title compounds was isolated as a foam colored pale yellow.

IR (film): 3070, 3050, 2940, 2860, 1750, 1600, 1590, 1575, 1430, 1260, 1110, 1035, 970, 915, 870, 820, 740 and 705 cm$^{-1}$.

EXAMPLE 13g (1S,5R,6S,7R)-1-Phenylacetylene-6-tert-butyldiphenylsilyloxymethyl-7-(tetrahydropyran-2-yloxy)-bicyclo[3.3.0]octan-3-one.

2.0 g (4.08 mmol) of the bicyclic, unsaturated ketone produced according to example 1h was reacted analogously to example 11g with use of phenylacetylene. After working up and purification, 1.78 g (3.00 mmol, 74%) of the title compound was isolated as a yellow oil.

IR (CHCl$_3$): 3070, 3050, 3000, 2940, 2860, 2220, 1735, 1600, 1590, 1425, 1260, 1110, 1075, 1020, 915, 870, 820, 740 and 700 cm$^{-1}$.

EXAMPLE 14

(4S,5R(5Z),6S,1R)-7-[4-Phenylacetylene-6-benzyloxymethyl-2-oxabicyclo[2.2.1]heptan-5-yl]-5-heptenoic acid.

14 mg of the ester mixture produced according to example 13 was saponified analogously to example 2 and, after working up and purification, 10.1 mg (22.7 micromol, 71%, relative to the initial material in example 13) of the title compound was isolated as a colorless oil.

IR (film): 3600-2400, 3080, 3060, 3030, 3000, 2930, 2880, 2230, 1730, 1705, 1600, 1490, 1455, 1110, 1070, 1005, 895, 755, 740 and 690 cm$^{-1}$.

EXAMPLE 15

(4S,5R(5Z),6S,1R)-7-[4-(2-Phenylethyl)-6-benzoyloxymethyl-2-oxabicyclo[2.2.1]heptan-5-yl]-5-heptenoic acid methyl (or benzyl) ester.

19.5 mg (52.3 micromol) of the alcohol produced according to example 15a was etherified analogously to example 1 and, after working up and purification, 23 mg of the title compounds was isolated as a colorless oil.

IR (film): 3080, 3060, 3030, 3000, 2930, 2870, 1735, 1600, 1495, 1455, 1240, 1205, 1115, 1095, 1020, 895, 740 and 700 cm$^{-1}$.

EXAMPLE 15a (4S,5R(5Z),6S,1R)-7-[4-(2-Phenylethyl)-6-hydroxymethyl-2-oxabicyclo[2.2.1]heptan-5-yl]-5-heptenoic acid methyl ester:

944 mg (1.55 mmol) of the bicyclic compound produced according to example 15b was reacted analogously to example 1a and, after working up and purification, 528 mg (1.42 mmol, 92%) of the title compound was isolated as a colorless oil.

IR (film): 3200–3600, 3060, 3020, 3000, 2940, 2860, 1735, 1605, 1450, 1435, 1240, 1155, 1025, 895, 750 and 700 cm$^{-1}$.

EXAMPLE 15b (4S,5R(5Z),6S,1R)-7-[4-(2-Phenylethyl)-6-tert-butyldiphenylsilyloxymethyl-2-oxabicyclo[2.2.1]heptan-5-yl]-5-heptenoic acid methyl ester:

1.11 g (1.77 mmol) of the diol produced in example 15c was reacted analogously to example 1b and, after working up and purification, 945 mg (1.55 mmol, 88%) of the title compound was isolated as a colorless oil.

IR (film): 3070, 3050, 3020, 3000, 2940, 2850, 1735, 1600, 1590, 1425, 1110, 895, 820, 740 and 700 cm$^{-1}$.

EXAMPLE 15c (1S,2R(5Z),3S,4R)-7-[1-Hydroxymethyl-1-(2-phenylethyl)-3-tert-butyldiphenylsilyloxymethyl-4-hydroxy-cyclopentan-2-yl]-5-heptenoic acid methyl ester.

1.62 g (2.27 mmol) of the compound produced in example 15d was reacted analogously to example 1c and, after working up and purification, 1.11 g (1.77 mmol, 78%) of the title compound was isolated as a colorless oil.

IR (film): 3200–3600, 3070, 3050, 3020, 3000, 2940, 2850, 1735, 1600, 1590, 1430, 1240, 1110, 1045, 820, 740 and 700 cm$^{-1}$.

EXAMPLE 15d (1S,2R(5Z),3S,4R)-7-[1-Hydroxymethyl-1-(2-phenylethyl)-3-tert-butyldiphenylsilyloxymethyl-4-(tetrahydropyran-2-yloxy)cyclopentan-2-yl]-5-heptenoic acid methyl ester (A) and (1R(5Z),2R,3S,4R)-7-[1-(2-phenylethyl)-2-hydroxymethyl-3-tert-butyldiphenylsilyloxymethyl-4-(tetrahydropyran-2-yloxy)cyclopentan-1-yl]-5-heptenoic acid methyl ester (B).

2.62 g (4.26 mmol) of the mixture of regioisomeric lactols isolated in example 15e was reacted analogously to example 1d and, after esterification, purification and chromatographic separation, 1.29 g (1.81 mmol, 42%) of title compound B as a nonpolar component was isolated in addition to 1.62 g (2.27 mmol, 53%) of title compound A as a polar component.

IR (film) of A: 3200–3600, 3070, 3050, 3020, 2940, 2855, 1735, 1600, 1590, 1430, 1240, 1200, 1110, 1030, 870, 820, 740 and 705 cm$^{-1}$.

EXAMPLE 15e (1S,4RS,6R,7S,8R)-1-(2-Phenylethyl)-4-hydroxy-7-tert-butyldiphenylsilyloxymethyl-8-(tetrahydropyran-2-yloxy)-3-oxabicyclo[4.3.0]nonane and (1R,3RS,6R,7S,8R)-1-(2-phenylethyl)-3-hydroxy-7-tert-butyldiphenylsilyloxymethyl-8-(tetrahydropyran-2-yloxy)-4-oxabicyclo[4.3.0]nonane:

2.70 g (4.40 mmol) of the mixture of both regioisomeric lactones produced in example 15f was reduced analogously to example 1e and, after working up, 2.62 g (4.26 mmol, 97%) of a mixture of the title compounds was isolated.

IR (film): 3200–3600, 3070, 3050, 3020, 2930, 2850, 1600, 1590, 1425, 1155, 1260, 1200, 1110, 1075, 1020, 910, 865, 820, 740 and 700 cm$^{-1}$.

EXAMPLE 15f (1S,6R,7S,8R)-1-(2-Phenylethyl)-7-tert-butyldiphenylsilyloxymethyl-8-(tetrahydropyran-2-yloxy)-3-oxabicyclo[4.3.0]nonan-4-one and (1R,6R,7S,8R)-1-(2-phenylethyl)-7-tert-butyldiphenylsilyloxymethyl-8-(tetrahydropyran-2-yloxy)-4-oxabicyclo[4.3.0]nonan-3-one.

3.14 g (5.26 mmol) of the ketone produced in example 15g was oxidized analogously to example 1f and, after working up and purification, 2.70 g (4.40 mmol, 84%) of an approximately 1:1 mixture of both title compounds was isolated as a colorless oil.

IR (film): 3070, 3050, 3015, 2940, 2850, 1745, 1600, 1590, 1425, 1110, 1040, 970, 870, 820, 740 and 705 cm$^{-1}$.

EXAMPLE 15g (1R,5R,6S,7R)-1-(2-Phenylethyl)-6-tert-butyldiphenylsilyloxymethyl-7-(tetrahydropyran-2-yloxy)-bicyclo[3.3.0]octan-3-one.

4.18 g (8.52 mmol) of the bicyclic unsaturated ketone produced in example 1h was reacted analogously to example 1g with phenethylmagnesium bromide with copper catalysis. After working up and purification, 3.15 g (5.27 mmol, 62%) of the title compound was isolated as a colorless oil.

IR (film): 3070, 3050, 3020, 2930, 2850, 1740, 1600, 1590, 1425, 1110, 1075, 1020, 870, 820, 740 and 700 cm$^{-1}$.

EXAMPLE 16

(4S,5R(5Z),6S,1R)-7-[4-(2-Phenylethyl)-6-benzyloxymethyl-2-oxabicyclo[2.2.1]heptan-5-yl]-5-heptenoic acid.

23 mg of the ester mixture produced according to example 15 was saponified analogously to example 2 and, after working up and purification, 21 mg (47 micromol, 90%, relative to the educt of example 15) of the title compound was isolated as a colorless oil.

IR (film): 3600–2400, 3080, 3060, 3020, 3000, 2930, 2860, 1730, 1705, 1600, 1495, 1455, 1240, 1205, 1115, 1090, 1025, 895, 740 and 700 cm$^{-1}$.

EXAMPLE 17

(4S,5R(5Z),6S,1R)-7-[4-(p-Fluorophenyl)-6-benzyloxymethyl-2-oxabicyclo[2.2.1]heptan-5-yl]-5-heptenoic acid methyl (or benzyl) ester.

17.5 mg (48.3 micromol) of the alcohol produced according to example 17a was reacted analogously to example 1 and, after working up and purification, 24 mg of the title compound was isolated as a colorless oil.

IR (film): 3060, 3020, 3000, 2930, 2870, 1735, 1600, 1510, 1455, 1110, 1075, 895, 820, 740 and 705 cm$^{-1}$.

EXAMPLE 17a (4S,5R(5Z),6S,1R)-7-[4-(p-Fluorophenyl)-6-hydroxy-2-oxabicyclo[2.2.1]heptan-5-yl]5-heptenoic acid methyl ester.

798 mg (1.33 mmol) of the bicyclic compound produced according to example 17b was reacted analogously to example 1a and, after working up and purification, 448 mg (1.24 mmol, 93%) of the title compound was isolated as a colorless oil.

IR (film): 3200–3600, 3080, 3060, 3020, 3000, 2950, 2870, 1735, 1600, 1510, 1435, 1220, 1020, 995, 895, 820 and 700 cm$^{-1}$.

EXAMPLE 17b (4S,5R(5Z),6S,1R)-7-[4-(p-Fluorophenyl)-6-tert-butyldiphenylsilyloxymethyl-2-oxabicyclo[2.2.1]heptan-5-yl]-5-heptenoic acid methyl ester.

1.15 g (1.86 mmol) of the diol produced according to example 17c was cyclized analogously to example 1b and, after working up and purification, 800 mg (1.33 mmol, 72%) of the title compound was isolated as a colorless oil.

IR (CHCl$_3$): 3070, 3050, 3000, 2950, 2930, 2860, 1735, 1605, 1590, 1510, 1425, 1230, 1110, 895, 830, 820, 740 and 705 cm$^{-1}$.

EXAMPLE 17c (1S,2R(5Z),3S,4R)-7-[1-Hydroxymethyl-1-(p-fluorophenyl)-3-tert-butyldiphenylsilyloxymethyl-4-hydroxy-cyclopentan-2-yl]-5-heptenoic acid methyl ester (A) and (1R,(5Z),2R,3S,4R)-7-[1-(p-fluorophenyl)-2-hydroxymethyl-3-tert-butyldiphenylsilyloxymethyl-4-hydroxy-cyclopentan-1-yl]-5-heptenoic acid methyl ester (B).

2.58 g (3.67 mmol) of a mixture of the regioisomeric compounds produced in example 17d was reacted analogously to example 1c and, after working up, purification and separation, 1.15 g (1.86 mmol, 51%) of title compound A, as well as 0.85 g (1.37 mmol, 37%) of title compound B were isolated respectively as colorless oil.

IR (CHCl$_3$) of A: 3700–3200, 3070, 3040, 3010, 2950, 2930, 2850, 1730, 1600, 1590, 1510, 1425, 1230, 1110, 1050, 820, 740 and 705 cm$^{-1}$.

EXAMPLE 17d (1S,2R,(5Z),3S,4R)-7-[1-Hydroxymethyl-1-(p-fluorophenyl)-3-tert-butyldiphenylsilyloxymethyl-4-(tetrahydropyran-2-yloxy)cyclopentan-2-yl]-5-heptenoic acid methyl ester and (1R,(5Z),2R,3S,4R)-7-[1-(p-fluorophenyl)-2-hydroxymethyl-3-tert-butyldiphenylsilyloxymethyl-4-(tetrahydropyran-2-yloxy)cyclopentan-1-yl]-5-heptenoic acid methyl ester.

2.55 g (4.22 mmol) of an approximately 1:1 mixture of the regioisomeric lactols produced in example 17e was reacted analogously to example 1d and, after formation of methyl ester and purification, 2.58 g (3.67 mmol, 87%) of a mixture of both title compounds was isolated as a colorless oil.

IR (film): 3200–3600, 3070, 3050, 3020, 2950, 2860, 1735, 1600, 1590, 1510, 1430, 1325, 1110, 1035, 870, 820, 740 and 705 cm$^{-1}$.

EXAMPLE 17e (1S,4RS,6R,7S,8R)-1-(p-Fluorophenyl)-4-hydroxy-7-tert-butyldiphenylsilyloxymethyl-8-(tetrahydropyran-2-yloxy)-3-oxabicyclo[4.3.0]nonane and (1S,3RS,6R,7S,8R)-1-(p-fluorophenyl)-3-hydroxy-7-tert-butyl-diphenylsilyloxymethyl-8-(tetrahydropyran-2-yloxy)-4-oxabicyclo[4.3.0]nonane:

Analogously to example 1e, 2.57 g (4.26 mmol) of an approximately 1:1 mixture of the regioisomeric lactones produced in example 17f was reduced and, after working up and purification, 2.55 g (4.22 mmol, 99%) of a mixture of both title compounds was isolated.

IR (film): 3200–3600, 3070, 3040, 3000, 2950, 2870, 1600, 1590, 1510, 1425, 1260, 1110, 1075, 1040, 910, 865, 820, 740 and 700 cm$^{-1}$.

EXAMPLE 17f (1S,6R,7S,8R)-1-(p-Fluorophenyl)-7-tert-butyldiphenylsilyloxymethyl-8-(tetrahydropyran-2-yloxy)-3-oxabicyclo[4.3.0]nonan-4-one and (1S,6R,7S,8R)-1-(p-fluorophenyl)-7-tert-butyldiphenylsilyloxymethyl-8-(tetrahydropyran-2-yloxy)-4-oxabicyclo[4.3.0]nonan-3-one.

2.80 g (4.77 mmol) of the bicyclic ketone produced according to example 17g was oxidized analogously to example 1f and, after working up and purification, 2.58 g (4.28 mmol, 90%) of an approximately 1:1 mixture of both title compounds was isolated.

IR (CHCl$_3$): 3070, 3050, 3000, 2950, 2860, 1745, 1605, 1590, 1510, 1230, 1110, 1030, 820, 740 and 700 cm$^{-1}$.

EXAMPLE 17g (1S,5R,6S,7R)-1-(p-Fluorophenyl)-7-tert-butyldiphenylsilyloxymethyl-7-(tetrahydropyran-2-yloxy)-bicyclo[3.3.0]octan-3-one.

4.06 g (8.27 mmol) of the bicyclic unsaturated ketone produced according to example 1h was reacted analogously to example 1g with p-fluorophenylmagnesium chloride with copper catalysis. After working up and purification, 2.80 g (4.77 mmol, 58%) of the title compounds was isolated as a colorless oil.

IR (film): 3090, 3040, 2940, 2850, 1740, 1600, 1590, 1510, 1425, 1235, 1110, 1075, 1020, 820, 740 and 700 cm$^{-1}$.

EXAMPLE 18

(4S,5R(5Z),6S,1R)-7-[4-(p-Fluorophenyl)-6-benzyloxymethyl-2-oxabicyclo[2.2.1]heptan-5-yl]-5-heptenoic acid.

24 mg of the ester mixture produced in example 17 was saponified analogously to example 2 and, after working up and purification, 20 mg (45.6 micromol, 94%, relative to the initial material in example 17) of the title compounds was isolated as a colorless oil.

IR (film): 3600–2400, 3090, 3060, 3030, 3000, 2930, 2870, 1725, 1710, 1605, 1510, 1450, 1230, 1160, 1040, 1025, 890, 830, 735, 695 and 640 cm$^{-1}$.

EXAMPLE 19

(4S,5R(5Z),6S,1R)-7-[4-Phenyl-6-tert-butyldiphenylsilyloxymethyl-2-oxabicyclo[2.2.1]heptan-5-yl]-5-heptenoic acid.

The colorless solution of 22.7 mg (39 micromol) of the compound, produced in example 3b, in 1 ml of methanol was mixed with 0.5 ml of a 5% aqueous lithium hydroxide solution and the originally heterogeneous mixture was stirred for 16 hours at 23° C. It neutralized by the addition of corresponding amounts of a 10% aqueous citric acid and purified by chromatography on an analytic thin-layer slab with use of a mixture of dichloromethane and ethanol. After elution of the suitable zone with a mixture of ethyl acetate and ethanol, 19.5 mg (34.3 micromol, 88%) of the title compound was isolated as a colorless oil.

IR (film): 3500-2400, 3070, 3050, 3030, 3010, 2950, 2930, 2860, 1730, 1710, 1600, 1590, 1470, 1430, 1110, 1075, 890, 825, 760, 740, 700, 615, 505 and 490 cm$^{-1}$.

EXAMPLE 20

(4S,5R(5Z),6S,1R)-7-[4-Phenyl-6-hydroxymethyl-2-oxabicyclo[2.2.1]heptan-5-yl]-5-heptenoic acid.

15 mg (43.5 micromol) of the compound produced in example 3a was saponified analogously to example 19 and, after working up and purification, 10.3 mg (31.2 micromol, 72%) of the title compound was isolated as a colorless oil.

IR (film): 3100-2400, 3080, 3060, 3030, 2930, 2870, 1710, 1600, 1500, 1445, 1230, 1200, 1040, 1000, 970, 890, 760 and 700 cm$^{-1}$.

EXAMPLE 21

(4S,5R(5Z),6S,1R)-7-[4-Phenyl-6-hexyloxymethyl-2-oxabicyclo[2.2.1]heptan-5-yl]-5-heptenoic acid methyl ester.

33.8 mg (98.1 micromol) of the compound produced in example 3a was dissolved in 3.5 ml of anhydrous tetrahydrofuran, mixed with 10 mg of a 50% sodium hydride dispersion in white oil and, after completion of hydrogen development, 140 microliters of 1-bromohexane was added. It was heated to 40°-50° C. and stirred for another 18 hours under an atmosphere of dry argon. It was mixed with water, acidified with a 10% citric acid and extracted several times with diethyl ether. The combined organic extracts were washed with water, dried on magnesium sulfate, filtered and concentrated by evaporation in a water jet vacuum. The residue was purified by chromatography on an analytic thin-layer slab with use of a chloroform/ethanol mixture. After elution of suitable zones, 16.4 mg (38.3 micromol, 39%) of the title compound was isolated in addition to the initial material and ester cleavage product.

IR (film): 3070, 3050, 3030, 3000, 2940, 2870, 1735, 1600, 1450, 1040, 895, 760 and 700 cm$^{-1}$.

EXAMPLE 22

(4S,5R(5Z),6S,1R)-7-[4-Phenyl-6-hexyloxymethyl-2-oxabicyclo[2.2.1]heptan-5-yl]-5-heptenoic acid.

16.4 mg (38.3 micromol) of the compound produced in example 21 was saponified analogously to example 19 and, after working up and purification, 10.0 mg (24.1 micromol, 63%) of the title compound was isolated as a colorless oil.

IR (film): 3600-2400, 3070, 3050, 3030, 3010, 2960, 2940, 2870, 1730, 1710, 1600, 1450, 1040, 900, 760 and 700 cm$^{-1}$.

EXAMPLE 23

(4S,5R(5Z),6R(1E,3R), 1R)-7-[4-Phenyl-6-(3-hydroxy-4,4-dimethyl-1-octenyl)-2-oxabicyclo[2.2.1]heptan-5-yl]-5-heptenoic acid methyl ester (A) and (4S,5R(5Z),6R(1E,3S),1R)-7-[4-phenyl-6-(3-hydroxy-4,4-dimethyl-1-octenyl)-2-oxabicyclo[2.2.1]heptan-5-yl]-5-heptenoic acid methyl ester (B).

108 mg (231 micromol) of the unsaturated ketone produced in example 23a was dissolved in 2.8 ml of anhydrous methanol, cooled under an atmosphere of dry argon to −40° C. and mixed with 53 mg of sodium borohydride. After 0.5 hours, it was quenched by adding 70 microliters of glacial acetic acid, allowed to heat to 23° C. and extracted several times with a total of 8 ml of diethyl ether. It was dried on magnesium sulfate and, after the removal of the solvent in a water jet vacuum, the residue obtained was chromatographed on 4 analytic silica gel slabs. A mixture of chloroform/ethanol was used as a mobile solvent, a mixture of ethyl acetate/ethanol was used as an eluant. 49 mg (105 micromol, 45%) of a nonpolar component, to which structure A was assigned was isolate, in addition to 31 mg (66 micromol, 29%) of a polar component, to which structure B was assigned.

IR (film) of A: 3200-3600, 3060, 2950, 2930, 2870, 1735, 1600, 1450, 1195, 1025, 995, 970, 895, 750 and 700 cm$^{-1}$.

IR (film) of B: 3200-3600, 3060, 2950, 2930, 2870, 1735, 1600, 1445, 1245, 1195, 995, 970, 895, 760 and 700 cm$^{-1}$.

EXAMPLE 23a (4S,5R(5Z),6R(1E),1R)-7-[4-Phenyl-6-(3-oxo-4,4-dimethyl-1-octenyl)-2-oxabicyclo[2.2.1]heptan-5-yl]-5-heptenoic acid methyl ester.

The solution of 96 mg of dimethyl-(2-oxo-3,3-dimethylheptyl)-phosphonate in 0.9 ml of anhydrous dimethoxyethane was instilled in the suspension of 8.9 mg of sodium hydride in 2.8 ml of anhydrous dimethoxyethane, cooled after the completion of the gas development under an atmosphere of dry argon to −30° C. and the solution of 104 mg (303 micromol) of the aldehyde produced in example 23b in 1.3 ml of anhydrous dimethoxyethane was instilled. It was allowed to heat within 6 hours to 22° C., mixed with 170 microliters of glacial acetic acid, diluted with 5 ml of diethyl ether, washed neutral with water and saturated sodium chloride solution and dried on magnesium sulfate. After removal of the solvent in a water jet vacuum, the residue was purified by chromatography on 6 analytic silica gel slabs. A mixture of n-hexane/ethyl acetate was used as a mobile solvent; ethyl acetate was used as an eluant. 108 mg (231 micromol, 76%) of the title compound was isolated as a colorless oil.

IR (film): 3060, 2955, 2930, 2870, 1735, 1685, 1620, 1450, 1195, 1045, 995, 900, 760 and 700 cm$^{-1}$.

EXAMPLE 23b (4S,5R(5Z),6S,1R)-7-[4-Phenyl-6-formyl-2-oxabicyclo[2.2.1]heptan-5-yl]-5-heptenoic acid methyl ester:

103 mg (299 micromol) of the alcohol produced according to example 3a was oxidized analogously to example 38b and, after working up and purification, 101 mg (295 micromol, 99%) of the title compound was isolated.

IR (film: 3060, 2950, 2870, 2720, 1735, 1715, 1600, 1500, 1445, 1435, 1245, 1165, 1015, 1000, 900, 765 and 700 cm$^{-1}$.

EXAMPLE 24

(4S,5R(5Z),6R(1E,3S),1R)-7-[4-Phenyl-6-(3-hydroxy-4,4-dimethyl-1-octenyl)-2-oxabicyclo[2.2.1]heptan-5-yl]-5-heptenoic acid.

48 mg (105 micromol) of the nonpolar alcohol produced according to example 23 was saponified analogously to example 2 and, after working up and purification, 44 mg (97 micromol, 92%) of the title compound was isolated as a colorless oil.

IR (film): 3600-2400, 3080, 3060, 3030, 3000, 2950, 2930, 2870, 1710, 1600, 1450, 1240, 1200, 995, 970, 890, 755 and 700 cm$^{-1}$.

EXAMPLE 25

(4S,5R(5Z),6R(1E,3R),1R)-7-[4-Phenyl-6-(3-hydroxy-4,4-dimethyl-1-octenyl)-2-oxabicyclo[2.2.1-]heptan-5-yl]-5-heptenoic acid.

31 mg (66 micromol) of the polar alcohol produced according to example 23 was saponified analogously to example 2 and, after working up and purification, 30 mg (60.8 micromol, 92%) of the title compound was isolated as a colorless oil.

IR (film): 3600–2400, 3090, 3060, 3030, 3000, 2960, 2930, 2870, 1710, 1605, 1450, 1240, 1195, 995, 970, 895, 760 and 700 cm$^{-1}$.

EXAMPLE 26

(4S,5R(5Z),6S,1R)-7-[4-Phenyl-6-[(E/Z)diphenylmethoxyiminomethyl]-2-oxabicyclo[2.2.1]heptan-5-yl]-5-heptenoic acid methyl ester.

19 mg (40 micromol) of the aldehyde produced according to example 23b was dissolved in 200 microliters of anhydrous ethanol, mixed with 12.2 mg of diphenylmethoxyhydroxyamine, a drop of pyridine and heated under an atmosphere of dry argon for 7 hours to 50° C. It was allowed to cool and purified by chromatography on an analytic silica gel slab. A mixture of chloroform/ethanol was used as a mobile solvent; ethyl acetate was used as an eluant. 20 mg (38 micromol, 95%) of the title compound was isolated as a colorless oil.

IR (film): 3080, 3060, 3025, 2940, 2870, 1735, 1600, 1495, 1450, 1020, 1000, 935, 895, 760, 740 and 700 cm$^{-1}$.

EXAMPLE 27

(4S,5R(5Z), 6S,1R)-7-[4-Phenylethyl)-6-[(E/Z)diphenylmethoxyiminomethyl]-2-oxabicyclo[2.2.1]heptan-5-yl]-5-heptenoic acid methyl ester.

18 mg (49 micromol) of the aldehyde produced according to example 27a was reacted analogously to example 26 and, after working up and purification, 26 mg (47 micromol, 97%) of the title compound was isolated as a colorless oil.

IR (film): 3080, 3060, 3030, 2940, 2865, 1735, 1600, 1495, 1450, 1020, 935, 895, 745 and 700 cm$^{-1}$.

EXAMPLE 27a (4S,5R(5Z),6R,1R)-7-[4-(2-Phenylethyl)-6-formyl-2-oxabicyclo[2.2.1]heptan-5-yl]-5-heptenoic acid methyl ester.

201 mg (540 micromol) of the alcohol produced according to example 15a was oxidized analogously to example 38b and, after working up and purification, 200 mg (540 micromol, 100%) of the title compound was isolated as a pale yellow oil.

IR (film): 3070, 3050, 3020, 2950, 2860, 2720, 1735, 1715, 1605, 1450, 1435, 1245, 1160, 1025, 900, 750 and 700 cm$^{-1}$.

EXAMPLE 28

(4S,5R(5Z),6S,1R)-7-[4-Phenyl-6-[(E,Z)diphenylmethoxyiminomethyl]-2-oxabicyclo[2.2.1]heptan-5-yl]-5-heptenoic acid.

20 mg (38 micromol) of the compound produced according to example 26 was saponified analogously to example 2 and, after working up and purification, 15 mg (29 micromol, 77%) of the title compound was isolated as a colorless oil.

IR (film): 3600–2500, 3090, 3060, 3030, 3010, 2940, 2880, 1730, 1710, 1605, 1495, 1450, 1000, 935, 900, 760, 745 and 700 cm$^{-1}$.

EXAMPLE 29

(4S,5R(5Z),6S,1R)-7-[4-(2-Phenylethyl)-6-[(E/Z)diphenylmethoxyiminomethyl]-2-oxabicyclo[2.2.1]heptan-5-yl]-5-heptenoic acid.

26 mg (47 micromol) of the compound produced according to example 27 was saponified analogously to example 2 and, after working up and purification, 20 mg (37 micromol, 79%) of the title compound was isolated as a colorless oil.

IR (film): 3600–2400, 3080, 3060, 3030, 3000, 2930, 2870, 1730, 1705, 1605, 1495, 1455, 1020, 935, 895, 745 and 700 cm$^{-1}$.

EXAMPLE 30

(4S,5R(5Z),6R(1E,3R),1R)-7-[4-Phenyl-6-(3-hydroxy-4-phenoxy-1-butenyl)-2-oxabicyclo[2.2.1]heptan-5-yl]-5-heptenoic acid methyl ester (A) and (4S,5R(5Z),6R(1E,3S),1R)-7-[4-phenyl-6-(3-hydroxy-4-phenoxy-1-butenyl)-2-oxabicyclo[2.2.1]heptan-5-yl]-5-heptenoic acid methyl ester (B).

54 mg (114 micromol) of the unsaturated ketone produced in example 30a was reduced analogously to example 23 and, after working up, purification and epimer separation, 26.6 mg (56 micromol, 49%) of a nonpolar alcohol, to which structure A was assigned was isolated, as well as 25 mg (52 micromol, 46%) of a polar alcohol, to which structure B was assigned.

IR (film) of the epimer mixture: 3600–3200, 3060, 3030, 3010, 2930, 2880, 1735, 1600, 1590, 1500, 1455, 1250, 1140, 1000, 970, 895, 760 and 700 cm$^{-1}$.

EXAMPLE 30a (4S,5R(5Z),6R(1E),1R)-7-[4-Phenyl-6-(3-oxo-4-phenoxy-1-butenyl)-2-oxabicyclo[2.2.1]heptan-5-yl]-5-heptenoic acid methyl ester.

84 mg (245 micromol) of the aldehyde produced according to example 23b was dissolved in 4 ml of anhydrous dimethoxyethane, cooled under an atmosphere of dry argon to 0° to 5° C., mixed with 147 mg of dimethyl-(2-oxo-3-phenoxy-propyl)-phosphonate lithium salt and allowed to stir for 8 hours at 23° C. It was poured into cold aqueous citric acid, extracted several times with diethyl ether, washed neutral with water and saturated sodium chloride solution and dried on magnesium sulfate. The residue remaining after the removal of the solvent in a water jet vacuum was purified by chromatography on 5 analytic silica gel slabs. A mixture of chloroform/ethanol was used as a mobile solvent; ethyl acetate was used as an eluant. 54 mg (114 micromol, 47%) of the title compound was isolated as a colorless oil.

IR (film): 3060, 3030, 2940, 2870, 1735, 1690, 1620, 1600, 1495, 1435, 1290, 1240, 1220, 1045, 1000, 900, 755 and 700 cm$^{-1}$.

EXAMPLE 31

(4S,5R(5Z),6R(1E,3R),1R)-7-[4-(p-Fluorophenyl)-6-(3-hydroxy-4-phenoxy-1-butenyl)-2-oxabicyclo[2.2.1-]heptan-5-yl]-5-heptenoic acid methyl ester (A) and (4S,5R(5Z),6R(1E,3S),1R)-7-[4-p-fluorophenyl)-6-(3-hydroxy-4-phenoxy-1-butenyl)-2-oxabicyclo[2.2.1]heptan-5-yl]-5-heptenoic acid methyl ester (B).

59 mg (120 micromol) of the unsaturated ketone produced in example 31a was reduced analogously to example 23 and, after working up and purification, 54 mg (109 micromol, 91%) of a mixture of both title compounds was isolated as a colorless oil.

IR (film): 3600–3200, 3060, 3040, 3010, 2940, 2920, 2870, 1730, 1600, 1585, 1510, 1490, 1240, 1160, 1035, 895, 835, 755 and 690 cm$^{-1}$.

The chromatographic separation yielded 24 mg (49 micromol, 41%) of the more nonpolar alcohol, to which structure A was assigned, as well as 29 mg (59 micromol, 49%) of the more polar alcohol, to which structure B was assigned.

EXAMPLE 31a (4S,5R(5Z),6R(1E),1R)-7-[4-(p-Flurophenyl)-6-(3-oxo-phenoxy-1-butenyl)-2-oxabicyclo[2.2.1]heptan-5-yl]-5-heptenoic acid methyl ester.

54 mg (150 micromol) of the aldehyde produced in example 31b was reacted analogously to example 30a with use of dimethyl-(2-oxo-3-phenoxy-propyl)-phosphonate lithium salt and, after working up and purification, 57 mg (116 micromol, 77%) of the title compound was isolated as a colorless oil.

IR (film): 3000, 2940, 2870, 1730, 1690, 1620, 1600, 1430, 1225, 1160, 895, 835, 755 and 690 cm$^{-1}$.

EXAMPLE 31b (4S,5R(5Z),6R,1R)-7-[4-(p-Fluorophenyl)-6-formyl-2-oxabicyclo[2.2.1]heptan-5-yl]-5-heptenoic acid methyl ester.

155 mg (428 micromol) of the alcohol produced in example 17a was oxidized analogously to example 38b and, after working up, 155 mg (428 micromol, 100%) of the title compound was isolated as a colorless oil.

IR (film): 3060, 2950, 2870, 2730, 1735, 1600, 1505, 1450, 1435, 1245, 1160, 1010, 1005, 900, 820, 760 and 700 cm$^{-1}$.

EXAMPLE 32

(4S,5R(5Z),6R(1E,3S),1R)-7-[4-Phenyl-6-(3-hydroxy-4-phenoxy-1-butenyl)-2-oxabicyclo[2.2.1]heptan-5-yl]-5-heptenoic acid.

25 mg (52 micromol) of the polar ester produced in example 30 was saponified analogously to example 2 and, after working up and purification, 19 mg (41 micromol, 79%) of the title compound was isolated as a colorless oil.

IR (film): 3600–2400, 3060, 3030, 3010, 2930, 1710, 1600, 1590, 1500, 1455, 1245, 1140, 995, 970, 895, 760 and 700 cm$^{-1}$.

EXAMPLE 33

(4S,5R(5Z),6R(1E,3R),1R)-7-[4-(p-Fluorophenyl)-6-(3-hydroxy-4-phenoxy-1-butenyl)-2-oxabicyclo[2.2.1]heptan-5-yl]-5-heptenoic acid.

24 mg (49 micromol) of the nonpolar ester produced in example 31 was saponified analogously to example 2 and, after working up and purification, 19 mg (40 micromol, 81%) of the title compound was isolated as a colorless oil.

IR (film): 3600–2400, 3060, 3040, 3010, 2930, 2880, 1710, 1600, 1585, 1515, 1495, 1300, 1240, 1160, 1040, 895, 835, 755, 690 and 585 cm$^{-1}$.

EXAMPLE 34

(4S,5R(5Z),6S(1E,3R),1R)-7-[4-Phenyl-6-(3-hydroxy-4-phenoxy-1-butenyl)-2-oxabicyclo[2.2.1]heptan-5-yl]-5-heptenoic acid:

26 mg (55 micromol) of the nonpolar ester produced in example 30 was saponified analogously to example 2 and, after working up and purification, 17 mg (37 micromol, 67%) of the title compound was isolated as a colorless oil.

IR (film): 3600–2400, 3060, 3030, 3010, 2930, 2880, 1730, 1710, 1600, 1590, 1500, 1455, 1245, 1040, 890, 755, 700 and 690 cm$^{-1}$.

EXAMPLE 35

(4S,5R(5Z),6R(1E,3S),1R)-7-[4-(p-Fluorophenyl)-6-(3-hydroxy-4-phenoxy-1-butenyl)-2-oxabicyclo[2.2.1]heptan-5-yl]-5-heptenoic acid.

29 mg (59 micromol) of the polar ester produced in example 31 was saponified analogously to example 2 and, after working up and purification, 24 mg (50 micromol, 85%) of the title compound was isolated as a colorless oil.

IR (film): 3600–2500, 3060, 3040, 3010, 2930, 2880, 1710, 1600, 1585, 1515, 1495, 1455, 1300, 1240, 1160, 1040, 895, 835, 755, 690 and 590 cm$^{-1}$.

EXAMPLE 36

(4S,5R(5Z),6S,1R)-7-[4-Methyl-6-(phenyl-p-benzyloxymethyl)-2-oxabicyclo[2.2.1]heptan-5-yl]-5-heptenoic acid methyl (or 4-phenylbenzyl) ester:

16.7 mg (59 micromol) of the alcohol obtained in example 1a was reacted analogously to example 1 with use of 4-phenylbenzyl chloride. After working up and purification, 26 mg of the title compounds was isolated as a colorless oil.

IR (film): 3070, 3030, 3010, 2960, 2930, 2880, 1735, 1600, 1485, 1455, 1230, 1110, 1020, 895, 830, 760 and 700 cm$^{-1}$.

EXAMPLE 37

(4S,5R(5Z),6S,1R)-7-[4-Methyl-6-(phenyl-p-benzyloxymethyl)-2-oxabicyclo[2.2.1]heptan-5-yl]-5-heptenoic acid.

26 mg of the ester mixture produced in example 36 was saponified analogously to example 2 and, after working up and purification, 18 mg (41 micromol, 69%) of the title compound was isolated as a colorless oil.

IR (film): 3600–2400, 3070, 3030, 3000, 2950, 2920, 2870, 1730, 1705, 1600, 1485, 1455, 1235, 1110, 1085, 1020, 1010, 895, 825, 760 and 695 cm$^{-1}$.

EXAMPLE 38

(4S,5R(5Z),6R(1E,3R),1R)-7-[4-Methyl-6-(3-hydroxy-1-octenyl)-2-oxabicyclo[2.2.1]heptan-5-yl]-5-heptenoic acid methyl ester (A) and (4S,5R(5Z),6R(1E,3S),1R)-7-[4-methyl-6-(3-hydroxy-1-octenyl)-2-oxabicyclo[2.2.1]heptan-5-yl]-5-heptenoic acid methyl ester (B).

37 mg (98 micromol) of the unsaturated ketone produced in example 38a was reduced analogously to example 23 and, after working up and purification, 37 mg (97 micromol, 100%) of a mixture of both title compounds was isolated as a colorless oil.

IR (film): 3600–3200, 2950, 2930, 2860, 1735, 1450, 1435, 1020, 965 and 890 cm$^{-1}$.

The chromatographic separation yielded 19 mg (50 micromol, 51%) of the more nonpolar alcohol, to which structure A was assigned, as well as 16.5 mg (44 micromol, 44%) of the more polar alcohol, to which structure B was assigned.

EXAMPLE 38a (4S,5R(5Z),6R(1E),1R)-7-[4-Methyl-6-(3-oxo-1-octenyl)-2-oxabicyclo[2.2.1]heptan-5-yl]-5-heptenoic acid methyl ester.

50 mg (178 micromol) of the aldehyde produced in example 38 b was reacted analogously to example 23a with use of dimethyl-(2-oxo-heptyl)-phosphonate and, after working up and purification, 37.6 mg (100 micromol, 56%) of the title compound was isolated as a colorless oil.

IR (film): 2950, 2930, 2870, 1735, 1690, 1670, 1620, 1450, 1435, 1240, 1195, 1160, 1020, 980 and 895 cm$^{-1}$.

EXAMPLE 38b (4S,5R(5Z),6R,1R)-7-[4-Methyl-6-formyl-2-oxabicyclo[2.2.1]heptan-5-yl]-5-heptenoic acid methyl ester.

To the solution of 63 microliters of freshly distilled oxalyl chloride, cooled under an atmosphere of dry argon to −60° C., in 1.6 ml of anhydrous dichloromethane were added the solution of 110 microliters of dimethyl sulfoxide in 310 microliters of dichloromethane and after about 2 minutes the solution of 168 mg (595 micromol) of the alcohol, produced in example 1a, in 630 microliters of dichloromethane. It was allowed to react for another 30–40 minutes, mixed with 440 microliters of triethylamine, allowed to heat to room temperature, diluted with 10 ml of diethyl ether, washed several times with water and saturated sodium chloride solution and dried on magnesium sulfate. After filtration and concentration by evaporation in a water jet vacuum, 155 mg (553 micromol, 93%) of the title compound was isolated as a pale yellow oil.

IR (film): 2950, 2930, 2870, 2720, 1735, 1715, 1450, 1435, 1245, 1215, 1195, 1160, 1010, 990, 970 and 895 cm$^{-1}$.

EXAMPLE 39

(4S,5S(5Z),6S(1E,3S),1S)-7-[4-Phenyl-6-(3-hydroxy-1-octenyl)-2-oxabicyclo[2.2.1]heptan-5-yl]-5-heptenoic acid methyl ester (A) and (4R,5S(5Z),6S(1E,3R),1S)-7-[4-Phenyl-6-(3-hydroxy-1-octenyl)-2-oxabicyclo[2.2.1]heptan-5-yl]-5-heptenoic acid methyl ester (B).

44 mg (100 micromol) of the unsaturated ketone produced in example 39a was reduced analogously to example 23 and, after working up and purification, 40 mg (91 micromol, 91%) of a mixture of both title compounds was isolated as a colorless oil.

IR (film): 3600–3200, 3060, 2950, 2930, 2860, 1730, 1600, 1450, 1435, 1265, 995, 970, 895, 735 and 700 cm$^{-1}$.

The chromatographic separation yielded 20 mg (45 micromol, 45%) of the more nonpolar alcohol, to which structure A was assigned, as well as 17 mg (39 micromol, 39%) of the more polar alcohol, to which structure B was assigned.

EXAMPLE 39a (4R,5S(5Z),6S(1E),1S)-7-[4-Phenyl-6-(3-oxo-1-octenyl)-2-oxabicyclo[2.2.1]heptan-5-yl]-5-heptenoic acid methyl ester.

43 mg (126 micromol) of the aldehyde produced in example 39b was reacted analogously to example 23a with use of dimethyl-(2-oxo-heptyl)-phosphonate and, after working up and purification, 44 mg (100 micromol, 80%) of the title compound was isolated as a colorless oil.

IR (film): 3060, 3000, 2950, 2930, 2870, 1735, 1690, 1670, 1625, 1600, 1500, 1450, 1435, 1245, 1195, 1170, 1045, 995, 975, 900, 760 and 700 cm$^{-1}$.

EXAMPLE 39 b (4R,5S(5Z),6S,1S)-7-[4-Phenyl-6-formyl-2-oxabicyclo[2.2.1]heptan-5-yl]-5-heptenoic acid methyl ester.

93 mg (270 micromol) of the alcohol produced according to example 5a was oxidized analogously to example 38b and, after working up and purification, 86 mg (251 micromol, 93%) of the title compound was isolated.

IR (film): 3060, 3030, 2940, 2870, 2720, 1735, 1715, 1600, 1500, 1450, 1435, 1245, 1165, 1015, 1000, 895, 765 and 700 cm$^{-1}$.

EXAMPLE 40

(4S,5R(5Z),6R(1E,3R),1R)-7-[4-Benzyl-6-(3-hydroxy-1-octenyl)-2-oxabicyclo[2.2.1]heptan-5-yl]-5-heptenoic acid methyl ester (A) and (4S,5R(5Z),6R(1E,3S),1R)-7-[4-benzyl-6-(3-hydroxy-1-octenyl)-2-oxabicyclo[2.2.1]heptan-5-yl]-5-heptenoic acid methyl ester (B).

55 mg (121 micromol) of the unsaturated ketone produced in example 40a was reduced analogously to example 23 and, after working up and purification, 51 mg (112 micromol, 93%) of a mixture of both title compounds was isolated as a colorless oil.

IR (film): 3600–3300, 3060, 3030, 2950, 2920, 2860, 1735, 1600, 1450, 1435, 1245, 1150, 1015, 995, 965, 895, 765 and 705 cm$^{-1}$.

The chromatographic separation yielded 27.7 mg (61 micromol, 50%) of the more nonpolar alcohol, to which structure A was assigned, as well as 21.2 mg (47 micromol, 39%) of the more polar alcohol, to which structure B was assigned.

EXAMPLE 40a (4S,5R(5Z),6R(1E),1R)-7-[4-Benzyl-6-(3-oxo-1-octenyl)-2-oxabicyclo[2.2.1]heptan-5-yl]-2-heptenoic acid methyl ester.

49 mg (137 micromol) of the aldehyde produced in example 40 b was reacted analogously to example 23a with use of dimethyl-(2-oxo-heptyl)-phosphonate and, after working up and purification, 55 mg (121 micromol, 88%) of the title compound was isolated as a colorless oil.

IR (film): 3060, 3030, 2950, 2930, 2860, 1735, 1690, 1670, 1620, 1450, 1245, 1160, 995, 900, 765 and 705 cm$^{-1}$.

EXAMPLE 40b (4S,5R(5Z),6R,1R)-7-[4-Benzyl-6-formyl-2-oxabicyclo[2.2.1]heptan-5-yl]-5-heptenoic acid methyl ester.

100 mg (279 micromol) of the alcohol produced according to example 7a was oxidized analogously to example 38b and, after working up and purification, 98 mg (275 micromol, 99%) of the title compound was isolated as a pale yellow oil.

IR (film): 3060, 2950, 2720, 1735, 1715, 1600, 1450, 1435, 1245, 1160, 1010, 995, 895, 760 and 700 cm$^{-1}$.

EXAMPLE 41

(4S,5R(5Z),6R(1E,3R),1R)-7-[4-(p-Phenyl-benzyl)-6-(3-hydroxy-1-octenyl)-2-oxabicyclo[2.2.1heptan-5-yl]-5-heptenoic acid methyl ester (A) and (4S,5R,(5Z),6R(1E,3S),1R)-7-[4-(p-phenyl-benzyl)-6-

(3-hydroxy-1-octenyl)-2-oxabicyclo[2.2.1]heptan-5-yl]-5-heptenoic acid methyl ester (B).

44 mg (83 micromol) of the unsaturated ketone produced in example 41a was reduced analogously to example 23 and, after working up and purification, 43 mg (81 micromol, 98%) of a mixture of both title compounds was isolated as a colorless oil.

IR (film): 3600–3200, 3060, 3030, 2930, 2870, 1735, 1600, 1455, 1200, 1110, 1010, 895, 850, 740 and 700 cm$^{-1}$.

The chromatographic separation yielded 23 mg (43 micromol, 52%) of the more nonpolar alcohol, to which structure A was assigned, as well as 19 mg (36 micromol, 43%) of the more polar alcohol, to which structure B was assigned.

EXAMPLE 41a (4S,5R(5Z),6R(1E),1R)-7-[4-(p-Phenyl-benzyl)-6-(3-oxo-1-octenyl)-2-oxabicyclo[2.2.1]heptan-5-yl]-5-heptenoic acid methyl ester.

43 mg (99 micromol) of the aldehyde produced in example 41b was reacted analogously to example 23a with use of dimethyl-(2-oxo-heptyl)-phosphonate and, after working up and purification, 44 mg (83 micromol, 84%) of the title compound was isolated as crystalline solid.

Melting point: 75°–76° C.

EXAMPLE 41b (4S,5R(5Z),6R, 1S)-7-[4-(p-Phenyl-benzyl)-6-formyl-2-oxabicyclo[2.2.1]heptan-5-yl]-5-heptenoic acid methyl acid ester.

103 mg (237 micromol) of the alcohol produced according to example 9a was oxidized analogously to example 38b and, after working up and purification, 87 mg (201 micromol, 85%) of the title compound was isolated as waxy solid.

IR (film): 3070, 3050, 3020, 2920, 2860, 2720, 1735, 1715, 1600, 1490, 1440, 1005, 895, 770, 740 and 700 cm$^{-1}$.

EXAMPLE 42

(4S,5R(5Z),6R(1E,3R),1R)-7-[4-(2-Phenylethyl)-6-(3-hydroxy-1-octenyl)-2-oxabicyclo[2.2.1]heptan-5-yl]-5-heptenoic acid methyl ester (A) and (4S,5R(5Z),6R(1E,3S),1R-7-[4-(2-phenylethyl)-6-(3-hydroxy-1-octenyl)-2-oxabicyclo[2.2.1]heptan-5-yl]-5-heptenoic acid methyl ester (B).

33.7 mg (72 micromol) of the unsaturated ketone produced in example 42a was reduced analogously to example 23 and, after working up and purification, 30 mg (64 micromol, 89%) of a mixture of both title compounds was isolated as a colorless oil.

IR (film): 3600–3200, 3080, 3060, 3020, 2930, 2860 1735, 1600, 1450, 1435, 1245, 1200, 1155, 1025, 1015, 970, 895, 755 and 700 cm$^{-1}$.

The chromatographic separation yielded 14 mg (30 micromol, 41%) of the more nonpolar alcohol, to which structure A was assigned, as well as 13 mg (28 micromol, 39%) of the more polar alcohol, to which structure B was assigned.

EXAMPLE 42a (4S, 5R(5Z),6R(1E),1R)-7-[4-(2-Phenylethyl)-6-(3-oxo-1-octenyl) -2-oxabicyclo[2.2.1]heptan-5-yl]-5-heptenoic acid methyl ester 52 mg (140 micromol) of the aldehyde produced in example 27a was reacted analogously to example 23a with use of dimethyl-(2-oxo-heptyl)-phosphonate and, after working up and purification, 33.7 mg (72 micromol, 52%) of the title compound was isolated as a colorless oil.

IR (film): 3080, 3060, 3020, 3000, 2950, 2920, 2860, 1735, 1690, 1670, 1620, 1450, 1435, 1245, 1170, 980, 900, 755 and 700 cm$^{-1}$.

EXAMPLE 43

(4S,5R(5Z),6R(1E,3R),1R)-7-[4-(p-Fluorophenyl)-6-(3-hydroxy-1-octenyl)-2-oxabicyclo[2.2.1]heptan-5-yl]-5-heptenoic acid methyl ester (A) and (4S,5R(5Z),6R(1E,3S),1R)-7-[4-(p-fluorophenyl)-6-(3-hydroxy-1-octenyl)-2-oxabicyclo[2.2.1]heptan-5-yl]-5-heptenoic acid methyl ester (B)

52 mg (114 micromol) of the unsaturated ketone produced in example 43a was reduced analogously to example 23 and, after working up and purification, 49 mg (107 micromol, 94%) of a mixture of both title compounds was isolated as a colorless oil.

IR (film): 3600–3200, 3050, 3000, 2950, 2930, 2860, 1735, 1600, 1510, 1230, 1160, 995, 970, 895, 830 and 735 cm$^{-1}$.

The chromatographic separation yielded 26 mg (57 micromol, 50%) of the more nonpolar alcohol, to which structure A was assigned, as well as 20 mg (44 micromol, 38%) of the more polar alcohol, to which structure B was assigned.

EXAMPLE 43a (4S,5R(5Z),6R(1E),1R)-7-[4-(p-Fluorophenyl)-6-(3-oxo-1-octenyl) -2-oxabicyclo[2.2.1]heptan-5-yl]-5-heptenoic acid methyl ester 46 mg (128 micromol) of the aldehyde produced in example 31b was reacted analogously to example 23a with use of dimethyl-(2-oxo-heptyl)-phosphonate and, after working up and purification, 52 mg (114 micromol, 89%) of the title compound was isolated as a colorless oil.

IR (film): 3000, 2950, 2930, 2860, 1735, 1690, 1670, 1620, 1510, 1435, 1230, 1160, 995, 975, 900 and 835 cm$^{-1}$.

EXAMPLE 44

(4S,5R(5Z),6R(1E,3R),1R)-7-[4-Methyl-6-(3-hydroxy-1-octenyl)-2-oxabicyclo[2.2.1] heptan-5-yl]-5-heptenoic acid 17.5 mg (46 micromol) of the nonpolar ester produced in example 38 was saponified analogously to example 2 and, after working up and purification, 15.7 mg (43 micromol, 94%) of the title compound was isolated as a colorless oil.

IR (film): 3600–2400, 2970, 2930, 2870, 1710, 1460, 1240, 1025, 970 and 890 cm$^{-1}$.

EXAMPLE 45

(4R,5S(5Z),6S(1E,3S),1S)-7-[4-Phenyl-6-(3-hydroxy-1-octenyl) -2-oxabicyclo[2.2.1]heptan-5-yl]-5-heptenoic acid 20 mg (45 micromol) of the nonpolar ester produced in example 39 was saponified analogously to example 2 and, after working up and purification, 19 mg (45 micromol, 90%) of the title compound was isolated as a colorless oil.

IR (film): 3600–2300, 3080, 3060, 3030, 3000, 2930, 2870, 1710, 1605, 1500, 1450, 1240, 1195, 1045, 995, 970, 890, 760 and 700 cm$^{-1}$.

EXAMPLE 46

(4S,5R(5Z),6R(1E,3R),1R)-7-[4-Benzyl-6-(3-hydroxy-1-octenyl) -2-oxabicyclo[2.2.1]heptan-5-yl]-5-heptenoic acid 27.7 mg (61 micromol) of the nonpolar ester produced in example 40 was saponified analogously to example 2 and, after working up and purification, 26 mg (59 micromol, 97%), of the title compound was isolated as a colorless oil.

IR (film): 3600–2400, 3090, 3070, 3030, 2940, 2870, 1710, 1605, 1455, 1245, 995, 970, 895, 765 and 705 cm$^{-1}$.

EXAMPLE 47

(4S,5R(5Z),6R(1E,3R),1R)-7-[4-(p-Phenyl-benzyl)-6-(3-hydroxy-2-ocetenyl)-2-oxabicyclo[2.2.1]heptan-5-yl]-5-heptenoic acid 23 mg (43 micromol) of the nonpolar ester produced in example 41 was saponified analogously to example 2 and, after working up and purification, 19.7 mg (38 micromol, 89%) of the title compound was isolated as crystalline solid.

IR (KBr): 3600–2200, 3010, 2930, 2870, 2850, 1690, 1600, 1490, 1265, 1200, 890, 765, 735 and 690 cm$^{-1}$.

EXAMPLE 48

(4S,5R(5Z),6R(1E,3R),1R)-7-[4-(2-Phenylethyl)-6-(3-hydroxy -1-octenyl)-2-oxabicyclo[2.2.1]heptan-5-yl]-5-heptenoic acid 14 mg(30 micromol) of the nonpolar ester produced in example 42 was saponified analogously to example 2 and, after working up and purification, 13 mg (29 micromol, 95%) of the title compound was isolated as a colorless oil.

IR (film: 3600–2400, 3080, 3060, 3020, 3000, 2930, 2860, 1725, 1710, 1605, 1455, 1240, 1030, 1115, 970, 890, 755 and 700 cm$^{-1}$.

EXAMPLE 49

(4S,5R(5Z),6R(1E,3R),1R)-7-[4-(p-Fluorophenyl)-6-(3-hydroxy-1-octenyl)-2-oxabicyclo[2.2.1]heptan-5-yl]-5-heptenoic acid 26 mg (57 micromol) of the nonpolar ester produced in example 43 was saponified analogously to example 2 and, after working up and purification, 21 mg (47 micromol, 83%) of the title compound was isolated as a colorless oil.

IR (film): 3600–2400, 3060, 3040, 3000, 2950, 2930, 2860, 1710, 1610, 1515, 1235, 1160, 995, 970, 895, 835 and 585 cm$^{-1}$.

EXAMPLE 50

(4S,5R(5Z),6R(1E,3S),1R)-7-[4-Methyl-6-(3-hydroxy-1-octenyl) -2-oxabicyclo[2.2.1]heptan-5-yl]-5-heptenoic acid 14.7 mg (39 micromol) of the polar ester produced in example 38 was saponified analogously to example 2 and, after working up and purification, 11.8 mg (32 micromol, 83%) of the title compound was isolated as a colorless oil.

IR (film): 3600–2400, 2960, 2930, 2870, 1730, 1710, 1460, 1240, 1025, 970 and 890 cm$^{-1}$.

EXAMPLE 51

(4R,5S(5Z),6S(1E,3R),1S)-7-[4-Phenyl-6-(3-hydroxy-1-octenyl) -2-oxabicyclo[2.2.1]heptan-5-yl]-5-heptenoic acid 17 mg (39 micromol) of the nonpolar ester produced in example 39 was saponified analogously to example 2 and, after working up and purification, 16 mg (38 micromol, 96%) of the title compound was isolated as a colorless oil.

IR(film): 3600–2400, 3080, 3060, 3030, 3000, 2950, 2930, 2860, 1710, 1605, 1500, 1450, 1295, 1240, 1195, 1045, 995, 970, 890, 760 and 700 cm$^{-1}$.

EXAMPLE 52

(4S,5R(5Z),6R(1E,3S),1R)-7-[4-Benzyl-6-(3-hydroxy-1-octenyl)-2-oxabicyclo[2.2.1] heptan-5-yl]-5-heptenoic acid 21.2 mg (47 micromol) of the polar ester produced in example 40 was saponified analogously to example 2 and, after working up and purification, 19 mg (43 micromol, 92%) of the title compound was isolated as a colorless oil.

IR (film): 3600–2400, 3090, 3070, 3030, 2930, 2870, 1730, 1710, 1605, 1455, 1245, 995, 970, 890, 765 and 705 cm$^{-1}$.

EXAMPLE 53

(4S,5R(5Z),6R(1E,3S),1R)-7-[4-(p-Phenyl-benzyl)-6-(3-hydroxy-1-octenyl)-2-oxabicyclo[2.2.1]heptan-5-yl]-5-heptenoic acid 19 mg (36 micromol) of the polar ester produced in example 41 was saponified analogously to example 2 and, after working up and purification, 14.6 mg (28 micromol, 78%) of the title compound was isolated as crystalline solid.

IR (KBr): 3600–2200, 3010, 2960, 2930, 2880, 2850, 1695, 1600, 1490, 1460, 1250, 1135, 1055, 1005, 970, 890, 770, 735 and 695 cm$^{-1}$.

EXAMPLE 54

(4S,5R(5Z),6R(1E,3S),1R)-7-[4-(2-Phenylethyl)-6-(3-hydroxy -1-octenyl)-2-oxabicyclo[2.2.1]heptan-5-yl]-5-heptenoic acid 13 mg (28 micromol) of the polar ester produced in example 42 was saponified analogously to example 2 and, after working up and purification, 11 mg (24 micromol, 86%) of the title compound was isolated as a colorless oil.

IR (film): 3600–2400, 3080, 3060, 3030, 3000, 2930, 2860, 1725, 1710, 1605, 1455, 1260, 1240, 1030, 970, 890, 755 and 700 cm$^{-1}$.

EXAMPLE 55

(4S,5R(5Z),6R(1E,3S),1R)-7-[4-(p-Fluorophenyl)-6-(3-hydroxy-1-octenyl)-2-oxabicyclo[2.2.1]heptan-5-yl]-5-heptenoic acid 20 mg (44 micromol) of the polar ester produced in example 43 was saponified analogously to example 2 and, after working up and purification, 18 mg (40 micromol, 92%) of the title compound was isolated as a colorless oil.

IR (film): 3600–2500, 3040, 3000, 2950, 2930, 2860, 1710, 1610, 1515, 1235, 1160, 995, 970, 895, 835 and 585 cm$^{-1}$.

EXAMPLE 56

(4S,5R(5Z),6R(1E,3R,4RS),1R)-7-[4-Methyl-6-(3-hydroxy-4-methyl-6-in-1-octenyl)-2-oxabicyclo[2.2.1]heptan-5-yl]-5-heptenoic acid methyl ester (A) and (4S,5R(5Z),6R(1E,3S,4RS),1R)-7-[4-methyl-6-(3-hdyroxy-4-methyl-6-in-1-octenyl)-2-oxabicyclo[2.2.1]heptan-5-yl]-5-heptenoic acid methyl ester (B)

53 mg (137 micromol) of the unsaturated ketone produced in example 56a was reduced analogously to example 23 and, after working up and purification, 52 mg (134 micromol, 98%) of a mixture of both title compounds was isolated as a colorless oil.

IR (film): 3600–3200, 2950, 2920, 2870, 1735, 1450, 1435, 1245, 1160, 1020, 970 and 890 cm$^{-1}$.

The chromatographic separation yielded 28 mg (72 micromol, 53%) of the more nonpolar alcohol, to which structure A was assigned, as well as 22 mg (57 micromol, 41%) of the more polar alcohol, to which structure B was assigned.

EXAMPLE 56a (4S,5R(5Z),6R(1E,4RS),1R)-7-[4-Methyl-6-(3-oxo-4-methyl-6-in-1-octenyl)-2-oxabicyclo[2.2.1]heptan-5-yl]-5-heptenoic acid methyl ester 50 mg (178 micromol) of the aldehyde produced in example 38b was reacted analogously to example 23a with use of racemic dimethyl-(2-oxo-3-methylhept-5-inyl)-phosphonate and, after working up and purification, 53 mg (137 micromol, 77%) of the title compound was isolated as a colorless oil.

IR (film): 2950, 2930, 2870, 1735, 1690, 1665, 1620, 1450, 1435, 1370, 1215, 1195, 1160, 1025, 975 and 895 cm$^{-1}$.

EXAMPLE 57

(4S,5R(5Z),6R(1E,3R,4RS),1R)-7-[4-(p-Phenyl-benzyl)-6-(3-hydroxy-4-methyl-6-in-1-octenyl)-2-oxabicyclo[2.2.1]heptan-5-yl]-5-heptenoic acid methyl ester (A) and (4S,5R(5Z),6R(1E,3S,4RS),1R)-7-[4-(p-phenyl-benzyl)-6-(3-hydroxy-4-methyl-6-in-1-octenyl)-2-oxabicyclo[2.2.1]heptan-5-yl]-5-heptenoic acid methyl ester (B)

44 mg (82 micromol) of the unsaturated ketone produced in example 57a was reduced analogously to example 23 and, after working up and purification, 43 mg (80 micromol, 97%) of a mixture of both title compounds was isolated.

IR (KBr): 3600–3200, 3010, 2960, 2930, 2870, 1735, 1600, 1490, 1245, 1120, 970, 895, 770, 735 and 695 cm$^{-1}$.

The chromatographic separation yielded 24.6 mg (45 micromol, 55%) of the more nonpolar alcohol, to which structure A was assigned, as well as 17 mg (31 micromol, 38%) of the more polar alcohol, to which structure B was assigned.

EXAMPLE 57a (4S,5R(5Z),6R(1E,4RS),1R)-7-[4-(p-Phenyl-benzyl)-6-(3-oxo-4-methyl-6-in-1-octenyl)-2-oxabicyclo[2.2.1]heptan-5-yl]-5-heptenoic acid methyl ester 43 mg (99 micromol) of the aldehyde produced in example 41b was reacted analogously to example 23a with use of racemic dimethyl-[2-oxo-3-methyl-hept-5-inyl]-phosphonate and, after working up and purification, 45 mg (84 micromol, 84%) of the title compound was isolated as a colorless oil.

Melting point: 82°–83° C.

EXAMPLE 58

(4S,5R(5Z),6R(1E,3R,4RS),1R)-7-[4-methyl-6-(3-hydroxy-4-methyl-6-in-1-octenyl)-2-oxabicyclo[2.2.1]heptan-5-yl]-5-heptenoic acid 28 mg (72 micromol) of the nonpolar ester produced in example 56 was saponified analogously to example 2 and, after working up and purification, 23.6 mg (63 micromol, 88%) of the title compound was isolated as a colorless oil.

IR (film): 3600–2400, 2960, 2930, 2870, 1730, 1710, 1455, 1240, 1020, 970 and 890 cm$^{-1}$.

EXAMPLE 59

(4S,5R(5Z),6R(1E,3R,4RS),1R)-7-[4-(p-Phenyl-benzyl)-6-(3-hydroxy-4-methyl-6-in-1-octenyl)-2-oxabicyclo[2.2.1]heptan-5-yl]-5-heptenoic acid 24.6 mg (45 micromol) of the nonpolar ester produced in example 57 was saponified analogously to example 2 and, after working up and purification, 20 mg (38 micromol, 84%) of the title compound was isolated as crystalline solid.

IR (KBr): 3600–2200, 3080, 3060, 3030, 2970, 2920, 1730, 1710, 1605, 1490, 1450, 1410, 1245, 1010, 995, 970, 890, 850, 770, 740 and 700 cm$^{-1}$.

EXAMPLE 60

(4S,5R(5Z),6R(1E,3S4RS),1R)-7-[4-Methyl-6-(3-hydroxy-4-methyl-6-in-1-octenyl)-2-oxabicyclo[2.2.1]heptan-5-yl]-5-heptenoic acid 22 mg (57 micromol) of the polar ester produced in example 56 was saponified analogously to example 2 and, after working up and purification, 20 mg (53 micromol, 84%) of the title compound was isolated as a colorless oil.

IR (film): 3600–2400, 2960, 2930, 2870, 1730, 1710, 1455, 1240, 1020, 970 and 885 cm$^{-1}$.

EXAMPLE 61

(4S,5R(5Z),6R(1E,3S,4RS),1R)-7-[4-(p-Phenyl-benzyl)-6-(3-hydroxy-4-methyl-6-in-1-octenyl)-2-oxabicyclo[2.2.1]heptan-5-yl]-5-heptenoic acid 17 mg (31 micromol) of the polar ester produced in example 57 was saponified analogously to example 2 and, after working up and purification, 12.4 mg (24 micromol, 76%) of the title compound was isolated as crystalline solid.

IR (KBr): 3600–2200, 3080, 3060, 3030, 2960, 2920, 1725, 1705, 1600, 1490, 1450, 1410, 1295, 1010, 995, 920, 890, 845, 765, 740 and 700 cm$^{-1}$.

EXAMPLE 62

(4R,5S(5Z),6R(1S)-7-[4-Phenyl-6-(N-morpholinomethyl)-2-oxabicyclo[2.2.1]heptan-5-yl]-5-heptenoic acid methyl ester 22 mg (54 micromol) of the bromide produced in example 62a was reacted analogously to example 63 and, after working up and purification, 15 mg (36 micromol, 67%) of the title compound was isolated as a colorless oil.

IR (film): 3080, 3060, 3030, 3000, 2950, 2870, 2810, 1735, 1670, 1600, 1440, 1225, 995, 895, 865 and 695 cm$^{-1}$.

EXAMPLE 62a (4R,5S(5Z),6S,1S)-7-[4-Phenyl-6-bromomethyl-2-oxabicyclo[2.2.1]heptan-5-yl]-5-heptenoic acid methyl ester 100 mg (290 micromol) of the alcohol produced in example 5a was bromated analogously to example 63a and, after working up and purification, 116 mg (285 micromol, 98%) of the title compound was isolated as a colorless oil.

IR (film): 3080, 3060, 3030, 3000, 2950, 2930, 2870, 1735, 1600, 1450, 1435, 1225, 1165, 995, 895, 765, 740, 705 and 640 cm$^{-1}$.

EXAMPLE 63

(4S,5R(5Z),6S,1R)-7-[4-Benzyl-6-(N-morpholinomethyl)-2-oxabicyclo[2.2.1]heptan-5-yl]-5-heptenoic acid methyl ester 17 mg (40 micromol) of the bromide produced according to example 63a was mixed with 205 microliters of morpholine and heated under an atmosphere of dry argon for 3 hours to 100° C. After the cooling, it was diluted with 10 ml of diethyl ether, washed several times with water, the organic phase was dried on magnesium sulfate, filtered, and the solvent was removed in a water jet vacuum. 14.2 mg (33 micromol, 83%) of the title compound was isolated as a colorless oil.

IR (film): 3060, 3030, 3000, 2950, 2930, 2870, 2815, 1730, 1670, 1605, 1440, 1225, 1000, 895, 865 and 695 cm$^{-1}$.

EXAMPLE 63a (4S,5R(5Z),6R,1R)-7-[4-Benzyl-6-bromomethyl-2-oxabicyclo[2.2.1]heptan-5-yl]-5-heptanoic acid methyl ester The solution of 66 mg (184 micromol) of the alcohol produced according to example 7a was dissolved in 1.4 ml of anhydrous acetonitrile, mixed with 305 mg of tetrabromomethane, 120 microliters of collidine, 241 mg of triphenylphosphine and stirred for 9 hours at 23° C. under an atmosphere of dry argon. It was mixed with 8 ml of diethyl ether, washed with ice-cold water, the organic phase was dried on magnesium sulfate, filtered and evaporated to dryness in a water jet vacuum. The residue was chromatographed on about 35 ml of silica gel. A gradient system of n-hexane/ethyl acetate was used as a mobile solvent. 77 mg (183 micromol, 99%) of the title compound was isolated as a colorless oil.

IR (film): 3080, 3060, 3020, 3000, 2950, 2930, 2860, 1735, 1605, 1450, 1435, 1220, 1165, 1015, 995, 895, 765, 735, 705 and 635 cm$^{-1}$.

EXAMPLE 64

(4S,5R(5Z),6S,1R)-7-[4-Phenylacetylene-6-(N-morpholinomethyl)-2-oxabicyclo[2.2.1]heptan-5-yl]-5-heptenoic acid methyl ester:

16 mg (37 micromol) of the bromide produced in example 64a was reacted analogously to example 63 and, after working up and purification, 14.5 mg (33 micromol, 90%) of the title compound was isolated as a colorless oil.

IR (film): 3060, 3030, 3000, 2950, 2860, 2810, 2230, 1730, 1670, 1600, 1440, 1220, 1110, 1000, 890, 865 and 690 cm$^{-1}$.

EXAMPLE 64a (4S,5R(5Z),6R,1R)-7-[4-Phenylacetylene-6-bromomethyl-2-oxabicyclo[2.2.1]heptan-5-yl]-5-heptenoic acid methyl ester 25 mg (68 micromol) of the alcohol produced in example 13a was reacted analogously to example 63a and, after working up and purification, 16.3 mg (38 micromol, 56%) of the title compound was isolated as a colorless oil.

IR (CHCl$_3$): 3080, 3060, 3020, 3000, 2950, 2880, 2230, 1725, 1600, 1490, 1435, 1300, 1220, 1165, 995, 895, 690 and 645 cm$^{-1}$.

EXAMPLE 65

(4S,5R(5Z),6S,1R)-7-[4-(2-Phenylethyl)-6-(N-morpholinomethyl)-2-oxabicyclo[2.2.1]heptan-5-yl]-5-heptenoic acid methyl ester 22 mg (51 micromol) of the bromide produced in example 65a was reacted analogously to example 63 and, after working up and purification, 20.6 mg (47 micromol, 91%) of the title compound was isolated as a colorless oil.

IR (film): 3080, 3060, 3030, 3000, 2950, 2870, 2810, 1735, 1665, 1600, 1440, 1220, 995, 895, 865 and 700 cm$^{-1}$.

EXAMPLE 65a (4S,5R(5Z),6R,1R)-7-[4-(2-Phenylethyl)-6-bromomethyl-2-oxabicyclo[2.2.1]heptan-5-yl]-5-heptenoic acid methyl ester 98 mg (263 micromol) of the alcohol produced in example 15a was bromated analogously to example 63a and, after working up and purification, 101 mg (232 micromol, 88%) of the title compound was isolated as a colorless oil.

IR (film): 3080, 3060, 3030, 3000, 2950, 2930, 2860, 1735, 1605, 1450, 1435, 1245, 1220, 1165, 1025, 980, 900, 750, 700 and 635 cm$^{-1}$.

EXAMPLE 66

(4R,5S(5Z),6R,1S)-7-[4-Phenyl-6-N-morpholinomethyl)-2-oxabicyclo[2.2.1]heptan-5-yl]-5-heptenoic acid 15 mg (36 micromol) of the ester produced in example 62 was saponified analogously to example 2 and, after working up and purification, 14 mg (35 micromol, 97%) of the title compound was isolated as colorless solid.

IR (KBr): 3600–3200, 3080, 3060, 3030, 3000, 2950, 2920, 2870, 2700–2300, 2100–1850, 1710, 1600, 1500, 1460, 1445, 1200, 1115, 1025, 1005, 900, 870, 760 and 700 cm$^{-1}$.

EXAMPLE 67

(4S,5R(5Z),6S,1R)-7-[4-Benzyl-6-(N-morpholinomethyl)-2-oxabicyclo[2.2.1]heptan-5-yl]-5-heptenoic acid 14.2 mg (33 micromol) of the ester produced in example 63 was saponified analogously to example 2 and, after working up and purification, 10 mg (24 micromol, 73%) of the title compound was isolated as a colorless oil.

IR (film): 3600–2300, 3080, 3060, 3030, 3000, 2930, 2870, 2810, 1720, 1605, 1495, 1455, 1265, 1245, 1120, 1005, 895, 870, 765 and 705 cm$^{-1}$.

EXAMPLE 68

(4S,5R(5Z),6S,1R)-7-[4-Phenylacetylene-6-(N-morpholinomethyl)-2-oxabicyclo[2.2.1]heptan-5-yl]-5-heptenoic acid 14.5 mg (33 micromol) of the ester produced in example 64 was saponified analogously to example 2 and, after working up and purification, 11.5 mg (27 micromol, 82%) of the title compound was isolated as a colorless oil.

IR (film): 3600–2400, 3080, 3060, 2930, 2880, 2860, 2810, 2240, 1720, 1600, 1490, 1480, 1445, 1140, 1120, 1005, 895, 870 and 695 cm$^{-1}$.

EXAMPLE 69

(4S,5R(5Z),6S,1R)-7-[4-(2-Phenylethyl)-6-N-morpholinomethyl)-2-oxabicyclo [2.2.1]heptan-5-yl]-5-heptenoic acid 20.6 mg (47 micromol) of the compound produced in example 65 was saponified analogously to example 2 and, after working up and purification, 16.5 mg (39 micromol, 82%) of the title compound was isolated as crystalline substance.

IR (KBr): (3600–2300, 3090, 3060, 3010, 2930, 2860, 1710, 1605, 1500, 1455, 1230, 1120, 1010, 890, 870 and 705 cm$^{-1}$.

EXAMPLE 70

(4R,5S(5Z),6R,1S)-7-[4-Phenyl-6-(1-imidazoylmethyl)-2-oxabicyclo[2.2.1]heptan-5-yl]-5-heptenoic acid methyl ester 26 mg (64 micromol) of the bromide produced in example 62a was reacted analogously to example 63 and, after working up and purification, 15 mg (38 micromol, 59%) of the title compound was isolated as a colorless oil.

IR (film): 3110, 3060, 3020, 3000, 2950, 2880, 1735, 1600, 1510, 1450, 1300, 1235, 1110, 1080, 1005, 900, 750, 700 and 665 cm$^{-1}$.

EXAMPLE 71

(4S,5R(5Z),6S,1R)-7-[4-Benzyl-6-(1-imidazoylmethyl)2-oxabicyclo[2.2.1]heptan-5-yl]-5-heptenoic acid methyl ester 15 mg (36 micromol) of the bromide produced in example 63a was reacted analogously to example 63 with use of imidazole and, after working up and purification, 9.2 mg (23 micromol, 64%) of the title compound was isolated as a colorless oil.

IR (film): 3115, 3060, 3030, 3000, 2940, 2870, 1735, 1605, 1510, 1455, 1235, 1110, 1085, 1000, 900, 760, 705 and 660 cm$^{-1}$.

EXAMPLE 72

(4S,5R(5Z),6S,1R)-7-[4-(2-Phenylethyl)-6-(1-imidazoylmethyl)-2-oxabicyclo[2.2.1]heptan-5-yl]-5-heptenoic acid methyl ester 19 mg (44 micromol) of the bromide produced in example 65a was reacted analogously to example 63 with use of imidazole and, after working up and purification, 18 mg (43 micromol, 97%) of the title compound was isolated as a colorless oil.

IR (film): 3110, 3080, 3060, 3030, 2970, 2930, 2870, 1735, 1605, 1455, 1320, 1295, 1235, 1110, 1075, 1010, 895, 750, 700 and 660 cm$^{-1}$.

EXAMPLE 73

(4R,5S(5Z),6R,1S)-7-[4-Phenyl-6-(1-imidazoylmethyl)-2-oxabicyclo[2.2.1]heptan-5-yl]-5-heptenoic acid 15 mg (38 micromol) of the ester produced in example 70 was saponified analogously to example 2 and, after working up and purification, 11 mg (29 micromol, 76%) of the title compound was isolated as colorless solid.

IR (KBr): 3600–3200, 3110, 3060, 3020, 3000, 2940, 2880, 2700–2200, 2100–1800, 1700, 1600, 1500, 1445, 1315, 1290, 1235, 1110, 1085, 1025, 1005, 900, 760, 750, 700 and 665 cm$^{-1}$.

EXAMPLE 74

(4S,5R(5Z),6S,1R)-7-[4-Benzyl-6-(1-imidazoylmethyl)-2-oxabicyclo[2.2.1]heptan-5-yl]-5-heptenoic acid 9.2 mg (23 micromol) of the ester produced in example 71 was saponified analogously to example 2 and, after working up and purification, 6.5 mg (16 micromol, 70%) of the title compound was isolated as a colorless oil.

IR (film): 3600–2300, 3120, 3060, 3030, 3000, 2930, 2860, 1710, 1605, 1510, 1455, 1235, 1110, 1085, 1005, 900, 760, 705 and 660 cm$^{-1}$.

EXAMPLE 75

(4S,5R(5Z),6S,1R)-7-[4-(2-Phenylethyl)-6-(1-imidazoylmethyl)-2-oxabicyclo[2.2.1]heptan-5-yl]-5-heptenoic acid 18 mg (43 micromol) of the compound produced in example 72 was saponified analogously to example 2 and, after working up and purification, 13.3 mg (33 micromol, 76%) of the title compound was isolated as a colorless oil.

IR (KBr): 3600–3000, 3100, 3080, 3060, 3020, 2970, 2920, 2870, 2700–2200, 2100–1800, 1700, 1600, 1455, 1320, 1290, 1255, 1235, 1110, 1080, 1030, 1010, 890, 750, 700, 660 and 630 cm$^{-1}$.

EXAMPLE 76

(4S,5R(5Z),6R(1E,3S,4S),1R)-7-[4-Benzyl-6-(3-hydroxy-4-methyl-6-in-1-nonenyl)-2-oxabicyclo[2.2.1-]heptan-5-yl]-5-heptenoic acid methyl ester (A) and
(4S,5R(5Z),6R(1E,3R,4S),1R)-7-[4-benzyl-6-(3-hydroxy-4-methyl-6-in-1-nonenyl)-2-oxabicyclo[2.2.1-]heptan-5-yl]-5-heptenoic acid methyl ester (B)

53 mg (111 micromol) of the unsaturated ketone produced in example 76a was reduced analogously to example 23 and, after working up and purification, 51 mg (107 micromol, 96%) of a mixture of both title compounds was isolated as a colorless oil.

IR (film): 3600–3200, 3080, 3060, 3030, 2970, 2920, 2870, 1735, 1600, 1450, 1435, 1245, 1155, 1015, 995, 970, 895, 765 and 705 cm−1.

The chromatographic separation yielded 33 mg (69 micromol, 62%) of the more nonpolar alcohol, to which structure A was assigned, as well as 15.5 mg (32 micromol, 29%) of the more polar alcohol, to which structure B was assigned.

EXAMPLE 76a (4S,5R(5Z),6R(1E,4S),1R)-7-[4-Benzyl-6-(3-oxo-4-methyl-6-in-1-nonenyl)-2-oxabicyclo[2.2.1]heptan-5-yl]-5-heptenoic acid methyl ester 49 mg (137 micromol) of the aldehyde produced in example 40b was reacted analogously to example 23a with use of dimethyl-(2-oxo-3S-methyl-oct-5-inyl)-phosphonate and, after working up and purification, 53 mg (111 micromol, 81%) of the title compound was isolated as a colorless oil.

IR (film): 3080, 3060, 3030, 2970, 2930, 2870, 1735, 1690, 1665, 1620, 1450, 1435, 1245, 1165, 995, 895, 765 and 705 cm−1.

EXAMPLE 77

(4S,5R(5Z),6R(1E,3R,4S),1R)-7-[4-Benzyl-6-(3-hydroxy-4-methyl-6-in-1-nonenyl)-2-oxabicyclo[2.2.1]heptan-5-yl]-5-heptenoic acid 33 mg (69 micromol) of the nonpolar ester produced in example 76 was saponified analogously to example 2 and, after working up and purification, 32 mg (68 micromol, 99%) of the title compound was isolated as a colorless oil.

IR (film): 3600–2400, 3090, 3060, 3030, 2980, 2930, 2880, 1710, 1605, 1495, 1455, 1245, 995, 970, 890, 765 and 705 cm−1.

EXAMPLE 78

(4S,5R(5Z),6R(1E,3S,4S),1R)-7-[4-Benzyl-6-(3-hydroxy-4-methyl-6-in-1-nonenyl)-2-oxabicyclo[2.2.1]heptan-5-yl]-5-heptenoic acid 15.5 mg (32 micromol) of the polar ester produced in example 76 was saponified analogously to example 2 and, after working up and purification, 14 mg (30 micromol, 94%) of the title compound was isolated as a colorless oil.

IR (film): 3600–2400, 3090, 3070, 3030, 2980, 2940, 2880, 1730, 1710, 1670, 1605, 1495, 1455, 1250, 1100, 1015, 995, 970, 890, 765 and 705 cm−1.

EXAMPLE 79

(4S,5R(5Z),6S,1R)-7-[4-(2-Phenylethyl)-6-((2-phenylaminocarbonyl)-hydrazino)-methyl)-2-oxabicyclo[2.2.1]heptan-5-yl]-5-heptenoic acid methyl ester 17.4 mg (47 micromol) of the aldehyde produced in example 27a was reacted analogously to example 26 with use of 4-phenylsemicarbazide and, after working up and purification, 21.3 mg (42 micromol, 90%) of the title compound was isolated as a colorless oil.

IR (film): 3370, 3200, 3140–3040, 3030, 2940, 2860, 1730, 1690, 1595, 1530, 1445, 1230, 1030, 980, 895, 755, 735 and 695 cm−1.

EXAMPLE 80

(4S,5R(5Z),6S,1R)-7-[4-(2-Phenylethyl)-6-((2-phenylaminocarbonyl)-hydrazino)-methyl)-2-oxabicyclo[2.2.1]heptan-5-yl]-5-heptenoic acid 21.3 mg (47 micromol) of the ester produced in example 79 was saponified analogously to example 2 and, after working up and purification, 18 mg (37 micromol, 78%) of the title compound was isolated as a colorless oil.

IR (film): 3500–2300, 3380, 3200, 3090, 3060, 3030, 3010, 2940, 2870, 1700, 1660, 1595, 1540, 1500, 1450, 1235, 900, 755 and 695 Cm−1.

EXAMPLE 81

(4R,5S(5Z),6R,1S)-7-[4-Phenyl-6-(1-pyrrolidinomethyl)-2-oxabicyclo[2.2.1]heptan-5-yl]-5-heptenoic acid pyrrolidineamide 22 mg (54 micromol) of the bromide produced in example 62a was reacted analogously to example 63 with use of pyrrolidine and, after working up and purification, 19 mg (44 micromol, 81%) of the title compound was isolated as a colorless oil.

IR (film): 3060, 3030, 2950, 2880, 2600, 1630, 1450, 1260, 1005, 895, 765, 705, 665, 620 and 450 cm−1.

EXAMPLE 82

(4S,5R(5Z),6S,1R)-7-[4-(2-Phenylethyl)-6-(N-pyrrolidinomethyl)-2-oxabicyclo[2.2.1]heptan-5-yl]-5-heptenoic acid pyrrolidineamide 18 mg (41 micromol) of the bromide produced in example 65a was reacted analogously to example 63 with use of pyrrolidine and, after working up and purification, 15 mg (32 micromol, 78%) of the title compound was isolated as a colorless oil.

IR (film): 3080, 3060, 3030, 2930, 2870, 2780, 1640, 1605, 1435, 895, 755 and 700 cm−1.

EXAMPLE 83

(4R,5S(5Z),6S,(1E,3S),1S)-7-[4-Phenyl-6-(3-hydroxy-4-(p-fluorophenoxy)-1-butenyl)-2-oxabicyclo[2.2.1]heptan-5-yl]-5-heptenoic acid methyl ester (A) and (4R,5S(5Z),6S(1E,3R),1S)-7-[4-phenyl-6-(3-hydroxy-4-(p-fluorophenoxy)-1-butenyl)-2-oxabicyclo[2.2.1]heptan-5-yl]-5-heptenoic acid methyl ester (B)

21 mg (43 micromol) of the unsaturated ketone produced in example 83a was reduced analogously to example 23 and, after working up and purification, 19 mg (38 micromol, 89%) of a mixture of both title compounds was isolated as a colorless oil.

IR (film): 3600–3200, 3080, 3060, 3030, 3010, 2930, 2870, 1735, 1600, 1505, 1250, 1210, 1040, 1030, 895, 830, 760 and 700 cm−1.

The chromatographic separation yielded 7.5 mg (15 micromol, 36%) of the more nonpolar alcohol, to which structure A was assigned, as well as 9 mg (18 micromol, 43%) of the more polar alcohol, to which structure B was assigned.

EXAMPLE 83a (4R,5S(5Z),6S,(1E),1S)-7-[4-Phenyl-6-(3-oxo-4-(p-fluorophenoxy)
-1-butenyl)-2-oxabicyclo[2.2.1]heptan-5-yl]-5-heptenoic acid methyl ester 43 mg (125 micromol) of the aldehyde produced in example 39b was reacted analogously to example 84a and, after working up and purification, 21 mg (43 micromol, 34%) of the title compound was isolated as a colorless oil.

IR (film): 3080, 3060, 3000, 2940, 2870, 1730, 1690, 1620, 1500, 1440, 1290, 1245, 1200, 1040, 1000, 895, 830, 765, 730 and 700 cm$^{-1}$.

EXAMPLE 84

(4S,5R(5Z),6R,(1E,3R),1R)-7-[4-(2-Phenylethyl)-6-(3-hydroxy
-4-(p-fluorophenoxy)-1-butenyl)-2-oxabicyclo[2.2.1-
]heptan-5-yl]-5-heptenoic acid methyl ester (A) and
(4S,5R(5Z),6R(1E,3S),1R)-7-[4-(2-phenylethyl)
-6-(3-hdyroxy-4-(p-fluorophenoxy)-1-butenyl)-2-
oxabicyclo[2.2.1]heptan-5-yl]-5-heptenoic acid methyl ester (B)

40 mg (77 micromol) of the unsaturated ketone produced in example 84a was reduced analogously to example 23 and, after working up and purification, 34 mg (65 micromol, 85%) of a mixture of both title compounds was isolated as a colorless oil.

IR (film): 3600–3200, 3080, 3060, 3020, 3000, 2930, 2860, 1735, 1600, 1505, 1450, 1435, 1250, 1210, 1030, 975, 895, 830, 760 and 700 cm$^{-1}$.

The chromatographic separation yielded 13 mg (25 micromol, 32%) of the more nonpolar alcohol, to which structure A was assigned, as well as 18 mg (34 micromol, 45%) of the more polar alcohol, to which structure B was assigned.

EXAMPLE 84a (4S,5R(5Z),6R(1E),1R)-7-[4-Phenylethyl)-6-(3-oxo-4-(p-fluorophenoxy)
-1-butenyl)-2-oxabicyclo[2.2.1]heptan-5-yl]-5-heptenoic acid methyl ester:

The solution of 47 mg of dimethyl-(2-oxo-3-(p-fluorophenoxy)propyl)-phosphonate in 500 microliters of anhydrous acetonitrile, was instilled in the solution of 7.6 mg of anhydrous lithium chloride in 500 microliters of anhydrous acetonitrile under an atmosphere of dry argon, mixed with 20 microliters of DBU and the solution of 55 mg (148 micromol) of the aldehyde, produced in example 27a, in 250 microliters of acetonitrile and stirred for 4 to 5 hours at 23° C. It was diluted with 10 ml of diethyl ether, washed neutral with 10% ammonium chloride solution, water and saturated sodium chloride solution, dried on magnesium sulfate and the residue obtained after filtration and concentration by evaporation in a water jet vacuum was chromatographed on two analytic silica gel slabs. A mixture of chloroform/diethyl ether was used as a mobile solvent; ethyl acetate was used as an eluant. 40 mg (77 micromol, 52%) of the title compound was isolated as a colorless oil.

IR (film): 3080, 3060, 3030, 3000, 2940, 2870, 1735, 1690, 1620, 1505, 1450, 1435, 1245, 1210, 1155, 1035, 980, 895, 830, 760, 730 and 700 cm$^{-1}$.

EXAMPLE 85

(4S,5R(5Z),6R(1E,3R),1R)-7-[4-(p-Fluorophenyl)-6-(3-hydroxy-4-(p-fluorophenoxy)-1-butenyl)-2-oxabicyclo[2.2.1]heptan-5-yl]-5-heptenoic acid methyl ester (A)
and
(4S,5R(5Z),6R(1E,3S),1R)-7-[4-(p-fluorophenyl)-6-(3-hydroxy-4-(p-fluorophenoxy)-1-butenyl)-2-oxabicyclo[2.2.1]heptan-5-yl]-5-heptenoic acid methyl ester (B)

39 mg (76 micromol) of the unsaturated ketone produced in example 85a was a reduced analogously to example 23 and, after working up and purification, 37 mg (72 micromol, 95%) of a mixture of both title compounds was isolated as a colorless oil.

IR (film): 3600–3200, 3050, 3000, 2970, 2940, 2870, 1730, 1600, 1505, 1245, 1220, 1160, 1035, 895, 830, 760 and 735 cm$^{-1}$.

The chromatographic separation yielded 15 mg (29 micromol, 38%) of the more nonpolar alcohol, to which structure A was assigned, as well as 19 mg (37 micromol, 49%) of the more polar alcohol, to which structure B was assigned.

EXAMPLE 85a (4S,5R(5Z),6R(1E),1R)-7-[4-(p-Fluorophenyl)-6-(3-oxo-4-(p
-fluorophenoxy)-1-butenyl)-2-oxabicyclo[2.2.1]heptan-5-yl]-5-heptenoic acid methyl ester 54 mg (150 micromol) of the aldehyde produced in example 31b was reacted analogously to example 84a with use of dimethyl-(2-oxo-3-(p-fluorophenoxy)-propyl)-phosphonate and, after working up and purification, 39 mg (76 micromol, 51%) of the title compound was isolated as a colorless oil.

IR, (film): 3010, 2940, 2870, 1730, 1715, 1690, 1620, 1505, 1435, 1220, 1200, 1160, 900 and 830 cm$^{-1}$.

EXAMPLE 86

(4R,5S(5Z),6S(1E,3R),1S)-7-[4-Phenyl-6-(3-hydroxy-4-(p
-fluorophenoxy)-1-butenyl)-2-oxabicyclo[2.2.1]heptan-5-yl]-5-heptenoic acid 9 mg (18 micromol) of the polar ester produced in example 83 was saponified analogously to example 2 and, after, working up and purification, 7 mg (15 micromol, 81%) of the title compound was isolated as a colorless oil.

IR (film): 3600–2400, 3080, 3060, 3030, 3010, 2930, 2870, 1710, 1600, 1505, 1250, 1210, 1035, 890, 830, 760 and 700 cm$^{-1}$.

EXAMPLE 87

(4S,5R(5Z),6R(1E,3R),1R)-7-[4-(2-Phenylethyl)-6-(3-hydroxy
-4-(p-fluorophenoxy)-1-butenyl)-2-oxabicyclo[2.2.1-
]heptan-5-yl]-5-heptenoic acid 13 mg (25 micromol) of the nonpolar compound produced in example 84 was saponified analogously to example 2 and, after working up and purification, 12 mg (24 micromol, 95%) of the title compound was isolated as a colorless oil.

IR (film): 3600–2200, 3030, 3010, 2930, 2870, 1725, 1710, 1605, 1505, 1250, 1210, 1030, 975, 890, 830, 760 and 700 cm$^{-1}$.

EXAMPLE 88

(4S,5R(5Z),6R(1E,3S),1R)-7-[4-(p-Fluorophenyl)-6-(3-hydroxy-4-(p-fluorophenoxy)-1-butenyl)-2-oxabicyclo[2.2.1]heptan-5-yl]-5-heptenoic acid methyl ester 14 mg (27 micromol) of the nonpolar ester produced in example 85 was saponified analogously to example 2 and, after working up and purification, 12 mg (24 micromol, 88%) of the title compound was isolated as a colorless oil.

IR (film): 3600–2500, 3070, 3050, 3000, 2930, 2880, 1710, 1610, 1600, 1505, 1295, 1220, 1160, 1035, 895, 830, 760, 585 and 510 cm$^{-1}$.

EXAMPLE 89

(4R,5S(5Z),6S(1E,3S),1S)-7-[4-Phenyl-6-(3-hydroxy-4-(p-fluorophenoxy)-1-butenyl)-2-oxabicyclo[2.2.1]heptan-5-yl]-5-heptenoic acid 7.5 mg (15 micromol) of the nonpolar ester produced in example 83 was saponified analogously to example 2 and, after working up and purification, 7 mg (15 micromol, 96%) of the title compound was isolated as a colorless oil.

IR (film): 3600–2400, 3080, 3060, 3030, 3010, 2930, 2880, 1710, 1600, 1505, 1250, 1210, 1040, 1030, 890, 830, 760 and 700 cm$^{-1}$.

EXAMPLE 90

(4S,5R(5Z),6R(1E,3S),1R)-7-[4-(2-Phenylethyl)-6-(3-hydroxy-4-(p-fluorophenoxy)-1-butenyl)-2-oxabicyclo[2.2.1]heptan-5-yl]-5-heptenoic acid 18 mg (34 micromol) of the polar compound produced in example 84 was saponified analogously to example 2 and, after working up and purification, 16 mg (31 micromol, 91%) of the title compound was isolated as a colorless oil.

IR (film): 3600-14 2400, 3080, 3060, 3030, 3000, 2930, 2870, 1725, 1710, 1505, 1455, 1250, 1210, 1030, 975, 890, 830, 760 and 700 cm$^{-1}$.

EXAMPLE 91

(4S,5R(5Z),6R(1E,3R),1R)-7-[4-(p-Fluorophenyl)-6-(3-hydroxy-4-(p-fluorophenoxy)-1-butenyl)-2-oxabicyclo[2.2.1]heptan-5-yl]-5-heptenoic acid 19 mg (37 micromol) of the polar ester produced in example 85 was saponified analogously to example 2 and, after working up and purification, 18 mg (36 micromol, 97%) of the title compound was isolated as a colorless oil.

IR (film): 3600–2500, 3080, 3030, 3010, 2980, 2940, 2880, 1710, 1610, 1605, 1510, 1460, 1300, 1225, 1165, 1040, 970, 895, 830, 760, 590 and 515 cm$^{-1}$.

EXAMPLE 92

(4R,5S(5Z),6R,1S)-7-[4-Phenyl-6-(1-piperidinomethyl)-2-oxabicyclo [2.2.1]heptan-5-yl]-5-heptenoic acid methyl ester 21 mg (52 micromol) of the bromide produced in example 62a was reacted analogously to example 63 with use of piperidine and, after working up and purification, 20 mg (49 micromol, 94%) of the title compound was isolated as a colorless oil.

IR (film): 3080, 3060, 3030, 3000, 2930, 2860, 1735, 1605, 1500, 1450, 1400, 1040, 895, 760 and 700 cm$^{-1}$.

EXAMPLE 93

(4R,5S(5Z),6R,1S)-7-[4-Phenyl-6-(1-piperidinomethyl)-2-oxabicyclo[2.2.2]heptan-5-yl]-5-heptenoic acid 20 mg (52 micromol) of the ester produced in example 92 was saponified analogously to example 2 and, after working up and purification, 15 mg (38 micromol, 78%) of the title compound was isolated as a colorless oil.

IR (film): 3600–2300, 3440, 3080, 3060, 3000, 2930, 2870, 1715, 1630, 1605, 1500, 1450, 1400, 1035, 895, 760 and 700 cm$^{-1}$.

EXAMPLE 94

(4S,5R(5Z),6S,1R)-7-[4-2-Phenylethyl)-6-(m-nitrobenzyl-oxymethyl)-2-oxabicyclo[2.2.2]heptan-5-yl]-5-heptenoic acid methyl (or m-nitrobenzyl) ester 18.7 mg (50 micromol) of the alcohol produced in example 15a was etherified analogously to example 1 with m-nitrobenzyl chloride and, after working up and purification, 20 mg of the title compounds was isolated as a colorless oil.

IR (film): 3080, 3060, 3020, 3000, 2930, 2860, 1735, 1600, 1530, 1350, 1100, 895, 810, 730 and 700 cm$^{-1}$.

EXAMPLE 95

(4S,5R(5Z),6S,1R)-7-[4-(2-Phenylethyl)-6-n-nitrobenzyloxymethyl)-2-oxabicyclo[2.2.1]heptan-5-yl]-5-heptenoic acid 20 mg of the ester mixture produced in example 94 was saponified analogously to example 2 and, after working up and purification, 13 mg (26 micromol, 53% relative to the educt of example 94) of the title compound was isolated as a colorless oil.

IR (film): 3600–2400, 3080, 3060, 3020, 3000, 2930, 2860, 1730, 1705, 1600, 1530, 1350, 1120, 1095, 890, 805, 730 and 700 cm$^{-1}$.

EXAMPLE 96

(4S,5R(5Z),6S,1R)-7-[4-(2-Phenylethyl)-6-(n-nitrobenzyloxymethyl)-2-oxabicyclo[2.2.1]heptan-5-yl]-5-heptenoic acid methyl (or o-fluorobenzyl) ester 19 mg (51 micromol) of the alcohol produced in example 15a was etherified analogously to example 1 with o-fluorobenzyl chloride and, after working up and purification, 27 mg of the title compounds was isolated as a colorless oil.

IR (film): 3080, 3060, 3030, 3000, 2930, 2870, 1735, 1620, 1605, 1585, 1490, 1455, 1230, 1120, 1085, 895, 760 and 700 cm$^{-1}$.

EXAMPLE 97

(4S,5R(5Z),6S,1R)-7-[4-Phenylethyl)-6-(o-flurobenzyloxymethyl)-2-oxabicyclo[2.2.2]heptan-5-yl]-5-heptenoic acid 27 mg of the ester mixture produced in example 96 was saponified analogously to example 2 and, after working up and purification, 18 mg (39 micromol, 76% relative to the educt of example 96) of the title compound was isolated as a colorless oil.

IR (film): 3600–2500, 3080, 3060, 3020, 3000, 2930, 2860, 1730, 1710, 1620, 1600, 1585, 1490, 1455, 1230, 1115, 1085, 890, 760 and 700 cm$^{-1}$.

EXAMPLE 98

(4S,5R(5Z),6S,1R)-7-[4-(2-Phenylethyl)-6-(m-fluorobenzyloxymethyl)-2-oxabicyclo[2.2.1]heptan-5-yl]-5-heptenoic acid methyl (or m-fluorobenzyl) ester 18 mg (48 micormol) of the alcohol produced in example 15a was etherified analogously to example 1 with m-fluorobenzyl chloride and, after working up and purification, 24 mg of the title compounds was isolated as a colorless oil.

IR (film): 3080, 3060, 3020, 3000, 2930, 2860, 1735, 1615, 1590, 1485, 1450, 1255, 1140, 895, 785, 750, 700 and 685 cm$^{-1}$.

EXAMPLE 99

(4S,5R(5Z),6S,1R)-7-[4-(2-Phenylethyl)-6-(m-fluorobenzyloxymethyl)-2-oxabicyclo[2.2.1]heptan-5-yl]-5-heptenoic acid 24 mg of the ester mixture produced in example 98 was saponified analogously to example 2 and, after working up and purification, 17 mg (36 micromol, 75% relative to the educt of example 98) of the title compound was isolated as a colorless oil.

IR (film): 3600-2400, 3080, 3060, 3020, 3000, 2930, 2860, 1725, 1710, 1615, 1590, 1485, 1450, 1250, 890, 785, 745, 700 and 685 cm$^{-1}$.

EXAMPLE 100

(4S,5R(5Z),6S,1R)-7-[4-(2-Phenylethyl)-6-(p-fluorobenzyloxymethyl)-2-oxabicyclo[2.2.2]heptan-5-yl]-5-heptenoic acid methyl (or p-fluorobenzyl) ester 19 mg (50 micromol) of the alcohol produced in example 15a was etherified analogously to example 1 with p-fluorobenzyl chloride and, after working up and purification, 21 mg of the title compounds was isolated as a colorless oil.

IR (film): 3080, 3060, 3020, 3000, 2930, 2860, 1735, 1605, 1510, 1220, 1150, 895, 825, 755 and 700 cm$^{-1}$.

EXAMPLE 101

(4S,5R(5Z),6S,1R)-7-[4-(p-Fluorophenyl)-6-(p-fluorobenzyloxymethyl)-2-oxabicyclo[2.2.1]heptan-5-yl]-5-heptenoic acid methyl (or p-fluorobenzyl)ester 18 mg (50 micromol) of the alcohol produced in example 17a was reacted analogously to example 1 and, after working up and purification, 26 mg of the title compounds was isolated as a colorless oil.

IR (film): 3080, 3060, 3030, 3000, 2940, 2860, 1735, 1605, 1510, 1225, 1145, 895, 820, 760 and 705 cm$^{-1}$.

EXAMPLE 102

(4S,5R(5Z),6S,1R)-7-[4-Phenyl-6-(p-fluorobenzyloxymethyl)-2-oxabicyclo[2.2.1]heptan-5-yl]-5-heptenoic acid methyl (or p-fluorobenzyl) ester 11.2 mg (33 micromol) of the alcohol produced in example 3a was reacted analogously to example 1 and, after working up and purification, 10 mg of the title compounds was isolated as a colorless oil.

IR (film): 3080, 3060, 3020, 3000, 2950, 2860, 1735, 1605, 1510, 1220, 1145, 900, 825, 760 and 700 cm$^{-1}$.

EXAMPLE 103

(4S,5R(5Z),6S,1R)-7-[4-(2-Phenylethyl)-6-(p-fluorobenzyloxymethyl)-2-oxabicyclo[2.2.1]heptan-5-yl]-5-heptenoic acid 21 mg of the ester mixture produced in example 100 was saponified analogously to example 2 and, after working up and purification, 16 mg (34 micromol, 68% relative to the educt of example 100) of the title compound was isolated as a colorless oil.

IR (film): 3600-2400, 3080, 3060, 3020, 3000, 2930, 2860, 1730, 1710, 1605, 1510, 1455, 1220, 1090, 890, 825, 755 and 700 cm$^{-1}$.

EXAMPLE 104

(4S,5R(5Z),6S,1R)-7-[4-(p-Fluorophenyl)-6-(p-fluorobenzyloxymethyl)-2-oxabicyclo[2.2.1]heptan-5-yl]-5-heptenoic acid 26 mg of the ester mixture produced in example 101 was saponified analogously to example 2 and, after working up and purification, 21 mg (46 micromol, 92% relative to the educt of example 101) of the title compound was isolated as a colorless oil.

IR (film): 3600-2500, 3070, 3040, 3000, 2930, 2870, 1725, 1710, 1600, 1510, 1220, 1160, 1090, 890 and 830 cm$^{-1}$.

EXAMPLE 105

(4S,5R(5Z),6S,1R)-7-[4-Phenyl-6-(p-flurobenzyloxymethyl)-2-oxabicyclo[2.2.1]heptan-5-yl]-5-heptenoic acid 10 mg of the ester mixture produced in example 102 was saponified analogously to example 2 and, after working up and purification, 9 mg (20 micromol, 59% relative to the educt of example 102) of the title compound was isolated as a colorless oil.

IR (film): 3600-2400, 3060, 3030, 3000, 2930, 2870, 1730, 1705, 1600, 1510, 1220, 1115, 1090, 895, 825, 760 and 700 cm$^{-1}$.

EXAMPLE 106

(4S,5R(5Z),6S,1R)-7-[4-(2-Phenylethyl)-6-(m-trifluoromethylbenzyloxymethyl)-2-oxabicyclo[2.21]heptan-5-yl]-5-heptenoic acid methyl (or m-trifluoromethylbenzyl) ester 17 mg (46 micromol) of the alcohol produced in example 15a was etherified analogously to example 1 with m-trifluoromethylbenzyl chloride and, after working up and purification, 23 mg of the title compounds was isolated as a colorless oil.

IR (film): 3080, 3060, 3030, 3000, 2930, 2860, 1735, 1605, 1495, 1330, 1200, 1165, 1130, 1070, 890, 750, 700 and 665 cm$^{-1}$.

EXAMPLE 107

(4S,5R(5Z),6S,1R)-7-[4-(2-Phenylethyl)-6-(m-trifluoromethylbenzyloxymethyl)-2-oxabicyclo[2.2.1]heptan-5-yl]-5-heptenoic aicd 23 mg of the ester mixture produced in example 106 was saponified analogously to example 2 and, after working up and purification, 17 mg (33 micromol, 72% relative to the educt of example 106) of the title compound was isolated as a colorless oil.

IR (film): 3600-2500, 3080, 3060, 3030, 3000, 2930, 2860, 1730, 1710, 1605, 1455, 1330, 1195, 1165, 1125, 1075, 890, 800, 755, 700 and 660 cm$^{-1}$.

EXAMPLE 108

(4S,5R(5Z),6S,1R)-7-[4-(2-Phenylethyl)-6-(p-trifluoromethylbenzyloxymethyl)-2-oxabicyclo[2.2.1]heptan-5-yl]-5-heptenoic acid methyl (or p-trifluoromethylbenzyl) ester 15 mg (40 micromol) of the alcohol produced in example 15a was etherified analogously to example 1 with p-trifluoromethylbenzyl chloride and, after working up and purification, 28 mg of the title compounds was isolated as a colorless oil.

IR (film): 3080, 3060, 3030, 3000, 2930, 2860, 1735, 1620, 1605, 1330, 1160, 1130, 1065, 1015, 895, 820, 760 and 700 cm$^{-1}$.

EXAMPLE 109

(4S,5R(5Z),6S,1R)-7-[4-(2-Phenylethyl)-6-(p-trifluoromethylbenzyloxymethyl)-2-oxabicyclo[2.2.1]heptan-5-yl]-5-heptenoic acid 28 mg of the ester mixture produced in example 108 was saponified analogously to example 2 and, after working up and purification, 19 mg (37 micormol, 91% relative to the educt of example 108) of the title compound was isolated as a colorless oil.

IR (film): 3600-2400, 3090, 3060, 3030, 3010, 2940, 2860, 1730, 1710, 1620, 1605, 1330, 1165, 1125, 1065, 1020, 890, 825, 755 and 705 cm$^{-1}$.

EXAMPLE 110

(4S,5R(5Z),6S,1R)-7-[4-[4-2-Phenylethyl)-6-(p-chlorobenzyloxymethyl)-2-oxabicyclo[2.2.1]heptan-5-yl]-5-heptenoic acid methyl (or p-chlorobenzyl) ester 18 mg (48 micromol) of the alcohol produced in example 15a was etherified analogously to example 1 with p-chlorobenzyl chloride and, after working up and purification, 30 mg of the title compounds was isolated as a colorless oil.

IR (film): 3080, 3060, 3030, 3000, 2930, 2860, 1735, 1600, 1495, 1450, 1235, 890, 810, 760 and 700 cm$^{-1}$.

EXAMPLE 111

(4S,5R(5Z),6S,1R)-7-[4(2-Phenylethyl)-6-(p-chlorobenzyloxymethyl)-2-oxabicyclo[2.2.1]heptan-5-yl]-5-heptenoic acid 30 mg of the ester mixture produced in example 110 was saponified analogously to example 2 and, after working up and purification, 18 mg (37 micromol, 77% relative to the educt of example 110) of the title compound was isolated as a colorless oil.

IR (film): 3600-2400, 3080, 3060, 3030, 3000, 2930, 2860, 1730, 1710, 1600, 1490, 1455, 1240, 1090, 1030, 890, 810, 755 and 700 cm$^{-1}$.

EXAMPLE 112

(4S,5R(5Z),6S,1R)-7-[4-(2-Phenylethyl)-6-(phenoxyethyloxymethyl)-2-oxabicyclo[2.2.1]heptan-5-yl]-5-heptenoic acid methyl (or phenoxyethyl) ester 17 mg (46 micromol) of the alcohol produced in example 15a was etherified analogously to example 1 with 1-chloro-2-phenoxyethane and, after working up and purification, 18 mg of the title compounds was isolated as a colorless oil.

IR (film): 3060, 3030, 3000, 2930, 2870, 1735, 1600, 1590, 1500, 1455, 1250, 1125, 890, 760, 700 and 690 cm$^{-1}$.

EXAMPLE 113

(4S,5R(5Z),6S,1R)-7-[4-(2-Phenylethyl)-6-(phenoxyethyloxymethyl)-2-oxabicyclo[2.2.1]heptan-5-yl]-5-heptenoic acid 18 mg of the ester mixture produced in example 112 was saponified analogously to example 2 and, after working up and purification, 11 mg (23 micromol, 50% relative to the educt of example 112) of the title compound was isolated as a colorless oil.

IR (film): 3600-2500, 3080, 3060, 3030, 3000, 2930, 2870, 1730, 1710, 1600, 1585, 1495, 1455, 1245, 1130, 890, 755, 700 and 690 cm$^{-1}$.

EXAMPLE 114

(4S,5R(5Z),6S,1R)-7-[4-(2-Phenylethyl)-6-N-anilinomethyl-2-oxabicyclo[2.2.1]heptan-5-yl]-5-heptenoic acid methyl ester 19 mg (44 micromol) of the bromide produced in example 65a was reacted analogously to example 63 with use of aniline and, after working up and purification, 17 mg (38 micromol, 87%) of the title compound was isolated as a colorless oil.

IR (film): 3440-3300, 3080, 3060, 3020, 2930, 2860, 1730, 1600, 1505, 1320, 1250, 895, 750 and 695 cm$^{-1}$.

EXAMPLE 115

(4S,5R(5Z),6S,1R)-7-[4-(2-Phenylethyl)-6-N-anilinomethyl-2-oxabicyclo[2.2.1]heptan-5-yl]-5-heptenoic acid 17 mg (38 micromol) of the ester produced in example 114 was saponified analogously to example 2 and, after working up and purification, 15 mg (35 micromol, 91%) of the title compound was isolated as a colorless oil.

IR (film): 3400, 3600-2300, 3080, 3060, 3030, 3000, 2930, 2860, 1725, 1710, 1605, 1510, 1495, 1325, 1255, 980, 890, 750, 700 and 695 cm$^{-1}$.

EXAMPLE 116

(4S,5R(5Z),6S,1R)-7-[4-(2-Phenylethyl)-6-(p-fluoro-N-anilinomethyl)-2-oxabicyclo[2.2.1]heptan-5-yl]-5-heptenoic acid methyl ester 19 mg (44 micromol) of the bromide produced in example 65a was reacted analogously to example 63 with use of p-fluoroaniline and, after working up and purification, 13 mg (28 micromol, 64%) of the title compound was isolated as a colorless oil.

IR (film): 3450-3300, 3080, 3060, 3030, 3000, 2930, 2870, 1735, 1610, 1605, 1515, 1220, 895, 820 and 700 cm$^{-1}$.

EXAMPLE 117

(4S,5R(5Z),6S,1R)-7-[4-(2-Phenylethyl)-6-p-fluoro-N-anilinomethyl)-2-oxabicyclo[2.2.1]heptan-5-yl]-5-heptenoic acid 13 mg (28 micromol) of the ester produced in example 116 was saponified analogously to example 2 and, after working up and purification, 11 mg (24 micromol, 87%) of the title compound was isolated as a colorless oil.

IR (film): 3390, 3600-2300, 3080, 3060, 3020, 3000, 2930, 2870, 1710, 1610, 1605, 1510, 1220, 890, 820 and 700 cm$^{-1}$.

EXAMPLE 118

(4S,5R(5Z),6S,1R)-7-[4-(p-Fluorophenyl)-6-phenoxymethyl-2-oxabicyclo[2.2.1]heptan-5-yl]-5-heptenoic acid methyl ester The solution of 36 mg (84.6 micromol) of the bromide, produced in example 118a, in 300 microliters of tetrahydrofuran was added to the clear solution of 90 mg of sodium phenolate in a mixture of 300 microliters of anhydrous methyl benzene and 300 microliters of tetrahydrofuran and heated for 28 hours to 80°–90° C. It was mixed with water, extracted several times with diethyl ether, washed neutral with water and saturated sodium chloride solution, dried on magnesium sulfate and the residue obtained after filtration and removal of the solvent was purified by chromatography on analytic silica gel slabs. A mixture of chloroform/diethyl ether was used as a mobile solvent; a mixture of ethyl acetate/ethanol was used as an eluant. In addition to the initial material and saponified ester, 18 mg (40.3 micromol, 48%) of the title compound was isolated as a pale yellow oil.

IR (film): 3080, 3060, 3030, 3000, 2950, 2930, 2870, 1735, 1600, 1510, 1445, 1230, 1110, 900, 820, 760 and 700 cm$^{-1}$.

EXAMPLE 118a (4S,5R(5Z),6S,1R)-7-[4-(p-Fluorophenyl)-6-bromomethyl-2-oxabicyclo[2.2.1]heptan-5-yl]-5-heptenoic acid methyl ester 28 mg (77 micromol) of the alcohol produced in example 17a was bromated analogously to example 63a and, after working up and purification, 32 mg (75 micromol, 97%) of the title compound was isolated as a colorless oil.

IR (film): 3080, 3060, 3030, 3000, 2950, 2860, 1735, 1600, 1505, 1450, 1435, 1220, 1165, 1010, 895, 825, 760, 700 and 635 cm$^{-1}$.

EXAMPLE 119

(4S,5R(5Z),6S,1R)-7-[4-(p-Fluorophenyl)-6-phenoxymethyl-2-oxabicyclo[2.2.1]heptan-5-yl]-5-heptenoic acid 18 mg (40.3 micromol) of the ester produced in example 118 was saponified analogously to example 2 and, after working up and purification, 14 mg (32.3 micromol, 82%) of the title compound was isolated as a colorless oil.

IR (film): 3600–2400, 3080, 3040, 2950, 2930, 2870, 1710, 1605, 1600, 1515, 1230, 1160, 895, 835, 720 and 580 cm$^{-1}$.

EXAMPLE 120

(1S,4R,5S(5Z),6R)-7-[4-(4-Fluorophenyl)-6-benzyloxymethyl-2-oxabicyclo[2.2.1]hept-5-yl]-5-heptenoic acid methyl (or benzyl) ester 17.5 mg (48.3 micromol) of the alcohol produced in example 120a was reacted analogously to example 1 and, after working up and purification, 22.6 mg of the title compounds was isolated as a colorless oil.

IR (film): 3060, 3020, 3000, 2930, 2870, 1735, 1600, 1510, 1455, 1110, 1075, 895, 820, 740 and 705 cm$^{-1}$.

EXAMPLE 120a (1S,4R,5S(5Z),6R)-7-[4-(4-Fluorophenyl)-6-hydroxymethyl-2-oxabicyclo[2.2.1]hept-5-yl]-5-heptenoic acid methyl ester 40.7 g (148 mmol) of enantiomeric Corey lactone was reacted analogously to examples 17a to 17g and 1h to 11 and 1.88 g (5.19 mmol, 3.5%) of the title compound was isolated as a colorless oil.

IR (film): 3600–3200, 3040, 3000, 2960, 2920, 2870, 1730, 1600, 1510, 1225, 1160, 1025, 890 and 830 cm$^{-1}$.

EXAMPLE 121

(1S,4R,5S(5Z),6R)-7-[4-(4-Fluorophenyl)-6-benzyloxymethyl-2-oxabicyclo[2.2.1]hept-5-yl]-5-heptenoic acid 22.6 mg of the ester mixture produced according to example 120 was saponified analogously to example 2 and, after working up and purification, 17.4 mg (39.7 micromol, 82%, relative to the initial material in example 120) of the title compound was isolated as a colorless oil.

IR (film): 3600–2400, 3090, 3060, 3020, 3000, 2940, 2870, 1725, 1710, 1605, 1510, 1450, 1230, 1160, 1090, 1030, 890, 830, 735, 690 and 640 cm$^{-1}$.

EXAMPLE 122

(1S,4R,5S(5Z),6R)-7-[4-(4-Fluorophenyl)-6-hexyloxymethyl-2-oxabicyclo[2.2.1]hept-5-yl]-5-heptenoic acid methyl ester 18.1 mg (50 micromol) of the alcohol produced in example 120a was etherified with use of 1-bromohexane analogously to example 1 and, after working up and purification, 25.5 mg (49 micromol, 98%) of the title compound was isolated as a colorless oil.

IR (film): 3040, 3000, 2960, 2930, 2860, 1730, 1605, 1515, 1230, 1160, 1120, 1090, 1030, 895 and 830 cm$^{-1}$.

EXAMPLE 123

(1S,4R,5S(5Z),6R)-7-[4-(4-Fluorophenyl)-6-hexyloxymethyl-2-oxabicyclo[2.2.1]hept-5-hept-5-yl]-5-heptenoic acid 25.5 mg of the ester produced according to example 122 was saponified analogously to example 2 and, after working up and purification, 20.0 mg (46.2 micromol, 94%) of the title compound was isolated as a colorless oil.

IR (film): 3600–2400, 3050, 3000, 2950, 2930, 2860, 1730, 1710, 1605, 1515, 1235, 1160, 1120, 1090, 1030, 895 and 830 cm$^{-1}$.

EXAMPLE 124

(1S,4R,5S(5Z),6R)-7-[4-Fluorophenyl)-6-[2-(4-bromophenoxy)-ethoxymethyl]-2-oxabicyclo[2.2.1]hept-5-yl]-5-heptenoic acid methyl ester 16.3 mg (45 micromol) of the alcohol produced in example 120a was etherified with use of 1-chloro-2-(4-bromophenyloxyl)-ethane analogoously to example 1 and, after working up and purification, 18.5 mg (34 micromol, 76%) of the title compound was isolated as a colorless oil.

IR (film): 3040, 3000, 2940, 2870, 1730, 1590, 1580, 1515, 1490, 1450, 1290, 1245, 895, 825 and 645 cm$^{-1}$.

EXAMPLE 125

(1S,4R,5S(5Z),6R)-7-[4-(4-Fluorophenyl)-6-[2-(4-bromophenoxy)-ethoxymethyl]-2-oxabicyclo[2.2.1-]hept-5-yl]-5-heptenoic acid 18.5 mg (34 micromol) of the ester produced according to example 124 was saponified analogously to example 2 and, after working up and purification, 15.4 mg (29 micromol, 85%) of the title compound was isolated as a colorless oil.

IR (film): 3600–2500, 3070, 3040, 3000, 2930, 2870, 1725, 1710, 1590, 1580, 1515, 1490, 1455, 1285, 1245, 895, 825 and 645 cm$^{-1}$.

EXAMPLE 126

(1S,4R,5S(5Z),6R)-7-[4-(4-Fluorophenyl)-6-(3-nitrobenzyloxymethyl]-2-oxabicyclo[2.2.1]hept-5-yl]-5-heptenoic acid methyl (or 3-nitrobenzyl) ester 19.4 mg (53 micromol) of the alcohol produced in example 120a was reacted analogously to example 1 and, after working up and purification, 19.9 mg of the title compounds was isolated as a colorless oil.

IR (film): 3070, 3050, 3000, 2930, 2870, 1735, 1610, 1595, 1530, 1510, 1230, 1160, 1120, 1095, 1030, 895, 830, 815 and 735 cm$^{-1}$.

EXAMPLE 127

(1S,4R,5S(5Z),6R)-7-[4-(4-Fluorophenyl)-6-(3-nitrobenzyloxymethyl]-2-oxabicyclo[2.2.1]hept-5-yl]-5-heptenoic acid 19.9 mg of the ester mixture produced according to example 126 was saponified analogously to example 2 and, after working up and purification, 15 mg (31 micromol, 58%, relative to the initial material in example 126) of the title compound was isolated as a colorless oil.

IR (film): 3600–2400, 3090, 3070, 3050, 3000, 2930, 2870, 1730, 1705, 1610, 1595, 1530, 1510, 1350, 1230, 1160, 1120, 1095, 1030, 895, 830, 815 and 730 cm$^{-1}$.

EXAMPLE 128

(1S,4R,5S(5Z),6R)-7-[4-(4-Fluorophenyl)-6-(4-chlorobenzyloxymethyl]-2-oxabicyclo[2.2.1]hept-5-yl]-5-heptenoic acid methyl (or 4-chlorobenzyl) ester 18.1 mg (50 micromol) of the alcohol produced in example 120a was reacted analogously to example 1 and, after working up and purification, 22 mg of the title compounds was isolated as a colorless oil.

IR (film): 3060, 3030, 3000, 2930, 2870, 1735, 1605, 1600, 1515, 1495, 1450, 1235, 1160, 1120, 1090, 1015, 895, 830, 820, 810 and 800 cm$^{-1}$.

EXAMPLE 129

(1S,4R,5S(5Z),6R)-7-[4-(4-Fluorophenyl)-6-(4-chlorobenzyloxymethyl]-2-oxabicyclo[2.2.1]hept-5-yl]-5-heptenoic acid 22 mg of the ester mixture produced according to example was saponified analogously to example 2 and, after working up and purification, 13.3 mg (28 micromol, 56%, relative to the initial material in example 128) of the title compound was isolated as a colorless oil.

IR (film): 3600–2400, 3050, 3000, 2930, 2870, 1725, 1710, 1605, 1600, 1515, 1490, 1410, 1230, 1160, 1120, 1090, 1015, 895, 830, 820, 810 and 800 cm$^{-1}$.

EXAMPLE 130

(1S,4R,5S(5Z),6R)-7-[4-(4-Fluorophenyl)-6-(4-fluorobenzyloxymethyl]-2-oxabicyclo[2.2.1]hept-5-yl]-5-heptenoic acid methyl (or 4-fluorobenzyl) ester 17.8 mg (49 micromol) of the alcohol produced in example 120a was reacted analogously to example 1 and, after working up and purification, 21 mg of the title compounds was isolated as a colorless oil.

IR (film): 3080, 3060, 3030, 3000, 2950, 2860, 1735, 1605, 1510, 1225, 1150, 895, 820, 760 and 705 cm$^{-1}$.

EXAMPLE 131

(1S,4R,5S(5Z),6R)-7-[4-Fluorophenyl)-6-(4-fluorobenzyloxymethyl]-2-oxabicyclo[2.2.1]hept-5-heptenoic acid 21 mg of the ester mixture produced according to example 130 was saponified analogously to example 2 and, after working up and purification, 18.1 mg (40 micromol, 81%, relative to the initial material in example 130) of the title compound was isolated as a colorless oil.

IR (film): 3600–2500, 3070, 3040, 3000, 2930, 2870, 1725, 1710, 1605, 1510, 1220, 1160, 1090, 1030, 1015, 895 and 830 cm$^{-1}$.

EXAMPLE 132

(1S,4R,5S(5Z),6R)-7-[4-(4-Fluorophenyl)-6-(4-trifluoromethylbenzyloxymethyl]-2-oxabicyclo[2.2.1]hept-5-yl]-5-heptenoic acid methyl (or 4-trifluoromethylbenzyl) ester 17.7 mg (49 micromol) of the alcohol produced in example was reacted analogously to example 1 and, after working up and purification, 26.5 mg of the title compounds was isolated as a colorless oil.

IR (film): 3040, 3000, 2940, 2870, 1735, 1620, 1610, 1515, 1325, 1240, 1165, 1125, 1065, 1020, 900, 830 and 825 cm$^{-1}$.

EXAMPLE 133

(1S,4R,5S(5Z),6R)-7-[4-(4-Fluorophenyl)-6-(4-trifluoromethylbenzyloxymethyl)-2-oxabicyclo[2.2.1]hept-5-yl]-5-heptenoic acid 26.5 mg of the ester mixture produced according to example 132 was saponified analogously to example 2 and, after working up and purification, 22.5 mg (44 micromol, 91%, relative to the initial material in example 132) of the title compound was isolated as a colorless oil.

IR (film): 3600–2500, 3040, 3000, 2940, 2870, 1725, 1710, 1620, 1610, 1515, 1325, 1235, 1165, 1125, 1065, 1020, 895, 830 and 825 cm$^{-1}$.

EXAMPLE 134

(1S,4R,5S(5Z),6R)-7-[4-(4-Fluorophenyl)-6-(4-phenylbenzyloxymethyl)-2-oxabicyclo[2.2.1]hept-5-yl]-5-heptenoic acid methyl ester 17 mg (47 micromol) of the alcohol produced in example 120a was reacted analogously to example 1 and, after working up and purification, 21 mg (40 micromol, 85%) of the title compound was isolated as a colorless oil.

IR (film): 3060, 3030, 3000, 2940, 2870, 1735, 1605, 1515, 1490, 1410, 1225, 1160, 1120, 1090, 1080, 1025, 1010, 895, 830, 760, 735 and 705 cm$^{-1}$.

EXAMPLE 135

(1S,4R,5S(5Z),6R)-7-[4-(4-Fluorophenyl)-6-(4-phenyl-benzyloxymethyl)-2-oxabicyclo[2.2.1]hept-5-yl]-5-heptenoic acid 21 mg (40 microl) of the ester produced according to example 134 was saponified analogously to example 2 and, after working up and purification, 16.5 mg (32 micromol, 80%) of the title compound was isolated as a colorless oil.

IR (film): 3600–2400, 3060, 3030, 3000, 2940, 2870, 1730, 1710, 1605, 1515, 1490, 1230, 1160, 1120, 1090, 1080, 1030, 1010, 895, 830, 760, 735 and 700 cm$^{-1}$.

EXAMPLE 136

(1S,4R,5S(5Z),6R)-7-[4-(4-Fluorophenyl)-6-(4-fluoroanilinomethyl)-2-oxabicyclo[2.2.1]hept-5-yl]-5-heptenoic acid methyl ester 28 mg (66 micromol) of the bromide produced in example 136a was reacted analogously to example 63 with use of 4-fluoroaniline and, after working up and purification, 20.5 mg (45 micromol, 68%) of the title compound was isolated as a colorless oil.

IR (film): 3450–3300, 3040, 3000, 2930, 2870, 1735, 1610, 1510, 1320, 1300, 1220, 1160, 895, 820 and 760 cm$^{-1}$.

EXAMPLE 136a (1S,4R,5S(5Z),6R)-7-[4-(4-Fluorophenyl)-6-bromomethyl-2-oxabicyclo[2.2.1]hept-5-yl]-5-heptenoic acid methyl ester 25.9 mg (71 micromol) of the alcohol produced in example 120a was bromated analogously to example 63a and, after working up and purification, 28 mg (66 micromol, 93%) of the title compound was isolated as a colorless oil.

IR (film): 3040, 2970, 2940, 2870, 1730, 1605, 1510, 1450, 1430, 1295, 1230, 1160, 1035, 900, 830 and 735 cm$^{-1}$.

EXAMPLE 137

(1S,4R,5S(5Z),6R)-7-[4-(4-Fluorophenyl)-6-(4-fluoroanilinomethyl)-2-oxabicyclo[2.2.1]hept-5-yl]-5-heptenoic acid 20.5 mg (45 micromol) of the ester produced according to example 136 was saponified analogously to example 2 and, after working up and purification, 18 mg (41 micromol, 91%) of the title compound was isolated as a colorless oil.

IR (film): 3600–2400, 3390, 3040, 3000, 2930, 2870, 1710, 1610, 1510, 1320, 1300, 1220, 1160, 895, 820 and 760 cm$^{-1}$.

EXAMPLE 138

(1S,4R,5S(5Z),6S)-7-[4-(4-Fluorophenyl)-6-[3(S)-hydroxy-4-phenoxy-1(E)-butenyl]-2-oxabicyclo[2.2.1-]hept-5-yl-5-heptenoic acid methyl ester (A) and (1S,4R,5S(5Z),6S)-7-[4-(4-fluorophenyl)-6-[3(R)-hydroxy-4-phenoxy-1-(E)-butenyl]-2-oxabicyclo[2.2.1-]hept-5-yl]-5-heptenoic acid methyl ester (B)

43 mg (87 micromol) of the unsaturated ketone produced in example 138a was reduced analogously to example 23 and, after working up and purification, 43 mg (87 micromol, 99%) of a mixture of both title compounds was isolated as a colorless oil.

IR (film): 3700–3100, 3050, 3000, 2970, 2940, 2930, 2870, 1730, 1595, 1585, 1510, 1490, 1450, 1430, 1290, 1230, 1160, 1080, 1035, 995, 970, 895, 830, 755, 735 and 690 cm$^{-1}$.

The chromatographic separation yielded 19.8 mg (40 micromol, 46%) of the more nonpolar alcohol, to which structure A was assigned, as well as 19.6 mg (40 micromol, 46%) of the more polar alcohol, to which structure B was assigned.

EXAMPLE 138a (1S,4R,5S(5Z),6S)-7-[4-(4-Fluorophenyl)-6-(3-oxo-4-phenoxy-1(E)-butenyl)-2-oxabicyclo[2.2.1]hept-5-yl]-5-heptenoic acid methyl ester.

47.4 mg (131 micromol) of the aldehyde produced in example 138b was reacted analogously to example 30a with use of dimethyl(2-oxo-3-phenoxy-propyl)-phosphonate lithium salt and, after working up and purification, 43.5 mg (88 micromol, 67%) of the title compound was isolated as a colorless oil.

IR (film): 3060, 3040, 3000, 2970, 2940, 2870, 1730, 1690, 1620, 1600, 1510, 1490, 1450, 1435, 1290, 1230, 1160, 1040, 995, 900, 835 755 and 690 cm$^{-1}$.

EXAMPLE 138b (1S,4R,5S(5Z),6S)-7-[4-(4-Fluorophenyl)-6-formyl-2-oxabicyclo[2.2.1]hept-5-yl]-5-heptenoic acid methyl ester 647 mg (1.79 mmol) of the alcohol produced in example 120a was oxidized analogously to example 38b and, after working up, 637 mg (1.77 mmol, 99%) of the title compound was isolated as a colorless oil, which was further reacted without purification.

EXAMPLE 139

(1S,4R,5S(5Z),6S)-7-[4-(4-Fluorophenyl)-6-[3(S)-hydroxy-4-phenoxy-1-(E)-butenyl]-2-oxabicyclo]2.2.1-]hept-5-yl]-5-heptenoic acid 19.8 mg (40 micromol) of the nonpolar ester produced in example 138 was saponfied analogously to example 2 and, after working up and purification, 15.9 mg (33 micromol, 83%) of the title compound was isolated as a colorless oil.

IR (film): 3700–2400, 3060, 3010, 2930, 2880, 1725, 1710, 1600, 1585, 1455, 1300, 1245, 1235, 1160, 1080, 1040, 995, 970, 895, 835, 755, 690 and 590 cm$^{-1}$.

EXAMPLe 140

(1S,4R,5S(5Z),6S)-7-[4-(4-Fluorophenyl)-6-[3-(R)-hydrozy-4-phenoxy-1-(E)-butenyl]-2-oxabicyclo[2.2.1-]hept-5-yl]-5-heptenoic acid 19.6 mg (39.6 micromol) of the polar ester produced in example 138 was saponified analogously to example 2 and, after working up and purification, 13.8 mg (28.7 micromol, 73%) of the title compound was isolated as a colorless oil.

IR (film): 3600–2400, 3050, 3040, 3000, 2930, 2880, 1725, 1710, 1600, 1585, 1455, 1300, 1250, 1235, 1160, 1080, 1040, 995, 970, 895, 840, 820, 755, 690 and 590 cm$^{-1}$.

EXAMPLE 141

(1S,4R,5S(5Z),6S)-7-[4-(4-Fluorophenyl)-6-[3(S)-hydroxy-1(E)-octenyl]-2-oxabicyclo[2.2.1]hept-5-yl]-5-heptenoic acid methyl ester (A) and
(1S,4R,5S(5Z),6S)-7-[4-(4-fluorophenyl)-6-[3(R)-hydroxy-1-(E)octenyl]-2-oxabicyclo[2.2.1]hept-5-yl]-5-heptenoic acid methyl ester (B)

43 mg (94 micromol) of the unsaturated ketone produced in example 141a was reduced analogously to example 23 and, after working up and purification, 42 mg (92 micromol, 97%) of a mixture of both title compounds was isolated as a colorless oil.

IR (film): 3600–3200, 3040, 3000, 2950, 2920, 2860, 1605, 1510, 1450, 1435, 1230, 1160, 995, 970, 895 and 830 cm$^{-1}$.

The chromatographic separation yielded 21 mg (46 micromol, 49%) of the more nonpolar alcohol, to which structure A was assigned, as well as 19 mg (41 micromol, 44%) of the more polar alcohol, to which structure B was assigned.

EXAMPLE 141a (1S,4R,5S(5Z),6S)-7-[4-(4-Fluorophenyl)-6-(3-oxo-1-(E)octenyl]-2 -oxabicyclo[2.2.1]hept-5-yl]-5-heptenoic acid methyl ester 47 mg (130 micromol) of the aldehyde produced in example 138b was reacted analogously to example 2a with use of dimethyl(2 -oxo-heptyl)-phosphonate and, after working up and purification, 43 mg (94 micromol, 72%) of the title compound was isolated as a colorless oil.

IR (film): 3040, 3000, 2950, 2920, 2860, 1730, 1690, 1665, 1620, 1510, 1450, 1430, 1230, 1160, 995, 900 and 835 cm$^{-1}$.

EXAMPLE 142

(1S,4R,5S(5Z),6S)-7-[4-(4-Fluorophenyl)-6-[3(S)-hydroxy-1(E)-octenyl]-2-oxabicyclo[2.2.1]hept-5-yl]-5-heptenoic acid 21 mg (46 micromol) of the nonpolar ester produced in example 141 was saponified analogously to example 2 and, after working up and purification, 19 mg (43 micromol, 93%) of the title compound was isolated as a colorless oil.

IR (film): 3600–2400, 3040, 3000, 2950, 2930, 2870, 2860, 1710, 1610, 1515, 1455, 1300, 1235, 1160, 995, 970, 895 and 835 cm$^{-1}$.

EXAMPLE 143

(1S,4R,5S(5Z),6S)-7-[4-(4-Fluorophenyl)-6-[3(R)-hydroxy-1(E)-octenyl]-2-oxabicyclo[2.2.1]hept-5-yl]-5-heptenoic acid 19 mg (41 micromol) of the polar ester produced in example 141 was saponified analogously to example 2 and, after working up and purification, 15.6 mg (35 micromol, 86%) of the title compound was isolated as a colorless oil.

IR (film): 3600–2400, 3040, 3000, 2940, 2870, 1725, 1710, 1610, 1515, 1455, 1300, 1230, 1160, 995, 970, 895 and 835 cm$^{-1}$.

EXAMPLE 144

(1S,4R,5S(5Z),6S)-7-[4-(4-Fluorophenyl)-6-[(1E,3R,4RS)-3-hydroxy-4,7-dimethyl-octa-1,6-dienyl]-2-oxabicyclo[2.2.1]hept-5-yl]-5-heptenoic acid methyl ester (A) and
(1S,4R,5S(5Z),6S)-7-[4-(4-fluorophenyl)-6-[1E,3S,4RS)-3-hydroxy-4,7-dimethyl-octa-1,6-dienyl]-2-oxabicyclo[2.2.1]hept-5-yl]-5-heptenoic acid methyl ester (B)

53 mg (110 micromol) of the unsaturated ketone produced in example 144a was reduced analogously to example 23 and, after working up and purification, 48 mg (99 micromol, 90%) of a mixture of both title compounds was isolated as a colorless oil.

IR (film): 3600–3200, 3040, 2960, 2920, 2870, 1735, 1605, 1510, 1450, 1435, 1230, 1160, 995, 970, 895, 835 and 735 cm$^{-1}$.

The chromatographic separation yielded 27 mg (56 micromol, 51%) of the more nonpolar alcohol, to which structure A was assigned, as well as 18 mg (37 micromol, 34%) of the more polar alcohol, to which structure B was assigned.

EXAMPLE 144b (1S,4R,5S(5Z),6S)-7-[4-(4-Fluorophenyl)-6-[(1E,4RS)-3-xo-4,7-dimethyl-octa-1,6-dienyl]-2-oxabicyclo[2.2.1-]hept-5-yl]-5-heptenoic acid methyl ester 48.6 mg (135 micromol) of the aldehyde produced in example 138b was reacted analogously to example 23a with use of dimethyl(2-oxo-3,6-dimethyl-5-heptenyl)-phosphonate and, after working up and purification, 53 mg (110 micromol, 81%) of the title compound was isolated as a colorless oil.

IR (film): 3040, 3000, 2960, 2930, 2870, 1735, 1690, 1665, 1620, 1510, 1450, 1435, 1370, 1230, 1160, 1040, 995, 975, 900 and 830 cm$^{-1}$.

EXAMPLE 145

(1S,4R,5S(5Z),6S)-7-[4-(4-Fluorophenyl)-6-[(1E,3S,4RS)-3-hydroxy-4,7-dimethyl-octa-1,6-dienyl]-2-oxabicyclo[2.2.1]hept-5-yl]-5-heptenoic acid 27 mg (56 micromol) of the nonpolar ester produced in example 144 was saponified analogously to example 2 and, after working up and purification, 23 mg (49 micromol, 87%) of the title compound was isolated as a colorless oil.

IR (film): 3600–2400, 3040, 2970, 2930, 2880, 1710, 1610, 1515, 1455, 1300, 1235, 1160, 995, 970, 895 and 835 cm$^{-1}$.

EXAMPLE 146

(1S,4R,5S(5Z),6S)-7-[4-(4-Fluorophenyl)-6-[(1E,3R,4RS)-3-hydroxy-4,7-dimethyl-octa-1.6-dienyl]-2-oxabicyclo[2.2.1]hept-5-yl]-5-heptenoic acid 18 mg (37 micromol) of the polar ester produced in example 144 was saponified analogously to example 2 and, after working up and purification, 16 mg (34 micromol, 92%) of the title compound was isolated as a colorless oil.

IR (film): 3600–2400, 3040, 2970, 2930, 2880, 1725, 1710, 1610, 1515, 1450, 1300, 1235, 1160, 995, 970, 895 and 835 cm$^{-1}$.

EXAMPLE 147

(1S,4R,5S(5Z),6R)-7-[4-(4-Fluorophenyl)-6-(3-phenylureidominomethyl)-2-oxabicyclo[2.2.1]hept-5-yl]-5-heptenoic acid methyl ester 18 mg (50 micromol) of the aldehyde produced in example 138b was reacted analogously to example 26 with use of 4-phenylsemicarbazide and, after working up and purification, 22.3 mg (45 micromol, 90%) of the title compound was isolated as a colorless oil.

IR (film): 3390, 3200, 3150–3050, 3010, 2940, 2880, 1730, 1690, 1595, 1535, 1515, 1450, 1235, 895, 830, 755 and 690 cm$^{-1}$.

EXAMPLE 148

(1S,4R,5S(5Z),6R)-7-[4-(4-Fluorophenyl)-6-(3-phenylureidoiminomethyl)-2-oxabicyclo[2.2.1]hept-5-yl]-5-heptenoic acid 22.3 mg (45 micromol) of the ester produced in example 147 was saponified analogously to example 2 and, after working up and purification, 18 mg (37.5 micromol, 83%) of the title compound was isolated as a colorless oil.

IR (film): 3600–2400, 3390, 3200, 3080, 3010, 2940, 2880, 1700, 1690, 1595, 1535, 1515, 1450, 1235, 895, 830, 755 and 690 cm$^{-1}$.

EXAMPLE 149

(1S,4R,5S(5Z),6R)-7-[4-(4-Fluorophenyl)-6-diphenylmethoxyiminomethyl-2-oxabicyclo[2.2.1]hept-5-yl]-5-heptenoic acid methyl ester 17.4 mg (48 micromol) of the aldehyde produced in example 138b was reacted analogously to example 26 and, after working up and purification, 25.7 mg (47 micromol, 98%) of the title compound was isolated as a colorless oil.

IR (film): 3090, 3060, 3030, 3000, 2930, 2870, 1735, 1605, 1515, 1495, 1450, 1300, 1235, 1160, 1040, 1020, 935, 895, 830, 740 and 700 cm$^{-1}$.

EXAMPLE 150

(1S,4R,5S(5Z),6R)-7-[4-(4-Fluorophenyl)-6-diphenylmethoxyiminomethyl-2-oxabicyclo[2.2.1]hept-5-yl]-5-heptenoic acid 25.7 mg (47 micromol) of the ester produced in example 149 was saponified analogously to example 2 and, after working up and purification, 24 mg (45 micromol, 97%) of the title compound was isolated as a colorless oil.

IR (film): 3600–2400, 3090, 3060, 3030, 3000, 2930, 2870, 1730, 1705, 1605, 1515, 1495, 1450, 1300, 1235, 1160, 1040, 1020, 1,000 935, 900, 830, 740 and 700 cm$^{-1}$.

EXAMPLE 151

(1S,4R,5S(5Z),6R)-7-[4-(4-Fluorophenyl)-6-(1-naphthylmethoxyiminomethyl)-2-oxabicyclo[2.2.1]hept-5-yl]-5-heptenoic acid methyl ester 17.9 mg (50 micromol) of the aldehyde produced in example 138b was reacted analogously to example 26 with use of 1-naphthylmethoxyamine and, after working up and purification, 24 mg (47 micromol, 93%) of the title compound was isolated as a colorless oil.

IR (film): 3060, 3040, 3000, 2940, 2870, 1730, 1605, 1595, 1510, 1450, 1435, 1365, 1230, 1160, 1035, 1010, 1000, 895, 830, 800, 790, 775 and 635 cm$^{-1}$.

EXAMPLE 152

(1S,4R,5S(5Z),6R)-7-[4-(4-Fluorophenyl)-6-(1-naphthylmethoxyiminomethyl)-2-oxabicyclo[2.2.1]hept-5-yl]-5-heptenoic acid 24 mg (47 micromol) of the ester produced according to example 151 was saponified analogously to example 2 and, after working up and purification, 20 mg (40 micromol, 85%) of the title compound was isolated as waxy solid.

IR (KBr): 3600–2400, 3070, 3050, 3010, 2940, 2880, 1730, 1705, 1610, 1600, 1515, 1230, 1160, 1040, 1015, 1000, 920, 900, 835, 800, 795, 780 and 585 cm$^{-1}$.

EXAMPLE 153

(1S,4R,5S(5Z),6S)-7-[4-(4-Fluorophenyl)-6-[3(S)-hydroxy-4-(4-fluorophenoxy)-1(E)-butenyl]-2-oxabicyclo[2.2.1]hept-5-yl]-5-heptenoic acid methyl ester (A) and (1S,4R,5S(5Z),6S)-7-[4-(4-fluorophenyl)-6-[3(R)-hydroxy-4-(4-flurophenoxy)-1(E)-butenyl]-2-oxabicyclo[2.2.1]hept-5-yl]-5-heptenoic acid methyl ester (B)

36 mg (70.5 micromol) of the unsaturated ketone produced in example 153a was reduced analogously to example 23 and, after working up and purification, 31 mg (60.5 micromol, 86%) of a mixture of both title compounds was isolated as a colorless oil.

IR (film): 3600–3200, 3050, 3000, 2970, 2940, 2870, 1735, 1605, 1510, 1245, 1220, 1160, 1035, 895, 830, 760 and 735 cm$^{-1}$.

The chromatographic separation yielded 11 mg (21.5 micromol, 30%) of the more nonpolar alcohol, to which structure A was assigned, as well as 16 mg (31 micromol, 44%) of the more polar alcohol, to which structure B was assigned.

EXAMPLE 153a (1S,4R,5S(5Z),6S)-7-(4-Fluorophenyl)-6-[3-oxo-4-(4-fluorophenoxy)-1(E)-butenyl]-2-oxabicyclo[2.2.1]hept-5-yl]-5-heptenoic acid methyl ester 55.4 mg (154 micromol) of the aldehyde produced in example 138b was reacted analogously to example 30a with use of dimethyl-(2-oxo-3-(p-fluorophenoxy)-propyl)-phosphonate and, after working up and purification, 36 mg (70.5 micromol, 46%) of the title compound was isolated as a colorless oil.

IR (film): 3070, 3040, 3000, 2970, 2940, 2870, 1730, 1690, 1620, 1510, 1505, 1435, 1290, 1220, 1200, 1160, 1040, 995, 900 and 830 cm$^{-1}$.

EXAMPLE 154

(1S,4R,5S(5Z),6S)-7-[4-(4-Fluorophenyl)-6-[3(S)-hydroxy-4-(4-fluorophenoxy)-1(E)-butenyl]-2-oxabicyclo[2.2.1]hept-5-yl]-5-heptenoic acid 11 mg (21.5 micromol) of the nonpolar ester produced in example 153 was saponified analogously to example 2 and, after working up and purification, 10 mg (20 micromol, 93%) of the title compound was isolated as a colorless oil.

IR (film): 3600–2400, 3080, 3030, 3010, 2980, 2940, 2870, 1710, 1610, 1605, 1510, 1460, 1300, 1225, 1165, 1035, 890, 835, 760, 590 and 520 cm$^{-1}$.

EXAMPLE 155

(1S,4R,5S(5Z),6S)-7-[4-(4-Fluorophenyl)-6-[3(R)-hydroxy-4-(4-fluorophenoxy)-1(E)-butenyl]-2-oxabicyclo[2.2.1]hept-5-yl]-5-heptenoic acid 16 mg (31 micromol) of the nonpolar ester produced in example 153 was saponified analogously to example 2 and, after working up and purification, 13 mg (26 micromol, 84%) of the title compound was isolated as a colorless oil.

IR (film): 3600–2400, 3080, 3030, 3010, 2980, 2940, 2880, 1710, 1610, 1605, 1510, 1460, 1300, 1225, 1165, 1040, 895, 830, 760, 590 and 520 cm$^{-1}$.

EXAMPLE 156

(1S,4R,5S(5Z),6S)-7-[4-(4-Fluorophenyl)-6-[3(S)-hydroxy-4-(4(RS)-fluoro-1(E)-octenyl]-2-oxabicyclo[2.2.1]hept-5-yl]-5-heptenoic acid methyl ester (A) and (1S,4R,5S(5Z),6S)-7-[4-(4-fluorophenyl)-6-[3(R)-hydroxy-4(RS)-fluoro-1(E)-octenyl]-2-oxabicyclo[2.2.1]hept-5-yl]-5-heptenoic acid methyl ester (B)

51 mg (107 micromol) of the unsaturated ketone produced in example 156a was reduced analogously to example 23 and, after working up and purification, 49 mg (103 micromol, 96%) of a mixture of both title compounds was isolated as a colorless oil.

IR (film): 3600–3200, 3040, 3000, 2950, 2930, 2860, 1735, 1605, 1510, 1450, 1435, 1230, 1160, 1040, 995, 970, 895 and 835 cm$^{-1}$.

The chromatographic separation yielded 26 mg (54.5 micromol, 51% of the more nonpolar alcohol, to which structure A was assigned, as well as 19 mg (40 micromol, 37%) of the more polar alcohol, to which structure B was assigned.

EXAMPLE 156a (1S,4R,5S(5Z),6S)-7-[4-(4-Fluorophenyl)-6-[3-oxo-4(RS)-fluoro-1(E)-octenyl]-2-oxabicyclo[2.2.1]hept-5-yl]-5-heptenoic acid methyl ester 48 mg (133 micromol) of the aldehyde produced in example 138b was reacted analogously to example 23a with use of dimethyl-(2-oxo-3-fluoroheptyl)-phosphonate and, after working up and purification, 51 mg (107 micromol, 81%) of the title compound was isolated as a colorless oil.

IR (film): 3040, 3020, 3000, 2950, 2920, 2870, 1730, 1690, 1615, 1510, 1450, 1430, 1310, 1290, 1230, 1160, 1045, 995, 975, 900 and 830 cm$^{-1}$.

EXAMPLE 157

(1S,4R,5S(5Z),6S)-7-[4-(4-Fluorophenyl)-6-[3(S)-hydroxy-4(RS)-fluoro-1(E)-octenyl]-2-oxabicyclo[2.2.1]hept-5-yl]-5-heptenoic acid 26 mg (55 micromol) of the nonpolar ester produced in example 156 was saponified analogously to example 2 and, after working up and purification, 24 mg (52 micromol, 95%) of the title compound was isolated as a colorless oil.

IR (film): 3600–2400, 3050, 3010, 2940, 2920, 2880, 1710, 1610, 1515, 1455, 1300, 1235, 1115, 1040, 995, 970, 895 and 835 cm$^{-1}$.

EXAMPLE 158

(1S,4R,5S(5Z),6S)-7-[4-(4-Fluorophenyl)-6-[3(R)-hydroxy-4(RS)-fluoro-1(E)-octenyl]-2-oxabicyclo[2.2.1]hept-5-yl]-5-heptenoic acid 19 mg (40 micromol) of the nonpolar ester produced in example 156 was saponified analogously to example 2 and, after working up and purification, 18 mg (39 micromol, 97%) of the title compound was isolated as a colorless oil.

IR (film): 3600–2400, 3050, 3010, 2940, 2920, 2880, 1725, 1710, 1610, 1515, 1300, 1235, 1115, 1040, 995, 970, 895 and 835 cm$^{-1}$.

EXAMPLE 159

(1S,4R,5S(5Z),6S)-7-[4-(4-Fluorophenyl)-6-[3(S)-hydroxy-4(RS)-fluoro-1(E)-nonenyl]-2-oxabicyclo[2.2.1]hept-5-yl]-5-heptenoic acid methyl ester (A) and (1S,4R,5S(5Z),6S)-7-[4-(4-fluorophenyl)-6-[3(R)-hydroxy-4(RS)-fluoro-1(E)-nonenyl]-2-oxabicyclo[2.2.1]hept-5-yl]-5-heptenoic acid methyl ester (B)

46 mg (94 micromol) of the unsaturated ketone produced in example 159a was reduced analogously to example 23 and, after working up and purification, 43 mg (88 micromol, 97%) of a mixture of both title compounds was isolated as a colorless oil.

IR (film): 3600–3200, 3080, 3040, 3000, 2960, 2930, 2870, 1735, 1605, 1510, 1435, 1230, 1160, 1040, 995, 970, 900 and 835 cm$^{-1}$.

The chromatographic separation yielded 24 mg (50 micromol, 52% of the more nonpolar alcohol, to which structure A was assigned, as well as 17 mg (34 micromol, 37%) of the more polar alcohol, to which structure B was assigned.

EXAMPLE 159a (1S,4R,5S(5Z),6S)-7-[4-(4-Fluorophenyl)-6-[3-oxo-4(RS)-fluoro-1(E)-nonenyl]-2-oxabicyclo[2.2.1]hept-5-yl]-5-heptenoic acid methyl ester 46 mg (128 micromol) of the aldehyde produced in example 138b was reacted analogously to example 23a with use of dimethyl-(2-oxo-3-fluorooctyl)-phosphonate and, after working up and purification, 46 mg (94 micromol, 74%) of the title compound was isolated as a colorless oil.

IR (film): 3070, 3040, 3000, 2950, 2920, 2860, 1735, 1690, 1615, 1510, 1450, 1435, 1230, 1160, 1045, 995, 900 and 830 cm$^{-1}$.

EXAMPLE 160

(1S,4R,5S(5Z),6S)-7-[4-(4-Fluorophenyl)-6-[3(S)-hydroxy-4(RS)-fluoro-1(E)-nonenyl]-2-oxabicyclo[2.2.1]hept-5-yl]-5-heptenoic acid 24 mg (50 micromol) of the nonpolar ester produced in example 159 was saponified analogously to example 2 and, after working up and purification, 21 mg (44 micromol, 88%) of the title compound was isolated as a colorless oil.

IR (film): 3600–2400, 3050, 3010, 2960, 2930, 1725, 1710, 1610, 1515, 1455, 1410, 1300, 1235, 1155, 1000, 975, 895 and 835 cm$^{-1}$.

EXAMPLE 161

(1S,4R,5S(5Z),6S)-7-[4-(4-Fluorophenyl)-6-[3(R)-hydroxy-4(RS)-fluoro-1(E)-nonenyl]-2-oxabicyclo[2.2.1]hept-5-yl]-5-heptenoic acid 17 mg (34 micromol) of the nonpolar ester produced in example 159 was saponified analogously to example 2 and, after working up and purification, 16 mg (33 micromol, 98%) of the title compound was isolated as a colorless oil.

IR (film): 3600–2400, 3050, 3010, 2950, 2930, 2870, 1710, 1610, 1515, 1455, 1410, 1300, 1235, 1155, 1045, 1000, 975, 895 and 835 cm$^{-1}$.

EXAMPLE 162

(1S,4R,5S(5Z),6S)-7-[4-(4-Fluorophenyl)-6-[3(S)-hydroxy-4,4-trimethylene-1(E)-nonen-7-inyl]-2-oxabicyclo[2.2.1]hept-5-yl]-5-heptenoic acid methyl ester (A) and (1S,4R,5S(5Z),6S)-7-[4-(4-fluorophenyl)-6-[3(R)-hydroxy-4,4-trimethylene-1(E)-nonen-7-inyl]-2- oxabicyclo[2.2.1]hept-5-yl]-5-heptenoic acid methyl ester (B)

30 mg (59 micromol) of the unsaturated ketone produced in example 162a was reduced analogously to example 23 and, after working up and purification, 28 mg (55 micromol, 93%) of a mixture of both title compounds was isolated as a colorless oil.

IR (film): 3600–3200, 3080, 3030, 2970, 2930, 2870, 1735, 1605, 1510, 1450, 1435, 1225, 1160, 1040, 995, 970, 895 and 835 cm$^{-1}$.

The chromatographic separation yielded 18 mg (35 micromol, 60%) of the more nonpolar alcohol, to which structure A was assigned, as well as 8 mg (16 micromol, 27%) of the more polar alcohol, to which structure B was assigned.

EXAMPLE 162a (1S,4R,5S(5Z),6S)-7-[4-(4-Fluorophenyl)-6-[3-oxo-4,4-trimethylene-1(E)-nonen-7-inyl]-2-oxabicyclo[2.2.1-]hept-5-yl]-5-heptenoic acid methyl ester 46 mg (128 micromol) of the aldehyde produced in example 138b was reacted analogously to example 23a with use of dimethyl(2-oxo-3,3-trimethylenon-oct-6-inyl)-phosphonate and, after working up and purification, 31 mg (61 micromol, 48%) of the title compound was isolated as a colorless oil.

IR (film): 3040, 2970, 2940, 2860, 1735, 1680, 1620, 1510, 1450, 1453, 1230, 1160, 995, 900 and 830 cm$^{-1}$.

EXAMPLE 163

(1S,4R,5S(5Z),6S)-7-[4-(4-Fluorophenyl)-6-[3(S)-hydroxy-4,4-trimethylene-1(E)-nonen-7-inyl]-2-oxabicyclo[2.2.1]hept-5-yl]-5-heptenoic acid 18 mg (35 micromol) of the nonpolar ester produced in example 162was saponified analogously to example 2 and, after working up and purification, 15 mg (30 micromol, 87%) of the title compound was isolated as a colorless oil.

IR (film): 3700–2400, 3040, 2980, 2940, 2880, 2840, 1710, 1610, 1515, 1445, 1435, 1410, 1300, 1230, 1160, 1040, 1015, 995, 970, 895 and 835 cm$^{-1}$.

EXAMPLE 164

(1S,4R,5S(5Z),6S)-7-[4-(4-Fluorophenyl)-6-[3(R)-hydroxy-4,4-trimethylene-1(E)-nonen-7-inyl]-2-oxabicyclo[2.2.1]hept-5-yl]-5-heptenoic acid 8 mg (16 micromol) of the polar ester produced in example 162was saponified analogously to example 2 and, after working up and purification, 7 mg (14 micromol, 88%) of the title compound was isolated as a colorless oil.

IR (film): 3600–2400, 3040, 2980, 2940, 2880, 2840, 1725, 1710, 1610, 1515, 1450, 1435, 1410, 1300, 1235, 1160, 1040, 1015, 995, 970, 890 and 835 cm$^{-1}$.

EXAMPLE 165

(1S,4R,5S(5Z),6S)-7-[4-(4-Fluorophenyl)-6-[3(S)-hydroxy-4,4-trimethylene-1(E)-nonen-6-inyl]-2-oxabicyclo[2.2.1]hept-5-yl]-5-heptenoic acid methyl ester (A) and (1S,4R,5S(5Z),6S)-7-[4-(4-fluorophenyl)-6-[3(R)-hydroxy-4,4-trimethylene-1(E)-nonen-6-inyl]-2-oxabicyclo[2.2.1]hept-5-yl]-5-heptenoic acid methyl ester (B)

50 mg (99 micromol) of the unsaturated ketone produced in example 165a was reduced analogously to example 23 and, after working up and purification, 46 mg (90 micromol, 91%) of a mixture of both title compounds was isolated as a colorless oil.

IR (film): 3600–3200, 3040, 2970, 2930, 2870, 1735, 1605, 1510, 1450, 1435, 1230, 1160, 1040, 995, 970, 895 and 835 cm$^{-1}$.

The chromatographic separation yielded 27 mg (53 micromol, 54%) of the more nonpolar alcohol, to which structure A was assigned, as well as 17 mg (33 micromol, 34%) of the more polar alcohol, to which structure B was assigned.

EXAMPLE 165a (1S,4R,5S(5Z),6S)-7-[4-(4-Fluorophenyl)-6-[3-oxo-4,4-trimethylene-1(E)-nonen-6-inyl]-2-oxabicyclo[2.2.1-]hept-5-yl]-5-heptenoic acid methyl ester 45 mg (125 micromol) of the aldehyde produced in example 138b was reacted analogously to example 23a with use of dimethyl(2-oxo-3,3-trimethylene-5-octinyl)-phosphonate and, after working up and purification, 50 mg (99 micromol, 79%) of the title compound was isolated as a colorless oil.

IR (film): 3070, 3040, 2970, 2940, 2870, 1730, 1685, 1620, 1510, 1450, 1430, 1230, 1160, 1045, 995, 900 and 830 cm$^{-1}$.

EXAMPLE 166

(1S,4R,5S(5Z),6S)-7-[4-(4-Fluorophenyl)-6-[3(S)-hydroxy-4,4-trimethylene-1(E)-nonen-6-inyl]-2-oxabicyclo[2.2.1]hept-5-yl]-5-heptenoic acid 26 mg (51 micromol) of the nonpolar ester produced in example 165 was saponified analogously to example 2 and, after working up and purification, 24 mg (49 micromol, 95%) of the title compound was isolated as a colorless oil.

IR (film): 3600–2400, 3040, 2980, 2940, 2880, 1710, 1610, 1515, 1455, 1430, 1405, 1320, 1300, 1235, 1160, 995, 970, 895 and 835 cm$^{-1}$.

EXAMPLE 167

(1S,4R,5S(5Z),6S)-7-[4-(4-Fluorophenyl)-6-[3(R)-hydroxy-4,4-trimethylene-1(E)-nonen-6-inyl]-2-oxabicyclo[2.2.1]hept-5-yl]-5-heptenoic acid 16 mg (31 micromol) of the nonpolar ester produced in example 165 was saponified analogously to example 2 and, after working up and purification, 15 mg (30 micromol, 98%) of the title compound was isolated as a colorless oil.

IR (film): 3600–2400, 3040, 2970, 2940, 2870, 1725, 1710, 1610, 1515, 1430, 1405, 1320, 1300, 1230, 1160, 1040, 995, 970, 895 and 835 cm$^{-1}$.

EXAMPLE 168

(1S,4R,5S(5Z),6S)-7-[4-(4-Fluorophenyl)-6-[(1E,3R,4RS,6Z)-3-hydroxy-4-methyl-7-chloro-octa-1,6-dienyl]-2-oxabicyclo[2.2.1]hept-5-yl]-5-heptenoic acid methyl ester (A) and (1S,4R,5S(5Z),6S)-7-[4-(4-fluorophenyl)-6-[(1E,3S,4RS,6Z)-3-hydroxy-4-methyl-7-chloro-octa-1,6-dienyl]-2-oxabicyclo[2.2.1]hept-5-yl]-5-heptenoic acid methyl ester (B)

52 mg (103 micromol) of the unsaturated ketone produced in example 168a was reduced analogously to example 23 and, after working up and purification, 52 mg (103 micromol, 99%) of a mixture of both title compounds was isolated as a colorless oil.

IR (film): 3600–3200, 3040, 2950, 2920, 2870, 1730, 1605, 1510, 1430, 1230, 1160, 995, 970, 895 and 830 cm$^{-1}$.

The chromatographic separation yielded 30 mg (59 micromol, 58%) of the more nonpolar alcohol, to which structure A was assigned, as well as 21 mg (42 micromol, 40%) of the more polar alcohol, to which structure B was assigned.

EXAMPLE 168a (1S,4R,5S(5Z),6S)-7-[4-(4-Fluorophenyl)-6-[(1E,4RS,6Z)-3-oxo-4-methyl-7-chloro-octa-1,6-dienyl]-2-oxabicyclo[2.2.1]hept-5-yl]-5-heptenoic acid methyl ester 48 mg (133 micromol) of the aldehyde produced in example 138b was reacted analogously to example 23a with use of dimethyl(2-oxo-3-methyl-6-chloro-hept-5(Z)-ene)-phosphonate and, after working up and purification, 52 mg (103 micromol, 78%) of the title compound was isolated as a colorless oil.

IR (film): 3040, 2970, 2940, 2930, 2870, 1730, 1690, 1665, 1620, 1510, 1450, 1430, 1360, 1225, 1160, 1040, 995, 975, 900 and 830 cm$^{-1}$.

EXAMPLE 169

(1S,4R,5S(5Z),6S)-7-[4-(4-Fluorophenyl)-6-[(1E,3R,4RS,6Z)-3-hydroxy-4-methyl-7-chloro-octa-1,6-dienyl]-2-oxabicyclo[2.2.1]hept-5-yl]-5-heptenoic acid 30 mg (59 micromol) of the nonpolar ester produced in example 168 was saponified analogously to example 2 and, after working up and purification, 25 mg (51 micromol, 86%) of the title compound was isolated as a colorless oil.

IR (film): 3600-2400, 3050, 3010, 2970, 2960, 2930, 2880, 1710, 1610, 1515, 1300, 1235, 1160, 1015, 995, 970, 895 and 835 cm$^{-1}$.

EXAMPLE 170

(1S,4R,5S(5Z),6S)-7-[4-(4-Fluorophenyl)-6-[(1E,3S,4RS)-3-hydroxy-4-methyl-7-chloro-octa-1,6-dienyl]-2-oxabicyclo[2.2.1]hept-5-yl]-5-heptenoic acid 21 mg (42 micromol) of the nonpolar ester produced in example 168 was saponified analogously to example 2 and, after working up and purification, 18 mg (37 micromol, 87%) of the title compound was isolated as a colorless oil.

IR (film): 3600-2400, 3060, 3020, 2970, 2930, 2280, 1710, 1610, 1515, 1455, 1410, 1300, 1235, 1160, 1015, 995, 970, 895 and 835 cm$^{-1}$.

EXAMPLE 171

(1S,4R,5S(5Z),6S)-7-[4-(4-Fluorophenyl)-6-[(1E,3R,4RS)-3-hydroxy-4,6-dimethyl-heptenyl]-2-oxabicyclo[2.2.1]hept-5-yl]-5-heptenoic acid methyl ester (A) and (1S,4R,5S(5Z),6S)-7-[4-(4-fluorophenyl)-6-[(1E,3S,4RS)-3-hydroxy-4,6-dimethyl-heptenyl]-2-oxabicyclo[2.2.1]hept-5-yl]-5-heptenoic acid methyl ester (B)

47 mg (100 micromol) of the unsaturated ketone produced in example 171a was reduced analogously to example 23 and, after working up and purification, 47 mg (99 micromol, 99%) of a mixture of both title compounds was isolated as a colorless oil.

IR (film): 3600-3250, 3040, 2950, 2920, 2860, 1735, 1605, 1450, 1435, 1365, 1230, 1160, 995, 970, 895 and 835 cm$^{-1}$.

The chromatographic separation yielded 28 mg (59 micromol, 59%) of the more nonpolar alcohol, to which structure A was assigned, as well as 18 mg (38 micromol, 38%) of the more polar alcohol, to which structure B was assigned.

EXAMPLE 171a (1S,4R,5S(5Z),6S)-7-[4-(4-Fluorophenyl)-6-[(1E,4RS,)-3-oxo-4,6-dimethyl-heptenyl]-2-oxabicyclo[2.2.1]hept-5-yl]-5-heptenoic acid methyl ester 47 mg (130 micromol) of the aldehyde produced in example 138b was reacted analogously to example 23a with use of dimethyl(2-oxo-3,5-dimethyl-hexyl)-phosphonate and, after working up and purification, 48 mg (102 micromol, 78%) of the title compound was isolated as a colorless oil.

IR (film): 3060, 3040, 2950, 2920, 2860, 1735, 1690, 1665, 1620, 1510, 1450, 1435, 1365, 1230, 1190, 1160, 1040, 995, 975, 900 and 830 cm$^{-1}$.

EXAMPLE 172

(1S,4R,5S(5Z),6S)-7-[4-(4-Fluorophenyl)-6-[(1E,3R,4RS)-3-hydroxy-4,6-dimethyl-heptenyl]-2-oxabicyclo[2.2.1]hept-5-yl]-5-heptenoic acid 28 mg (69 micromol) of the nonpolar ester produced in example 171 was saponified analogously to example 2 and, after working up and purification, 24 mg (52 micromol, 76%) of the title compound was isolated as a colorless oil.

IR (film): 3600-2400, 3050, 3010, 2960, 2930, 2870, 1725, 1710, 1610, 1515, 1460, 1300, 1235, 1165, 995, 970, 895 and 835 cm$^{-1}$.

EXAMPLE 173

(1S,4R,5S(5Z),6S)-7-[4-(4-Fluorophenyl)-6-[(1E,3S,4RS)-3-hydroxy-4,6-dimethyl-heptenyl]-2-oxabicyclo[2.2.1]hept-5-yl]-5-heptenoic acid 18 mg (38 micromol) of the nonpolar ester produced in example 171 was saponified analogously to example 2 and, after working up and purification, 17 mg (37 micromol, 97%) of the title compound was isolated as a colorless oil.

IR (film): 3600-2400, 3050, 3010, 2960, 2930, 2870, 1710, 1610, 1515, 1460, 1385, 1300, 1235, 1165, 995, 970, 895 and 835 cm$^{-1}$.

EXAMPLE 174

(1S,4R,5S(5Z),6S)-7-[4-(4-Fluorophenyl)-6-(2-pyridyl-2-vinyl)-2-oxabicyclo[2.2.1]hept-5-yl]-5-heptenoic acid methyl ester The pale yellow solution of 26.4 mg of 2-picolyltriphenylphosphonium chloride-sodium amide in 250 microliters of anhydrous tetrahydrofuran was mixed with the solution of 19 mg (53 micromol) of the aldehyde, produced in example 138b, in 200 microliters of anhydrous tetrahydrofuran and allowed to react for two hours at 25° C. under an atmosphere of dry argon. The reaction solution was directly applied on two analytic thin-layer slabs, developed with a mixture of trichloromethane/ethanol and eluted with trichloromethane. 19 mg (44 micromol, 82%) of the title compound was isolated as a colorless oil.

IR (film): 3430, 3040, 3000, 2970, 2930, 2870, 2540, 1595, 1585, 1565, 1515, 1465, 1430, 1295, 1225, 1040, 995, 970, 900, 835, 760, 590 and 530 cm$^{-1}$.

EXAMPLE 175

(1S,4R,5S(5Z),6S)-7-[4-(4-Fluorophenyl)-6-(2-vinyl)-2-oxabicyclo[2.2.1]hept-5-yl]-5-heptenoic acid 19 mg (44 micromol) of the ester produced in example 174 was saponified analogously to example 2 and, after working up and purification, 16 mg (38 micromol, 86%) of the title compound was isolated as a colorless oil.

IR (film): 3600–2300, 3430, 3040, 3000, 2970, 2930, 2870, 2540, 2100–1800, 1725, 1710, 1650, 1595, 1585, 1565, 1515, 1470, 1430, 1295, 1230, 1040, 995, 970, 900, 835, 760, 585 and 530 cm$^{-1}$.

EXAMPLE 176

(1S,4R,5S(5Z),6S)-7-[4-(4-Fluorophenyl)-6-(2-phenylvinyl)-2-oxabicyclo[2.2.1]hept-5-yl]-5-heptenoic acid methyl ester 18 mg (50 micromol) of the ester produced in example 138b was reacted analogously to example 174 with use of benzyltriphenylphosphonium bromide-sodium amide and, after working up and purification, 17 mg (40 micromol, 81%) of the title compound was isolated as a colorless oil.

IR (film): 3080, 3060, 3020, 3000, 2970, 2940, 2870, 1735, 1595, 1510, 1445, 1435, 1230, 1195, 1160, 1040, 995, 965, 895, 835, 745 and 695 cm$^{-1}$.

EXAMPLE 177

(1S,4R,5S(5Z),6S)-7-[4-(4-Fluorophenyl)-6-(2-phenylvinyl)-2-oxabicyclo[2.2.1]hept-5-yl]-5-heptenoic acid 17 mg (40 micromol) of the ester produced in example 176 was saponified analogously to example 2 and, after working up and purification, 15 mg (36 micromol, 89%) of the title compound was isolated as a colorless oil.

IR (film): 3600–2400, 3080, 3060, 3030, 3010, 2980, 2940, 2880, 1730, 1710, 1610, 1600, 1515, 1450, 1410, 1300, 1230, 1160, 1040, 995, 965, 895, 835, 745, 695, 585 and 520 cm$^{-1}$.

EXAMPLE 178

(1S,4R,5S(5Z),6S)-7-[4-(4-Fluorophenyl)-6-[1(E/Z),-4(E)-pentadienyl]2-oxabicyclo[2.2.1]hept-5-yl]-5-heptenoic acid methyl ester 20 mg (55 micromol) of the ester produced in example 138b was reacted analogously to example 174 with use of crotyltriphenylphosphonium bromide-sodium amide and, after working up and purification, 7 mg (18 micromol, 32%) of the title compound was isolated as a colorless oil.

IR (film): 3040, 3010, 2930, 2870, 1735, 1610, 1515, 1450, 1410, 1300, 1235, 1160, 995, 900 and 835 cm$^{-1}$.

EXAMPLE 179

(1S,4R,5S(5Z),6S)-7-[4-(4-Fluorophenyl)-6-[1(E/Z),-4(E)-pentadienyl]2-oxabicyclo[2.2.1]hept-5-yl]-5-heptenoic acid 7 mg (13 micromol, 72%) of the ester produced in example 178 was saponified analogously to example 2 and, after working up and purification, 5 mg (13 micromol, 72%) of the title compound was isolated as a colorless oil.

IR (film): 3600–2400, 3040, 3010, 2930, 2880, 1730, 1710, 1610, 1515, 1450, 1410, 1300, 1235, 1160, 990, 900 and 835 cm$^{-1}$.

EXAMPLE 180

(1S,4R,5S(5Z),6R)-7-[4-(4-Fluorophenyl)-6-(4-trifluoromethylbenzyloxyiminomethyl)-2-oxabicyclo[2.2.1]hept-5-yl]-5-heptenoic acid methyl ester 17.9 mg (49 micromol) of the aldehyde produced in example 138b was reacted analogously to example 26 with use of p-trifluoromethylphenylmethoxyamine and, after working up and purification, 22.8 mg (43 micromol, 87%) of the title compound was isolated as a colorless oil.

IR (film): 3070, 3040, 2940, 2870, 1735, 1620, 1605, 1510, 1435, 1415, 1325, 1230, 1160, 1125, 1065, 1015, 900, 830 and 820 cm$^{-1}$.

EXAMPLE 181

(1S,4R,5S(5Z),6R)-7-[4-(4-Fluorophenyl)-6-(4-methylbenyloxyiminomethyl)-2-oxabicyclo[2.2.1]hept-5-yl]-5-heptenoic acid 22 mg (43 micromol) of the ester produced according to example 180 was saponified analogously to example 2 and, after working up and purification, 19 mg (37 micromol, 85%) of the title compound was isolated as a colorless oil.

IR (film): 3600–2400, 3050, 3010, 2930, 2880, 1730, 1710, 1620, 1610, 1515, 1415, 1325, 1235, 1165, 1125, 1065, 1015, 900, 835 and 820 cm$^{-1}$.

EXAMPLE 182

(1S,4R,5S(5Z),6R)-7-[4-(4-Fluorophenyl)-6-(4-fluorobenyloxyiminomethyl)-2-oxabicyclo[2.2.1]hept-5-yl]-5-heptenoic acid methyl ester 19.3 mg (53.5 micromol) of the aldehyde produced in example 138b was reacted analogously to example 26 with use of p-trifluorophenylmethoxyamine and, after working up and purification, 23.6 mg (48.8 micromol, 91%) of the title compound was isolated as a colorless oil.

IR (film): 3070, 3040, 3000, 2940, 2870, 1735, 1605, 1510, 1435, 1365, 1220, 1160, 1040, 1015, 1000, 900 and 830 cm$^{-1}$.

EXAMPLE 183

(1S,4R,5S(5Z),6R)-7-[4-(4-Fluorophenyl)-6-(4-fluorobenyloxyiminomethyl)-2-oxabicyclo[2.2.1]hept-5-yl]-5-heptenoic acid 23.6 mg (48.8 micromol) of the ester produced according to example 182 was saponified analogously to example 2 and, after working up and purification, 22 mg (46.9 micromol, 96%) of the title compound was isolated as a colorless oil.

IR (film): 3600–2400, 3070, 3040, 3010, 2930, 2880, 1730, 1710, 1605, 1515, 1225, 1160, 1040, 1015, 1000, 900, 835 and 820 cm$^{-1}$.

EXAMPLE 184

(1S,4R,5S(5Z),6R)-7-[4-(4-Fluorophenyl)-6-(benzyloxyiminomethyl)-2-oxabicyclo[2.2.1]hept-5-yl]-5-heptenoic ester 17.1 mg (47.4 micromol) of the aldehyde produced in example 138b was reacted analogously to example 26 with use of phenylmethoxyamine and, after working up and purification, 17.8 mg (38.2 micromol, 81%) of the title compound was isolated as a colorless oil.

IR (film): 3090, 3060, 3030, 3000, 2940, 2920, 2870, 1735, 1605, 1510, 1450, 1430, 1365, 1230, 1160, 1040, 1015, 1000, 900, 835, 750, 735 and 700 cm$^{-1}$.

EXAMPLE 185

(1S,4R,5S(5Z),6R)-7-[4-(4-Fluorophenyl)-6-(benzyloxyiminomethyl)-2-oxabicyclo[2.2.1]hept-5-yl]-5-heptenoic acid 17.8 mg (38.2 micromol) of the ester produced according to example 184 was saponified analogously to example 2 and, after working up and purification, 17 mg (31.4 micromol, 82%) of the title compound was isolated as a colorless oil.

IR (film): 3600–2400, 3090, 3060, 3030, 3010, 2930, 2880, 1730, 1710, 1610, 1515, 1455, 1235, 1165, 1045, 1015, 1000, 900, 835, 820, 735 and 700 cm$^{-1}$.

EXAMPLE 186

(1S,4R,5S(5Z),6R(3S,4S))-7-[4-(4-Fluorophenyl)-6-(3-hydroxy-4-methyl-nona-1,6-diinyl)-2-oxabicyclo[2.2.1]hept-5-yl]-5-heptenoic acid methyl ester 3 mg (6.4 micromol) of the ester produced according to example 187 was dissolved in 1 ml of dichloromethane, cooled to 0°–5° C. and mixed with an ethereal solution of diazomethane. After removal of the solvent, 3 mg (6.4 micromol, 100%) of the title compound was isolated as a colorless oil.

IR (film): 3600–3200, 3050, 3010, 2970, 2940, 2880, 2230, 1735, 1610, 1595, 1515, 1445, 1435, 1290, 1235, 1165, 1040, 1020, 990, 895, 835 and 820 cm$^{-1}$.

EXAMPLE 187

(1S,4R,5S(5Z),6R(3S,4S))-7-[4-(4-Fluorophenyl)-6-(3-hydroxy-4-methyl-nona-1,6-diinyl)-2-oxabicyclo[2.2.1]hept-5-yl]-5-heptenoic acid 26 mg (46.3 micromol) of nonpolar alcohol A produced according to example 190 was dissolved in a mixture of 460 microliters of anhydrous dimethyl sulfoxide and 190 microliters of anhydrous tetrahydrofuran, mixed with 15.6 mg of potassium t.-butanolate and stirred for 2.5 hours at 23° C. under an atmosphere of dry argon. It was mixed with ice water, acidified by adding a saturated citric acid solution, extracted with diethyl ether, dried on magnesium sulfate and the residue obtained after filtration and removal of the solvent was purified by chromatography on 2 analytic thin-layer slabs. A mixture of trichloromethane and ethanol was used as a mobile solvent; a mixture of ethyl acetate and ethanol was used as an eluant. 11.5 mg (24.6 micromol, 53%) of the title compound was isolated as a colorless oil.

IR (film): 3700–2400, 3050, 3010, 2980, 2940, 2880, 2230, 1710, 1610, 1595, 1515, 1445, 1435, 1410, 1290, 1235, 1165, 1040, 1020, 990, 900, 835 and 820 cm$^{-1}$.

EXAMPLE 188

(1S,4R,5S(5Z),6R(3R,4S))-7-[4-(4-Fluorophenyl)-6-(3-hydroxy-4-methyl-nona-1,6-diinyl)-2-oxabicyclo[2.2.1]hept-5-yl]-5-heptenoic acid methyl ester 2.7 mg (5.8 micromol) of the acid produced according to example 139 was reacted analogously to example 186 and, after removal of the solvent, 2.7 mg (5.8 micromol, 100%) of the title compound was isolated as a colorless oil.

IR (film): 3600–3200, 3050, 3010, 2980, 2940, 2880, 2230, 1735, 1610, 1515, 1445, 1435, 1410, 1295, 1230, 1165, 1040, 1020, 990, 900, 835 and 820 cm$^{-1}$.

EXAMPLE 189

(1S,4R,5S(5Z),6R)(3R,4S))-7-[4-(4-Fluorophenyl)-6-(3-hydroxy-4-methyl-nona-1,6-diinyl)-2-oxabicyclo[2.2.1]hept-5-yl]-5-heptenoic acid 38 mg (67.7 micromol) of polar alcohol B produced according to example 190 was reacted analogously to example 187 and, after working up and purification, 17.3 mg (37.1 micromol, 55%) of the title compound was isolated as a colorless oil.

IR (film): 3700–2400, 3050, 3010, 2980, 2940, 2880, 2230, 1710, 1610, 1515, 1445, 1435, 1410, 1295, 1235, 1165, 1040, 1020, 990, 900, 835 and 820 cm$^{-1}$.

EXAMPLE 190

(1S,4R,5S(5Z),6R(1E/Z,3S,4S))-7-[4-(4-Fluorophenyl)-6-(2-bromo-3-hydroxy-4-methyl-non-1-en-6inyl)-2-oxabicyclo[2.2.1]hept-5-yl]-5-heptenoic acid methyl ester (A) and (1S,4R,5S(5Z),6R(1E/Z,3R,4S))-7-[4-(4-fluorophenyl)-6-(2-bromo-3-hydroxy-4-methyl-non-1-en-6-inyl)-2-oxabicyclo[2.2.1]hept-5-yl]-5-yl]-5-heptenoic acid methyl ester (B)

80 mg (143 micromol) of the unsaturated ketone produced in example 190a was reduced analogously to example 23 and, after working up and purification, 66 mg (118 micromol, 82%) of a mixture of both title compounds was isolated as a colorless oil.

IR (film): 3600–3200, 3040, 2970, 2930, 2870, 1735, 1605, 1510, 1450, 1430, 1230, 1160, 1040, 990, 895, 830 and 735 cm$^{-1}$.

The chromatographic separation yielded 26 mg (46.3 micromol, 32% of the more nonpolar alcohol, to which structure A was assigned, as well as 38 mg (67.7 micromol, 47%) of the more polar alcohol, to which structure B was assigned.

EXAMPLE 190a (1S,4R,5S(5Z),6R(1E/Z,4S))-7-[4-(4-Fluorophenyl)-6-(2-bromo-3-oxo-4-methyl-non-1-en-6inyl)-2-oxabicyclo[2.2.1]hept-5-yl]-5-heptenoic acid methyl ester:

The solution of 62 mg of dimethyl-(2-oxo-3S-methyl-oct-5-in)-phosphonate in 650 microliters of anhydrous tetrahydrofuran was instilled in a suspension consisting of 12.4 mg of a 50% sodium hydride dispersion in white oil and 1.1 ml of anhydrous tetrahydrofuran at 0° C. under an atmosphere of dry argon, mixed after 30 minutes with 47.5 mg of fine powdered N-bromosuccinimide and the solution of 77.7 mg (215 micromol) of the aldehyde, produced according to example 138b in 750 microliters of anhydrous tetrahydrofuran was instilled after 1 hour. It was allowed to heat to 23° C., stirred for another 5 hours, diluted with diethyl ether, washed until the neutral reaction with a 10% sodium bicarbonate solution and water, dried on magnesium sulfate and the residue obtained after filtration and removal of the solvent was purified by chromatography on 3 analytic thin-layer slabs. A mixture of chloroform and diethyl ether was used as a mobile solvent; ethyl acetate was used as an eluant. 80 mg (143 micromol, 66%) of the title compound was isolated as a colorless oil.

IR (film): 3040, 3010, 2970, 2930, 2870, 1730, 1680, 1600, 1510, 1450, 1430, 1230, 1160, 1040, 985, 900 and 830 cm$^{-1}$.

EXAMPLE 191

(1S,4R,5S(5Z),6R(1E/Z,3R,4S))-7-[4-(4-Fluorophenyl)-6-(2-bromo-3-hydroxy-4-methyl-non-1-en-6inyl)-2-oxabicyclo[2.2.1]hept-5-yl]-5-heptenoic acid 7.3 mg (13 micromol) of polar ester B produced according to example 190 was saponified analogously to example 2 and, after working up and purification, 5.1 mg (9.3 micromol, 72%) of the title compound was isolated as a colorless oil.

IR (film): 3600–2400, 3040, 3010, 2960, 2930, 2870, 1735, 1605, 1510, 1450, 1410, 1305, 1230, 1160, 1040, 990, 895, 830 and 730 cm$^{-1}$.

EXAMPLE 192

(1S,4R,5S(5Z),6R(1E/Z,3S,4S))-7-[4-(4-Fluorophenyl)-6-(2-bromo-3-hydroxy-4-methyl-non-1-en-6inyl)-2-oxabicyclo[2.2.1]hept-5-yl]-5-heptenoic acid:

8.1 mg (14.4 micromol) of nonpolar alcohol A produced according to example 190 was saponified analogously to example 2 and, after working up and purification, 7.5 mg (13.7 micromol, 95%) of the title compound was isolated as a colorless oil.

IR (film): 3600–2300, 3050, 3010, 2970, 2930, 2880, 1735, 1605, 1510, 1455, 1410, 1305, 1235, 1160, 1040, 990, 895, 830 and 730 cm$^{-1}$.

EXAMPLE 193

(1S,4R,5S(5Z),6S(1E,3S,4S))-7-[4-(4-Fluorophenyl)-6-(3-hydroxy-4-methyl-non-1-en-6inyl)-2-oxabicyclo[2.2.1]hept-5-yl]-5-heptenoic acid methyl ester (A) and (1S,4R,5S(5Z),6S(1E,3R,4S))-7-[4-(4-fluorophenyl)-6-(3-hydroxy-4-methyl-non-1-en-6-inyl)-2-oxabicyclo[2.2.1]hept-5-yl]-5-heptenoic acid methyl ester (B)

40 mg (83.2 micromol) of the unsaturated ketone produced in example 193a was reduced analogously to example 23 and, after working up and purification, 39 mg (80,8 micromol, 97%) of a mixture of both title compounds was isolated as a colorless oil.

IR (film): 3600–3200, 3040, 2970, 2930, 2870, 1730, 1605, 1510, 1450, 1435, 1230, 1160, 995, 970, 895, 830 and 735 cm$^{-1}$.

The chromatographic separation yielded 16.4 mg (34 micromol, 41%) of the more nonpolar alcohol, to which structure A was assigned, as well as 20 mg (41 micromol, 50%) of the more polar alcohol to which structure B was assigned.

EXAMPLE 193a (1S,4R,5S(5Z),6S(1E,4S)-7-[4-(4-Fluorophenyl)-6-(3-oxo-4-methyl-non-1-en-6inyl)-2-oxabicyclo[2.2.1]hept-5-yl]-5-heptenoic acid methyl ester 49.3 mg (136 micromol) of the aldehyde produced in example 138b was reacted analogously to example 23a with use of dimethyl-(2-oxo-3S-methyl-oct-5-ine)-phosphonate and, after working up and purification, 37 mg (77 micromol, 57%) of the title compound was isolated as a colorless oil.

IR (film): 3060, 3040, 2970, 2930, 2870, 1735, 1690, 1665, 1620, 1510, 1450, 1430, 1230, 1160, 1040, 995, 975, 900 and 835 cm$^{-1}$.

EXAMPLE 194

(1S,4R,5S(5Z),6S(1E,3S,4S))-7-[4-(4-Fluorophenyl)-6-(3-methyl-non-1-en-6inyl)-2-oxabicyclo[2.2.1]hept-5-yl]-5-heptenoic acid 16 mg (33.2 micromol) of the aldehyde produced in example 193 was saponified analogously to example 2 and, after working up and purification, 15 mg (32 micromol, 97%) of the title compound was isolated as a colorless oil.

IR (film): 3700–2400, 3070, 3050, 3010, 2970, 2930, 2880, 2100, 1710, 1610, 1515, 1455, 1410, 1320, 1300, 1235, 1165, 1040, 1015, 995, 975, 895, 835 and 820 cm$^{-1}$.

EXAMPLE 195

(1S,4R,5S(5Z),6S(1E,3R,4S))-7-[4-(4-Fluorophenyl)-6-(3-hydroxy-4-methyl-non-1-en-6inyl)-2-oxabicyclo[2.2.1]hept-5-yl]-5-heptenoic acid 20 mg (41.4 micromol) of the aldehyde produced according to example 193 was saponified analogously to example 2 and, after working up and purification, 16 mg (34.1 micromol, 82%) of the title compound was isolated as a colorless oil.

IR (film): 3700–2300, 3070, 3040, 3000, 2970, 2930, 2880, 1710, 1610, 1515, 1455, 1410, 1320, 1300, 1235, 1160, 995, 970, 895 and 835 cm$^{-1}$.

EXAMPLE 196

(1S,4R,5S(5Z),6R)-7-[4-(4-cyanobenzyloxymethyl)-2-oxabicyclo[2.2.1]hept-5-yl]-5-heptenoic methyl (or 4-cyanobenzyl) ester 19.6 mg (54.1 micromol) of the alcohol produced in example 120a was reacted analogously to example 1 with 4-bromomethylbenzonitrile and, after working up and purification, 23 mg of the title compounds was isolated as a colorless oil.

IR (film): 3050, 3040, 3010, 2930, 2860, 2220, 1730, 1605, 1510, 1435, 1360, 1225, 1160, 1120, 1090, 1030, 895, 830 and 815 cm$^{-1}$.

EXAMPLE 197

(1S,4R,5S(5Z),6R)-7-[4-(4-Fluorophenyl)-6-(4-cyanobenzyloxymethyl)-2-oxabicyclo[2.2.1]hept-5-yl]-5-heptenoic acid 23 mg of the ester mixture produced according to example 196 was saponified analogously to example 2 and, after working up and purification, 18 mg (38.8 micromol, 72%, relative to the initial material in example 196) of the title compound was isolated as a colorless oil.

IR (film): 3600–2400, 3070, 3050, 3010, 2930, 2870, 2230, 1725, 1710, 1610, 1515, 1410, 1230, 1160, 1125, 995, 930, 920, 895, 835 and 820 cm$^{-1}$.

EXAMPLE 198

(1S,4R,5S(5Z),6R)-7-[4-(4-Fluorophenyl)-6-(3-cyanobenzyloxymethyl)-2-oxabicyclo[2.2.1]hept-5-yl]-5-heptenoic acid methyl (or 3-cyanobenzyl) ester 18.4 mg (50.8 micromol) of the alcohol produced in example 120a was reacted analogously to example 1 with 3-bromomethylbenzonitrile and, after working up and purification, 25 mg of the title compound was isolated as a colorless oil.

IR (film): 3060, 3040, 3000, 2940, 2860, 2230, 1730, 1605, 1510, 1435, 1230, 1160, 1090, 1030, 895, 830, 795, 730 and 685 cm$^{-1}$.

EXAMPLE 199

(1S,4R,5S(5Z),6R)-7-[4-(4-Fluorophenyl)-6-(3-cyanobenzyloxymethyl)-2-oxabicyclo[2.2.1]hept-5-yl]-5-heptenoic acid 25 mg (50.8 micromol) of the alcohol produced in example 198 was saponified analogously to example 2 and, after working up and purification, 16.8 mg (36.2 micromol, 71%, relative to the initial material in example 198) of the title compound was isolated as a colorless oil.

IR (film): 3600–2400, 3050, 3010, 2930, 2870, 2230, 1725, 1710, 1605, 1515, 1230, 1160, 1120, 1090, 1030, 890, 835, 795 and 690 cm$^{-1}$.

EXAMPLE 200

(1S,4R,5S(5Z),6R,)-7-[4-(4-Fluorophenyl)-6-(3-phenylpropoxymethyl)-2-oxabicyclo[2.2.1]hept-5-yl]-5-heptenoic acid methyl ester 19.4 mg (53.5 micromol) of the alcohol produced in example 120a was reacted analogously to example 1 with 3-bromo-1-phenylpropane and, after working up and purification, 23.4 mg of the title compound was isolated as a colorless oil.

IR (film): 3080, 3060, 3020, 2930, 2860, 1730, 1600, 1510, 1450, 1230, 1160, 1115, 1025, 895, 830, 735 and 700 cm$^{-1}$.

EXAMPLE 201

(1S,4R,5S(5Z),6R)-7-[4-(4-Fluorophenyl)-6-(3-phenyl-propoxymethyl)-2-oxabicyclo[2.2.1]hept-5-yl]-5-heptenoic acid 23.4 mg of the ester produced according to example 200 was saponified analogously to example 2 and, after working up and purification, 17 mg (36.4 micromol, 68%, relative to the initial material in example 200) of the title compound was isolated as a colorless oil.

IR (film): 3700–2400, 3090, 3060, 3030, 3000, 2940, 2870, 1725, 1710, 1515, 1455, 1230, 1160, 1120, 1030, 895, 835, 745 and 700 cm$^{-1}$.

EXAMPLE 202

(1S,4R,5S(5Z),6R)-7-[4-(4-Fluorophenyl)-6-[2-(4-fluorophenoxy)-ethoxymethyl]-2-oxabicyclo[2.2.1-]hept-5-yl]-5-heptenoic acid methyl (or 2-(4-fluorophenoxy)-ethyl)ester 21.4 mg (59 micromol) of the alcohol produced in example 120a was reacted analogously to example 1 with 4-fluorophenoxy-2-ethyl bromide and, after working up, 21 mg of the title compounds was isolated as a colorless oil.

IR (film): 3070, 3050, 3010, 2940, 2870, 1735, 1605, 1505, 1455, 1255, 1220, 1210, 1130, 895, 830 and 745 cm$^{-1}$.

EXAMPLE 203

(1S,4R,5S(5Z),6R)-7-[4-(4-Fluorophenyl)-6-[2-(4-fluorophenoxy)-ethoxymethyl]-2-oxabicyclo[2.2.1-]hept-5-yl]-5-heptenoic acid 21 mg of the ester mixture produced according to example 202 was saponified analogously to example 2 and, after working up and purification, 10.6 mg (21.8 micromol, 37%, relative to the initial material in example 202) of the title compound was isolated as a colorless oil.

IR (film): 3600–2400, 3070, 3050, 3010, 2930, 2870, 1730, 1710, 1605, 1505, 1455, 1250, 1220, 1210, 1130, 895, 830 and 745 cm$^{-1}$.

EXAMPLE 204

(1S,4R,5S(5Z),6R)-7-[4-(4-Fluorophenyl)-6-[2-(methoxycarbonylmethoxy)-ethoxymethyl]-2-oxabicyclo[2.2.1-]hept-5-yl]-5-heptenoic acid methyl ester 2.5 mg (5.5 micromol) of the acid produced according to example 205 was esterified analogously to example 186 and, after removal of the solvent, 2.5 mg (5.5 micromol, 100%) of the title compound was isolated as a colorless oil.

IR (film): 3070, 3050, 3010, 2940, 2880, 1735, 1605, 1505, 1455, 1250, 1215, 1125, 895, 830 and 745 cm$^{-1}$.

EXAMPLE 205

(1S,4R,5S(5Z),6R)-7-[4-(4-Fluorophenyl)-6-[2-(carboxymethoxy)-ethoxymethyl]-2-oxabicyclo[2.2.1]hept-5-yl]-5-heptenoic acid 18.4 mg (50.8 micromol) of the alcohol produced in example 120a was reacted analogously to example 1 with 6-chloro-3-oxahexanoic acid ethyl ester and, after working up and purification, 12.8 mg (28.4 micromol, 56%) of the title compound was isolated as a colorless oil.

IR (film): 3700–2300, 3050, 3010, 2930, 2880, 1720, 1605, 1515, 1430, 1230, 1120, 1030, 895 and 835 cm$^{-1}$.

EXAMPLE 206

(1S,4R,5S(5Z),6R)-7[4-(4-Fluorophenyl)-6-(cyclohexylmethoxyiminomethyl)-2-oxabicyclo[2.2.1]hept-5-yl]-5-heptenoic acid methyl ester 23.8 mg (66 micromol) of the aldehyde produced in example 138b was reacted analogously to example 26 with use of cyclohexylmethoxyamine and, after working up and purification, 21 mg (44.5 micromol, 67%) of the title compound was isolated as a colorless oil.

IR (film): 3050, 3010, 2920, 2850, 1735, 1605, 1510, 1450, 1230, 1160, 1040, 1000, 900, 830 and 735 cm$^{-1}$.

EXAMPLE 207

(1S,4R,5S(5Z),6R)-7-[4-(4-Fluorophenyl)-6-(cyclohexylmethoxyiminomethyl)-2-oxabicyclo[2.2.1]hept-5-yl]-5-heptenoic acid 21 mg (44.5 micromol) of the ester produced according to example 206 was saponified analogously to example 2 and, after working up and purification, 20 mg (43.7 micromol, 98%) of the title compound was isolated as a colorless oil.

IR (film): 3600–2400, 3070, 3050, 3010, 2930, 2850, 2635, 1730, 1710, 1610, 1515, 1450, 1235, 1160, 1040, 1025, 995, 895, 835 and 820 cm$^{-1}$.

EXAMPLE 208

(1S,4R,5S(5Z),6R(3S,4S))-4-[4-(4-Fluorophenyl)-6-(3-hydroxyoct-1-inyl)-2-oxabicyclo[2.2.1]hept-5-yl]-5-heptenoic acid methyl ester 4.1 mg (9.3 micromol) of the acid produced according to example 209 was esterified analogously to example 186 and, after removal of the solvent, 4 mg (8.8 micromol, 95%) of the title compound was isolated as a colorless oil.

IR (film): 3600–3200, 3050, 3020, 2950, 2930, 2860, 2230, 1735, 1610, 1515, 1455, 1410, 1295, 1230, 1165, 1045, 1015, 995, 895 and 830 cm$^{-1}$.

EXAMPLE 209

(1S,4R,5S(5Z),6R(3S,4S))-7-[4-(4-Fluorophenyl)-6-(3-hydroxyoct-1-inyl)-2-oxabicyclo[2.2.1]hept-5yl]-5-heptenoic acid 24 mg (44.6 micromol) of nonpolar alcohol A produced according to example 212 was reacted analogously to example 187 and, after working up and purification, 13.8 mg (31.2 micromol, 70%) of the title compound was isolated as a colorless oil.

IR (film): 3600–2500, 3050, 3010, 2950, 2930, 2870, 2860, 2230, 1710, 1610, 1515, 1455, 1410, 1235, 1160, 1045, 1015, 990, 900 and 830 cm$^{-1}$.

EXAMPLE 210

(1S,4R,5S(5Z),6R(3R,4S))-7-[4-(4-Fluorophenyl)-6-(3-hydroxyoct-1-inyl)-2-oxabicyclo[2.2.1]hept-5-yl]-5-heptenoic acid methyl ester 2.9 mg (6.6 micromol) of the acid produced according to example 211 was esterified analogously to example 186 and, after removal of the solvent, 3 mg (6.6 micromol, 100%) of the title compound was isolated as a colorless oil.

IR (film): 3600–3200, 3050, 3020, 2950, 2930, 2860, 2230, 1735, 1610, 1515, 1450, 1410, 1300, 1230, 1160, 1040, 1010, 995, 895 and 830 cm⁻¹.

EXAMPLE 211

(1S,4R,5S(5Z),6R(3R,4S))-7-[4-(4-Fluorophenyl)-6-(3-hydroxyoct-1-inyl)-2-oxabicyclo[2.2.1]hept-5-yl]-5-heptenoic acid 17 mg (31.6 micromol) of polar alcohol B produced according to example 212 was reacted analogously to example 187 and, after working up and purification, 10.2 mg (23 micromol, 73%) of the title compound was isolated as a colorless oil.

IR (film): 3700–2400, 3070, 3050, 3010, 2950, 2930, 2870, 2860, 2230, 1710, 1610, 1515, 1455, 1410, 1295, 1235, 1160, 1045, 1015, 990, 895 and 830 cm⁻¹.

EXAMPLE 212

(1S,4R,5S(5Z),6R(1E/Z,3S,4S))-7-[4-(4-Fluorophenyl)-6-(2-bromo-3-hydroxy-oct-1-enyl)-2-oxabicyclo[2.2.1-]hept-5-yl]-5-heptenoic acid methyl ester (A) and (1S,4R,5S(5Z),6R(1E/Z,3R,4S))-7-[4-(4-fluorophenyl)-6-(2-bromo-3-hydroxy-oct-1enyl)-2-oxabicyclo[2.2.1-]hept-5-yl]-5-heptenoic acid methyl ester (B)

80 mg (149 micromol) of the unsaturated ketone produced in example 212a was reduced analogously to example 23 and, after working up and purification, 67 mg (125 micromol, 84%) of a mixture of both title compounds was isolated as a colorless oil.

IR (film): 3600–3300, 3070, 3050, 3010, 2960, 2930, 2860, 1735, 1605, 1515, 1455, 1410, 1305, 1235, 1160, 1040, 995, 940, 895, 835 and 725 cm⁻¹.

The chromatographic separation yielded 37 mg (68.8 micromol, 46%) of the more nonpolar alcohol, to which structure A was assigned, as well as 27 mg (50.2 micromol, 34%) of the more polar alcohol, to which structure B was assigned.

EXAMPLE 212a (1S,4R,5S(5Z),6R(1E,Z,4S))-7-[4-(4-Fluorophenyl)-6-(2-bromo-3-oxo-oct-1-enyl)-2-oxabicyclo[2.2.1]hept-5-yel]-5-heptenoic acid methyl ester 80.7 mg (224 micromol) of the aldehyde produced in example 138b was reacted analogously to example 190a with use of dimethyl-(2-oxo-heptyl)-phosphonate and, after working up and purification, 80 mg (149 micromol, 67%) of the title compound was isolated as a colorless oil.

IR (film): 3070, 3050, 3010, 2950, 2930, 2870, 1735, 1685, 1600, 1510, 1450, 1435, 1365, 1305, 1230, 1160, 1045, 990, 900 and 830 cm⁻¹.

EXAMPLE 213

(1S,4R,5S(5Z),6R(1E/Z,3S,4S))-7-(4-(4-Fluorophenyl)-6-(2-bromo-3-hydroxy-oct-1-enyl)-2-oxabicyclo[2.2.1]hept-5-yl]-5-heptenoic acid:

12.6 mg (23.4 micromol) of nonpolar ester A produced according to example 212 was saponified analogously to example 2 and, after working up and purification, 12 mg (22.9 micromol, 98%) of the title compound was isolated as a colorless oil.

IR (film): 3600–2400, 3050, 3010, 2950, 2930, 2870, 2860, 1710, 1605, 1515, 1455, 1410, 1305, 1235, 1160, 1045, 995, 895, 830 and 725 cm⁻¹.

EXAMPLE 214

(1R,4S,5R(5Z),6S)-7-[4-(4-Fluorophenyl)-6-(4-cyanobenzyloxymethyl)-2-oxabicyclo[2.2.1]hept-5-yl]-5-heptenoic acid 19 mg of the ester mixture produced according to example 214a was saponified analogously to example 2 and, after working up and purification, 14.8 mg (31.9 micromol, 72%, relative to the initial material in example 214a) of the title compound was isolated as a colorless oil.

IR (film): 3600–2400, 3070, 3050, 3010, 2930, 2870, 2230, 1725, 1710, 1610, 1515, 1410, 1230, 1160, 1125, 995, 930, 920, 895, 835 and 820 cm⁻¹.

EXAMPLE 214a (1R,4S,5R(5Z),6S)-7-[4-(4-Fluorophenyl)-6-(4-cyanobenzyloxymethyl)-2-oxabicyclo[2.2.1]hept-5-yl]-5-heptenoic acid methyl (or 4-cyanobenzyl) ester 16.1 mg (44.4 micromol) of the alcohol produced in example 17a was reacted analogously to example 1 with 4-bromomethylbenzonitrile and, after working up and purification, 19 mg of the title compounds was isolated as a colorless oil.

IR (film): 3050, 3040, 3010, 2930, 2860, 2220, 1730, 1605, 1510, 1435, 1360, 1225, 1160, 1120, 1090, 1030, 895, 830 and 815 cm⁻¹.

EXAMPLE 215

(1S,4R,5S(5Z),6R(1E/Z,3R,4S))-7-[4-(4-Fluorophenyl)-6-(2-bromo-3-hydroxy-oct-1-enyl)-2-oxabicyclo[2.2.1]hept-5-yl]-5-heptenoic acid 8.8 mg (16.4 micromol) of polar ester B produced according to example 212 was saponified analogously to example 2 and, after working up and purification, 8.3 mg (15.9 micromol, 97%) of the title compound was isolated as a colorless oil.

IR (film); 3600–2400, 3050, 3010, 2950, 2930, 2870, 2860, 1710, 1610, 1515, 1455, 1410, 1300, 1235, 1165, 1040, 995, 940, 895, 835 and 725 cm⁻¹.

EXAMPLE 216

(1S,4R,5S(5Z),6R)-7-[4-(4-Fluorophenyl)-6-[(1E,3S,4RS)-3-hydroxy-4,7-dimethyl-octa-1-in-6-enyl]-2-oxabicyclo[2.2.1]hept-5-yl]-5-heptenoic acid methyl ester 3.3 mg (7 micromol) of the acid produced according to example 217 was esterified analogously to example 186 and, after removal of the solvent, 3.2 mg (6.6 micromol, 94%) of the title compound was isolated as a colorless oil.

IR (film): 3050, 3010, 2960, 2930, 2870, 2230, 1735, 1605, 1515, 1455, 1235, 1160, 1040, 1020, 1000, 900 and 830 cm⁻¹.

EXAMPLE 217

(1S,4R,5S(5Z),6R)-7-[4-(4-Fluorophenyl)-6-[(1E,3S,4RS)-3-hydroxy-4,7-dimethyl-octa-1-in-6-enyl]-2-oxabicyclo[2.2.1]hept-5-yl]-5-heptenoic acid 27 mg (47.9 micromol) of nonpolar alcohol A produced according to example 220 was reacted analogously to example 187 and, after working up and purification, 18 mg (38.4 micromol, 80%) of the title compound was isolated as a colorless oil.

IR (film): 3600–2500, 3070, 3050, 3010, 2960, 2930, 2880, 2230, 1710, 1610, 1515, 1455, 1235, 1165, 1040, 1020, 990, 940, 900 and 830 cm$^{-1}$.

EXAMPLE 218

(1S,4R,5S(5Z),6R)-7-[4-(4-Fluorophenyl)-6[(1E,3R,4RS)-3-hydroxy-4,7-dimethyl-octa-1-in-6-enyl]-2-oxabicyclo[2.2.1]hept-5-yl]-5-heptenoic acid methyl ester 3 mg (6.4 micromol) of the acid produced according to example 219 was esterified analogously to example 186 and, after removal of the solvent, 3 mg (6.2 micromol, 97%) of the title compound was isolated as a colorless oil.

IR (film): 3600–3200, 3050, 3010, 2960, 2930, 2880, 2230, 1730, 1610, 1515, 1455, 1410, 1375, 1300, 1265, 1235, 1160, 1040, 1020, 995, 940, 895, 830 and 815 cm$^{-1}$.

EXAMPLE 219

(1S,4R,5S(5Z),6R)-7-[4-(4-Fluorophenyl)-6-[(1E,3R,4RS)-3-hydroxy-4,7-dimethyl-octa-1-in-6-enyl]-2-oxabicyclo]2.2.1]hept-5-yl]-5-heptenoic acid 18 mg (31.9 micromol) of polar alcohol B produced according to example 220 was reacted analogously to example 187 and, after working up and purification, 10.6 mg (22.6 micromol, 71%) of the title compound was isolated as a colorless oil.

IR (film): 3700–2400, 3050, 3010, 2960, 2930, 2880, 2230, 1710, 1610, 1515, 1455, 1410, 1375, 1295, 1265, 1235, 1160, 1040, 1020, 990, 940, 895, 830 and 815 cm$^{-1}$.

EXAMPLE 220

(1S,4R,5S(5Z),6R)-7-[4-(4-Fluorophenyl)-6-[(1E/Z,3S,4RS)-2-bromo-3-hydroxy-4,7-dimethyl-oct-1,6-dienyl]-2-oxabicyclo[2.2.1]hept-5-yl]-5-heptenoic acid methyl ester (a) and
(1S,4R,5S(5Z),6R)-7-[4-(4-fluorophenyl)-6-[(1E/Z,3R,4RS)-2-bromo-3-hydroxy-4,7-dimethyl-oct-1,6-dienyl]-2-oxabicyclo[2.2.1]hept-5-yl]-5-heptenoic acid methyl ester (B)

50 mg (89 micromol) of the unsaturated ketone produced in example 220a was reduced analogously to example 23 and, after working up and purification, 48 mg (85.2 micromol, 96%) of a mixture of both title compounds was isolated as a colorless oil.

IR (film): 3600–3200, 3050, 3010, 2960, 2920, 2870, 1730, 1605, 1510, 1450, 1435, 1375, 1230, 1160, 1040, 990, 895, 830 and 735 cm$^{-1}$.

The chromatographic separation yielded 27 mg (47.9 micromol, 54%) of the more nonpolar alcohol, to which structure A was assigned, as well as 18 mg (31.9 micromol, 36%) of the more polar alcohol, to which structure B was assigned.

EXAMPLE 220a (1S,4R,5S(5Z),6R)-7-[4-(4-Fluorophenyl)-6-[(1E/Z,4RS)-2-bromo-3-oxo-4,7-dimethyl-oct-1,6-dienyl]-2-oxabicyclo[2.2.1]hept-5-yl]-5-heptenoic acid methyl ester 67.9 mg (188 micromol) of the aldehyde produced in example 138b was reacted analogously to example 190a with use of dimethyl-(2-oxo-3-(RS),6-dimethyl-hept-5-enyl)-phosphonate and, after working up and purification, 50 mg (89 micromol, 47%) of the title compound was isolated as a colorless oil.

IR (film): 3070, 3050, 3010, 2970, 2930, 2870, 1735, 1680, 1600, 1510, 1450, 1435, 1370, 1305, 1230, 1160, 1045, 985, 900 and 835 cm$^{-1}$.

EXAMPLE 221

(1S,4R,5S(5Z),6R)-7-[4-(4-Fluorophenyl)-6-[(1E/Z,3R,4RS)-2-bromo-3-hydroxy-4,7-dimethyl-oct-1,6-dienyl]-2-oxabicyclo[2.2.1]hept-5-yl]-5-heptenoic acid 12 mg (21.3 micromol) of polar ester B produced according to example 220 was saponified analogously to example 2 and, after working up and purification, 9.3 mg (16.9 micromol, 79%) of the title compound was isolated as a colorless oil.

IR (film): 3600–2400, 3050, 3010, 2950, 2920, 2870, 1710, 1605, 1510, 1455, 1420, 1375, 1230, 1160, 1045, 995, 895, 830 and 730 cm$^{-1}$.

EXAMPLE 222

(1S,4R,5S(5Z),6R)-7-(4-Fluorophenyl)-6-[(1E/Z,3S,4RS)-2-bromo-3-hydroxy-4,7-dimethyl-oct-1,6-dienyl]-2-oxabicyclo[2.2.1]hept-5-yl]-5-heptenoic acid 13.7 mg (24.3 micromol) of nonpolar ester A produced according to example 220 was saponified analogously to example 2 and, after working up and purification, 11.8 mg (21.5 micromol, 88%) of the title compound was isolated as a colorless oil.

IR (film): 3600–2400, 3050, 3010, 2950, 2930, 2870, 1710, 1605, 1515, 1455, 1420, 1305, 1230, 1160, 1040, 995, 895, 830 and 730 cm$^{-1}$.

EXAMPLE 223

(1S,4R,5S(5Z),6R)-7-[4-(4-Fluorophenyl)-6-[(3S)-3-hydroxy-3-cyclohexyl-prop-1-inyl]-2-oxabicyclo[2.2.1-]hept-5-yl]-5-heptenoic acid methyl ester 3.5 mg (7.7 micromol) of the acid produced according to example 224 was esterified analogously to example 186 and, after removal of the solvent, 3.5 mg (7.5 micromol, 97%) of the title compound was isolated as a colorless oil.

IR (film): 3600–3200, 3050, 3010, 2940, 2860, 2230, 1735, 1605, 1510, 1445, 1265, 1230, 1160, 1015, 995, 895 and 835 cm$^{-1}$.

EXAMPLE 224

(1S,4R,5S(5Z),6R)-7-[4-(4-Fluorophenyl)-6-[(3S)-3-hydroxy-3-cyclohexyl-prop-1-inyl]-2-oxabicyclo[2.2.1-]hept-5-yl]-5-heptenoic acid 29.6 mg (53.9 micromol) of nonpolar alcohol A produced according to example 227 was reacted analogously to example 187 and, after working up and purification, 13.8 mg (30.4 micromol, 56%) of the title compound was isolated as a colorless oil.

IR (film): 3600–2400, 3050, 3010, 2930, 2850, 2230, 1710, 1605, 1510, 1450, 1265, 1230, 1160, 1015, 990, 895, 830 and 735 cm$^{-1}$.

EXAMPLE 225

(1S,4R,5S(5Z),6R)-7-[4-(4-Fluorophenyl)-6-[(3R)-3-hydroxy-3-cyclohexyl-prop-1-inyl]-2-oxabicyclo[2.2.1-]hept-5-yl]-5-heptenoic acid methyl ester 2.8 mg (6.2 micromol) of the acid produced according to example 226 was esterified analogously to example 185 and, after removal of the solvent, 2.9 mg (6.2 micromol, 100%) of the title compound was isolated as a colorless oil.

IR (film): 3600–3200, 3070, 3050, 3010, 2940, 2850, 2230, 1735, 1605, 1515, 1450, 1410, 1295, 1235, 1160, 1045, 1010, 990, 940, 895 and 830 cm$^{-1}$.

EXAMPLE 226

(1S,4R,5S(5Z),6R)-7-[4-(4-Fluorophenyl)-6-[(3R)-3-hydroxy-3-cyclohexyl-prop-1-inyl]-2-oxabicyclo[2.2.1-]hept-5-yl]-5-heptenoic acid 23.5 mg (42.8 micromol) of polar alcohol B produced according to example 227 was reacted analogously to example 187 and, after working up and purification, 11.5 mg (25.3 micromol, 59%) of the title compound was isolated as a colorless oil.

IR (film): 3700–2400, 3070, 3050, 3010, 2930, 2850, 2230, 1710, 1610, 1515, 1450, 1410, 1295, 1235, 1160, 1045, 1015, 990, 940, 895, 830 and 815 cm$^{-1}$.

EXAMPLE 227

(1S,4R,5S(5Z),6R)-7-[4-(4-Fluorophenyl-6-[(1E/Z,3S)-2-bromo-3-hydroxy-3-cyclohexyl-prop-1-enyl]-2-oxabicyclo[2.2.1]hept-5-yl]-5-heptenoic acid methyl ester (A) and
(1S,4R,5S(5Z),6R)-7-[4-(4-fluorophenyl)-6-[(1E/Z,3R)-2-bromo-3-hydroxy-3-cyclohexyl-prop-1-enyl]-2-oxabicyclo[2.2.1]hept-5-yl]-5-heptenoic acid methyl ester (B)

60 mg (110 micromol) of the unsaturated ketone produced in example 227 a was reduced analogously to example 23 and, after working up and purification, 57.8 mg (105 micromol, 96%) of a mixture of both title compounds was isolated as a colorless oil.

IR (film): 3600–3200, 3050, 3000, 2930, 2850, 1730, 1605, 1510, 1450, 1230, 1160, 990, 895, 830 and 735 cm$^{-1}$.

The chromatographic separation yielded 29.6 mg (53.9 micromol, 49%) of the more nonpolar alcohol, to which structure A was assigned, as well as 23.5 mg (42.8 micromol, 39%) of the more polar alcohol, to which structure B was assigned.

EXAMPLE 227a (1S,4R,5S(5Z),6R)-7-[4-(4-Fluorophenyl)-6-[(1E/Z)-2-bromo-3-oxo-3-cyclohexyl-prop-1-enyl]-2-oxabicyclo[2.2.1]hept-5-yl]-5-heptenoic acid methyl ester 70.7 mg (196 micromol) of the aldehyde produced in example 138b was reacted analogously to example 190a with use of dimethyl-(2-oxo-2-cyclohexyl-ethyl)-phosphonate and, after working up and purification, 60 mg (110 micromol, 56%) of the title compound was isolated as a colorless oil.

IR (film): 3050, 3000, 2930, 2850, 1735, 1680, 1600, 1510, 1445, 1435, 1370, 1305, 1235, 1160, 1045, 985, 900 and 830 cm$^{-1}$.

EXAMPLE 228

(1S,4R,5S(5Z),6R)-7-[4-(4-Fluorophenyl)-6-[(1E/Z,3R)-2-bromo-3-hydroxy-3-cyclohexyl-prop-1-enyl]-2-oxabicyclo[2.2.1]hept-5-yl]-5-heptenoic acid 14.7 mg (26.7 micromol) of polar ester B produced according to example 227 was saponified analogously to example 2 and, after working up and purification, 12.6 mg (23.5 micromol, 88%) of the title compound was isolated as a colorless oil.

IR (film): 3600–2400, 3070, 3040, 3010, 2930, 2850, 1710, 1600, 1510, 1450, 1435, 1230, 1160, 1045, 985, 900, 830 and 735 cm$^{-1}$.

EXAMPLE 229

(1S,4R,5S(5Z),6R)-7-[4-(4-Fluorophenyl)-6-[(1E/Z,3R)-2-bromo-3-hydroxy-3-cyclohexyl-prop-1-enyl]-2-oxabicyclo[2.2.1]hept-5-yl]-5-heptenoic acid 13.4 mg (24.4 micromol) of nonpolar ester A produced according to example 227 was saponified analogously to example 2 and, after working up and purification, 11.6 mg (21.7 micromol, 89%) of the title compound was isolated as a colorless oil.

IR (film): 3600–2400, 3040, 3010, 2930, 2850, 1710, 1605, 1510, 1450, 1435, 1225, 1160, 1040, 995, 895, 830 and 735 cm$^{-1}$.

EXAMPLE 230

(1S,4R,5S(5Z),6S)-7-[4-(4-Fluorophenyl)-6-[(1E,3S)-3-hydroxy-3-cyclohexyl-prop-1-enyl]-2-oxabicyclo[2.2.1-]hept-5-yl]-5-heptenoic acid methyl ester (A) and
(1S,4R,5S(5Z),6S)-7-[4-(4-fluorophenyl)-6-[(1E,3R)-3-hydroxy-3-cyclohexyl-prop-1-enyl]-2-oxabicyclo[2.2.1-]hept-5-yl]-5-heptenoic acid methyl ester (B)

39 mg (83.2 micromol) of the unsaturated ketone produced in example 230a was reduced analogously to example 23 and, after working up and purification, 33 mg (70 micromol, 84%) of a mixture of both title compounds was isolated as a colorless oil.

IR (film): 3600–3200, 3040, 3010, 2920, 2850, 1730, 1605, 1510, 1450, 1230, 1160, 995, 970, 895, 835 and 735 cm$^{-1}$.

The chromatographic separation yielded 19 mg (40.4 micromol, 49%) of the more nonpolar alcohol, to which structure A was assigned, as well as 14 mg (29.7 micromol, 36%) of the more polar alcohol, to which structure B was assigned.

EXAMPLE 230a (1S,4R,5S(5Z),6S)-7-[4-(4-Fluorophenyl)-6-[(1E)-3-oxo-3-cyclohexyl-prop-1-enyl]-2-oxabicyclo[2.2.1]hept-5-yl]-5-heptenoic acid methyl ester 50.3 mg (140 micromol) of the aldehyde produced in example 138b was reacted analogously to example 23a with use of dimethyl(2-oxo-2-cyclohexyl-ethyl)-phosphonate and, after working up and purification, 39 mg (83.2 micromol, 60%) of the title compound was isolated as a colorless oil.

IR (film): 3070, 3050, 3010, 2930, 2850, 1735, 1690, 1660, 1620, 1510, 1445, 1370, 1310, 1230, 1160, 995, 900 and 835 cm$^{-1}$.

EXAMPLE 231

(1S,4R,5S(5Z),6S)-7-[4-(4-Fluorophenyl)-6-[(1E,3S)-3-hydroxy-3-cyclohexyl-prop-1-enyl]-2-oxabicyclo[2.2.1-]hept-5-yl]-5-heptenoic acid 19 mg (40.4 micromol) of nonpolar ester A produced according to example 230 was saponified analogously to example 2 and, after working up and purification, 18 mg (39.4 micromol, 98%) of the title compound was isolated as waxy material.

IR (KBr): 3700–2300, 3050, 3010, 2930, 2860, 1710, 1610, 1515, 1450, 1235, 1160, 995, 970, 895 and 835 cm$^{-1}$.

EXAMPLE 232

(1S,4R,5S(5Z),6S)-7-[4-(4-Fluorophenyl)-6-[(1E,3R)-3-hydroxy-3-cyclohexyl-prop-1-enyl]-2-oxabicyclo[2.2.1]hept-5-yl]-5-heptenoic acid 14 mg (29.7 micromol) of polar ester B produced according to example 230 was saponified analogously to example 2 and, after working up and purification, 12 mg (26.3 micromol, 88%) of the title compound was isolated as a colorless oil.

IR (film): 3700–2400, 3050, 3010, 2930, 2850, 1710, 1610, 1515, 1450, 1410, 1300, 1235, 1160, 995, 970, 895 and 835 cm$^{-1}$.

EXAMPLE 233

(1S,4R,5S(5Z),6R)-7-[4-(4-Fluorophenyl)-6-[3(S)-hydroxy-4,4-trimethylene-nona-1,7-diinyl]-2-oxabicyclo[2.2.1]hept-5-yl]-5-heptenoic acid methyl ester 2.6 mg (5.3 micromol) of the acid produced according to example 234 was esterified analogously to example 186 and, after removal of the solvent, 2.3 mg (4.5 micromol, 86%) of the title compound was isolated as a colorless oil.

IR (film): 3600–3200, 3040, 3000, 2980, 2940, 2870, 2230, 1735, 1610, 1515, 1450, 1410, 1300, 1230, 1160, 1040, 1015, 995, 895 and 835 cm$^{-1}$.

EXAMPLE 234

(1S,4R,5S(5Z),6R)-7-[4-(4-Fluorophenyl)-6-[3(S)-hydroxy-4,4-trimethylene-nona-1,7-diinyl]-2-oxabicyclo[2.2.1]hept-5-yl]-5-heptenoic acid 17 mg (28.9 micromol) of nonpolar alcohol A produced according to example 237 was reacted analogously to example 187 and, after working up and purification, 8.7 mg (17.7 micromol, 61%) of the title compound was isolated as a colorless oil.

IR (film): 3600–2400, 3040, 3020, 2980, 2940, 2880, 2230, 1710, 1610, 1515, 1450, 1410, 1295, 1230, 1160, 1040, 1015, 995, 970, 895 and 835 cm$^{-1}$.

EXAMPLE 235

(1S,4R,5S(5Z),6R)-7-[4-(4-Fluorophenyl)-6-[3(S)-hydroxy-4,4-trimethylene-nona-1,7-diinyl]-2-oxabicyclo[2.2.1]hept-5-yl]-5-heptenoic acid methyl ester 2.2 mg (4.5 micromol) of the acid produced according to example 236 was esterified analogously to example 186 and, after removal of the solvent, 2.2 mg (4.3 micromol, 96%) of the title compound was isolated as a colorless oil.

IR (film): 3600–3200, 3050, 2980, 2940, 2870, 2230, 1735, 1610, 1515, 1450, 1435, 1410, 1300, 1235, 1160, 1040, 1020, 995, 895 and 835 cm$^{-1}$.

EXAMPLE 236

(1S,4R,5S(5Z),6R)-7-[4-(4-Fluorophenyl)-6-[3(S)-hydroxy-4,4-trimethylene-nona-1,7-diinyl]-2-oxabicyclo[2.2.1]hept-5-yl]-5-heptenoic acid 9.2 mg (15.7 micromol) of polar alcohol B produced according to example 237 was reacted analogously to example 187 and, after working up and purification, 4.8 mg (9.7 micromol, 62%) of the title compound was isolated as a colorless oil.

IR (film): 3600–2400, 3040, 2980, 2940, 2870, 2230, 1710, 1610, 1515, 1445, 1435, 1410, 1295, 1235, 1160, 1035, 1015, 995, 970, 895 and 835 cm$^{-1}$.

EXAMPLE 235

(1S,4R,5S(5Z),6R)-7-[4-(4-Fluorophenyl)-6-[(1E/Z,3S)-2-bromo-3-hydroxy-4,4-trimethylene-non-1-en-7-inyl]-2-oxabicyclo[2.2.1]hept-5-yl]-5-heptenoic acid methyl ester (A) and
(1S,4R,5S(5Z),6R)-7-[4-(4-fluorophenyl)-6-[(1E/Z,3R)-2-bromo-3-hydroxy-4,4-trimethylene-non-1-en-7-inyl]-2-oxabicyclo[2.2.1]hept-5-yl]-5-heptenoic acid methyl ester (B)

32 mg (54.6 micromol) of the unsaturated ketone produced in example 237a was reduced analogously to example 23 and, after working up and purification, 28.5 mg (48.5 micromol, 89%) of a mixture of both title compounds was isolated as a colorless oil.

IR (film): 3600–3200, 3050, 2940, 2860, 1730, 1605, 1510, 1435, 1230, 1160, 1040, 1015, 990, 895 and 835 cm$^{-1}$.

The chromatographic separation yielded 17 mg (28.9 micromol, 53%) of the more nonpolar alcohol, to which structure A was assigned, as well as 9.2 mg (15.7 micromol, 29%) of the more polar alcohol, to which structure B was assigned.

EXAMPLE 237a (1S,4R,5S(5Z),6R)-7-[4-(4-Fluorophenyl)-6-[(1E/Z)-2-bromo-3-oxo-4,4-trimethylene-non-1-en-7-inyl]-2-oxabicyclo[2.2.1]hept-5-yl]-5-heptenoic acid methyl ester 65.1 mg (181 micromol) of the aldehyde produced in example 138b was reacted analogously to example 190a with use of dimethyl-(2-oxo-3,3-trimethylene-oct-6-inyl)-phosphonate and, after working up and purification, 32 mg (54.6 micromol, 30%) of the title compound was isolated as a colorless oil.

IR (film): 3050, 2940, 2870, 1735, 1675, 1605, 1515, 1435, 1230, 1160, 1045, 900 and 835 cm$^{-1}$.

EXAMPLE 238

(1S,4R,5S(5Z),6R)-7-[4-(4-Fluorophenyl)-6-[(1E/Z,3R)-2-bromo-3-hydroxy-4,4-trimethylene-non-1-en-7-inyl]-2-oxabicyclo[2.2.1]hept-5-yl]-5-heptenoic acid 9.9 mg (16.8 micromol) of polar ester B produced according to example 237 was saponified analogously to example 2 and, after working up and purification, 8.3 mg (14.5 micromol, 86%) of the title compound was isolated as a colorless oil.

IR (film): 3600–2400, 3050, 3010, 2950, 2930, 2860, 1710, 1605, 1510, 1440, 1230, 1160, 1040, 1015, 990, 900 and 835 cm$^{-1}$.

EXAMPLE 239

(1S,4R,5S(5Z),6R)-7-[4-(4-Fluorophenyl)-6-[(1E/Z,3S)-2-bromo-3-hydroxy-4,4-trimethylene-non-1-en-7inyl]-2-oxabicyclo-[2.2.1]hept-5-yl]-5-heptenoic acid 10.5 mg (17.9 micromol) of nonpolar ester A produced according to example 237 was saponified analogously to example 2 and, after working up and purification, 8.8 mg (15.3 micromol, 86%) of the title compound was isolated as a colorless oil.

IR (film): 3600–2300, 3070, 3050, 3010, 2940, 2860, 1715, 1605, 1515, 1440, 1235, 1160, 1040, 1010, 990, 895 and 835 cm$^{-1}$.

EXAMPLE 240

(1S,4R,5S(5Z),6R)-7-[4-(4-Fluorophenyl)-6-(1-naphthylmethyloxymethyl)-2-oxabicyclo[2.2.1]hept-5-yl]-5-heptenoic acid methyl (or 1-naphthylmethyl) ester 16.4 mg (45.2 micromol) of the alcohol produced in example 120a was reacted analogously to example 1 with 1-chloromethylnaphthyl and, after working up and purification, 22.3 mg of the title compounds was isolated as a colorless oil.

IR (film); 3070, 3050, 3010, 2930, 2870, 1735, 1605, 1595, 1515, 1230, 1160, 1115, 1095, 1075, 1030, 970, 895, 835, 800, 795 and 775 cm$^{-1}$.

EXAMPLE 241

(1S,4R,5S(5Z),6R)-7-[4-(4-Fluorophenyl)-6-(1-naphthylmethyloxymethyl)-2-oxabicyclo[2.2.1]hept-5-yl]-5-heptenoic acid 22.3 mg of the ester mixture produced according to example 240 was saponified analogously to example 2 and, after working up and purification, 12 mg (24.6 micromol, 54%, relative to the initial material in example 240) of the title compound was isolated as a colorless oil.

IR (film): 3600–2500, 3070, 3050, 3010, 2930, 2870, 1730, 1710, 1605, 1595, 1515, 1235, 1160, 1115, 1095, 1075, 1030, 975, 895, 835, 800, 795 and 775 cm$^{-1}$.

EXAMPLE 242

(1S,4R,5S(5Z),6R)-7-[4-(4-Fluorophenyl)-6-(2-naphthylmethyloxymethyl)-2-oxabicyclo[2.2.1]hept-5-yl]-5-heptenoic acid methyl (or 1-naphthylmethyl) ester 16.9 mg (46.6 micromol) of the alcohol produced in example 120a was reacted analogously to example 1 with 2-bromomethylnaphthyl and, after working up and purification, 23.4 mg of the title compounds was isolated as a colorless oil.

IR (film): 3040, 3010, 2930, 2870, 1735, 1605, 1510, 1230, 1160, 1125, 1090, 890, 855, 830, 815 and 750 cm$^{-1}$.

EXAMPLE 243

(1S,4R,5S(5Z),6R)-7-[4-(4-Fluorophenyl)-6-(2-naphthylmethyloxymethyl)-2-oxabicyclo[2.2.1]hept-5-yl]-5-heptenoic acid 23.4 mg of the ester mixture produced according to example 242 was saponified analogously to example 2 and, after working up and purification, 20 mg (40.9 micromol, 88%, relative to the initial material in example 242) of the title compound was isolated as a colorless oil.

IR (film): 3600–2400, 3050, 3010, 2930, 2870, 1730, 1705, 1605, 1515, 1230, 1160, 1125, 1090, 895, 855, 830, 820 and 750 cm$^{-1}$.

EXAMPLE 244

(1S,4R,5S(5Z),6R)-7-[4-(4-Fluorophenyl)-6-(2,4-bistrifluoromethylbenzyloxymethyl)-2-oxabicyclo[2.2.1]hept-5-yl]-5-heptenoic acid methyl (or 2,4-bis-trifluoromethylbenzyl) ester 17.6 mg (48.5 micromol) of the alcohol produced in example 120a was reacted analogously to example 1 with 2,4-bistrifluoromethylbenzyl bromide and, after working up and purification, 29.6 of the title compounds was isolated as a colorless oil.

IR (film): 3070, 3050, 3010, 2930, 2870, 1735, 1625, 1605, 1515, 1345, 1300, 1275, 1235, 1175, 1130, 1085, 1055, 910, 900 and 835 cm$^{-1}$.

EXAMPLE 245

(1S,4R,5S(5Z),6R)-7-[4-(4-Fluorophenyl)-6-(2,4-bistrifluoromethylbenzyloxymethyl)-2-oxabicyclo[2.2.1]hept-5-yl]-5-heptenoic acid 29.6 mg of the ester mixture produced according to example 244 was saponified analogously to example 2 and, after working up and purification, 22 mg (38.3 micromol, 79%, relative to the initial material in example 242) of the title compound was isolated as a colorless oil.

IR (film): 3600–2400, 3050, 3000, 2930, 2870, 1730, 1710, 1630, 1610, 1515, 1345, 1300, 1275, 1235, 1175, 1130, 1085, 1055, 910, and 835 cm$^{-1}$.

EXAMPLE 246

(1S,4R,5S(5Z), 6R)-7-[4-(4-Fluorophenyl)-6-3,5-bistrifluoromethylbenzyloxymethyl)-2-oxabicyclo[2.2.1]hept-5-yl]-5-heptenoic acid methyl (or 3,5-bis-trifluoromethylbenzyl) ester 17.7 mg (48.8 micromol) of the alcohol produced in example 120a was reacted analogously to example 1 with 3,5-bistrifluoromethylbenzyl bromide and, after working up and purification, 26.5 of the title compounds was isolated as a colorless oil.

IR (film): 3050, 3000, 2940, 2870, 1735, 1620, 1605, 1510, 1455, 1435, 1380, 1355, 1280, 1230, 1175, 1130, 900, 885, 835 705 and 680 cm$^{-1}$.

EXAMPLE 247

(1S,4R,5S(5Z),6R)-7-[4-(4-Fluorophenyl)-6-(3,5-bistrifluoromethylbenzyloxymethyl)-2-oxabicyclo[2.2.1]hept-5-yl]-5-heptenoic acid 26.5 mg of the ester mixture produced according to example 246 was saponified analogously to example 2 and, after working up and purification, 23 mg (40 micromol, 82%, relative to the initial material in example 246) of the title compound was isolated as a colorless oil.

IR (film): 3700–2400, 3050, 3010, 2930, 2870, 1730, 1710, 1625, 1610, 1515, 1385, 1355, 1280, 1235, 1175, 1135, 890, 845, 835, 820, 705 and 685 cm$^{-1}$.

EXAMPLE 248

(1S,4R,5S(5Z),6R)-7-[4-(4-Fluorophenyl)-6-(3-methylbenzyloxymethyl)-2-oxabicyclo[2.2.1]hept-5-yl]-5-heptenoic acid methyl (or 3-methylbenzyl) ester 16.9 mg (46.6 micromol) of the alcohol produced in example 120a was reacted analogously to example 1 with 3-methylbenzyl bromide and, after working up and purification, 23.7 mg of the title compounds was isolated as a colorless oil.

IR (film): 3050, 3010, 2930, 2870, 1735, 1605, 1595, 1515, 1235, 1160, 1115, 1090, 1025, 975, 895, 835, 785 and 700 cm$^{-1}$.

EXAMPLE 249

(1S,4R,5S(5Z),6R)-7-[4-(4-Fluorophenyl)-6-(3-methylbenzyloxymethyl)-2-oxabicyclo[2.2.1]hept-5-yl]-5-heptenoic acid 23.7 mg of the ester mixture produced according to example 248 was saponified analogously to example 2 and, after working up and purification, 17.4 mg (38.4 micromol, 82%, relative to the initial material in example 248) of the title compound was isolated as a colorless oil.

IR (film); 3700–2400, 3050, 3010, 2930, 2870, 1730, 1710, 1610, 1595, 1515, 1235, 1160, 1115, 1090, 1030, 975, 895, 835, 785 and 695 cm$^{-1}$.

EXAMPLE 250

(1S,4R,5S(5Z),6R)-7-[4-(4-Fluorophenyl)-6-(4-methylbenzyloxymethyl)-2-oxabicyclo[2.2.1]hept-5-yl]-5-heptenoic acid methyl (or 4-methylbenzyl) ester 18.5 mg (51 micromol) of the alcohol produced in example 120a was reacted analogously to example 1 was 4-methylbenzyl bromide and, after working up and purification, 24.2 mg of the title compounds was isolated as a colorless oil.

IR (film): 3050, 3000, 2950, 2930, 2870, 1735, 1610, 1595, 1515, 1455, 1410, 1360, 1295, 1230, 1160, 1120, 1090, 1030, 1020, 970, 895, 830, 815 and 805 cm$^{-1}$.

EXAMPLE 251

(1S,4R,5S(5Z),6R)-7-[4-(4-Fluorophenyl)-6-(4-methylbenzyloxymethyl)-2-oxabicyclo[2.2.1]hept-5-yl]-5-heptenoic acid 24.2 mg of the ester mixture produced according to example 250 was saponified analogously to example 2 and, after working up and purification, 19.9 mg (44 micromol, 86%, relative to the initial material in example 250) of the title compound was isolated as a colorless oil.

IR (film): 3600–2400, 3050, 3010, 2940, 2870, 1730, 1710, 1610, 1515, 1455, 1410, 1360, 1300, 1230, 1160, 1115, 1090, 1030, 1020, 970, 895, 830, 820 and 805 cm$^{-1}$.

EXAMPLE 252

(1S,4R,5S(5Z),6R)-7-[4-(4-Fluorophenyl)-6-(4-benzyloxy)-benzyloxymethyl)-2-oxabicyclo[2.2.1]hept-5-yl]-5-heptenoic acid methyl (or 4-(benzyloxy)benzyl) ester 21.4 mg (59 micromol) of the alcohol produced in example 120a was reacted analogously to example 1 with 4-benzyloxybenzyl chloride and, after working up and purification, 32 mg of the title compounds was isolated as a colorless oil.

IR (film): 3060, 3030, 3010, 2930, 2860, 1735, 1610, 1585, 1515, 1450, 1300, 1235, 1165, 1115, 1090, 1080, 1025, 895, 830, 820, 740 and 700 cm$^{-1}$.

EXAMPLE 253

(1S,4R,5S(5Z),6R)-7-[4-(4-Fluorophenyl)-6-(4-benzyloxy)-benzyloxymethyl)-2-oxabicyclo[2.2.1]hept-5-yl]-5-heptenoic acid 32 mg of the ester mixture produced according to example 252 was saponified analogously to example 2 and, after working up and purification, 25.8 mg (47.4 micromol, 80%, relative to the initial material in example 252) of the title compound was isolated as a colorless oil.

IR (film): 3600–2400, 3060, 3030, 3000, 2930, 2860, 1730, 1705, 1610, 1585, 1510, 1450, 1300, 1235, 1170, 1160, 1115, 1090, 1080, 1025, 895, 830, 820, 740 and 695 cm$^{-1}$.

EXAMPLE 254

(1S,4R,5S(5Z),6S)-7-[4-(2-Phenylethinyl)-6[3(S)-hydroxy-1(E)-octenyl]-2-oxabicyclo[2.2.1]hept-5-yl]-5-heptenoic acid 17 mg (36.6 micromol) of nonpolar ester A produced according to example 256 was saponified analogously to example 2 and, after working up and purification, 16 mg (35.5 micromol, 97%) of the title compound was isolated as a colorless oil.

IR (film): 3600–2300, 3080, 3060, 3010, 2950, 2930, 2880, 2860, 2230, 1710, 1600, 1490, 1455, 1445, 1405, 1305, 1240, 1200, 1120, 1015, 995, 970, 895, 755 and 690 cm$^{-1}$.

EXAMPLE 255

(1S,4R,5S(5Z),6S)-7-[4-(2-Phenylethinyl)-6[3(R)-hydroxy-1(E)-octenyl]-2-oxabicyclo[2.2.1]hept-5-yl]-5-heptenoic acid 16 mg (34.4 micromol) of polar ester B produced according to example 256 was saponified analogously to example 2 and, after working up and purification, 12.7 mg (28.2 micromol, 82%) of the title compound was isolated as a colorless oil.

IR (film): 3700–2400, 3080, 3060, 3010, 2960, 2930, 2870, 2860, 2230, 1710, 1600, 1490, 1455, 1445, 1300, 1240, 1200, 1015, 995, 970, 895, 755 and 695 cm$^{-1}$.

EXAMPLE 256

(1S,4R,5S(5Z),6S)-7-[4-(2-Phenylethinyl)-6[3(S)-hydroxy-1(E)-octenyl]-2-oxabicyclo[2.2.1]hept-5-yl]-5-heptenoic acid methyl ester (A) and
(1S,4R,5S(5Z),6S)-7-[4-(2-phenylethinyl)-6[3(R)-hydroxy-1(E)-octenyl]-2-oxabicyclo[2.2.1-hept-5-yl]-5-heptenoic acid methyl ester (B)

39 mg (84.3 micromol) of the unsaturated ketone produced in example 246a was reduced analogously to example 23 and, after working up and purification, 36.5 mg (78.6 micromol, 93%) of a mixture of both title compounds was isolated as a colorless oil.

IR (film): 3600–3200, 3070, 3050, 3010, 2950, 2930, 2860, 2220, 1735, 1595, 1490, 1440, 1360, 1300, 1240, 1195, 1155, 1070, 1010, 995, 970, 895, 755 and 690 cm$^{-1}$.

The chromatographic separation yielded 17 mg (36.6 micromol, 43%) of the more nonpolar alcohol, to which structure A was assigned, as well as 16 mg (34.3 micromol, 41%) of the more polar alcohol, to which structure B was assigned.

EXAMPLE 256a (1S,4R,5S(5Z),6S)-7-[4-(2-Phenylethinyl)-6[3-oxo-1(E)octenyl]-2-oxabicyclo[2.2.1]hept-5-yl]-5-heptenoic acid methyl ester 52 mg (142 micromol) of the aldehyde produced in example 256b was reacted analogously to example 23a with use of dimethyl(2-oxo-heptyl)-phosphonate and, after working up and purification, 39 mg (84.3 micromol, 59%) of the title compound was isolated as a colorless oil.

IR (film): 3070, 3050, 2950, 2930, 2970, 2230, 1735, 1690, 1670, 1620, 1595, 1490, 1450, 1440, 1365, 1310, 1240, 1190, 1170, 1070, 1010, 995, 975, 895, 755 and 690 cm$^{-1}$.

EXAMPLE 256b (1S,4R,5S(5Z),6S)-7-[4-(2-Phenylethinyl)-6-formyl-2-oxabicyclo[2.2.1]hept-5-yl]-5-heptenoic acid methyl ester 55.7 mg (151 micromol) of the alcohol produced in example 256c was oxidized analogously to example 38b and, after working up, 52 mg (142 micromol, 94%) of the title compound was isolated as a colorless oil.

IR (film): 3080, 3050, 3010, 2950, 2930, 2870, 2720, 2230, 1735, 1715, 1595, 1490, 1360, 1310, 1245, 1190, 1170, 1070, 1025, 980, 895, 755 and 690 cm$^{-1}$.

EXAMPLE 256c (1S,4R,5S(5Z),6R)-7-[4-(2-Phenylethinyl)-6-hydroxymethyl-2-oxabicyclo[2.2.1]hept-5-yl]-5-heptenoic acid methyl ester 5.3 g (19.2 mmol) of enantiomeric Corey lactone was reacted analogously to examples 11a to 11g and 1h to 11 and 208 mg (564 micromol, 2.9%) of the title compound was isolated as a colorless oil.

IR (film): 3600–3200, 3070, 3050, 2950, 2930, 2870, 2230, 1735, 1490, 1440, 1365, 1300, 1245, 1200, 1155, 1065, 1025, 1000, 890, 755 and 690 cm$^{-1}$.

EXAMPLE 257

(1S,4R,5S(5Z),6R)-7-[4-(2-Phenylethinyl)-6-benzyloxymethyl-2-oxabicyclo[2.2.1]hept-5-yl]-5-heptenoic acid methyl (or benzyl) ester 17.8 mg (48.3 micromol) of the alcohol produced in example 256c was reacted analogously to example 1 with benzyl chloride and, after working up and purification, 18 mg of the title compounds was isolated as a colorless oil.

IR (film): 3090, 3060, 3020, 3000, 2930, 2870, 2230, 1730, 1595, 1490, 1450, 1360, 1305, 1210, 1150, 1110, 1070, 1005, 895 755, 735 and 695 cm$^{-1}$.

EXAMPLE 258

(1S,4R,5S(5Z),6R)-7-[4-(2-Phenylethinyl)-6-benzyloxymethyl-2-oxabicyclo[2.2.1]hept-5-yl]-5-heptenoic acid 18 mg of the ester mixture produced according to example 257 was saponified analogously to example 2 and, after working up and purification, 16.7 mg (37.6 micromol, 78%, relative to the initial material in example 257) of the title compound was isolated as a colorless oil.

IR (film): 3600–2400, 3080, 3060, 3030, 3000, 2930, 2870, 2230, 1730, 1705, 1600, 1490, 1450, 1440, 1365, 1305, 1240, 1210, 1110, 1070, 1005, 895, 755, 735 and 695 cm$^{-1}$.

EXAMPLE 259

(1S,4R,5S(5Z),6R)-7-[4-(2-Phenylethinyl)-6-(4-cyanobenzyloxymethyl)-2-oxabicyclo[2.2.1]hept-5-yl]-5-heptenoic acid methyl (or 4-cyanobenzyl) ester 16.9 mg (45.9 micromol) of the alcohol produced in example 256c was reacted analogously to example 1 with 4-bromomethylbenzonitrile and, after working up and purification, 20 mg of the title compounds was isolated as a colorless oil.

IR (film): 3060, 3000, 2940, 2870, 2220, 1730, 1610, 1600, 1440, 1360, 1210, 1105, 1005, 895, 755 and 690 cm$^{-1}$.

EXAMPLE 260

(1S,4E,5S(5Z),6R)-7-[4-(2-Phenylethinyl)-6-(4-cyanobenzyloxymethyl)-2-oxabicyclo[2.2.1]hept-5-yl]-5-heptenoic acid 20 mg of the ester mixture produced according to example 259 was saponified analogously to example 2 and, after working up and purification, 18 mg (38 micromol, 84%, relative to the initial material in example 259) of the title compound was isolated as a colorless oil.

IR (film): 3600–2300, 3080, 3050, 3000, 2930, 2870, 2850, 2230, 1710, 1610, 10,, 1490, 1445, 1310, 1280, 1210, 1110, 1005, 895, 820, 760 and 690 cm$^{-1}$.

EXAMPLE 261

(1S,4R,5S(5Z),6S(1E,3S,4S))-7-[4-(2-Phenylethinyl)-6-(3-hydroxy-4-methyl-non-1-en-6-inyl)-2-oxabicyclo[2.2.1]hept-5-yl]-5-heptenoic acid 11.2 mg (22.9 micromol) of nonpolar ester A produced according to example 263 was saponified analogously to example 2 and, after working up and purification, 10 mg (21.1 micromol, 92%) of the title compound was isolated as a colorless oil.

IR (film): 3600–2500, 3070, 3050, 3030, 3010, 2970, 2930, 2850, 230, 1710, 1605, 1490, 1455, 1390, 1240, 1195, 1015, 990, 970, 895, 755 and 690 cm$^{-1}$.

EXAMPLE 262

(1S,4R,5S(5Z),6S))-7-[4-(Phenylethinyl)-6-(3-hydroxy-4-methyl-non-1-en-6-inyl)-2-oxabicyclo[2.2.1]hept-5-yl]-5-heptenoic acid 18.1 mg (37 micromol) of polar ester B produced according to example 263 was saponified analogously to example 2 and, after working up and purification, 14.7 mg (31 micromol, 84%) of the title compound was isolated as a colorless oil.

IR (film): 3600–2400, 3080, 3050, 3030, 3010, 2970, 2930, 2850, 2230, 1710, 1600, 1490, 1455, 1390, 1240, 1200, 1015, 990, 970, 890, 755 and 690 cm$^{-1}$.

EXAMPLE 263

(1S,4R,5S(5Z),6S(1E,3S,4S))-7-[4-(2Phenylethinyl)-6-(3-hydroxy-4-methyl-non-1-en-6-inyl)-2-oxabicyclo[2.2.1]hept-5-yl]-5-heptenoic acid methyl ester (A)
and
(1S,4R,5S(5Z),6S(1E,3R,4S))-7-[4-(2-phenylethinyl)-6-(3-hydroxy-4-methyl-non-1-en-6-inyl)-2-oxabicyclo[2.2.1]hept-5-yl]-5-heptenoic acid methyl ester (B)

32 mg (65.8 micromol) of the unsaturated ketone produced in example 263a was reduced analogously to example 23 and, after working up and purification, 31.1 mg (63.6 micromol, 97%) of a mixture of both title compounds was isolated as a colorless oil.

IR (film): 3600–3200, 3080, 3050, 2970, 2950, 2930, 2870, 2850, 2220, 1730, 1595, 1450, 1435, 1265, 1195, 1155, 1010, 995, 970, 890, 755, 735 and 690 cm$^{-1}$.

The chromatographic separation yielded 11.2 mg (22.9 micromol, 35%) of the more nonpolar alcohol, to which structure A was assigned, as well as 18.1 mg (37.0 micromol, 56%) of the more polar alcohol, to which structure B was assigned.

EXAMPLE 263a (1S,4R,5S(5Z),6S(1E,4S))-7-[4-(2-Phenylethinyl)-6-(3-oxo-4-methyl-non-1-en-6-inyl)-2-oxabicyclo[2.2.1]hept-5-yl]-5-heptenoic acid methyl ester 48.6 mg (133 micromol) of the aldehyde produced in example 256b was reacted analogously to example 23a with use of dimethyl(2-oxo-3S-methyl-oct-5-ine)-phosphonate and, after working up and purification, 32 mg (65.8 micromol, 50%) of the title compound was isolated as a colorless oil.

IR (film): 3080, 3050, 2970, 2930, 2870, 2230, 1735, 1685, 1665, 1615, 1450, 1435, 1240, 1160, 1040, 1015, 985, 895, 755, 735 and 695 cm$^{-1}$.

EXAMPLE 264

(1S,4R,5S(5Z),6R(3S,4S))-7-[4-(2-Phenylethinyl)-6-(3-hydroxy-4-methyl-nona-1,6-diinyl)-2-oxabicyclo[2.2.1]hept-5-yl]-5-heptenoic acid methyl ester 2.5 mg (5.3 micromol) of the acid produced according to example 265 was esterified analogously to example 186 and, after removal of the solvent, 2.5 mg (5.1 micromol, 97%) of the title compound was isolated as a colorless oil.

IR (film): 3600–3200, 3080, 3060, 3030, 3010, 2970, 2930, 2880, 2230, 1735, 1605, 1490, 1450, 1410, 1320, 1290, 1270, 1240, 1160, 1020, 990, 895, 760 and 690 cm$^{-1}$.

EXAMPLE 265

(1S,4R,5S(5Z),6R(3S,4S))-7-[4-(2-Phenylethinyl)-6-(3-hydroxy-4-methyl-nona-1,6-diinyl)-2-oxabicyclo[2.2.1]hept-5-yl]-5heptenoic acid 23.9 mg (42.1 micromol) of nonpolar alcohol A produced according to example 268 was reacted analogously to example 187 and, after working up and purification, 11.7 mg (24.8 micromol, 59%) of the title compound was isolated as a colorless oil.

IR (film): 3600–2400, 3060, 3030, 3010, 2970, 2940, 2880, 2230, 1705, 1600, 1490, 1455, 1445, 1410, 1320, 1305, 1280, 1240, 1155, 1020, 990, 895, 760 and 690 cm$^{-1}$.

EXAMPLE 266

(1S,4R,5S(5Z),6R(3R,4S))-7-[4-(2-Phenylethinyl)-6-(3-hydroxy-4-methyl-nona-1,6-diinyl)-2-oxabicyclo[2.2.1]hept-5-yl]-5-heptenoic acid methyl ester 2.9 mg (6.1 micromol) of the acid produced according to example 267 was esterified analogously to example 186 and, after removal of the solvent, 3 mg (6.1 micromol, 100%) of the title compound was isolated as a colorless oil.

IR (film): 3600–3200, 3070, 3050, 3030, 3010, 2970, 2930, 2880, 2230, 1735, 1600, 1490, 1450, 1410, 1320, 1305, 1290, 1270, 1240, 1160, 1020, 990, 895, 760 and 690 cm$^{-1}$.

EXAMPLE 267

(1S,4R,5S(5Z),6R(3R,4S))-7-[4-(2-Phenylethinyl)-6-(3-hydroxy-4-methyl-nona-1,6-diinyl)-2-oxabicyclo[2.2.1]hept-5-yl]-5-heptenoic acid 25.7 mg (45 micromol) of polar alcohol B produced according to example 268 was reacted analogously to example 187 and, after working up and purification, 15.5 mg (32.8 micromol, 73%) of the title compound was isolated as a colorless oil.

IR (film): 3700–2400, 3080, 3060, 3030, 3010, 2970, 2930, 2880, 2230, 1710, 1600, 1490, 1455, 1445, 1410, 1320, 1305, 1290, 1270, 1240, 1155, 1020, 990, 895, 760 and 690 cm$^{-1}$.

EXAMPLE 268

(1S,4R,5S(5Z),6R(1E/Z,3S,4S))-7-[4-(2-Phenylethinyl)-6-(2-bromo-3-hydroxy-4-methyl-non-1-en-6-inyl)-2-oxabicyclo[2.2.1]hept-5-yl]-5-heptenoic acid methyl ester (A) and
(1S,4R,5S(5Z),6R(1E/Z,3R,4S))-7-[4-(2-phenylethinyl)-6-(2-bromo-3-hydroxy-4-methyl-non-1-en-6-inyl)-2-oxabicyclo[2.2.1]hept-5-yl]-5-heptenoic acid methyl ester (B)

58 mg (102 micromol) of the unsaturated ketone produced in example 268a was reduced analogously to example 23 and, after working up and purification, 52.8 mg (93 micromol, 91%) of a mixture of both title compounds was isolated as a colorless oil.

IR (film): 3600–3200, 3080, 2050, 2970, 2950, 2930, 2880, 2230, 1735, 1595, 1490, 1450, 1435, 1315, 1240, 1200, 1155, 1025, 1010, 990, 895, 755, 735 and 690 cm$^{-1}$.

The chromatographic separation yielded 23.9 mg (42.1 micromol, 41%) of the more nonpolar alcohol, to which structure A was assigned, as well as 25.7 mg (45 micromol, 45%) of the more polar alcohol, to which structure B was assigned.

EXAMPLE 268a (1S,4R,5S(5Z),6R(1E/Z,4S))-7-[4-(2-Phenylethinyl)-6-(2-bromo-3-oxo-4-methyl-non-1-en-6-inyl)-2-oxabicyclo[2.2.1]hept-5-yl]-5-heptenoic acid methyl ester 39.5 mg (108 micromol) of the aldehyde produced in example 256b was reacted analogously to example 190a with use of dimethyl-(2-oxo-3S-methyl-oct-5-ine)-phosphate and, after working up and purification, 58 mg (102 micromol, 94%) of the title compound was isolated as a colorless oil.

IR (film): 3080, 3050, 2970, 2950, 2930, 2880, 2230, 1730, 1685, 1600, 1485, 1450, 1435, 1310, 1265, 1240, 1160, 1070, 1015, 985, 895, 755, 735 and 690 cm$^{-1}$.

EXAMPLE 269

(1S,4R,5S(5Z),6R(1E/Z,3S,4S))-7-[4-(2-Phenylethinyl)-6-(2-bromo-3-hydroxy-4-methyl-non-1-en-6-inyl)-2-oxabicyclo[2.2.1]hept-5-yl]-5-heptenoic acid 10.2 mg (18 micromol) of nonpolar ester A produced according to example 268 was saponified analogously to example 2 and, after working up and purification, 8.5 mg (15.4 micromol, 85%) of the title compound was isolated as a colorless oil.

IR (film): 3700–2400, 3070, 3050, 2970, 2950, 2930, 2880, 2230, 1705, 1595, 1490, 1450, 1435, 1315, 1240, 1200, 1160, 1025, 1010, 990, 895, 755 and 695 cm$^{-1}$.

EXAMPLE 270

(1s,4r,5s(5z),6r(1e/z,3r,4s))-7-[4-(2-Phenylethinyl)-6-(2-bromo-3-hydroxy-4-methyl-non-1-en-6-inyl)-2-oxabicyclo[2.2.1]hept-5-yl]-5-heptenoic acid 12.3 mg (21.7 micromol) of polar ester B produced according to example 268 was saponified analogously to example 2 and, after working up and purification, 10.6 mg (19.1 micromol, 88%) of the title compound was isolated as a colorless oil.

IR (film): 3600–2400, 3080, 3050, 2970, 2950, 2930, 2880, 2230, 1710, 1595, 1495, 1450, 1435, 1315, 1240, 1200, 1160, 1025, 1010, 990, 895, 755, 735 and 690 cm$^{-1}$.

EXAMPLE 271

(1S,4R,5S(5Z),6R)-7-[4-(2-Phenylethinyl)-6-(4-benzyloxy)benzyloxymethyl)-2-oxabicyclo[2.2.1]hept-5-yl]-5-heptenoic acid methyl (or 4-(benzyloxy) benzyl) ester 28 mg (76 micromol) of the alcohol produced in example 256c was reacted analogously to example 1 with 4-benzyloxybenzyl chloride and, after working up and purification, 36 mg of the title compounds was isolated as a colorless oil.

IR (film): 3070, 3030, 3010, 2930, 2880, 2230, 1735, 1610, 1580, 1510, 1445, 1295, 1240, 1170, 1110, 1080, 1025, 1005, 895, 825, 760, 740 and 695 cm$^{-1}$.

EXAMPLE 272

(1S,4R,5S(5Z),6R)-7-[4-(2-Phenylethinyl)-6-(4-benzyloxy)benzyloxymethyl)-2-oxabicyclo[2.2.1]hept-5-yl]-5-heptenoic acid 36 mg of the ester mixture produced according to example 271 was saponified analogously to example 2 and, after working up and purification, 28.4 mg (51.6 micromol, 68%, relative to the initial material in example 271) of the title compound was isolated as a colorless oil.

IR (film): 3600–2400, 3060, 3030, 3010, 2930, 2880, 2230, 1730, 1710, 1610, 1585, 1510, 1300, 1240, 1170, 1105, 1080, 1025, 1005, 895, 825, 760, 740 and 695 cm$^{-1}$.

EXAMPLE 273

(1S,4R,5S,6R)-7-[4-(4-Fluorophenyl)-6-(4-fluorobenzyloxymethyl)-2-oxabicyclo[2.2.1]hept-5-yl]-3-oxa-5(Z)heptenoic acid 9.2 mg of the ester mixture produced according to example 274 was saponified analogously to example 2 and, after working up and purification, 5.8 mg (12.6 micromol, 31%, relative to the initial material in example 274) of the title compound was isolated as a colorless oil.

IR (film): 3700–2400, 3070, 3040, 2930, 2870, 1730, 1605, 1510, 1225, 1115, 895 and 830 cm$^{-1}$.

EXAMPLE 274

(1S,4R,5S,6R)-7-[4-(4-Fluorophenyl)-6-(4-fluorobenzyloxymethyl)-2-oxabicyclo[2.2.1]hept-5-yl]-3-oxa-5(Z)-heptenoic acid-t-butyl (or 4-fluorobenzyl) ester 16.5 mg (40 micromol) of the alcohol produced in example 274a was reacted analogously to example 1 and, after working up and purification, 9.2 mg of the title compounds was isolated as a colorless oil.

IR (film): 3050, 2980, 2930, 2870, 1745, 1605, 1510, 1370, 1265, 1225, 1160, 1120, 1030, 830 and 735 cm$^{-1}$.

(1S,4R,5S,6R)-7-[4-(4-Fluorophenyl)-6-hydroxymethyl-2-oxabicyclo[2.2.1]hept-5-yl]-3-oxa-5(Z)-heptenoic acid-tert-butyl ester 686 mg (1.06 mmol) of the compound produced in example 274b was reacted analogously to example 1a and, after working up and purification, 385 mg (947 micromol, 89%) of the title compound was isolated as a colorless oil.

IR (film): 3600–3200, 3040, 2970, 2920, 2870, 1740, 1605, 1510, 1365, 1230, 1160, 1130, 1025, 970, 895 and 735 cm$^{-1}$.

EXAMPLE 274b (1S,4R,5S,6R)-7-[4-(4-Fluorophenyl)-6-tert-butyldiphenylsilyloxymethyl-2-oxabicyclo[2.2.1]hept-5-yl]-3-oxa-5(Z)heptenoic acid-t-butyl ester 580 mg (1.09 mmol) of the alcohol produced in example 274c was reacted analogously to example 1 with bromoacetic acid-tert-butyl ester and, after working up and purification, 686 mg (1.06 mmol, 97%) of the title compound was isolated as a colorless oil.

IR (film): 3050, 3040, 3010, 2970, 2930, 2850, 1745, 1605, 1590, 1510, 1470, 1425, 1390, 1365, 1295, 1225, 1160, 1130, 1110, 940, 895, 830, 820, 740 and 700 cm$^{-1}$.

EXAMPLE 274c (1S,4R,5S,6R)-4-[4-(4-Fluorophenyl)-6-tert-butyldiphenylsilyloxymethyl-2-oxabicyclo[2.2.1]hept-5-yl]-2(Z)butenol 620 mg (1.11 mmol) of ester A produced in example 274d was reduced analogously to example 274j and, after working up, 581 mg (1.09 mmol, 99%) of the title compound was isolated as a colorless oil.

IR (film): 3600–3200, 3070, 3040, 3010, 2950, 2930, 2860, 1605, 1590, 1510, 1470, 1425, 1265, 1230, 1160, 1110, 1025, 1015, 895, 830, 820, 735 and 700 cm$^{-1}$.

EXAMPLE 274d (1S,4R,5S,6R)-4-[4-(4-Fluorophenyl)-6-tert-butyldiphenylsilyloxymethyl-2-oxabicyclo[2.2.1]hept-5-yl]-2(Z)butenoic acid methyl ester (A) and
(1S,4R,5S,6R)-4-[4-(4-fluorophenyl)-6-tert-butyldiphenylsilyloxymethyl-2-oxabicyclo[2.2.1]hept-5-yl]-2(E)-butenoic acid methyl ester (B)

The solution of 1.25 ml of bis-(2,2,2-trifluoroethyl)-methoxycarbonylmethyl-phosphonate in 30 ml of anhydrous tetrahydrofuran was mixed with 1.96 g of 18-crown-6, cooled under at atmosphere of dry argon to −70° C. and 5.9 ml of a 1M solution of sodium hexamethyl-disilazide in tetrahydrofuran was instilled. It was allowed to react for 15 minutes and then the solution of 748 mg (1.48 mmol) of the aldehyde, produced in example 274e, in 15 ml of anhydrous tetrahydrofuran was instilled and allowed to stir for 2.5 hours −70° C. to −60° C. Then, it was poured on a saturated ammonium chloride solution, extracted several times with diethyl ether, washed with water and saturated sodium chloride solution, dried on magnesium sulfate and the residue obtained after filtration and removal of the solvent was purified by chromatography on about 100 ml of silica gel with use of a gradient system of n-hexane and ethyl acetate. 622 mg (1.11 mmol, 75%) of title compound A as well as 54 mg (96.6 micromol, 7%) of title compound B were isolated.

IR (film) of A: 3070, 3040, 2950, 2930, 2860, 1720, 1645, 1605, 1590, 1510, 1425, 1230, 1205, 1170, 1110, 1085, 1025, 895, 820, 740 and 700 cm$^{-1}$.

IR (film) of B: 3070, 3040, 2950, 2930, 2860, 1720, 1655, 1645, 1605, 1590, 1510, 1425, 1265, 1230, 1160, 1110, 1085, 1025, 1015, 895, 830, 820, 740 and 700 cm$^{-1}$.

EXAMPLE 274e (1S,4R,5S,6R)-4-[4-(4-Fluorophenyl)-6-tert-butyldiphenylsilyloxymethyl-2-oxabicyclo[2.2.1]hept-5-yl]-1-oxoethane 748 mg (1.48 mmol) of the alcohol produced in example 274f was oxidized analogously to example 38b and, after working up, 748 mg (1.48 mmol, 100%) of the title compound was isolated as a pale yellow oil, which was further reacted without purification.

EXAMPLE 274f (1S,4R,5S,6R)-2-[4-(4-Fluorophenyl)-6-tert-butyldiphenylsilyloxymethyl-2-oxabicyclo[2.2.1]hept-5-yl]-1-hydroxyethane 1.03 g (1.68 mmol) of the benzoate produced in example 274g was saponified analogously to example 2 and, after working up and purification, 748 mg (1.48 mmol, 88%) of the title compound was isolated as a colorless oil.

IR (film): 3600–3200, 3070, 3050, 2920, 2850, 1605, 1590, 1510, 1465, 1425, 1260, 1230, 1160, 1110, 1075, 1065, 1015, 975, 93, 895, 830, 820, 740 and 700 cm$^{-1}$.

EXAMPLE 274g (1S,4R,5S,6R)-2-[4-(4-Fluorophenyl)-6-tert-butyldiphenylsilyloxymethyl-2-oxabicyclo[2.2.1]hept-5-yl]-1-benzoyloxy-ethane 1.11 g (1.76 mmol) of the diol produced in example 274h was reacted analogously to example 1b and, after working up and purification, 1.03 g (1.68 mmol, 95%) of the title compound was isolated as a colorless oil.

IR (film): 3070, 3050, 2950, 2930, 2850, 1775, 1715, 1600, 1585, 1510, 1465, 1450, 1425, 1270, 1230, 1110, 1070, 1020, 830, 820, 740 and 705 cm$^{-1}$.

EXAMPLE 274h (1R,2S,3R,4S)-2-[1-Hydroxymethyl-1-(4-fluorophenyl)-3-tert-butyl-diphenylsilyloxymethyl-4-hydroxy-cyclopentan-2-yl]-1-benzoyloxyethane 1.79 g (2.17 mmol) of the benzoate produced in example 274i was reacted analogously to example 1c and, after working up and purification, 1.11 g (1.76 mmol, 81%) of the title compound was isolated as a colorless oil.

IR (film): 3700–3100, 3070, 3040, 2950, 2930, 2860, 1715, 1600, 1585, 1510, 1470, 1450, 1425, 1270, 1235, 1110, 1070, 1045, 825, 740 and 705 cm$^{-1}$.

EXAMPLE 274i (1R,2S,3R,4S)-2-[1-tert-Butyldimethylsilyloxymethyl-1-(4-fluorophenyl)-3-tert-butyldiphenylsilyloxymethyl-4-(tetrahydropyran-2-yloxy)-cyclopentan-2yl]-1-benzoyloxyethane 1.70 g (2.36 mmol) of the alcohol produced in example 274j was dissolved in 17 ml of anhydrous pyridine, mixed with 850 microliters of benzoyl chloride and allowed to rest for 4 hours at 23° C. under an atmosphere of dry argon. It was diluted with diethyl ether, washed several times with ice water, dried on magnesium sulfate and the residue obtained after filtration and removal of the solvent was purified by chromatography on about 75 ml of silica gel. A gradient system of a n-hexane and diethyl ether was used as a mobile solvent. 1.79 g (2.17 mmol, 92%) of the title compound was isolated as a colorless oil.

IR (film): 3070, 3050, 2950, 2860, 1715, 1600, 1585, 1510, 1475, 1450, 1425, 1270, 1250, 1110, 1025, 875, 840, 740 and 705 cm$^{-1}$.

EXAMPLE 274j (1R,2S,3,RS)-2-[1-tert-Butyldimethylsilyloxymethyl-1-(4-fluorophenyl)-3-tert-butyldiphenylsilyloxymethyl-4-(tetrahydropyran-2-yloxy)-cyclopentan-2-yl]-1-hydroxyethane 1.77 g (2.36 mmol) of the compound produced in example 274k was dissolved in 30 ml of anhydrous toluene, cooled under an atmosphere of dry argon to 0°–5° C., mixed with 8.3 ml of a 1M solution of diisobutylaluminum hydride in toluene and allowed to react for 30 minutes. The working up took place analogously to example 1e, 1.70 g (2.36 mmol, 100%) of the title compound was isolated as a colorless oil.

IR (film):L 3600–3400, 3070, 3050, 2940, 2860, 1605, 1590, 1470, 1425, 1265, 1250, 1235, 1165, 1130, 1110, 1075, 1025, 875, 840, 740 and 705 cm$^{-1}$.

EXAMPLE 274k (1r,2S,3R,4S)-2-[1-tert-Butyldimethylsilyloxymethyl-1-(4-fluorophenyl)-3-tert-butyldiphenylsilyloxymethyl-4-(tetrahydropyran-2-cyclopentan-2-yl]-ethanoic acid methyl ester 1.55 g (2.44 mmol) of the hydroxyester produced in example 274l was reacted analogously to example 11 with use of tert-butyldimethylchlorosilane and, after working up and chromatographic purification, 1.77 g (2.36 mmol, 97%) of the title compound was isolated as a colorless oil.

IR (film): 3070, 3040, 2940, 2850, 1735, 1600, 1585, 1510, 1465, 1425, 1250, 1235, 1160, 1110, 1075, 1030, 1020, 875, 840, 740 and 700 cm$^{-1}$.

EXAMPLE 274l (1R,2S,3R,4S)-2-[1-Hydroxymethyl-1-(4-fluorophenyl)-3-tert-butyldiphenylsilyloxymethyl-4-(tetrahydropyran-2-yloxy)cyclopentan-2-yl]-ethanoic acid methyl ester 1.48 g (2.46 mmol) of the lactone produced according to example 274m was dissolved in 15 ml of tetrahydrofuran, mixed with 15 ml of 1 n potassium hydroxide solution and allowed to stir vigorously for 16 hours at 23° C. The organic solvent was distilled off to a very large extent, the aqueous phase was acidified with ice-cold saturated citric acid to pH 4 to 5, quickly extracted several times with ice-cold dichloromethane and the combined extracts were instilled in a precooled ethereal solution of diazomethane. Then, it was dried on magnesium sulfate and, after filtration and removal of the solvent, 1.55 g (2.44 mmol, 99%) of the title compound was isolated as a pale yellow oil, which was quickly further reacted without purification.

EXAMPLE 274m (1R,6S,7R,8S)-1-(4-Fluorophenyl)-7-tert-butyldiphenylsilyloxymethyl-8-(tetrahydropyran-2-yloxy)-3-oxabicyclo[4.3.0]nonan-4-one 1.007 g (1.66 mmol) of (1R,4RS,6S,7R,8S)-1-(4-fluorophenyl)-4-hydroxy-7-tert-butyldiphenylsilyloxymethyl-8-(tetrahydropyran-2yloxy)-3-oxabicyclo[4.3.0]nonane, which was produced analogously to example 1f to 1l of enantiomeric Corey lactone (cf. example 120a), was dissolved in 20 ml of anhydrous acetone, cooled under an atmosphere of dry argon to −30° C., mixed with 1 ml of a standardized Jones solution and stirred for 2 hours at −30° C. The working up took place analogously to example 1i. 994 mg (1.65 mmol, 99%) of the title compound was isolated as a pale yellow oil.

IR (film): 3070, 3040, 2940, 2850, 1750, 1605, 1580, 1510, 1465, 1425, 1260, 1235, 1110, 1080, 1030, 970, 820, 740, and 700 cm$^{-1}$.

EXAMPLE 275

(1S,4R,5S,6R)-7-[4-(4-Fluorophenyl)-6-(4-fluorobenzyloxymethyl)-2-oxabicyclo[2.2.1]hept-5-yl]-3-oxa-5(E)-heptenoic acid 17.4 mg of the ester mixture produced according to example 276 was saponified analogously to example 2 and, after working up and purification, 12.2 mg (26.6 micromol, 54%) relative to the initial material in example 276) of the title compound was isolated as colorless oil.

IR (film): 3600–2400, 3070, 3040, 2920, 2860, 1730, 1605, 1515, 1225, 1160, 1115, 970, 900 and 830 cm$^{-1}$.

EXAMPLE 276

(1S,4R,5S,6R)-7-[4-(4-Fluorophenyl)-6-(4-fluorobenzyloxymethyl)-2-oxabicyclo[2.2.1]hept-5-yl]-3-oxa-5(E)-heptenoic acid-t-butyl (or 4-fluorobenzyl) ester 20.2 mg (49 micromol) of the alcohol produced in example 276a was reacted analogously to example 1 and, after working up and purification, 17.4 mg of the title compounds was isolated as a colorless oil.

IR (film): 3070, 3040, 2980, 2930, 2860, 1745, 1605, 1510, 1365, 1225, 1160, 1125, 1025, 970, 895, and 830 cm$^{-1}$.

EXAMPLE 276a (1S,4R,5S,6R)-7-[4-(4-Fluorophenyl)-6-hydroxymethyl-2-oxabicyclo[2.2.1]hept-5-yl]-3-oxa-5(E)-heptenoic acid-t-butyl ester 3.88 mg (602 micromol) of the compound produced in example 276b was reacted analogously to example 1a and, after working up and purification, 218 mg (536 micromol, 89%) of the title compound was isolated as a colorless oil.

IR (film): 3600–3200, 3070, 3040, 2970, 2920, 2870, 1740, 1605, 1510, 1365, 1300, 1230, 1160, 1130, 1025, 970, 895 and 835 cm$^{-1}$.

EXAMPLE 276b (1S,4R,5S,6R)-7-[4-(4-Fluorophenyl)-6-tert-butyldiphenylsilyloxymethyl-2-oxabicyclo[2,2,1]hept-5-yl]-3-oxa-5(E)-heptenoic acid-t-butyl ester 364 mg (686 micromol) of compound A produced in example 276c was etherified analogously to example 1 with bromoacetic acid-tert-butyl ester and, after working up and purification, 388 mg (602 micromol, 88%) of the title compound was isolated as a colorless oil.

IR (film): 3090, 3070, 3040, 3010, 2950, 2930, 2860, 1745, 1605, 1590, 1510, 1470, 1425, 1390, 1365, 1295, 1225, 1160, 1130, 1110, 895, 830, 820, 740 and 700 cm$^{-1}$.

EXAMPLE 276c (1S,4R,5S,6R)-4-[4-(4-Fluorophenyl)-6-tert-butyldiphenylsilyloxymethyl-2-oxabicyclo[2.2.1]hept-5-yl]-2(E)-butenol (A) and
(1S,4R,5S,6R)-4-[4-(4-fluorophenyl)-6-tert-butyldiphenylsilyloxymethyl-2-oxabicyclo[2.2.1]hept-5-yl]-2(Z)butenol (B)

506 mg (883 micromol) of the compounds produced in example 276d was reduced analogously to example 274j and, after working up and chromatographic separation on about 100 ml of silica gel with use of a gradient system of n-hexane and ethyl acetate, 374 mg (705 micromol, 80%) of title compound A, as well as 25 mg (47 micromol, 5%) of title compound B were each isolated as colorless oil.

IR (film) of A: 3600–3200, 3070, 3050, 3010, 2950, 2920, 2850, 1605, 1590, 1510, 1470, 1425, 1265, 1230, 1160, 1110, 1025, 1000, 970, 895, 825, 735 and 705 cm$^{-1}$.

IR (film) of B: 3600–3200, 3070, 3050, 3010, 2950, 2920, 2850, 1605, 1590, 1510, 1470, 1425, 1265, 1230, 1160, 1110, 1025, 1015, 1000, 890, 830, 820, 735 and 705 cm$^{-1}$.

EXAMPLE 276d (1S,4R,5S,6R)-4-[4-(4-Fluorophenyl)-6-tert-butyldiphenylsilyloxymethyl-2-oxabicyclo[2.2.1]hept-5-yl]-2(E)-butenoic acid ethyl ester and
(1S,4R,5S,6R)-4-[4-(4-fluorophenyl)-6-tert-butyldiphenylsilyloxymethyl-2-oxabicyclo[2.2.1]hept-5-yl]-2(Z)butenoic acid ethyl ester 683 mg (1.16 mmol) of the diols produced in example 276e was reacted analogously to example 1b and, after working up and purification, 516 mg (901 micromol, 78%) of the title compounds was isolated as a colorless oil.

IR (film): 3070, 3050, 3010, 2950, 2930, 2860, 1715, 1650, 1605, 1590, 1510, 1465, 1425, 1390, 1365, 1315, 1265, 1230, 1160, 1110, 895, 830, 820, 740 and 705 cm$^{-1}$.

EXAMPLE 276e (1R,2S,3R,4S)-4-[1-Hydroxymethyl-1-(4-fluorophenyl)-3-tert-butyldiphenylsilyloxymethyl-4-hydroxy-cyclopentan-2-yl]-2(E)butenoic acid ethyl ester and
(1R,2S,3R,4S)-4-[1-hydroxymethyl-1-(4-fluorophenyl)-3-tert-butyldiphenylsilyloxymethyl-4-hydroxycyclopentan-2-yl]-2(Z)-butenoic acid ethyl ester 902 mg (1.34 mmol) of the ester mixture produced in example 276f was reacted analogously to example 1c and, after working up and purification, 683 mg (1.16 mmol, 86%) of the title compounds was isolated as a colorless oil.

IR (film): 3600–3200, 3070, 3050, 2950, 2930, 2850, 1710, 1645, 605, 1585, 1510, 1465, 1425, 1265, 1235, 1160, 1110, 1045, 825, 740 and 700 cm$^{-1}$.

EXAMPLE 276f (1R,2S,3R,4S)-4-[1-Hydroxymethyl-1-(4-fluorophenyl)-3-tert-butyldiphenylsilyloxymethyl-4-(tetrahydropyran-2-yloxy)cyclopentan-2-yl]-2(E)-butenoic acid ethyl ester and
(1R,2S,3R,4S)-4-[1-hydroxymethyl-1-(4-fluorophenyl)-3-tert-butyldiphenylsilyloxymethyl-4-(tetrahydropyran-2-yloxy)cyclopentan-2-yl]-2(Z)-butenoic acid ethyl ester 969 mg (1.60 mmol) of (1R,4RS,6S,7R,8S)-1(4-fluorophenyl-4-hydroxy-7-tert-butyldiphenylsilyloxymethyl-8-(tetrahydropyran-2-yloxy)-3-oxabicyclo[4.3.0]nonane, which was produced from enantiomeric Corey lactone analogously to examples 1f to 11 (cf. example 120a), was dissolved in 3 ml of anhydrous toluene, mixed with 1.67 g of ethoxycarbonylethyltriphenylphosphorane and heated under an atmosphere of dry argon for 36 hours to 80° C. After the cooling, it was purified directly by chromatography on about 70 ml of silica gel with use of a gradient system of n-hexane and diethyl ether. 902 mg (1.34 mmol, 84%) of a mixture of both title compounds was isolated as a colorless oil.

IR (film): 3600–3400, 3070, 3040, 2940, 2860, 1710, 1645, 1600, 1585, 1510, 1465, 1425, 1365, 1265, 1230, 1200, 1160, 1110, 1070, 1030, 870, 820, 755 and 700 cm$^{-1}$.

EXAMPLE 277

(1S,4R,5S,6R)-7-[4-(4-Fluorophenyl)-6-[2-(4-fluorophenoxy)ethoxymethyl]-2-oxabicyclo[2.2.1]hept-5-yl]-3-oxa-5(E)-heptenoic acid 20.3 mg (50 micromol) of the alcohol produced according to example 276a was reacted analogously to example 1 and, after working up and purification, 9.2 mg (19 micromol, 38%) of the title compound was isolated as a colorless oil.

IR (film): 3600–2400, 3070, 30650, 2930, 2870, 1735, 1605, 1510, 1455, 1250, 1225, 1210, 1130, 895, 830, and 745 cm$^{-1}$.

EXAMPLE 278

(1Sm,4R,5S,6R)-7-[4-(4-Fluorophenyl)-6-[2-(4-fluorophenoxy)ethoxymethyl]-2-oxabicyclo[2.2.1]hept-5-yl]-3-oxa-5(E)-heptenoic acid methyl ester 3 mg (6 micromol) of the acid produced in example 277 was esterified analogously to example 186 and, after working up, 3 mg of the title compound was isolated as a colorless oil.

IR (film): 3070, 3050, 2930, 2870, 1745, 1605, 1510, 1455, 1295, 1250, 1225, 1210, 1166, 1130, 1030, 970, 895, 830 and 745 cm$^{-1}$.

EXAMPLE 279

(1S,4R,5S,6R)-7-[4-(4-Fluorophenyl)-6-[2-(4-fluorophenoxy)ethoxymethyl]-2-oxabicyclo[2.2.1]hept-5-yl]-3-oxa-5(Z)-heptenoic acid 17.7 mg (44 micromol) of the alcohol produced according to example 274a was reacted analogously to example 1 and, after working up and purification, 8.7 mg (18 micromol, 41%) of the title compound was isolated as a colorless oil.

IR (film): 3700–2400, 3070, 3050, 3010, 2920, 2870, 1730, 1605, 1510, 1455, 1295, 1250, 1220, 1210, 1160, 1130, 1100, 1030, 895, 830 and 745 cm$^{-1}$.

EXAMPLE 280

(1S,4R,5S,6R)-7-[4-(4-Fluorophenyl)-6-[2-(4-fluorophenoxy)ethoxymethyl]-2-oxabicyclo[2.2.1]hept-5-yl]-3-oxa-5(Z)-heptenoic acid methyl ester 3.1 mg (6 micromol) of the acid produced in example 277 was esterified analogously to example 186 and, after working up, 3 mg of the title compound was isolated as a colorless oil.

IR (film): 3110, 3070, 3050, 3010, 2930, 2870, 1745, 1605, 1510, 1455, 1425, 1295, 1250, 1225, 1210, 1160, 1130, 1100, 1030, 895, 830 and 745 cm$^{-1}$.

EXAMPLE 281

(1S,4R,5S,6S)-7-[4-(4-Fluorophenyl)-6-[3(S)-hydroxy-1(E)octenyl]-2-oxabicyclo[2.2.1]hept-5-yl]-3-oxa-5(E)-heptenoic acid 12 mg (24 micromol) of nonpolar ester A produced according to example 283 was saponified analogously to example 2 and, after working up and purification, 9.4 mg (21 micromol, 88%) of the title compound was isolated as a colorless oil.

IR (film): 3600–2400, 3040, 2950, 2930, 2870, 2860, 1725, 1605, 1515, 1455, 1425, 1230, 1160, 1115, 995, 970, 895, 835 and 755 cm$^{-1}$.

EXAMPLE 282

(1S,4R,5S,6S,)-7-[4-(4-Fluorophenyl)-6-[3(R)-hydroxy-1(E)octenyl]-2-oxabicyclo[2.2.1]hept-5-yl]-3-oxa-5(E)-heptenoic acid 13 mg (26 micromol) of polar ester B produced according to example 283 was saponified analogously to example 2 and, after working up and purification, 9.5 mg (21 micromol, 82%) of the title compound was isolated as a colorless oil.

IR (film): 3600–2400, 3040, 2950, 2930, 2860, 1725, 1610, 1515, 1425, 1235, 1160, 1115, 1000, 970, 895, 835 and 755 cm$^{-1}$.

EXAMPLE 283

(1S,4R,5S,6S)-7-[4-(4-Fluorophenyl)-6-[3(S)-hydroxy-1(E)octenyl]-2-oxabicyclo[2.2.1]hept-5yl]-3-oxa-5(E)-heptenoic acid-t-butyl ester (A) and
(1S,4R,5S,6S)-7-[4-(4-Fluorophenyl)-6-[3(R)-hydroxy-1(E)-octenyl]-2-oxabicyclo[2.2.1]hept-5-yl]-3-oxa-5(E)-heptenoic acid-t-butyl ester (B)

26.7 mg (53 micromol) of the unsaturated ketone produced in example 283a was reduced analogously to example 23 and, after working up and purification, 26 mg (52 micromol, 98%) of a mixture of both title compounds was isolated as a colorless oil.

IR (film): 3600–3200, 3040, 2970, 2950, 2930, 2860, 1745, 1605, 1510, 1365, 1230, 1160, 1130, 965, 895 and 835 cm$^{-1}$.

The chromatographic separation yielded 12 mg (24 micromol, 45%) of the more nonpolar alcohol, to which structure A was assigned, as well as 13 mg (26 micromol, 48%) of the more polar alcohol, to which structure B was assigned.

EXAMPLE 283a (1S,4R,5S,6S)-7-[4-(4-Fluorophenyl)-6-[3-oxo-1(E)-octenyl]-2-oxabicyclo[2.2.1]hept-5yl]-3-oxa-5(E)-heptenoic acid-t-butyl ester 40.9 mg (101 micromol) of the aldehyde produced in example 283b was reacted analogously to example 23a with use of dimethyl(2-oxo-heptyl)-phosphonate and, after working and purification, 26.7 mg (53 micromol, 53%) of the title compound was isolated as a colorless oil.

IR (film): 3040, 2970, 2950, 2930, 2870, 1745, 1690, 1670, 1620, 1510, 1365, 1225, 1160, 1130, 995, 970, 900 and 835 cm$^{-1}$.

EXAMPLE 283b (1S,4R,5S,6S)-7-[4-(4-Fluorophenyl)-6-formyl-2-oxabicyclo[2.2.1]hept-5-yl]-3-oxa-5(E)-heptenoic acid-t-butyl ester 83 mg (204 micromol) of the alcohol produced in example 276a was oxidized analogously to example 38b and, after working up, 83 mg (204 micromol, 100%) of the title compound was isolated as a colorless oil, which was further reacted without purification.

EXAMPLE 284

(1S,4R,5S,6S)-7-[4-(4-Fluorophenyl)-6-[3(S)-hydroxy-1(E)octenyl]-2-oxabicyclo[2.2.1]hept-5yl]-3-oxa-5(Z)-heptenoic acid 18 mg (36 micromol) of nonpolar ester A produced according to example 286 was saponified analogously to example 2 and, after working up and purification, 12 mg (27 micromol, 75%) of the title compound was isolated as a colorless oil.

IR (film): 3700–2400, 3070, 3050, 3010, 2950, 2930, 2870, 2860, 1730, 1610, 1515, 1455, 1425, 1300, 1230, 1160, 1120, 1000, 970, 895 and 835 cm$^{-1}$.

EXAMPLE 285

(1S,4R,5S,6S)-7-[4-(4-Fluorophenyl)-6-[3(R)-hydroxy-1(E)octenyl]-2-oxabicyclo[2.2.1]hept-5yl]-3-oxa-5(Z)-heptenoic acid 22 mg (44 micromol) of polar ester B produced according to example 286 was saponified analogously to example 2 and, after working up and purification, 15 mg (34 micromol, 76 %) of the title compound was isolated as a colorless oil.

IR (film): 3600–2400, 3070, 3040, 3020, 2950, 2930, 2870, 2860, 1730, 1610, 1515, 1455, 1430, 1300, 1235, 1160, 1120, 1000, 970, 895 and 835 cm$^{-1}$.

EXAMPLE 286

(1S,4R,5S,6S)-7-[4-(4-Fluorophenyl)-6-[3(S)-hydroxy-1(E)octenyl]-2-oxabicyclo[2.2.1]hept-5yl]-3-oxa-5(Z)-heptenoic acid-t-butyl ester (A) and
(1S,4R,5S,6S)-7-[4-(4-fluorophenyl)-6-[3(R)-hydroxy-1(E)-octenyl]-2-oxabicyclo[2.2.1]hept-5-yl]-3-oxa-5(Z)-heptenoic acid-t-butyl ester (B)

42 mg (84 micromol) of the unsaturated ketone produced in example 286a was reduced analogously to example 23 and, after working up and purification, 42 mg (84 micromol, 100%) of a mixture of both title compounds was isolated as a colorless oil.

IR (film): 3600–3200, 3050, 2970, 2950, 2930, 2860, 1745, 1605, 1510, 1455, 1365, 1230, 1160, 1125, 995, 970, 940, 895 and 835 cm$^{-1}$.

The chromatographic separation yielded 18 mg (36 micromol, 43%) of the nonpolar alcohol, to which structure A was assigned, as well as 22 mg (44 micromol, 52%) of the more polar alcohol, to which structure B was assigned.

EXAMPLE 286a (1S,4R,5S,6S)-7-[4-(4-Fluorophenyl)-6-[3-oxo-1(E)-octenyl]-2-oxabicyclo[2.2.1]hept-5-yl]-3-oxa-5(Z)-heptenoic acid-t-butyl ester 48.6 mg (120 micromol) of the aldehyde produced in example 286b was reacted analogously to example 23a with use of dimethyl(2-oxo-heptyl)-phosphonate and, after working up and purification, 42 mg (84 micromol, 70%) of the title compound was isolated as a colorless oil.

IR (film): 3050, 2970, 2950, 2930, 2870, 1745, 1690, 1670, 1625, 1515, 1450, 1370, 1230, 1160, 1130, 1040, 995, 975, 940, 900 and 835 cm$^{-1}$.

EXAMPLE 286B (1S,4R,5S,6S)-7-[4-(4-fluorophenyl)-6-formyl-2-oxabicyclo[2.2.1]hept-5-yl]-3-oxa-5(Z)-heptenoic acid-t-butyl ester 186 mg (458 micromol) of the alcohol produced in example 274a was oxidized analogously to example 38b and, after working up, 185 mg (457 micromol, 100%) of the title compound was isolated as a colorless oil, which was further reacted without purification.

EXAMPLE 287

(1S,4R,5S(5E),6S(1E,3S,4S))-7-[4-(4(Fluorophenyl)-6-(3-hydroxy-4-methyl-non-1-en-6-inyl)-2-oxabicyclo[2.2.1]hept-5-yl]-3-oxa-5-heptenoic acid 11.2 mg (21 micromol) of nonpolar ester A produced according to example 289 was saponified analogously to example 2 and, after working up and purification, 9.8 mg (21 micromol, 99%) of the title compound was isolated as a colorless oil.

IR (film): 3600–2400, 3040, 2970, 2930, 2880, 1730, 1605, 1515, 1455, 1430, 1230, 1160, 1115, 995, 970, 895, 835 and 760 cm$^{-1}$.

EXAMPLE 288

(1S,4R,5S(5E),6S(1E,3R,4S))-7-[4-(4-Fluorophenyl)-6-(3-hydroxy-4-methyl-non-1-en-6-inyl)-2-oxabicyclo[2.2.1]hept-5-yl]-3-oxa-5-heptenoic acid 12.8 mg (24 micromol) of polar ester B produced according to example 289 was saponified analogously to example 2 and, after working up and purification, 11 mg (23 micromol, 97%) of the title compound was isolated as a colorless oil.

IR (film): 3600–2400, 3070, 3040, 2970, 2920, 2870, 1725, 1605, 1515, 1455, 1430, 1230, 1160, 1110, 995, 970, 895, 835 and 755 cm$^{-1}$.

EXAMPLE 289

(1S,4R,5S(5E),6S(1E,3S,4S))-7-[4-(4-Fluorophenyl)-6-(3-hydroxy-4-methyl-non-1-en-6-inyl)-2-oxabicyclo[2.2.1]hept-5-yl]-3-oxa-5-heptenoic acid-t-butyl ester (A) and
(1S,4R,5S(5E),6S(1E,3R,4S))-7-[4-(4-fluorophenyl)-6-(3-hydroxy-4-methyl-non-1-en-6-inyl)-2-oxabicyclo[2.2.1]hept-5-yl]-3-oxa-5-heptenoic acid-t-butyl ester (B)

29 mg (55 micromol) of the unsaturated ketone produced in example 289a was reduced analogously to example 23 and, after working up and purification, 26 mg (23 micromol, 90%) of a mixture of both title compounds was isolated as a colorless oil.

IR (film): 3600-3200, 3050, 2970, 2930, 2870, 1745, 1605, 1510, 1450, 1370, 1230, 1160, 1130, 970, 895, and 835 cm$^{-1}$.

The chromatographic separation yielded 11.2 mg (21 micromol, 38%) of the more nonpolar alcohol, to which structure A was assigned, as well as 12.8 mg (24 micromol), 44%) of the more polar alcohol, to which structure B was assigned.

EXAMPLE 289a (1S,4R,5S(5E),6S(1E,4S))-7-[4-(4-Fluorophenyl)-6-(3-oxo-4-methyl-non-1-en-6-inyl)-2-oxabicyclo[2.2.1]hept-5-yl]-3-oxa-5-heptenoic acid-t-butyl ester 42.8 mg (106 micromol) of the aldehyde produced in example 283b was reacted analogously to example 23a with use of dimethyl(2-oxo-3(S)-methyl-oct-5-inyl)-phosphonate and, after working up and purification, 29 mg (55 micromol, 52%) of the title compound was isolated as a colorless oil.

IR (film): 3070, 3040, 2970, 2930, 2870, 1745, 1690, 1665, 1620, 1510, 1450, 1365, 1225, 1160, 1130, 1040, 995, 970, 940, 900 and 835 cm$^{-1}$.

EXAMPLE 290

(1S,4R,5S(5Z),6S(1E,3S,4S))-7-[4-(4-Fluorophenyl)-6-(3-hydroxy-4-methyl-non-1-en-6-inyl)-2-oxabicyclo[2.2.1]hept-5-yl]-3-oxa-5-heptenoic acid 15 mg (28 micromol) of nonpolar ester A produced according to example 292 was saponified analogously to example 2 and, after working up and purification, 13.2 mg (28 micromol, 100%) of the title compound was isolated as a colorless oil.

IR (film): 3600-2400, 3070, 3050, 3010, 2970, 2930, 2920, 2880, 2240, 1730, 1605, 1515, 1455, 1430, 1410, 1230, 1160, 1115, 995, 970, 940, 910, 895, 830 and 730 cm$^{-1}$.

EXAMPLE 291

(1S,4R,5S(5Z),6S(1E,3S,4S))-7-[4-(4-Fluorophenyl)-6-(3-hydroxy-4-methyl-non-1-en-6-inyl)-2-oxabicyclo[2.2.1]hept-5-yl]-3-oxa-5-heptenoic acid 23 mg (44 micromol) of polar ester B produced according to example 292 was saponified analogously to example 2 and, after working up and purification, 16.4 mg (35 micromol, 80%) of the title compound was isolated as a colorless oil.

IR (film): 3600-2400, 3070, 3040, 3010, 2970, 2930, 2920, 2880, 2240, 1730, 1605, 1510, 1455, 1430, 1230, 1160, 1115, 995, 970, 940, 910, 895, 835 and 735 cm$^{-1}$.

EXAMPLE 292

(1S,4R,5S(5Z),6S(1E,3S,4S))-7-[4-(4-Fluorophenyl)-6-(3-hydroxy-4-methyl-non-1-en-6-inyl)-2-oxabicyclo[2.2.1]hept-5-yl]-3-oxa-5-heptenoic acid-t-butyl ester (A) and
(1S,4R,5S(5Z),6S(1E,3R,4S))-7-[4-(4-fluorophenyl)-6-(3-hydroxy-4-methyl-non-1-en-6-inyl)-2-oxabicyclo[2.2.1]hept-5-yl]-3-oxa-5-heptenoic acid-t-butyl ester (B)

45 mg (86 micromol) of the unsaturated ketone produced in example 292a was reduced analogously to example 23 and, after working up and purification, 41 mg (78 micromol, 91%) of a mixture of both title compounds was isolated as a colorless oil.

IR (film): 3600-3200, 3050, 2970, 2930, 2870, 1745, 1605, 1510, 1450, 1370, 1230, 1160, 1125, 970, 940, 895 and 835 cm$^{-1}$.

The chromatographic separation yielded 15 mg (28 micromol, 33%) of the more nonpolar alcohol, to which structure A was assigned, as well as 23 mg (44 micromol 51%) of the more polar alcohol, to which structure B was assigned.

EXAMPLE 292a (1S,4R,5S(5Z),6S(1E,4S))-7-[4-(4-Fluorophenyl)-6-(3-oxo-4-methyl-non-1-en-6-inyl)-2-oxabicyclo[2.2.1]hept-5-yl]-3-oxa-5-heptenoic acid-t-butyl ester 43.7 mg (108 micromol) of the aldehyde produced in example 286b was reacted analogously to example 23a with use of dimethyl(2-oxo-3(S)-methyl-oct-5-inyl)-phosphonate and, after working up and purification, 45 mg (86 micromol, 79%) of the title compound was isolated as a colorless oil.

IR (film): 3070, 3050, 3010, 2970, 2930, 2870, 1745, 1690, 1665, 1620, 1510, 1455, 1365, 1225, 1160, 1130, 1040, 995, 975, 945, 900 and 835 cm$^{-1}$.

EXAMPLE 293

(1S,4R,5S(5Z),6R)-7-[4-(4-Phenylphenyl)-6-[1-butylaminocarbonyloxymethyl]-2-oxabicyclo[2.2.1]hept-5-heptenoic acid methyl ester The solution of 20 mg (48 micromol) of the alcohol, produced in example 293a, in 400 microliters of anhydrous dimethylformamide was mixed with 6 mg of copper(I) chloride, 10 microliters of n-butyl isocyanate, and stirred for 2 hours at 25° C. under an atmosphere of dry argon. It was diluted with diethyl ether, washed with water, dried on magnesium sulfate and the residue obtained after filtration and removal of the solvent was purified by chromatography on two analytic thin-layer slabs. A mixture of n-hexane and ethyl acetate was used as a mobile solvent; diethyl ether was used as an eluant. 16 mg (31 micromol, 65%) of the title compound was isolated as a colorless oil.

IR (film): 3340, 3060, 3030, 2950, 2930, 2870, 1720, 1600, 1505, 1485, 1245, 1145, 1115, 1005, 970, 895, 830, 765, 730 and 695 cm$^{-1}$.

EXAMPLE 293a (1S,4R,5S(5Z),6R)-7-[4-(4-Phenylphenyl)-6-hydroxymethyl-2-oxabicyclo[2.2.1]hept-5-heptenoic acid methyl ester 13.7 mg (49.6 mmol) of enantiomeric Corey lactone was reacted analogously to examples 17a to 17g and 1h to 1l and 1.44 g (3.41 mmol, 6.9%) of the title compound was isolated as a colorless oil.

IR (film): 3600-2400, 3080, 3060, 3030, 3000, 2930, 2870, 1730, 1710, 1600, 1505, 1455, 1295, 1250, 1210, 1130, 1095, 895, 830, 765, 750, 730 and 700 cm$^{-1}$.

EXAMPLE 294

(1S,4R,5S(5Z),6R)-7-[4-(4-Phenylphenyl)-6-[1-butylaminocarbonyloxymethyl]-2-oxabicyclo[2.2.1]hept-5-yl]-5-heptenoic acid 16 mg (31 micromol) of the ester produced according to example 293 was saponified analogously to example 2 and, after working up and purification, 13.7 mg (27 micromol, 88%) of the title compound was isolated as a colorless oil.

IR (film): 3600–2400, 3330, 3080, 3050, 3030, 2950, 2930, 2870, 1710, 1600, 1525, 1505, 1490, 1455, 1250, 1225, 1145, 1035, 1020, 1010, 970, 895, 835, 765, 730 and 700 cm⁻¹.

EXAMPLE 295

(1S,4R,5S(5Z),6R)-7-[4-(4-Phenylphenyl)-6-[2-(4fluorophenoxy)-ethoxymethyl]-2-oxabicyclo[2.2.1]hept-5-yl]-5-heptenoic acid methyl (or 2-(4-fluorophenoxy)-ethyl) ester 20.6 mg (49 micromol) of the alcohol produced in example 293a was reacted analogously to example 1 with 4-fluorophenoxy-2-ethyl bromide and, after working up and purification, 15 mg of the title compound was isolated as a colorless oil.

IR (film): 3080, 3050, 3030, 3000, 2930, 2870, 1745, 1600, 1510, 1490, 1455, 1295, 1250, 1215, 1125, 1095, 1010, 895, 830, 765, 745, 730 and 700 cm⁻¹.

EXAMPLE 296

(1S,4R,5S(5Z),6R)-7-[4-(4-Phenylphenyl)-6-[2-(4fluorophenyl)-ethoxymethyl]-2-oxabicyclo[2.2.1]hept-5-yl]-5-heptenoic acid 15 mg of the ester mixture produced according to example 295 was saponified analogously to example 2 and, after working up and purification, 10.7 mg (19.6 micromol, 22%, relative to the initial material in example 295) of the title compound was isolated as a colorless oil.

IR (film): 3600–2500, 3080, 3060, 3030, 3000, 2930, 2870, 1730, 1710, 1600, 1505, 1490, 1455, 1295, 1250, 1210, 1130, 1095, 1010, 895, 830, 765, 750, 730 and 700 cm⁻¹.

EXAMPLE 297

(1S,4R,5S(5Z),6R)-7-[4-(4-Phenylphenyl)-6-(benzyloxymethyl)-2-oxabicyclo[2.2.1]hept-5-yl]-5-heptenoic acid methyl (or benzyl ester 19.4 mg (46 micromol) of the alcohol produced in example 293a was reacted analogously to example 1 with benzyl chloride and, after working up and purification, 24 mg of the title compounds was isolated as a colorless oil.

IR (film): 3090, 3060, 3030, 3010, 2930, 2870, 1745 1600, 1490, 1450, 1405, 1365, 1300, 1240, 1210, 1115, 1095, 1075, 1010, 895, 835, 765, 730 and 695 cm⁻¹.

EXAMPLE 298

(1S,4R,5S(5Z),6R)-7-[4-(4-Phenylphenyl)-6-benzyloxymethyl)-2-oxabicyclo[2.2.1]hept-5-yl]-5-heptenoic acid 24 mg of the ester mixture produced according to example 297 was saponified analogously to example 2 and, after working up and purification, 20.4 mg (41 micromol, 89%, relative to the initial material in example 297) of the title compound was isolated as a colorless oil.

IR (film): 3600–2400, 3060, 3030, 3000, 2930, 2870, 1730, 1705, 1600, 1490, 1450, 1405, 1365, 1300, 1240, 1205, 1120, 1095, 1070, 1010, 895, 835, 765, 730 and 695 cm⁻¹.

EXAMPLE 299

(1S,4R,5S(5Z),6R)-7-[4-(4-Phenylphenyl)-6-[4-cyanobenzyloxymethyl)-2-oxabicyclo[2.2.1]hept-5-yl]-5-heptenoic acid methyl (or 4-cyanobenzyl) ester 19.6 mg (47 micromol) of the alcohol produced in example 293a was reacted analogously to example 1 with 4-cyanobenzyl bromide and, after working up and purification, 16.5 mg of the title compounds was isolated as a colorless oil.

IR (film): 3080, 3060, 3030, 3000, 2930, 2870, 2230, 1745, 1610, 1600, 1490, 1450, 1405, 1365, 1240, 1210, 1125, 1110, 1095, 1020, 1010, 970, 895, 835, 820, 765, 730 and 695 cm⁻¹.

EXAMPLE 300

(1S,4R,5S(5Z),6R)-7-[4-(4-Phenylphenyl)-6-(4-cyanobenzyloxymethyl)-2-oxabicyclo[2.2.1]hept-5-yl]-5-heptenoic acid 16.5 mg of the ester mixture produced according to example 299 was saponified analogously to example 2 and, after working up and purification, 14.7 mg (28 micromol, 61%, relative to the initial material in example 299) of the title compound was isolated as a colorless oil.

IR (film): 3600–2400, 3060, 3030, 3000, 2930, 2870, 2230, 1725, 1705, 1610, 1600, 1490, 1450, 1405, 1365, 1240, 1210, 1125, 1110, 1095, 1020, 1010, 970, 895, 835, 820, 765, 730 and 700 cm⁻¹.

EXAMPLE 301

(1S,4R,5S(5Z),6R)-7-[4-(4-Phenylphenyl)-6-(3-nitrobenzyloxymethyl)-2-oxabicyclo[2.2.1]hept-5-yl]-5-heptenoic acid methyl (or 3-nitrobenzyl) ester 19.4 mg (46 micromol) of the alcohol produced in example 293a was reacted analogously to example 1 with 3-nitrobenzyl chloride and, after working up and purification, 21 mg of the title compounds was isolated as a colorless oil.

IR (film): 3080, 3060, 3030, 3010, 2930, 2870, 1740, 1600, 1580, 1530, 1490, 1450, 1350, 1240, 1210, 1125, 1095, 1010, 895, 835, 805, 765, 730 and 700 cm⁻¹.

EXAMPLE 302

(1S,4R,5S(5Z),6R)-7-[4-(4-Phenylphenyl)-6-(3-nitrobenzyloxymethyl)-2-oxabicyclo[2.2.1]hept-5-yl]-5-heptenoic acid 21 mg of the ester mixture produced according to example 301 was saponified analogously to example 2 and, after working up and purification, 15.2 mg (28 micromol, 61%, relative to the initial material in example 301) of the title compound was isolated as a colorless oil.

IR (film): 3600–2400, 3060, 3030, 3000, 2930, 2870, 1730, 1710, 1600, 1580, 1530, 1490, 1450, 1350, 1240, 1210, 1125, 1095, 1010, 895, 835, 810, 765, 730 and 700 cm⁻¹.

EXAMPLE 303

(1S,4R,5S(5Z),6R)-7-[4-(4-Phenylphenyl)-6-(4-fluorobenzyloxymethyl)-2-oxabicyclo[2.2.1]hept-5-yl]-5-heptenoic acid methyl (or 4-fluorobenzyl) ester 19.5 mg (46 micromol) of the alcohol produced in example 293a was reacted analogously to example 1 with 4-fluorobenzyl chloride and, after working up and purification, 26 mg of the title compounds was isolated as a colorless oil.

IR (film): 3070, 3050, 3030, 3010, 2930, 2870, 1745, 1600, 1510, 1490, 1445, 1405, 1295, 1220, 1155, 1115, 1090, 1015, 1010, 970, 895, 835, 765, 730 and 700 cm$^{-1}$.

EXAMPLE 304

(1S,4R,5S(5Z),6R)-7-[4-(4-Phenylphenyl)-6-(4-fluorobenzyloxymethyl)-2-oxabicyclo[2.2.1]hept-5-yl]-5-heptenoic acid 26 mg of the ester mixture produced according to example 303 was saponified analogously to example 2 and, after working up and purification, 20.7 mg (40 micromol, 87%, relative to the initial material in example 303) of the title compound was isolated as a colorless oil.

IR (film): 3600–2400, 3050, 3030, 3010, 2930, 2870, 1730, 1705, 1600, 1510, 1490, 1450, 1405, 1295, 1225, 1155, 1115, 1090, 1010, 970, 895, 830, 765, 730 and 700 cm$^{-1}$.

EXAMPLE 305

(1S,4R,5S(5Z),6R)-7-[4-(4-Phenylphenyl)-6-[phenylaminocarbonyloxymethyl]-2-oxabicyclo[2.2.1]hept-5-yl]-5-heptenoic acid methyl ester 19.6 of the alcohol produced in example 293a was reacted analogously to example 293 with phenyl isocyanate and, after working up and purification, 24 mg (45 micromol, 95%) of the title compound was isolated as a colorless oil.

IR (film): 3400, 3080, 3050, 3030, 2950, 2930, 2880, 1740, 1600, 1540, 1500, 1485, 1445, 1405, 1315, 1220, 1055, 1030, 895, 835, 765, 735 and 695 cm$^{-1}$.

EXAMPLE 306

(1S,4R,5S(5Z),6R)-7-[4-(4-Phenylphenyl)-6-[phenylaminocarbonyloxymethyl]-2-oxabicyclo[2.2.1]hept-5-yl]-5-heptenoic acid 24 mg (45 micromol) of the ester produced according to example 305 was saponified analogously to example 2 and, after working up and purification, 17.7 mg (34 micromol, 72%) of the title compound was isolated as a colorless oil.

IR (film): 3600–2400, 3050, 3030, 3010, 2930, 2870, 1730, 1705, 1600, 1510, 1490, 1450, 1405, 1295, 1225, 1155, 1115, 1090, 1010, 970, 895, 830, 765, 730 and 700 cm$^{-1}$.

EXAMPLE 307

(1S,4R,5S(5Z),6S)-7-[4-(4-Phenylphenyl)-6-[(1E,3S)-3-hydroxy-3-cyclohexyl-prop-1-enyl]-oxabicyclo[2.2.1]hept-5-yl]-5-heptenoic acid methyl ester (A) and (1S,4R,5S(5Z),6S)-7-[4-(4-phenylphenyl)-6-[(1E,3R)-3-hydroxy-3-cyclohexyl-prop-1-enyl]-2-oxabicyclo[2.2.1]hept-5-yl]-5-heptenoic acid methyl ester (B)

42.5 mg (81 micromol) of the unsaturated ketone produced in example 307a was reduced analogously to example 23 and, after working up and purification, 34 mg (64 micromol, 79%) of a mixture of both title compounds was isolated as a colorless oil.

IR (film): 3600–3200, 3050, 3030, 2920, 2850, 1735, 1600, 1485, 1455, 1245, 1195, 1005, 995, 970, 895, 835, 765, 730 and 695 cm$^{-1}$.

The chromatographic separation yielded 17.5 mg (33 micromol, 41%) of the more nonpolar alcohol, to which structure A was assigned, as well as 12.6 mg (24 micromol, 30%) of the more polar alcohol, to which structure B was assigned.

EXAMPLE 307a (1S,4R,5S(5Z),6S)-7-[4-(4-Phenylphenyl)-6-[(1E)-3-oxo-3cyclohexyl-prop-1-enyl]-2-oxabicyclo[2.2.1]hept-5-yl]-5-heptenoic acid methyl ester 50.4 mg (120 micromol) of the aldehyde produced in example 307b was reacted analogously to example 23a with use of dimethyl(2-oxo-2-cyclohexyl-ethyl)-phosphonate and, after working up and purification, 42.5 mg (81 micromol, 67%) of the title compound was isolated as a colorless oil.

IR (film): 3050, 3030, 2920, 2850, 1735, 1685, 1600, 1485, 1455, 1245, 1150, 1000, 970, 895, 835, 765, 730 and 695 cm$^{-1}$.

EXAMPLE 307b (1S,4R,5S(5Z),6S)-7-[4-(4-Phenylphenyl)-6-formyl-2-oxabicyclo[2.2.1]hept-5-yl]-5-heptenoic acid methyl ester 258 mg (613 micromol) of the alcohol produced in example 293a was oxidized analogously to example 38b and, after working up, 256 mg (612 micromol, 100%) of the title compound was isolated as a colorless oil, which was further reacted without purification.

EXAMPLE 308

(1S,4R,5S(5Z),6S)-7-[4-(4-Phenylphenyl)-6-[(1E,3S)-3-hydroxy-3-cyclohexyl-prop-1-enyl]-2-oxabicyclo[2.2.1]hept-5-yl]-5-heptenoic acid 17.5 mg (33 micromol) of nonpolar ester A produced according to example 307 was saponified analogously to example 2 and, after working up and purification, 17 mg (33 micromol, 100%) of the title compound was isolated as a colorless oil.

IR (film): 3600–2400, 3080, 3060, 3030, 3000, 2930, 2850, 1710, 1600, 1490, 1450, 1405, 1295, 1240, 1195, 1005, 995, 970, 910, 890, 840, 765, 730 and 695 cm$^{-1}$.

EXAMPLE 309

(1S,4R,5S(5Z),6S)-7-[4-(4-Phenylphenyl)-6-[(1E,3S)-3-hydroxy-3-cyclohexyl-prop-1-enyl]-2-oxabicyclo[2.2.1]hept-5-yl]-5-heptenoic acid 12.6 mg (24 micromol) of polar ester B produced according to example 307 was saponified analogously to example 2 and, after working up and purification, 12 mg (23 micromol, 98%) of the title compound was isolated as a colorless oil.

IR (film): 3600–2400, 3080, 3050, 3030, 3000, 2930, 2850, 1715, 1600, 1490, 1445, 1405, 1300, 1240, 1195, 1010, 995, 970, 910, 890, 835, 765, 730 and 700 cm$^{-1}$.

EXAMPLE 310

(1S,4R,5S(5Z),6S(1E,3S,4S))-7-[4-(4-Phenylphenyl)-6-(3-hydroxy-4-methyl-non-1-en-6-inyl)-2-oxabicyclo[2.2.1]hept-5-yl]-5-heptenoic acid methyl ester (A) and (1S,4R,5S(5Z),6S(1E,3R,4S))-7-[4-(4-phenylphenyl)-6-(3-hydroxy-4-methyl-non-1-en-6-inyl)-2-oxabicyclo[2.2.1]hept-5-yl]-5-heptenoic acid methyl ester (B)

41.6 mg (77 micromol) of the unsaturated ketone produced in example 310a was reduced analogously to example 23 and, after working up and purification, 36 mg (67 micromol, 86%) of a mixture of both title compounds was isolated as a colorless oil.

IR (film): 3600–3200, 3060, 3030, 2970, 2930, 2880, 1745, 1600, 1490, 1450, 1405, 1320, 1295, 1245, 1195, 1110, 995, 970, 895, 835, 765, 730 and 695 cm$^{-1}$.

The chromatographic separation yielded 15.8 mg (29 micromol, 38%) of the more nonpolar alcohol, to which structure A was assigned, as well as 17.3 mg (32 micromol, 42%) of the more polar alcohol, to which structure B was assigned.

EXAMPLE 310a (1S,4R,5S(5Z),6S(1E,4S))-7-[4-(4-Phenylphenyl)-6-(3-oxo-4-methyl-non-1-en-6-inyl)-2-oxabicyclo[2.2.1]hept-5-yl]-5-heptenoic acid methyl ester 51.8 mg (124 micromol) of the aldehyde produced according to example 307b was reacted analogously to example 23a with use of dimethyl(2-oxo-3(S)-methyl-oct-5-ine)-phosphonate and, after working up and purification, 41.6 mg (77 micromol, 62%) of the title compound was isolated as a colorless oil.

IR (film): 3060, 3030, 2970, 2930, 2880, 1735, 1685, 1600, 1490, 1450, 1430, 1245, 1195, 995, 970, 895, 835, 765, 730 and 700 cm$^{-1}$.

EXAMPLE 311

(1S,4R,5S(5Z),6S(1E,3S,4S))-7-[4-(4-Phenylphenyl)-6-(3-hydroxy-4-methyl-non-1-en-6-inyl)-2-oxabicyclo[2.2.1]hept-5-yl]-5-heptenoic acid 15.8 mg (29 micromol) of nonpolar ester A produced according to example 310 was saponified analogously to example 2 and, after working up and purification, 13.7 mg (26 micromol, 90%) of the title compound was isolated as a colorless oil.

IR (film): 3700–2400, 3080, 3060, 3030, 2970, 2930, 2880, 1710, 1600, 1490, 1450, 1405, 1320, 1295, 1245, 1195, 1110, 995, 970, 895, 835, 765, 730 and 700 cm$^{-1}$.

EXAMPLE 312

(1S,4R,5S(5Z),6S(1E,3S,4S))-7-[4-(4-Phenylphenyl)-6-(3-hydroxy-4-methyl-non-1-en-6-inyl)-2-oxabicyclo[2.2.1]hept-5-yl]-5-heptenoic acid 17.3 mg (32 micromol) of polar ester B produced according to example 310 was saponified analogously to example 2 and, after working up and purification, 16.6 mg (32 micromol, 99%) of the title compound was isolated as a colorless oil.

IR (film): 3600–2400, 3080, 3050, 3030, 2970, 2930, 2880, 1710, 1600, 1490, 1455, 1405, 1320, 1295, 1245, 1195, 1105, 995, 970, 910, 895, 835, 765, 730 and 695 cm$^{-1}$.

EXAMPLE 313

(1S,4R,5S(5Z),6R(1E/Z,3S,4S))-7-[4-(4-Phenylphenyl)-6-(2-bromo-3-hydroxy-4-methyl-non-1-en-6-inyl)-2-oxabicyclo[2.2.1]hept-5-yl]-5-heptenoic acid methyl ester (A) and
(1S,4R,5S(5Z),6R(1E/Z,3R,4S))-7-[4-(4-phenylphenyl)-6-(2-bromo-3-hydroxy-4-methyl-non-1-en-6-inyl)-2-oxabicyclo[2.2.1]hept-5-yl]-5-heptenoic acid methyl ester (B)

61.3 mg (99 micromol) of the unsaturated ketone produced in example 313a was reduced analogously to example 23 and, after working up and purification, 58.7 mg (95 micromol, 96%) of a mixture of both title compounds was isolated as a colorless oil.

IR (film): 3600–3200, 3060, 3030, 2970, 2930, 2870, 1730, 1600, 1485, 1450, 1435, 1315, 1265, 1035, 990, 895, 835, 765, 735 and 700 cm$^{-1}$.

The chromatographic separation yielded 24.5 mg (40 micromol, 40%) of the more nonpolar alcohol, to which structure A was assigned, as well as 33 mg (53 micromol, 54%) of the more polar alcohol, to which structure B was assigned.

EXAMPLE 313a (1S,4R,5S(5Z),6R(1E/Z,4S))-7-[4-(4-Phenylphenyl)-6-(2-bromo-3-oxo-4-methyl-non-1-en-6-inyl)-2-oxabicyclo[2.2.1]hept-5-yl]-5-heptenoic acid methyl ester 67.5 mg (161 micromol) of the aldehyde produced according to example 307b was reacted analogously to example 190a with use of dimethyl(2-oxo-3(S)-methyl-oct-5-ine)-phosphonate and, after working up and purification, 61.3 mg (99 micromol, 62%) of the title compound was isolated as a colorless oil.

IR (film): 3060, 3030, 2970, 2930, 2870, 1730, 1685, 1600, 1485, 1450, 1435, 1240, 1150, 985, 900, 835, 765, 730 and 695 cm$^{-1}$.

EXAMPLE 314

(1S,4R,5S(5Z),6R(1E,3R,4S))-7-[4-(4-Phenylphenyl)-6-(2-bromo-3-hydroxy-4-methyl-non-1-en-6-inyl)-2-oxabicyclo[2.2.1]hept-5-yl]-5-heptenoic acid 6.3 mg (10 micromol) of polar ester B produced according to example 313 was saponified analogously to example 2 and, after working up and purification, 5.5 mg (9 micromol, 88%) of the title compound was isolated as a colorless oil.

IR (film): 3600–2400, 3050, 3030, 2970, 2930, 2870, 1710, 1605, 1485, 1450, 1435, 1315, 1265, 1240, 1195, 1035, 990, 895, 835, 765, 735 and 695 cm$^{-1}$.

EXAMPLE 315

(1S,4R,5S(5Z),6R(1E/Z,3S,4S))-7-[4-(4-Phenylphenyl)-6-(2-bromo-3-hydroxy-4-methyl-non-1-en-6-inyl)-2-oxabicyclo[2.2.1]hept-5-yl]-5-heptenoic acid 5.7 mg (9 micromol) of nonpolar ester A produced according to example 313 was saponified analogously to example 2 and, after working up and purification, 4.8 mg (8 micromol, 86%) of the title compound was isolated as a colorless oil.

IR (film): 3600–2400, 3050, 3030, 2970, 2930, 2870, 1715, 1605, 1485, 1450, 1435, 1315, 1265, 1240, 1195, 1035, 990, 895, 835, 765, 735 and 695 cm$^{-1}$.

EXAMPLE 316

(1S,4R,5S(5Z),6R(3R,4S))-7-[4-(4-Phenylphenyl)-6-(3-hydroxy-4-methyl-nona-1,6-diinyl)-2-oxabicyclo[2.2.1]hept-5-yl]-5-heptenoic acid 26 mg (42 micromol) of polar alcohol B produced according to example 313 was saponified analogously to example 186 and, after working up and purification, 18 mg (34 micromol, 82%) of the title compound was isolated as a colorless oil.

IR (film): 3600–2400, 3050, 3030, 2970, 2930, 2880, 2230, 1705, 1600, 1485, 1450, 1435, 1405, 1320, 1240, 1145, 1020, 1005, 990, 895, 835, 765, 735 and 695 cm$^{-1}$.

EXAMPLE 317

(1S,4R,5S(5Z),6R(3R,4S))-7-[4-(4-Phenylphenyl)-6-(3-hydroxy-4-methyl-nona-1,6-diinyl)-2-oxabicyclo[2.2.1-]hept-5-yl]-5-heptenoic acid methyl ester 2.7 mg (5 micromol) of the acid produced according to example 316 was esterified analogously to example 186 and, after removal of the solvent, 2.7 mg (5 micromol, 97%) of the title compound was isolated as a colorless oil.

IR (film): 3600–3200, 3050, 3030, 2970, 2930, 2870, 2230, 1745, 1600, 1485, 1445, 1435, 1405, 1320, 1240, 1145, 1020, 1005, 990, 895, 835, 765, 735, 730 and 700 cm$^{-1}$.

EXAMPLE 318

(1S,4R,5S(5Z),6R(3S,4S))-7-[4-(4-Phenylphenyl)-6-(3-hydroxy-4-methyl-nona-1,6-diinyl)-2-oxabicyclo[2.2.1-]hept-5-yl]-5-heptenoic acid 18 mg (29 micromol) of nonpolar ester A produced according to example 313 was reacted analogously to example 187 and, after working up and purification, 13.2 mg (25 micromol, 87%) of the title compound was isolated as a colorless oil.

IR (film): 3600–2400, 3080, 3050, 3030, 2970, 2930, 2880, 2230, 1710, 1600, 1525, 1485, 1450, 1435, 1405, 1320, 1290, 1240, 1145, 1020, 1005, 990, 940, 895, 835, 765, 730 and 695 cm$^{-1}$.

EXAMPLE 319

(1S,4R,5S(5Z),6R(3S,4S))-7-[4-(4-Phenylphenyl)-6-(3-hydroxy-4-methyl-nona-1,6-diinyl)-2-oxabicyclo[2.2.1-]hept-5-yl]-5-heptenoic acid methyl ester 3.1 mg (6 micromol) of the acid produced according to example 318 was esterified analogously to example 186 and, after removal of the solvent, 3.1 mg (6 micromol, 98%) of the title compound was isolated as a colorless oil.

IR (film): 3600–3200, 3070, 3050, 3030, 2970, 2930, 2880, 2230, 1740, 1600, 1485, 1450, 1435, 1405, 1320, 1290, 1240, 1145, 1020, 1000, 940, 895, 835, 765, 730 and 695 cm$^{-1}$.

EXAMPLE 320

(1S,4R,5S(5Z),6S)-7-[4-(4-Phenylphenyl)-6-(3(S)-hydroxy-1(E)-octenyl]-2-oxabicyclo[2.2.1]hept-5-yl]-5-heptenoic acid methyl ester (A) and
(1S,4R,5S(5Z),6S))-7-[4-(4-phenylphenyl)-6-[3(R)-hydroxy-1(E)octenyl]-2-oxabicyclo[2.2.1]hept-5-yl]-5-heptenoic acid methyl ester (B)

41.6 mg (81 micromol) of the unsaturated ketone produced in example 320a was reduced analogously to example 23 and, after working up and purification, 35.3 mg (64 micromol, 85%) of a mixture of both title compounds was isolated as a colorless oil.

IR (film): 3600–3200, 3060, 3030, 2950, 2930, 2860, 1735, 1600, 1485, 1450, 1435, 1245, 1195, 995, 970, 895, 835, 765, 730 and 695 cm$^{-1}$.

The chromatographic separation yielded 18.7 mg (36 micromol, 45%) of the more nonpolar alcohol, to which structure A was assigned, as well as 14.3 mg (28 micromol, 34%) of the more polar alcohol, to which structure B was assigned.

EXAMPLE 320a (1S,4R,5S(5Z),6S)-7-[4-(4-Phenylphenyl)-6-[3-oxo-1(E)octenyl]-2-oxabicyclo[2.2.1]hept-5-yl]-5-heptenoic acid methyl ester 49.8 mg (118 micromol) of the aldehyde produced in example 307b was reacted analogously to example 23a with use of dimethyl(2-oxo-heptyl)-phosphonate and, after working up and purification, 41.4 mg (80 micromol, 68%) of the title compound was isolated as a colorless oil.

IR (film): 3060, 3030, 2950, 2930, 2860, 1740, 1690, 1600, 1485, 1440, 1245, 1195, 1005, 995, 970, 895, 765, 730 and 695 cm$^{-1}$.

EXAMPLE 321

(1S,4R,5S(5Z),6S)-7-[4-(4-Phenylphenyl)-6-[3(R) hydroxy-1(E)octenyl]-2-oxabicyclo[2.2.1]hept-5-yl]-5-heptenoic acid 14.3 mg (28 micromol) of polar ester B produced according to example 320 was saponified analogously to example 2 and, after working up and purification, 13.8 mg (27 micromol, 96%) of the title compound was isolated as a colorless oil.

IR (film): 3600–2400, 3080, 3060, 3030, 3010, 2950, 2930, 2870, 2860, 1710, 1600, 1490, 1455, 1405, 1295, 1240, 1195, 1045, 1010, 995, 970, 910, 835, 765 and 700 cm$^{-1}$.

EXAMPLE 322

(1S,4R,5S(5Z),6S)-7-[4-(4-Phenylphenyl)-6-[3(R) hydroxy-1(E)octenyl]-2-oxabicyclo[2.2.1]hept-5-yl]-5-heptenoic acid 18.7 mg (36 micromol) of nonpolar ester A produced according to example 320 was saponified analogously to example 2 and, after working up and purification, 18.1 mg (36 micromol, 100%) of the title compound was isolated as a colorless oil.

IR (film): 3600–2400, 3060, 3030, 2950, 2930, 2870, 1710, 1600, 1490, 1450, 1405, 1295, 1240, 1195, 1010, 995, 970, 910, 835, 765 and 700 cm$^{-1}$.

EXAMPLE 323

(1S,4R,5S(5Z),6R)-7-[4-(4-Phenylphenyl)-6-(4-fluorobenzyloxyiminomethyl)-2-oxabicyclo[2.2.1]hept-5-yl]-5-heptenoic acid methyl ester 19.9 mg (48 micromol) of the aldehyde produced in example 307b was reacted analogously to example 26a with use of p-fluorophenylmethoxyamine and, after working up and purification, 17 mg (31 micromol, 66%) of the title compound was isolated as a colorless oil.

IR (film): 3060, 3030, 2940, 2870, 1730, 1600, 1510, 1485, 1220, 1155, 1045, 1005, 995, 900, 835, 765, 730 and 595 cm$^{-1}$.

EXAMPLE 324

(1S,4R,5S(5Z),6R)-7-[4-(4-Phenylphenyl)-6-(4-fluorobenzyloxyiminomethyl)-2-oxabicyclo[2.2.1]hept-5-yl]-5-heptenoic acid 17 mg (31 micromol) of the ester produced according to example 323 was saponified analogously to example 2 and, after working up and purification, 16 mg (30 micromol, 98%) of the title compound was isolated as a colorless oil.

IR (film): 3600–2500, 3060, 3030, 3010, 2930, 2880, 1730, 1705, 1600, 1510, 1490, 1445, 1405, 1295, 1220, 1155, 1045, 1005, 995, 895, 835, 765, 730 and 700 cm$^{-1}$.

EXAMPLE 325

(1S,4R,5S(5Z),6R)-7-[4-(4-Phenylphenyl)-6--(cyclohexylmethoxyiminomethyl)-2-oxabicyclo[2.2.1-]hept-5-yl]-5-heptenoic acid methyl ester 18.3 mg (44 micromol) of the aldehyde produced in example 307b was reacted analogously to example 26 with use of cyclohexylmethoxyamine and, after working up and purification, 18 mg (34 micromol, 78%) of the title compound was isolated as a colorless oil.

IR (film): 3060, 3030, 3000, 2920, 2850, 1735, 1600, 1485, 1445, 1240, 1190, 1160, 1035, 1000, 900, 835, 765, 730 and 695 cm$^{-1}$.

EXAMPLE 326

(1S,4R,5S(5Z),6R)-7-[4-(4-Phenylphenyl)-6--(cyclohexylmethoxyiminomethyl)-2-oxabicyclo[2.2.1-]hept-5-yl]-5-heptenoic acid 18 mg (34 micromol) of the ester produced according to example 325 was saponified analogously to example 2 and, after working up and purification, 17 mg (33 micromol, 97%) of the title compound was isolated as a colorless oil.

IR (film): 3600–2400, 3080, 3050, 3030, 3000, 2930, 2850, 1730, 1705, 1600, 1490, 1450, 1405, 1295, 1240, 1190, 1080, 1040, 1025, 1010, 995, 900, 835, 765, 730 and 700 cm$^{-1}$.

EXAMPLE 327

(1S,4R,5S,6R)-7-[4-(4-Fluorophenyl)-6-(4-fluorobenzyloxymethyl)-2-oxabicyclo[2.2.1]hept-5-yl]-3-oxaheptanoic acid 19.5 mg (48 micromol) of the alcohol produced in example 327a was reacted analogously to example 1 and, after working up and purification, 17.5 mg (38 micromol, 80%) of the title compound was isolated as a colorless oil.

IR (film): 3600–2400, 3070, 3040, 2930, 2860, 1725, 1605, 1510, 1425, 1365, 1225, 1160, 1115, 1025, 900, and 830 cm$^{-1}$.

EXAMPLE 327a (1S,4R,5S,6R)-7-[4-(4-Fluorophenyl)-6-hydroxymethyl-2--oxabicyclo[2.2.1]hept-5-yl]-3-oxaheptanoic acid-t-butyl ester 84 mg (207 micromol) of the alcohol produced in example 276a was dissolved in 3 ml of ethyl acetate, mixed with 30 mg of palladium on carbon (10%) and hydrogenated under normal pressure, until a clearly slowed-down absorption of hydrogen took place. It was filtered, concentrated by evaporation in a water jet vacuum and the residue obtained was purified by chromatography on 4 analytic thin-layer slabs. A mixture of trichloromethane and acetone was used as a mobile solvent; a mixture of ethanol and ethyl acetate was used as an eluant. 49 mg (129 micromol, 58%) of the title compound was isolated as a colorless oil.

IR (film): 3700–3200, 3050, 2980, 2930, 2860, 1740, 1605, 1510, 1365, 1230, 1160, 1135, 1020, 895, 830, 815 and 735 cm$^{-1}$.

EXAMPLE 328

(1S,4R,5S,6R)-7-[4-(4-Fluorophenyl)-6-(4-fluorobenzyloxymethyl)-2-oxabicyclo[2.2.1]hept-5-yl]-3-oxaheptanoic acid methyl ester 2.9 mg (6 micromol) of the acid produced according to example 327 was esterified analogously to example 186 and, after removal of the solvent, 3 mg (6 micromol, 100%) of the title compound was isolated as a colorless oil.

IR (film): 3070, 3050, 2930, 2860, 1745, 1605, 1515, 1425, 1365, 1225, 1160, 1120, 1100, 1025, 895 and 830 cm$^{-1}$.

EXAMPLE 329

(1S,4R,5S,6R)-7-[4-(4-Fluorophenyl)-6-(4-cyanobenzyloxymethyl)-2-oxabicyclo[2.2.1]hept-5-yl]-3-oxaheptanoic acid 19 mg (47 micromol) of the alcohol produced in example 327a was reacted analogously to example 1 and, after working up and purification, 12.1 mg (26 micromol, 56%) of the title compound was isolated as a colorless oil.

IR (film): 3600–2400, 3070, 3050, 2930, 2860, 2215, 1725, 1610, 1515, 1415, 1230, 1160, 1125, 1100, 1020, 895, 830 and 815 cm$^{-1}$.

EXAMPLE 330

(1S,4R,5S,6R)-7-[4-(4-Fluorophenyl)-6-(4-cyanobenzyloxymethyl)-2-oxabicyclo[2.2.1]hept-5-yl]-3-oxaheptanoic acid methyl ester 3.4 mg (7 micromol) of the acid produced according to example 329 was esterified analogously to example 186 and, after removal of the solvent, 3.3 mg (7 micromol, 94%) of the title compound was isolated as a colorless oil.

IR (film): 3070, 3050, 2930, 2860, 2215, 1740, 1610, 1515, 1415, 1230, 1160, 1125, 1110, 1100, 1020, 895, 830 and 820 cm$^{-1}$.

EXAMPLE 331

(1S,4R,5S(5Z),6R(1E/Z,3S,4S))-7-[4-(4-Fluorophenyl)-6-(2-bromo-3-hydroxy-4-methyl-non-1-en-6inyl)-2-oxabicyclo[2.2.1]hept-5-yl]-3-oxa-5-heptenoic acid-t-butyl ester (A) and
(1S,4R,5S(5Z),6R-(1E/Z,3R,4S))-7-[4-(4-fluorophenyl)-6-(2-bromo-3-hydroxy-4-methyl-non-1-en-6-inyl)-2-oxabicyclo[2.2.1]hept-5-yl]-3-oxa-5-heptenoic acid-t-butyl ester (B)

92 mg (151 micromol) of the unsaturated ketone produced in example 331a was reduced analogously to example 23 and, after working up and purification, 77 mg (126 micromol, 84%) of a mixture of both title compounds was isolated as a colorless oil.

IR (film): 3600–3200, 3060, 3050, 2970, 2930, 2870, 1745, 1605, 1515, 1450, 1370, 1230, 1160, 1125, 1040, 995, 940, 895, 835 and 735 cm$^{-1}$.

The chromatographic separation yielded 29 mg (48 micromol, 32%) of the more nonpolar alcohol, to which structure A was assigned, as well as 46 mg (77 micromol, 50%) of the more polar alcohol, to which structure B was assigned.

EXAMPLE 331a (1S,4R,5S(5Z),6R(1E/Z,4S))-7-[4-(4-Fluorophenyl)-6-(2-bromo-3-oxo-4-methyl-non-1-en-6-inyl)-2-oxabicyclo[2.2.1]hept-5-yl]-3-oxa-5-heptenoic acid-t-butyl ester 88 mg (218 micromol) of the aldehyde produced in example 286b was reacted analogously to example 190a with use of dimethyl-(2-oxo-3(S)-methyl-oct-5-inyl)-phosphonate and, after working up and purification, 92 mg (151 micromol, 70%) of the title compound was isolated as a colorless oil.

IR (film): 3050, 2970, 2930, 2870, 1745, 1690, 1600, 1510, 1455, 1365, 1230, 1160, 1130, 1040, 990, 940, 905, 835 and 735 cm$^{-1}$.

EXAMPLE 332

(1S,4R,5S(5Z),6R(1E/Z,3R,4S))-7-[4-(4-Fluorophenyl)-6-(2-bromo-3-hydroxy-4-methyl-non-1-en-6-inyl)-2-oxabicyclo[2.2.1]hept-5-yl]-3-oxa-5-heptenoic acid 8.3 mg (14 micromol) of polar ester B produced according to example 331 was saponified analogously to example 2 and, after working up and purification, 6.5 mg (12 micromol, 85%) of the title compound was isolated as a colorless oil.

IR (film): 3600–2400, 3050, 2970, 2930, 2870, 1710, 1605, 1510, 1455, 1365, 1230, 1160, 1125, 1040, 995, 940, 895, 835 and 735 cm$^{-1}$.

EXAMPLE 333

(1S,4R,5S(5Z),6R(1E/Z,3S,4S))-7-[4-(4-Fluorophenyl)-6-(2-bromo-3-hydroxy-4-methyl-non-1-en-6-inyl)-2-oxabicyclo[2.2.1]hept-5-yl]-3-oxa-5-heptenoic acid 5.1 mg (8 micromol) of nonpolar ester A produced according to example 331 was saponified analogously to example 2 and, after working up and purification, 4.2 mg (8 micromol, 96%) of the title compound was isolated as a colorless oil.

IR (film): 3600–2400, 3050, 2970, 2930, 2870, 1710, 1605, 1510, 1455, 1370, 1230, 1160, 1125, 1035, 995, 940, 895, 835 and 735 cm$^{-1}$.

EXAMPLE 334

(1S,4R,5S(5Z),6R(3R,4S))-7-[4-(4-Fluorophenyl)-6-(3-hydroxy-4-methyl-nona-1,6-diinyl)-2-oxabicyclo[2.2.1]hept-5-yl]-3-oxa-5-heptenoic acid 31 mg (51 micromol) of polar alcohol B produced according to example 331 was reacted analogously to example 187 and, after working up and purification, 12 mg (25 micromol, 49%) of the title compound was isolated as a colorless oil.

IR (film): 3600–2400, 3050, 3010, 2970, 2930, 2870, 2230, 1710, 1605, 1515, 1450, 1230, 1160, 1125, 1040, 990, 900, 835 and 735 cm$^{-1}$.

EXAMPLE 335

(1S,4R,5S(5Z),6R(1E/Z,3R,4S))-7-[4-(4-Fluorophenyl)-6-(2-bromo-3-hydroxy-4-methyl-non-1-en-6-inyl)-2-oxabicyclo[2.2.1]hept-5-yl]-3-oxa-5-heptenoic acid methyl ester 4 mg (9 micromol) of the acid produced according to example 334 was esterified analogously to example 186 and, after removal of the solvent, 4 mg (8 micromol, 97%) of the title compound was isolated as a colorless oil.

IR (film): 3600–3200, 3050, 3010, 2970, 2930, 2870, 2230, 1740, 1605, 1515, 1450, 1230, 1160, 1130, 1035, 995, 900, 835 and 735 cm$^{-1}$.

EXAMPLE 336

(1S,4R,5S(5Z),6R(3S,4S))-7-[4-(4-Fluorophenyl)-6-(3-hydroxy-4-methyl-nona-1,6-diinyl)-2-oxabicyclo[2.2.1]hept-5-yl]-3-oxa-5-heptenoic acid 19.6 mg (32 micromol) of nonpolar ester A produced according to example 331 was reacted analogously to example 187 and, after working up and purification, 8.2 mg (17 micromol, 54%) of the title compound was isolated as a colorless oil.

IR (film): 3600–2400, 3050, 2970, 2930, 2870, 2230, 1710, 1605, 1510, 1455, 1230, 1160, 1120, 1035, 995, 895, 835 and 735 cm$^{-1}$.

EXAMPLE 337

(1S,4R,5S(5Z),6R(3S,4S))-7-[4-(4-Fluorophenyl)-6-(3-hydroxy-4-methyl-nona-1,6-diinyl)-2-oxabicyclo[2.2.1]hept-5-yl]-3-oxa-5-heptenoic acid methyl ester 2.7 mg (6 micromol) of the acid produced according to example 336 was esterified analogously to example 186 and, after removal of the solvent, 2.8 mg (6 micromol, 100%) of the title compound was isolated as a colorless oil.

IR (film): 3600–3200, 3050, 3010, 2970, 2930, 2870, 2230, 1745, 1605, 1515, 1455, 1230, 1160, 1120, 1040, 995, 895, 835 and 735 cm$^{-1}$.

EXAMPLE 338

(1S,4R,5S(5Z),6R)-7-[4-(4-Fluorophenyl)-6--(cyclohexylmethoxyiminomethyl)-2-oxabicyclo[2.2.1]hept-5-yl]-3-oxa-5-heptenoic acid-t-butyl ester 16.3 mg (40 micromol) of the aldehyde produced in example 286b was reacted analogously to example 26 with use of cyclohexylmethoxyamine and, after working up and purification, 16.1 mg (31 micromol, 78%) of the title compound was isolated as a colorless oil.

IR (film): 3070, 3040, 3010, 2930, 2850, 1745, 1610, 1515, 1450, 1430, 1235, 1165, 1115, 1040, 1025, 1000, 945, 900, 835 and 820 cm$^{-1}$.

EXAMPLE 339

(1S,4R,5S(5Z),6R)-7-[4-(4-Fluorophenyl)-6--(cyclohexylmethoxyiminomethyl)-2-oxabicyclo[2.2.1]hept-5-yl]-3-oxa-5-heptenoic acid 16.1 mg (31 micromol) of the ester produced according to example 338 was saponified analogously to example 2 and, after working up and purification, 12.8 mg (28 micromol, 90%) of the title compound was isolated as a colorless oil.

IR (film): 3600–2400, 3070, 3050, 302, 2930, 2850, 1730, 1610, 1515, 1450, 1235, 1160, 1115, 1040, 1025, 1000, 900, 835 and 820 cm$^{-1}$.

EXAMPLE 340

(1S,4R,5S(5Z),6R)-7-[4-(4-Fluorophenyl)-6-(4-fluorobenzyloxyiminomethyl)-2-oxabicyclo[2.2.1]hept-5-yl]-3-oxa-5-heptenoic acid methyl ester 16.8 mg (42 micromol) of the aldehyde produced in example 286b was reacted analogously to example 26 with use of p-fluorophenylmethoxyamine and, after working up and purification, 17.6 mg (33 micromol, 80%) of the title compound was isolated as a colorless oil.

IR (film): 3070, 3050, 3010, 2930, 2880, 1745, 1605, 1515, 1430, 1415, 1365, 1225, 1160, 1120, 1100, 1040, 1015, 945, 900 and 835 cm$^{-1}$.

EXAMPLE 341

(1S,4R,5S(5Z),6R)-7-[4-(4-Fluorophenyl)-6-(4-fluorobenzyloxyiminomethyl)-2-oxabicyclo[2.2.1]hept-5-yl]-3-oxa-5-heptenoic acid 17.6 mg (33 micromol) of the ester produced according to example 340 was saponified analogously to example 2 and, after working up and purification, 12.8 mg (27 micromol, 82%) of the title compound was isolated as a colorless oil.

IR (film): 3600–2400, 3070, 3050, 3020, 2930, 2880, 1730, 1605, 1515, 1430, 1225, 1160, 1120, 1045, 1015, 945, 900 and 835 cm$^{-1}$.

EXAMPLE 342

(1S,4R,5S,6R)-7-[4-(4-Fluorophenyl)-6-(benzyloxymethyl)-2-oxabicyclo[2.2.1]hept-5-yl]-3-oxa-5(Z)-heptenoic acid 19 mg (47 micromol) of the alcohol produced in example 274a was reacted analogously to example 1 and, after working up and purification, 14.5 mg (33 micromol, 70%) of the title compound was isolated as a colorless oil.

IR (film): 3700–2300, 3090, 3060, 3030, 2920, 2870, 1725, 1605, 1515, 1455, 1230, 1160, 1115, 1100, 1030, 900, 835, 740 and 700 cm$^{-1}$.

EXAMPLE 343

(1S,4R,5S,6R)-7-[4-(4-Fluorophenyl)-6-(benzyloxymethyl)-2-oxabicyclo[2.2.1]hept-5-yl]-3-oxa-5(Z)-heptenoic acid methyl ester 3.1 mg (7 micromol) of the acid produced in example 342 was esterified analogously to example 186 and, after removal of the solvent, 3.1 mg (7 micromol, 97%) of the title compound was isolated as a colorless oil.

IR (film): 3090, 3060, 3030, 2970, 2920, 2870, 1745, 1605, 1515, 1455, 1430, 1230, 1160, 1115, 1100, 1030, 975, 900, 835, 740 and 700 cm$^{-1}$.

EXAMPLE 344

(1S,4R,5R,(5Z),6S)-7-[4-(4-Phenylphenyl)-6-trifluoromethylcarbonylamino-2-oxabicyclo[2.2.1]hept-5-yl]-5-heptenoic acid 15 mg (30 micromol) of ester B produced in example 344a was saponified analogously to example 2 and, after working up and purification, 12 mg (25 micromol, 83%) of the title compound was isolated as a colorless oil.

IR (film): 3700–2600, 3430, 3310, 3080, 3060, 3030, 2940, 2880, 1710, 1600, 1555, 1490, 1215, 1185, 1115, 1005, 900, 840, 815, 730 and 695 cm$^{-1}$.

EXAMPLE 344a (1S,4R,5R(5Z),6S)-7-[4-(4-Phenylphenyl)-6-amino-2-oxabicyclo[2.2.1]hept-5yl]-5-heptenoic acid methyl ester (A) and (1S,4R,5R(5Z),6S)-7-[4-(4-phenylphenyl)-6-trifluoromethylcarbonylamino-2-oxabicyclo[2.2.1]hept-5-yl]-5-heptenoic acid methyl ester (B)

The solution, cooled to 0°–5° C., of 409 mg (903 micromol) of the acid chloride, produced in example 344b, in 1.4 ml of dichloromethane was mixed with the solution of 71.7 mg of sodium azide in 240 microliters of water and, after the addition of 0.9 mg of tetrabutylammonium hydrogen sulfate, stirred for 1 hour with ice cooling. The organic phase was separated, the aqueous phase was washed several times with dichloromethane and the combined organic extracts were stored on anhydrous magnesium sulfate for 2 days. After filtration and concentration by evaporation of the volume to about 2 ml, it was mixed with 300 microliters of trifluoroacetic acid and refluxed for 24 hours. The residue obtained after removal of the solvent was purified by chromatography on about 75 ml of silica gel with use of a gradient system of dichloromethane and methanol. 277 mg (683 micromol, 76%) of title compound A as well as 103 mg (205 micromol, 23%) of title compound B were each isolated as a colorless oil.

IR (film) of A: 3360, 3290, 3050, 3030, 2930, 2860, 1730, 1605, 1485, 1265, 1075, 1045, 1005, 895, 835, 765, 735 and 700 cm$^{-1}$.

IR (film) of B: 3300, 3060, 3030, 2940, 2880, 1725, 1705, 1600, 1550, 1485, 1440, 1210, 1180, 1155, 1005, 900, 840, 765, 730 and 695 cm$^{-1}$.

EXAMPLE 344b (1S,4R,5S(5Z),6S)-7-[4-(4-Phenylphenyl)-6-chlorocarbonyl-2-oxabicyclo[2.2.1]hept-5-yl]-5-heptenoic acid methyl ester The solution of 400 mg (921 micromol) of the acid, produced in example 344c, in 10 ml of anhydrous dichloromethane was cooled under an atmosphere of dry argon to 0°–5° C., mixed with 160 microliters of thionyl chloride, allowed to heat to 23° C. and stirred for another 6 hours. After removal of the solvent in a vacuum, 409 mg (903 micromol, 98%) of the title compound was isolated as a pale yellow oil, which was further reacted without purification.

EXAMPLE 344c (1S,4R,5S(5Z),6S)-7-[4-(4-Phenylphenyl)-6-hydroxycarbonyl-2-oxabicyclo[2.2.1]hept-5-yl]-5-heptenoic acid methyl ester The solution of 540 mg (1.28 mmol) of the alcohol produced according to example 293a was oxidized analogously to example 274m and, after working up and performed analogously to example 1i and purification performed chromatographically on about 70 mg of silica gel with use of a gradient system of n-hexane and acetone, 400 mg (921 micromol, 72%) of the title compound was isolated as a colorless oil.

IR (film): 3700–2500, 3050, 3030, 2950, 2870, 1730, 1700, 1600, 1485, 1440, 1300, 1220, 1170, 1005, 990, 895, 835, 765, 730 and 695 cm$^{-1}$.

EXAMPLE 345

(1S,4R,5R(5Z),6S)-7-[4-(4-Phenylphenyl)-6-(3,5-dichloro-2-hydroxybenzenesulfonamino)-2-oxabicyclo[2.2.1]hept-5-yl]-5-heptenoic acid methyl ester 22 mg (54.2 micromol) of the amine produced according to in example 544a was dissolved in 800 microliters of anhydrous dichloromethane, mixed with 100 microliters of triethylamine, 17 mg of 3,5-dichloro-2-hydroxy-benzenesulfonic acid chloride and stirred for 5 hours at 23° C. under an atmosphere of dry argon. The chromatographic purification took place on an analytic thin-layer slab. A mixture of chloroform and acetone was used as a mobile solvent; a mixture of ethanol and ethyl acetate was used as an eluant. 11 mg (17 micromol, 31%) of the title compound was isolated as a colorless oil.

IR (film): 3450–3150, 3280, 3080, 3060, 3030, 2940, 2870, 1730, 1600, 1580, 1485, 1465, 1265, 1240, 1160, 1070, 1000, 900, 870, 835, 805, 765, 735, 700 and 580 cm$^{-1}$.

EXAMPLE 346

(1S,4R,5R(5Z),6S)-7-[4-(4-Phenylphenyl)-6-(3,5-dichloro-2-hydroxybenzenesulfonamino)-2-oxabicyclo[2.2.1]hept-5-yl]-5-heptenoic acid 11 mg (17 micromol) of the ester produced according to example 345 was saponified analogously to example 2 and, after working up and purification, 10 mg (16 micromol, 95%) of the title compound was isolated as a colorless oil.

IR (film): 3700–2400, 3270, 3080, 3060, 3030, 2930, 2870, 1710, 1600, 1580, 1485, 1465, 1415, 1315, 1300, 1240, 1150, 1090, 1075, 1010, 995, 900, 870, 835, 765, 735, 695 and 580 cm$^{-1}$.

EXAMPLE 347

(1S,4R,5R(5Z),6S)-7-[4-(4-Phenylphenyl)-6-(4-methylbenzenesulfonamino)-2-oxabicyclo[2.2.1]hept-5-yl]-5-heptenoic acid methyl ester 25 mg (50 micromol) of the amine produced according to example 344a was reacted analogously to example 345 with use of 4-methylbenzenesulfonic acid chloride and, after purification, 15.7 mg (28 micromol, 46%) of the title compound was isolated as a colorless oil.

IR (film): 3300, 3060, 3030, 2940, 2880, 1725, 1715, 1600, 1550, 1485, 1435, 1330, 1215, 1180, 1160, 1090, 1005, 900, 835, 765, 735, 700 and 660 cm$^{-1}$.

EXAMPLE 348

(1S,4R,5R(5Z),6S)-7-[4-(4-Phenylphenyl)-6-(4-methylbenzenesulfonamino)-2-oxabicyclo[2.2.1]hept-5-yl]-5-heptenoic acid 15.7 mg (28 micromol) of the ester produced according to example 347 was saponified analogously to example 2 and, after working up and purification, 12.9 mg (24 micromol, 84%) of the title compound was isolated as a colorless oil.

IR (film): 3700–2400, 3270, 3050, 3010, 2940, 2880, 1710, 1600, 1555, 1435, 1325, 1230, 1160, 1090, 1005, 905, 835, 815, 765, 735, 700 and 660 cm$^{-1}$.

EXAMPLE 349

(1S,4R,5R(5Z),6S)-7-[4-(4-Phenylphenyl)-6-(4-fluorobenzenesulfonamino)-2-oxabicyclo[2.2.1]hept-5-yl]-5-heptenoic acid methyl ester 22.7 mg (56 micromol) of the amine produced according to example 344a was reacted analogously to example 345 with use of 4-fluorobenzenesulfonic acid chloride and, after purification, 15 mg (27 micromol, 48%) of the title compound was isolated as a colorless oil.

IR (film): 3300, 3060, 3030, 2940, 2880, 1725, 1710, 1595, 1550, 1490, 1435, 1330, 1215, 1165, 1155, 1090, 1005, 900, 840, 765, 735, 700 and 660 cm$^{-1}$.

EXAMPLE 350

(1S,4R,5R(5Z),6S)-7-[4-(4-Phenylphenyl)-6-(4-fluorobenzenesulfonamino)-2-oxabicyclo[2.2.1]hept-5-yl]-5-heptenoic acid 15 mg (27 micromol) of the ester produced according to example 349 was saponified analogously to example 2 and, after working up and purification, 11.4 mg (21 micromol, 77%) of the title compound was isolated as a colorless oil.

IR (film): 3700–2500, 3300, 3060, 3030, 2940, 2880, 1710, 1600, 1550, 1490, 1435, 1325, 1215, 1160, 1155, 1090, 1005, 900, 835, 765, 735, 700 and 660 cm$^{-1}$.

EXAMPLE 351

(1S,4R,5R(5Z),6S)-7-[4-(4-Phenylphenyl)-6-(naphthalene-2-sulfonamino)-2-oxabicyclo[2.2.1]hept-5-yl]-5-heptenoic acid methyl ester 23.3 mg (57.5 micromol) of the amine produced according to example 344a was reacted analogously to example 345 with use of naphthalene-2-sulfonic acid chloride and, after purification, 18.4 mg (31 micromol, 54%) of the title compound was isolated as a colorless oil.

IR (film): 3280, 3060, 3030, 2940, 2870, 1730, 1600, 1485, 1435, 1330, 1265, 1245, 1160, 1130, 1090, 1075, 1005, 900, 835, 815, 765, 735, 700 and 660 cm$^{-1}$.

EXAMPLE 352

(1S,4R,5R(5Z),6S)-7-[4-(4-Phenylphenyl)-6-(naphthalene-2-sulfonamino)-2-oxabicyclo[2.2.1]hept-5-yl]-5-heptenoic acid 18.4 mg (31 micromol) of the ester produced according to example 351 was saponified analogously to example 2 and, after working up and purification, 14.9 mg (26 micromol, 83%) of the title compound was isolated as a colorless oil.

IR (film): 3700–2500, 3280, 3060, 3030, 2940, 2880, 1705, 1600, 1485, 1435, 1330, 1265, 1245, 1160, 1130, 1090, 1075, 1005, 895, 835, 815, 765, 735, 695 and 660 cm$^{-1}$.

EXAMPLE 353

(1S,4R,5R(5Z),6S)-7-[4-(4-Phenylphenyl)-6-(quinoline-8-sulfonamino)-2-oxabicyclo[2.2.1]hept-5-yl]-5-heptenoic acid methyl ester 22.5 mg (55.5 micromol) of the amine produced according to example 344a was reacted analogously to example 345 with use of quinoline-8-sulfonic acid chloride and, after purification, 20 mg (33.5 micromol, 60%) of the title compound was isolated as a colorless oil.

IR (film): 3280, 3060, 3030, 2940, 2870, 1730, 1615, 1595, 1560, 1490, 1370, 1330, 1210, 1170, 1145, 1090, 1070, 1005, 900, 835, 790, 765, 735, 700 and 675 cm$^{-1}$.

EXAMPLE 354

(1S,4R,5R(5Z),6S)-7-[4-(4-Phenylphenyl)-6-(quinoline-8-sulfonamino)-2-oxabicyclo[2.2.1]hept-5-yl]-5-heptenoic acid 20 mg (33.5 micromol) of the ester produced according to example 353 was saponified analogously to example 2 and, after working up and purification, 17 mg (29 micromol, 87%) of the title compound was isolated as a colorless oil.

IR (film): 3700–2500, 3420, 3250, 3060, 3030, 3010, 2930, 2870, 1710, 1615, 1595, 1565, 490, 1450, 1405, 1330, 1215, 1165, 1145, 1090, 1005, 995, 970, 895, 830, 790, 765, 700, 675 and 580 cm$^{-1}$.

EXAMPLE 355

(1S,4R,5R(5Z),6S)-7-[4-(4-Phenylphenyl)-6-(hexylcarbonylamino)-2-oxabicyclo[2.2.1]hept-5-yl]-5-heptenoic acid methyl ester 20.9 mg (51.5 micromol) of the amine produced according to example 344a was reacted analogously to example 345 with use of n-heptanoic acid chloride and, after purification, 21.7 mg (41.9 micromol, 81%) of the title compound was isolated as a colorless oil.

IR (film): 3290, 3060, 3030, 2950, 2930, 2860, 1735, 1715, 1640, 1540, 1485, 1450, 1435, 1365, 1245, 1215, 1165, 1125, 1050, 1005, 970, 900, 835, 765, 730 and 700 cm$^{-1}$.

EXAMPLE 356

(1S,4R,5R(5Z),6S)-7-[4-(4-Phenylphenyl)-6-(hexylcarbonylamino)-2-oxabicyclo[2.2.1]hept-5-yl]-5-heptenoic acid 21.7 mg (41.9 micromol) of the ester produced according to example 355 was saponified analogously to example 2 and, after working up and purification, 21 mg (41.7 micromol, 99%) of the title compound was isolated as a colorless oil.

IR (film): 3700–2500, 3450, 3060, 3030, 3010, 2960, 2930, 2870, 1710, 1645, 1545, 1490, 1455, 1405, 1380, 1300, 1245, 1220, 1125, 1050, 1010, 975, 900, 835, 765, 730 and 695 cm$^{-1}$.

EXAMPLE 357

(1S,4R,5R(5Z),6S)-7-[4-(4-Phenylphenyl)-6-(4-fluorophenylcarbonylamino)-2-oxabicyclo[2.2.1]hept-5-yl]-5-heptenoic acid methyl ester 20.2 mg (49.8 micromol) of the amine produced according to example 344a was reacted analogously to example 345 with use of 4-fluorobenzoic acid chloride and, after purification, 24.7 mg (46.8 micromol, 94%) of the title compound was isolated as a colorless oil.

IR (film): 3310, 3060, 3030, 2940, 2870, 1735, 1715, 1655, 1630, 1605, 1535, 1500, 1440, 1315, 1235, 1160, 1095, 1045, 1005, 970, 900, 850, 765, 735 and 700 cm$^{-1}$.

EXAMPLE 358

(1S,4R,5R(5Z),6S)-7-[4-(4-Phenylphenyl)-6-(4-fluorophenylcarbonylamino)-2-oxabicyclo[2.2.1]hept-5-yl]-5-heptenoic acid 24.7 mg (46.8 micromol) of the ester produced according to example 357 was saponified analogously to example 2 and, after working up and purification, 18 mg (35 micromol, 75%) of the title compound was isolated as a colorless oil.

IR (film): 3700–2500, 3330, 3060, 3030, 3010, 2940, 2880, 1710, 1635, 1605, 1540, 1505, 1235, 1160, 1095, 1010, 970, 900, 850, 765, 735 and 700 cm$^{-1}$.

EXAMPLE 359

(1S,4R,5R(5Z),6S)-7-[4-(4-Phenylphenyl)-6-(perfluorobenzenesulfonamino)-2-oxabicyclo[2.2.1]hept-5-yl]-5-heptenoic acid methyl ester 19 mg (46.9 micromol) of the amine produced according to example 344a was reacted analogously to example 345 with use of perfluorobenzenesulfonic acid chloride and, after purification, 19.5 mg (30.7 micromol, 65%) of the title compound was isolated as a colorless oil.

IR (film): 3260, 3060, 3030, 2940, 2880, 1735, 1710, 1645, 1610, 1515, 1495, 1440, 1360, 1295, 1170, 1100, 990, 900, 835, 765, 735, 700, 645 and 605 cm$^{-1}$.

EXAMPLE 360

(1S,4R,5R(5Z),6S)-7-[4-(4-Phenylphenyl)-6-(perfluorobenzenesulfonamino)-2-oxabicyclo[2.2.1]hept-5-yl]-5-heptenoic acid 19.5 mg (30.7micromol) of the ester produced according to example 359 was saponified analogously to example 2 and, after working up and purification, 16.8 mg (27 micromol, 88%) of the title compound was isolated as a colorless oil.

IR (film): 3700–2500, 3260, 3060, 3030, 2940, 2880, 1705, 1640, 1610, 1515, 1495, 1445, 1365, 1295, 1170, 1095, 990, 900, 835, 765, 735, 700, 645 and 605 cm$^{-1}$.

EXAMPLE 361

(1S,4S,5S(5Z),6R)-7-[4-(4-Fluorophenyl)-6-(4-methylbenzenesulfonamino)-2-oxabicyclo[2.2.1]hept-5-yl]-5-heptenoic acid methyl ester 38 mg (109 micromol) of the amine produced according to example 361a was reacted analogously to example 345 with use of 4-methylbenzenesulfonic acid chloride and, after purification, 36.7 mg (73.2 micromol, 67%) of the title compound was isolated as a colorless oil.

IR (film): 3270, 3060, 3010, 2940, 2970, 1730, 1710, 1600, 1515, 1435, 1325, 1230, 1160, 1090, 1000, 970, 900, 830, 815, 735 and 665 cm$^{-1}$.

EXAMPLE 361a (1R,4S,5S(5Z),6R)-7-[4-(4-Fluorophenyl)-6-amino-2-oxabicyclo[2.2.1]hept-5-yl]-5-heptenoic acid methyl ester (A) and
(1R,4S,5S(5Z),6R)-7-[4-(4-fluorophenyl)-6-trifluoromethylcarbonylamino-2-oxabicyclo[2.2.1]hept-5-yl]-5heptenoic acid methyl ester (B)

142 mg (392 micromol) of the alcohol produced according to example 17a was reacted analogously to examples 344c to 344a and, after working up and purification, 38 mg (109 micromol, 28%) of title compound A as well as 47 mg (102 micromol, 26%) of title compound B each were isolated as a colorless oil.

IR (film) of A: 3340, 3040, 3010, 2940, 2870, 1735, 1605, 1510, 1435, 1360, 1230, 1200, 1160, 1100, 1035, 1000, 895, 835 and 720 cm$^{-1}$.

IR (film) of B: 3310, 3070, 3010, 2950, 2880, 1725, 1705, 1605, 1550, 1515, 1435, 1365, 1300, 1220, 1180, 1160, 1090, 1045, 1005, 970, 945, 900, 835 and 725 cm$^{-1}$.

37 mg (80.5 micromol) of title compound B was dissolved in a mixture of 500 microliters of methanol and 200 microliters of water, mixed with 30 mg of potassium carbonate and stirred for 24 hours at 50° C. It was neutralized by adding a diluted citric acid solution and purified by chromatography on two analytic thin-layer slabs. A mixture of chloroform and acetone was used as a mobile solvent; a mixture of acetone and ethyl acetate was used as an eluant.

22 mg (60.4 micromol, 75%) of title compound A was isolated as a colorless oil.

EXAMPLE 362

(1R,4S,5S(5Z),6R)-7-[4-(4-Fluorophenyl)-6-(4-methyl-benzenesulfonamino-2-oxabicyclo[2.2.1]hept-5-yl]-5-heptenoic acid 36.7 mg (73.2 micromol) of the ester produced according to example 361 was saponified analogously to example 2 and, after working up and purification, 27.8 mg (57 micromol, 78%) of the title compound was isolated as a colorless oil.

IR (film): 3700–2400, 3270, 3050, 3010, 2940, 2980, 1710, 1600, 1515, 1435, 1410, 1325, 1310, 1235, 1160, 1090, 1000, 975, 905, 835, 815, 735 and 665 cm$^{-1}$.

EXAMPLE 363

(1R,4S,5S(5Z),6R)-7-[4-(4-Fluorophenyl)-6-(naphtha-lene-2-sulfonamino)-2-oxabicyclo[2.2.1]hept-5-yl]-5-heptenoic acid methyl ester 20 mg (57.6 micromol) of the amine produced according to example 361a was reacted analogously to example 345 with use of naphthalene-2-sulfonic acid chloride and, after purification, 16 mg (30 micromol, 52%) of the title compound was isolated as a colorless oil.

IR (film): 3270, 3060, 3010, 2940, 2870, 1730, 1605, 1590, 1510, 1435, 1325, 1230, 1160, 1095, 1075, 1000, 900, 860, 830, 820, 735 and 660 cm$^{-1}$.

EXAMPLE 364

(1R,4S,5S(5Z),6R)-7-[4-(4-Fluorophenyl)-6-(naphtha-lene-2-sulfonamino)-2-oxabicyclo[2.2.1]hept-5-yl]-5-heptenoic acid 16 mg (30 micromol) of the ester produced according to example 363 was saponified analogously to example 2 and, after working up and purification, 15.3 mg (29 micromol, 97%) of the title compound was isolated as a colorless oil.

IR (film): 3700–2500, 3270, 3060, 3010, 2930, 2870, 1705, 1605, 1590, 1515, 1455, 1435, 1410, 1325, 1235, 1160, 1130, 1095, 1075, 1000, 975, 900, 865, 830, 815, 750, 660 and 550 cm$^{-1}$.

EXAMPLE 365

(1S,4R,5R(5Z),6S)-7-[4-(4-Phenylphenyl)-6-(3-phenyl-propylcarbonylamino)-2-oxabicyclo[2.2.1]hept-5-yl]-5-heptenoic acid methyl ester 19.7 mg (48 micromol) of the amine produced according to example 344a was reacted analogously to example 345 with use of 4-phenylbutyric acid chloride and, after purification, 22.8 mg (41 micromol, 85%) of the title compound was isolated as a colorless oil.

IR (film): 3300, 3080, 3060, 3030, 2940, 2870, 1730, 1635, 1535, 1485, 1450, 1245, 1160, 1005, 900, 835, 765, 730 and 700 cm$^{-1}$.

EXAMPLE 366

(1S,4R,5R(5Z),6S)-7-[4-(4-Phenylphenyl)-6-(3-phenyl-propylcarbonylamino)-2-oxabicyclo[2.2.1]hept-5-yl]-5-heptenoic acid 22.8 mg (41 micromol) of the ester produced according to example 365 was saponified analogously to example 2 and, after working up and purification, 21 mg (39 micromol, 95%) of the title compound was isolated as a colorless oil.

IR (film): 3430, 3060, 3030, 2930, 2860, 1705, 1635, 1540, 1490, 1450, 1150, 1005, 970, 900, 835, 765, 730 and 695 cm$^{-1}$.

EXAMPLE 367

(1S,4R,5R(5Z),6S)-7-[4-(4-Phenylphenyl)-6-(2-phenox-yethylcarbonylamino)-2-oxabicyclo[2.2.1]hept-5-yl]-5-heptenoic acid methyl ester 17.2 mg (42 micromol) of the amine produced according to example 344a was reacted analogously to example 345 with use of 3-phenoxypropyl chloride and, after purification, 17.7 mg (32 micromol, 76%) of the title compound was isolated as a colorless oil.

IR (film): 3300, 3060, 3030, 2940, 2870, 1735, 1640, 1600, 1540, 1490, 1240, 1170, 1040, 1005, 895, 835, 765, 755, 730 and 695 cm$^{-1}$.

EXAMPLE 368

(1S,4R,5R(5Z),6S)-7-[4-(4-Phenylphenyl)-6-(3-phenyl-propylcarbonylamino)-2-oxabicyclo[2.2.1]hept-5-yl]-5-heptenoic acid 17.7 mg (32 micromol) of the ester produced according to example 367 was saponified analogously to example 2 and, after working up and purification, 14 mg (26 micromol, 81%) of the title compound was isolated as a colorless oil.

IR (film): 3430, 3060, 3030, 2930, 2860, 1705, 1640, 1600, 1550, 1495, 1490, 1240, 1040, 1005, 900, 835, 765, 755, 730 and 690 cm$^{-1}$.

EXAMPLE 369

(1S,4R,5S(5Z),6S)-7-[4-(4-Phenylphenyl)-6-[4(S)-hydroxy-4(RS)-phenyl-1(E)-pentenyl]-2-oxabicy-clo[2.2.1]hept-5-yl]-5-heptenoic acid methyl ester (A)
and
(1S,4R,5S(5Z),6S)-7-[4-(4-phenylphenyl)-6-[3(R)-hydroxy-4(RS)-phenyl-1(E)-pentenyl]-2-oxabicy-clo[2.2.1]hept-5-yl]-5-heptenoic acid methyl ester (B)

62 mg (113 micromol) of the unsaturated ketone produced in example 369a was reduced analogously to example 23 and, after working up and purification, 54 mg (98 micromol, 87%) of a mixture of both title compounds was isolated as a colorless oil.

IR (film): 3600–3200, 3080, 3060, 3030, 2960, 2870, 1735, 1600, 1485, 1450, 1245, 1195, 1005, 995, 970, 895, 835, 765, 730 and 700 cm$^{-1}$.

The chromatographic separation yielded 20.1 mg (36 micromol, 32%) of the more nonpolar alcohol, to which structure A was assigned, as well as 30.1 mg (55 micromol, 48%) of the more polar alcohol, to which structure B was assigned.

EXAMPLE 369a (1S,4R,5S(5Z),6S)-7-[4-(4-Phenylphenyl)-6-(3-oxo-4(RS)-phenyl-1(E)-pentenyl]-2-oxabicyclo[2.2.1]hept-5-yl]-3-oxa-5-heptenoic acid methyl ester 54.1 mg (129 micromol) of the aldehyde produced in example 307b was reacted analogously to example 23a with use of dimethyl-(2-oxo-3(RS)-phenylbutyl)-phosphonate and, after working up and purification, 62 mg (113 micromol, 87%) of the title compound was isolated as a colorless oil.

IR (film): 3080, 3050, 3030, 2970, 2940, 2870, 1735, 1690, 1670, 1620, 1600, 1485, 1445, 1310, 1240, 1195, 1165, 1075, 1030, 995, 970, 900, 835, 765, 730 and 700 cm$^{-1}$.

EXAMPLE 370

(1S,4R,5S(5Z),6S)-7-[4-(4-Phenylphenyl)-6-[3(R)-hydroxy-4(RS)-phenyl-1(E)-pentenyl]-2-oxabicyclo[2.2.1]hept-5-yl]-5-heptenoic acid 30.1 mg (55 micromol) of polar ester B produced according to example 369 was saponified analogously to example 2 and, after working up and purification, 25.4 mg (47 micromol, 86%) of the title compound was isolated as waxy solid.

IR (KBr): 3430, 3080, 3060, 3030, 2970, 2930, 2870, 1705, 1600, 1485, 1450, 1400, 1240, 1195, 1005, 995, 970, 895, 835, 765, 730 and 700 cm$^{-1}$.

EXAMPLE 371

(1S,4R,5S(5Z),6S)-7-[4-(4-Phenylphenyl)-6-[3(S)-hydroxy-4(RS)-phenyl-1(E)-pentenyl]-2-oxabicyclo[2.2.1]hept-5-yl]-5-heptenoic acid 20.1 mg (36 micromol) of nonpolar ester A produced according to example 369 was saponified analogously to example 2 and, after working up and purification, 19 mg (35 micromol, 98%) of the title compound was isolated as a colorless oil.

IR (film): 3430, 3060, 3030, 2950, 2870, 1705, 1600, 1550, 1485, 1400, 1240, 1040, 1005, 995, 970, 895, 835, 765, 730 and 700 cm$^{-1}$.

EXAMPLE 372

(1S,4R,5S(5Z),6S)-7-[4-(4-Phenylphenyl)-6-[3(S)-hydroxy-5-phenyl-1(E)-pentenyl]-2-oxabicyclo[2.2.1]hept-5-yl]-5-heptenoic acid methyl ester (A) and
(1S,4R,5S(5Z),6S)-7-[4-(4-phenylphenyl)-6-[3(R)-hydroxy-5-phenyl-1(E)-pentenyl]-2-oxabicyclo[2.2.1]hept-5-heptenoic acid methyl ester (B)

65 mg (118 micromol) of the unsaturated ketone produced in example 372a was reduced analogously to example 23 and, after working up and purification, 59 mg (107 micromol, 91%) of a mixture of both title compounds was isolated as a colorless oil.

IR (film): 3600-3200, 3080, 3050, 3020, 2940, 2860, 1735, 1600, 1485, 1450, 1435, 1245, 1195, 1165, 1045, 1005, 995, 970, 895, 835, 765, 730 and 700 cm$^{-1}$.

The chromatographic separation yielded 30 mg (54 micromol, 46%) of the more nonpolar alcohol, to which structure A was assigned, as well as 26.7 mg (48 micromol, 41%) of the more polar alcohol, to which structure B was assigned.

EXAMPLE 372a (1S,4R,5S(5Z),6S)-7-[4-(4-Phenylphenyl)-6-(3-oxo-5-phenyl]-1(E)-pentenyl]-2-oxabicyclo[2.2.1]hept-5-yl]-3-oxa-5-heptenoic acid methyl ester 55.5 mg (133 micromol) of the aldehyde produced in example 307b was reacted analogously to example 23a with use of dimethyl-(2-oxo-4-phenylbutyl)-phosphonate and, after working up and purification, 65 mg (118 micromol, 89%) of the title compound was isolated as a colorless oil.

IR (film): 3080, 3060, 3030, 2940, 2870, 1735, 1690, 1665, 1620, 1600, 1485, 1445, 1310, 1450, 1435, 1365, 1240, 1190, 1170, 995, 975, 900, 835, 765, 730 and 700 cm$^{-1}$.

EXAMPLE 373

(1S,4R,5S(5Z),6S)-7-[4-(4-Phenylphenyl)-6-[3(R)-hydroxy-5-phenyl-1(E)-pentenyl]-2-oxabicyclo[2.2.1]hept-5-yl]-5-heptenoic acid 26.7 mg (48 micromol) of polar ester B produced according to example 372 was saponified analogously to example 2 and, after working up and purification, 21.7 mg (40 micromol, 84%) of the title compound was isolated as waxy solid.

IR (film): 3700-2600, 3080, 3060, 3030, 2930, 2870, 1705, 1600, 1490, 1450, 1405, 1195, 1125, 1095, 1005, 995, 970, 890, 765, 730 and 700 cm$^{-1}$.

EXAMPLE 374

(1S,4R,5S(5Z),6S)-7-[4-(4-Phenylphenyl)-6-[3(S)-hydroxy-5-phenyl-1(E)-pentenyl]-2-oxabicyclo[2.2.1]hept-5-yl]-5-heptenoic acid 30 mg (54 micromol) of nonpolar ester A produced according to example 372 was saponified analogously to example 2 and, after working up and purification, 24.5 mg (46 micromol, 85%) of the title compound was isolated as a colorless oil.

IR (film): 3700-2600, 3080, 3060, 3030, 2930, 2870, 1710, 1600, 1490, 1450, 1405, 1345, 1195, 1125, 1095, 1005, 995, 970, 895, 765, 730 and 700 cm$^{-1}$.

EXAMPLE 375

(1S,4R,5S(5Z),6S)-7-[4-(4-Phenylphenyl)-6-[3(S),5-dihydroxy-4(RS)-phenyl-1(E)-pentenyl]-2-oxabicyclo[2.2.1]hept-5-yl]-5-heptenoic acid methyl ester (A) and
(1S,4R,5S(5Z),6S)-7-[4-(4-phenylphenyl)-6-[3(R),5-dihydroxy-4(RS)-phenyl-1(E)-pentenyl]-2-oxabicyclo[2.2.1]hept-5-yl]-5-heptenoic acid methyl ester (B)

33.6 mg (42 micromol) of the unsaturated ketone produced in example 375a was reduced analogously to example 23. The diastereoisomeric alcohols isolated after working up and chromatographic purification were separately subjected to a silyl ether cleavage and analogously to example 1a. After renewed working up and chromatographic purification, 15.3 mg (27 micromol, 64%) of the more nonpolar alcohol, to which structure A was assigned, as well as 8.2 mg (14 micromol, 34%) of the more polar alcohol, to which structure B was assigned, were isolated.

IR (film) of A: 3600-3200, 3060, 3030, 2940, 2880, 1730, 1600, 1485, 1450, 1425, 1265, 1195, 1110, 995, 970, 835, 765, 735 and 700 cm$^{-1}$.

EXAMPLE 375a (1S,4R,5S(5Z),6S)-7-[4-(4-Phenylphenyl)-6-(3-oxo-4(RS)-phenyl-5(tert-butyldiphenylsilyloxy)-1(E)-pentenyl]-2-oxabicyclo[2.2.1]hept-5-yl]-3-oxa-5-heptenoic acid methyl ester 54 mg (129 micromol) of the aldehyde produced in example 307b was reacted analogously to example 23a with use of dimethyl-(2-oxo-34(RS)-phenyl-4-(tert-butyldiphenylsilyloxy)butyl)-phosphonate and, after working up and purification, 33.6 mg (42 micromol, 32%) of the title compound was isolated as a colorless oil.

IR (film): 3050, 3030, 2940, 2860, 1735, 1690, 1665, 1620, 1600, 1485, 1450, 1425, 1190, 1110, 995, 970, 900, 820, 765, 735 and 700 cm$^{-1}$.

EXAMPLE 376

(1S,4R,5S(5Z),6S)-7-[4-(4-Phenylphenyl)-6-[3(R),5-dihydroxy-4(RS)-phenyl-1(E)-pentenyl]-2-oxabicyclo[2.2.1]hept-5-yl]-5-heptenoic acid 8.2 mg (14 micromol) of polar ester B produced according to example 375 was saponified analogously to example 2 and, after working up and purification, 6.6 mg (12 micromol, 85%) of the title compound was isolated as waxy solid.

IR (film): 3700–2400, 3080, 3050, 3030, 2930, 2880, 1710, 1600, 1485, 1450, 1405, 1295, 1240, 1195, 1045, 1005, 995, 970, 890, 835, 765, 735 and 700 cm$^{-1}$.

EXAMPLE 377

(1S,4R,5S(5Z),6S)-7-[4-(4-Phenylphenyl)-6-[3(S),5-dihydroxy-4(RS)-phenyl-1(E)-pentenyl]-2-oxabicyclo[2.2.1]hept-5-yl]-5-heptenoic acid 15.3 mg (27 micromol) of nonpolar ester A produced according to example 375 was saponified analogously to example 2 and, after working up and purification, 14 mg (25 micromol, 94%) of the title compound was isolated as a colorless oil.

IR (film): 3700–2400, 3080, 3060, 3030, 2930, 2880, 1705, 1600, 1490, 1450, 1400, 1240, 1195, 1045, 1005, 995, 970, 890, 835, 765, 730 and 700 cm$^{-1}$.

EXAMPLE 378

(1S,4R,5S,6R)-7-[4-(4-Fluorophenyl)-6-(4-cyanobenzyloxymethyl)-2-oxabicyclo[2.2.1]hept-5-yl]-3-oxa-5(Z)-heptenoic acid-tert-butyl ester 13.2 mg (32 micromol) of the alcohol produced in example 274a was reacted analogously to example 1 with 4-cyanobenzyl bromide and, after working up and purification, 13.7 mg (26 micromol, 82%) of the title compound was isolated as a colorless oil.

IR (film): 3050, 2980, 2930, 2870, 2230, 1745, 1610, 1510, 1365, 1230, 1160, 1125, 1030, 945, 895, 835, 820 and 735 cm$^{-1}$.

EXAMPLE 379

(1S,4R,5S,6R)-7-[4-(4-Fluorophenyl)-6-(4-cyanobenzyloxymethyl)-2-oxabicyclo[2.2.1]hept-5-yl]-3-oxa-5(Z)-heptenoic acid 13.7 mg (26 micromol) of the ester produced according to example 378 was saponified analogously to example 2 and, after working up and purification, 10.5 mg (23 micromol, 88%) of the title compound was isolated as a colorless oil.

IR (film): 3600–2500, 3070, 3040, 2920, 2870, 2230, 1725, 1610, 1510, 1230, 1160, 1115, 1030, 1020, 975, 895, 835 and 820 cm$^{-1}$.

EXAMPLE 380

(1S,4R,5S,6R)-7-[4-(4-Fluorophenyl)-6-(4-cyanobenzyloxymethyl)-2-oxabicyclo[2.2.1]hept-5-yl]-3-oxa-5(E)-heptenoic acid 11.2 mg (28 micromol) of the alcohol produced in example 276a was reacted analogously to example 1 with 4-cyanobenzyl bromide and, after working up and purification, 10 mg (21 micromol, 77%) of the title compound was isolated as a colorless oil.

IR (film): 3600–2500, 3040, 2920, 2860, 2220, 1720, 1610, 1510, 1420, 1370, 1230, 1160, 1115, 1100, 1030, 970, 895, 830 and 820 cm$^{-1}$.

EXAMPLE 381

(1S,4R,5S,6R)-7-[4-(4-Fluorophenyl)-6-(4-cyanobenzyloxymethyl)-2-oxabicyclo[2.2.1]hept-5-yl]-3-oxa-5(E)-heptenoic acid methyl ester 3 mg (6 micromol) of the acid produced in example 380 was esterified analogously to example 186 and, after removal of the solvent, 3 mg (6 micromol, 99%) of the title compound was isolated as a colorless oil.

IR (film): 3070, 3040, 2920, 2860, 2220, 1735, 1605, 1510, 1420, 1230, 1160, 1105, 1025, 970, 895, 830 and 820 cm$^{-1}$.

EXAMPLE 382

(1S,4R,5S,6R)-7-[4-(4-Fluorophenyl)-6-(naphth-2-ylmethoxymethyl)-2-oxabicyclo[2.2.1]hept-5-yl]-3-oxa-5(E)-heptenoic acid-tert-butyl ester 11.7 mg (29 micromol) of the alcohol produced in example 276a was reacted analogously to example 1 with 2-bromomethylnaphthalene and, after working up and purification, 15.6 mg (28 micromol, 98%) of the title compound was isolated as a colorless oil.

IR (film): 3050, 2970, 2920, 2860, 1745, 1600, 1510, 1365, 1225, 1160, 1125, 1030, 970, 895, 830, 820 and 820 cm$^{-1}$.

EXAMPLE 383

(1S,4R,5S,6R)-7-[4-(4-Fluorophenyl)-6-(naphth-2-ylmethoxymethyl)-2-oxabicyclo[2.2.1]hept-5-yl]-3-oxa-5(E)-heptenoic acid 15.6 mg (28 micromol) of the ester produced according to example 382 was saponified analogously to example 2 and, after working up and purification, 10.8 mg (22 micromol, 79%) of the title compound was isolated as a colorless oil.

IR (film): 3600–2400, 3050, 2920, 2860, 1730, 1605, 1510, 1230, 1160, 1120, 1030, 970, 895, 830, 820 and 750 cm$^{-1}$.

EXAMPLE 384

(1S,4R,5S,6R)-7-[4-(4-Fluorophenyl)-6-(naphth-2-ylmethoxymethyl)-2-oxabicyclo[2.2.1]hept-5-yl]-3-oxa-5(Z)-heptenoic acid-tert-butyl ester 14.3 mg (35 micromol) of the alcohol produced in example 274a was reacted analogously to example 1 with 2-bromomethylnaphthalene and, after working up and purification, 18.2 mg (33 micromol, 95%) of the title compound was isolated as a colorless oil.

IR (film): 3050, 2970, 2920, 2860, 1745, 1600, 1510, 1365, 1230, 1160, 1120, 1030, 945, 895, 830, 820, and 750 cm$^{-1}$.

EXAMPLE 385

(1S,4R,5S,6R)-7-[4-(4-Fluorophenyl)-6-(naphth-2-ylmethoxymethyl)-2-oxabicyclo[2.2.1]hept-5-yl]-3-oxa-5(Z)-heptenoic acid 18.2 mg (33 micromol) of the ester produced according to example 384 was saponified analogously to example 2 and, after working up and purification, 12.9 mg (26 micromol, 79%) of the title compound was isolated as a colorless oil.

IR (film): 3700–2500, 3050, 3010, 2920, 2860, 1725, 1605, 1510, 1230, 1160, 1125, 1100, 1030, 975, 950, 895, 830, 820 and 750 cm$^{-1}$.

EXAMPLE 386

(1S,4R,5S,6S)-7-[4-(4-Fluorophenyl)-6-(3(S)-hydroxy-4(RS)-phenyl-1(E)-pentenyl]-2-oxabicyclo[2.2.1]hept-5-yl]-3-oxa-5(Z)-heptenoic acid-tert-butyl ester (A) and (1S,4R,5S,6S)-7-[4-(4-phenylphenyl)-6-[3(R)-hydroxy-4(RS)-phenyl-1(E)-pentenyl)-2-oxabicyclo[2.2.1]hept-5-yl]-3-oxa-5(Z)-heptenoic acid-tert-butyl ester (B)

39 mg (73 micromol) of the unsaturated ketone produced in example 386a was reduced analogously to example 23 and, after working up and purification, 34 mg (63 micromol, 87%) of a mixture of both title compounds was isolated as a colorless oil.

IR (film): 3600–3200, 3060, 3020, 2970, 2930, 2870, 1740, 1600, 1510, 1450, 1370, 1230, 1160, 1125, 1000, 970, 945, 895, 835, 735 and 700 cm$^{-1}$.

The chromatographic separation yielded 13.1 mg (24 micromol, 33%) of the more nonpolar alcohol, to which structure A was assigned, as well as 18.7 mg (35 micromol, 48%) of the more polar alcohol, to which structure B was assigned.

EXAMPLE 386a (1S,4R,5S,6S)-7-[4-(4-Fluorophenyl)-6-(3-oxo-4(RS)-phenyl-1(E)-pentenyl]-2-oxabicyclo[2.2.1]hept-5-yl]-3-oxa-5(Z)-heptenoic acid-tert-butyl ester 56.8 mg (140 micromol) of the aldehyde produced in example 286b was reacted analogously to example 23a with use of dimethyl-(2-oxo-3(RS)-phenylbutyl)-phosphonate and, after working up and purification, 39 mg (73 micromol, 52%) of the title compound was isolated as a colorless oil.

IR (film): 3060, 3020, 2970, 2930, 2870, 1740, 1690, 1665, 1620, 1600, 1510, 1450, 1370, 1230, 1160, 1125, 1040, 1000, 975, 940, 900, 835, 765 and 700 cm$^{-1}$.

EXAMPLE 387

(1S,4R,5S,6S)-7-[4-(4-Fluorophenyl)-6-(3(R)-hydroxy-4(RS)-phenyl-1(E)-pentenyl]-2-oxabicyclo[2.2.1]hept-5-yl]-3-oxa-5(Z)-heptenoic acid 18.7 mg (35 micromol) of polar ester B produced according to example 386 was saponified analogously to example 2 and, after working up and purification, 12.8 mg (27 micromol, 76%) of the title compound was isolated as a colorless oil.

IR (film): 3600–3200, 3080, 3050, 3020, 2970, 2930, 2870, 1730, 1610, 1510, 1450, 1230, 1160, 1110, 1015, 995, 970, 895, 835 and 700 cm$^{-1}$.

EXAMPLE 388

(1S,4R,5S,6S)-7-[4-(4-Fluorophenyl)-6-[3(S)-hydroxy-4(RS)-phenyl-1(E)-pentenyl)-2-oxabicyclo[2.2.1]hept-5-yl]-3-oxa-5(Z)-heptenoic acid 13.1 mg (24 micromol) of nonpolar ester A produced according to example 386 was saponified analogously to example 2 and, after working up and purification, 8.5 mg (18 micromol, 74%) of the title compound was isolated as a colorless oil.

IR (film): 3600–3200, 3080, 3060, 3020, 2970, 2930, 2870, 1725, 1605, 1510, 1450, 1425, 1230, 1160, 1105, 1015, 995, 940, 970, 895, 835 and 700 cm$^{-1}$.

We claim:

1. A 2-oxabicyclic[2.2.1]heptane derivative of formula I

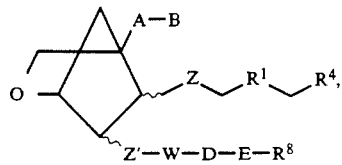

or an enantiomer thereof, wherein

A is —(CH$_2$)$_n$—, (E)— or (Z)—CH=CH—, or C≡C—, n is 0–7,

B is —OR$^2$, halogen, —C≡N, N$_3$, or —COOR$^3$,

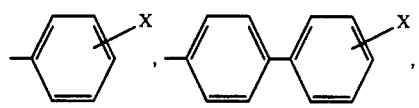

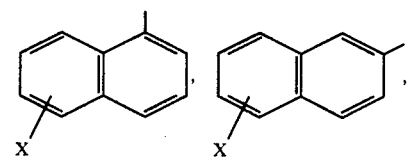

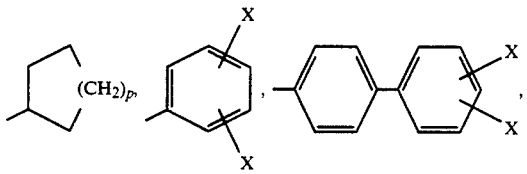

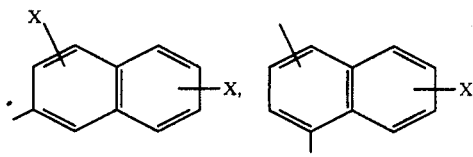

or a 5- or 6-membered heterocyclic radical with at least one N, O or S atom,

R$^1$ is oxygen, a direct bond or a —CH$_2$ group,

R$^2$ is hydrogen, C$_1$–C$_{10}$-alkyl, C$_5$–C$_{12}$-aryl substituted by X or C$_7$–C$_{16}$-aralkyl substituted by X, R$^3$ is hydrogen, C$_1$–C$_{10}$-alkyl, C$_5$–C$_6$-cycloalkyl, C$_6$–C$_{12}$-aryl or C$_7$–C$_{16}$-aralkyl, X is hydrogen C$_1$–C$_5$-alkyl,

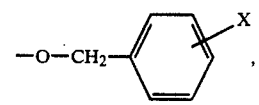

—OR$^2$, halogen, —C≡N, —N$_3$, —NO$_2$, —COOR$^3$, trifluoromethyl or phenyl,

R$^4$ is

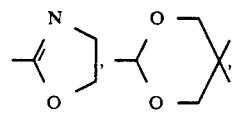

—COOR$^5$, wherein

R$^5$ is hydrogen, or C$_1$—C$_{10}$-alkyl unsubstituted or substituted by halogen, phenyl, C$_1$–C$_4$-alkoxy or di-($C_1$-$C_4$)-alkylamino, $C_5$-$C_6$-cycloalkyl, $C_7$-$C_{16}$-aralkyl, phenacyl or $C_6$-$C_{12}$-aryl substituted by X or a 5- or 6-member heterocyclic radical with at least one N, O or S atom, or —CONHR$^6$, wherein $R^6$ is hydrogen, $C_1$-$C_{10}$-alkanoyl or $C_1$-$C_{10}$-alkanesulfonyl or CONR$^2$R$^3$ or

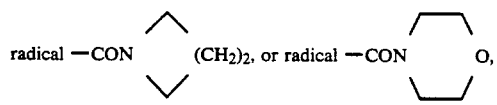

t is 2 or 3,

Z and Z′ are identical or different and are —($CH_2$)$_p$—, (E)-CH=CH, —CH=CR$^7$, or —C≡C, p is 0 to 5, W is a direct bond

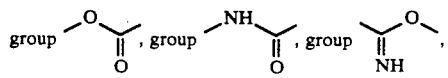

a free of functionally modified hydroxymethylene group or a free or functionally modified

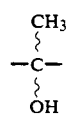

group wherein the OH group is respectively in the α- or β-position,

D is a direct bond,

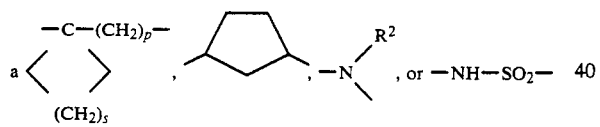

group, a straight-chain saturated $C_1$-$C_5$-alkylene group, a $C_2$-$C_5$-branched saturated or a straight-chain or branched unsaturated alkylene group, unsubstituted or substituted by fluorine atoms, s is 2 to 4, E is a direct bond, —C≡C— or —CH=CR$^7$—, wherein R$^7$ is hydrogen, $C_1$-$C_5$-alkyl, halogen or trifluoromethyl, R$^8$ is hydrogen, $C_1$-$C_{10}$-alkyl, $C_3$-$C_{10}$-cycloalkyl, $C_7$-$C_{16}$-aralkyl unsubstituted or substituted by X, $C_6$-$C_{12}$-aryl unsubstituted or substituted by X or a 5- or 6-member heterocyclic radical with at least one N, O or S atom, or, if E represents a direct bond,

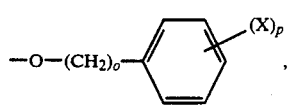

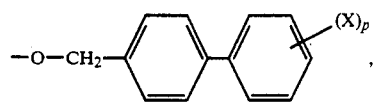

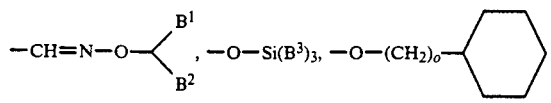

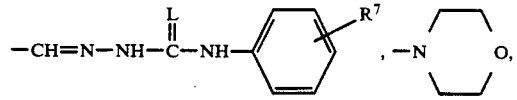

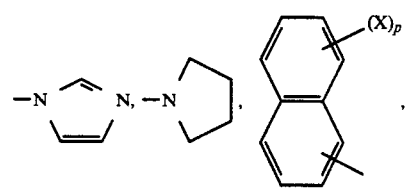

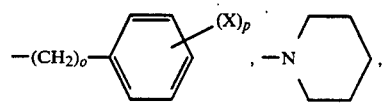

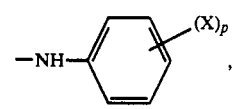

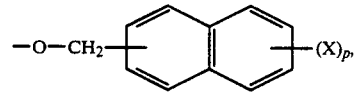

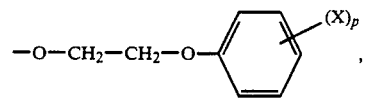

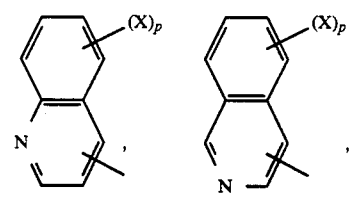

—O—($CH_2$)$_s$—L—($CH_2$)$_o$—X, wherein X is the same or different in radicals —(X)$_p$, if p=2 or 3, o is 0 to 5, B$^1$ and B$^2$ are the same or different and are, except for halogen, B, each B$^3$ is the same or different and is $C_1$-$C_4$-alkyl, phenyl or $C_7$-$C_{16}$-aralkyl, L is oxygen or sulfur, and if R$^5$ is hydrogen, a salt thereof with a physiologically compatible base, or an α-, β-, or γ-cyclodextrin clathrate thereof, or a compound of formula I encapsulated in liposomes.

2. A compound of claim 1, wherein

D is a direct bond, a straight-chain saturated $C_{1-5}$-alkylene group, —NR$^2$— or —NH—SO$_2$.

3. A compound of claim 1, wherein

A—B is 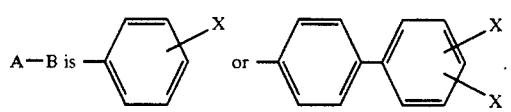

4. A compound of claim 1, wherein $R^8$ is hydrogen, $C_{1-10}$-alkyl, $C_{3-10}$-cycloalkyl,

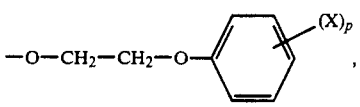

$C_{6-12}$-aryl, unsubstituted or substituted by X, $C_{7-16}$-aralkyl, unsubstituted or substituted by X, or

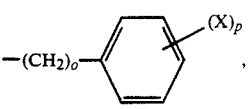

5. A compound of claim 1, wherein
$R^4$ is —COOR$^5$ or

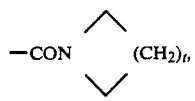

$R^5$ is H, $C_{1-5}$-alkyl or $C_{7-8}$-aralkyl, unsubstituted or substituted by halogen.

6. A pharmaceutical composition comprising an effective amount of a compound of claim 1 and a pharmaceutically acceptable excipient.

7. A pharmaceutical composition of claim 6, wherein the amount of the compound is 0.1–100 mg.

* * * * *